(12) United States Patent
Mun et al.

(10) Patent No.: US 12,108,662 B2
(45) Date of Patent: *Oct. 1, 2024

(54) COMPOUND FOR ORGANIC ELECTRONIC ELEMENT, ORGANIC ELECTRONIC ELEMENT USING SAME AND ELECTRONIC DEVICE THEREFOR

(71) Applicant: DUK SAN NEOLUX CO., LTD., Cheonan-si (KR)

(72) Inventors: Soung Yun Mun, Cheonan-si (KR); Jae Taek Kwon, Cheonan-si (KR); Jong Gwang Park, Cheonan-si (KR); Yun Suk Lee, Seongnam-si (KR); Won Sam Kim, Hwaseong-si (KR); Seul Gi Kim, Daejeon (KR); Jin Bae Jeon, Cheonan-si (KR); Jung Hwan Park, Hwaseong-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 262 days.

This patent is subject to a terminal disclaimer.

(21) Appl. No.: 16/304,346

(22) PCT Filed: May 24, 2017

(86) PCT No.: PCT/KR2017/005413
§ 371 (c)(1),
(2) Date: Nov. 26, 2018

(87) PCT Pub. No.: WO2017/204556
PCT Pub. Date: Nov. 30, 2017

(65) Prior Publication Data
US 2019/0296248 A1    Sep. 26, 2019

(30) Foreign Application Priority Data

May 26, 2016  (KR) .................. 10-2016-0065005
Jul. 4, 2016  (KR) .................. 10-2016-0084282
May 19, 2017  (KR) .................. 10-2017-0062429

(51) Int. Cl.
*H10K 85/60*    (2023.01)
*C07C 211/54*    (2006.01)
(Continued)

(52) U.S. Cl.
CPC .......... *H10K 85/636* (2023.02); *C07C 211/54* (2013.01); *C07D 209/82* (2013.01);
(Continued)

(58) Field of Classification Search
CPC .. H10K 85/622; H10K 85/626; H10K 85/631; H10K 85/633; H10K 85/636;
(Continued)

(56) References Cited

U.S. PATENT DOCUMENTS

2002/0121860 A1* 9/2002 Seo .............................. 313/506
2003/0157364 A1* 8/2003 Senoo .......................... 428/690
(Continued)

FOREIGN PATENT DOCUMENTS

KR    10-2015-0007476 A    1/2015
KR    10-2015-0124902 A    11/2015
(Continued)

OTHER PUBLICATIONS

Pang et al. "A full-color, low-power, wearable display for mobile applications", SPIE, Mar. 29, 2012 (Year: 2012).*
(Continued)

*Primary Examiner* — Dylan C Kershner
*Assistant Examiner* — Seokmin Jeon
(74) *Attorney, Agent, or Firm* — Vorys, Sater, Seymour and Pease LLP; Mih Suhn Koh

(57) ABSTRACT

Provided are an organic electronic element and an electronic device therefor, wherein the organic electronic element has a mixture of a compound according to the present invention
(Continued)

used as material for an organic layer thereof, thereby enabling the achievement of high light-emitting efficiency and low driving voltage of the organic electronic element, and enabling the life of the element to be greatly extended.

16 Claims, 7 Drawing Sheets

(51) Int. Cl.
    *C07D 209/82*     (2006.01)
    *C07D 307/91*     (2006.01)
    *C07D 333/76*     (2006.01)
    *C07D 409/12*     (2006.01)
    *C09K 11/06*     (2006.01)
    *H10K 50/00*     (2023.01)
    *H10K 50/11*     (2023.01)
    *H10K 50/15*     (2023.01)
    *H10K 50/17*     (2023.01)
    *H10K 99/00*     (2023.01)
    *H10K 101/10*     (2023.01)

(52) U.S. Cl.
    CPC ......... *C07D 307/91* (2013.01); *C07D 333/76* (2013.01); *C07D 409/12* (2013.01); *C09K 11/06* (2013.01); *H10K 50/00* (2023.02); *H10K 50/11* (2023.02); *H10K 85/622* (2023.02); *H10K 85/626* (2023.02); *H10K 85/633* (2023.02); *H10K 85/654* (2023.02); *H10K 85/6572* (2023.02); *H10K 99/00* (2023.02); *H10K 50/15* (2023.02); *H10K 50/17* (2023.02); *H10K 85/6574* (2023.02); *H10K 85/6576* (2023.02); *H10K 2101/10* (2023.02)

(58) Field of Classification Search
    CPC ............... H10K 85/654; H10K 85/657; H10K 85/6572; H10K 85/6574; H10K 85/6576; H10K 50/00; H10K 50/11; H10K 50/15; H10K 50/156; H10K 50/17; H10K 2101/10
See application file for complete search history.

(56) References Cited

U.S. PATENT DOCUMENTS

| 2006/0103298 | A1* | 5/2006 | Lee ............................ 313/504 |
| 2007/0252516 | A1* | 11/2007 | Kondakova .................. 313/504 |
| 2009/0167162 | A1* | 7/2009 | Lin .............................. 313/504 |
| 2010/0187977 | A1* | 7/2010 | Kai .............................. 313/504 |
| 2011/0006670 | A1* | 1/2011 | Katakura ..................... 313/504 |
| 2011/0163302 | A1* | 7/2011 | Lin ................................ 257/40 |
| 2012/0181521 | A1* | 7/2012 | Yabunouchi ................... 257/40 |
| 2013/0234119 | A1 | 9/2013 | Mizuki et al. |
| 2015/0179941 | A1* | 6/2015 | Miyata .................. H01L 51/006 |
| 2015/0364699 | A1* | 12/2015 | Sisk ..................... H01L 51/0072 |
| 2016/0164046 | A1* | 6/2016 | Uezawa ................. H01L 51/56 |
| 2017/0047527 | A1* | 2/2017 | Lee ..................... H01L 51/0072 |
| 2017/0294489 | A1* | 10/2017 | Lim .................... H01L 27/3211 |

FOREIGN PATENT DOCUMENTS

| KR | 10-2016-0007965 A | 1/2016 |
| KR | 10-2016-0034527 A | 3/2016 |
| KR | 10-2016-0038814 A | 4/2016 |
| KR | 10-1614739 B1 | 4/2016 |

OTHER PUBLICATIONS

Machine-translate English version of WO 2013/105747, Junghwang Park, Jul. 18, 2013 (Year: 2013).*
English translation of CN 104650029 A combined with the original CN 104650029 A, Yinkui Li, May 27, 2015 (Year: 2015).*
English translation of KR 2013/0024521 and the original KR 2013/0024521, Soung Yun Mun (Year: 2013).*
Huiqing Pang et al. "A full-color, low-power, wearable display for mobile applications", SPIE, Mar. 29, 2012 (Year: 2012).*
English translation of JP 2002/234888 A and the original JP 2002/234888 A, Yoshiyuki Totani, Aug. 23, 2002 (Year: 2002).*
English translation of KR20150031892 and the original KR20150031892, Feb. 3, 2020, SoungYun Mun (Year: 2020).*
Non-Final Office Action for corresponding KR Patent Application No. 10-2017-0062429, 17 pages, issued Jan. 21, 2019.

* cited by examiner

COMPOUND FOR ORGANIC ELECTRONIC ELEMENT, ORGANIC ELECTRONIC ELEMENT USING SAME AND ELECTRONIC DEVICE THEREFOR

BACKGROUND

Technical Field

The present invention relates to compound for organic electronic element, organic electronic element using the same, and an electronic device thereof.

Background Art

In general, organic light emitting phenomenon refers to a phenomenon that converts electronic energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function.

In the case of a polycyclic compound containing a heteroatom, the difference in properties according to the material structure is so large that it is applied to various layers as a material of an organic electronic element. In particular, it has characteristics of different band gaps (HOMO, LUMO), electronical characteristics, chemical properties, and physical properties depending on the number of rings, fused positions and the type and arrangement of heteroatoms, therefore application development for layers of various organic electronic elements using the same has been progressed.

As a representative example thereof, in the following Patent Documents 1 to 4, the performance of the 5-membered cyclic compound in the polycyclic compound has been reported depending on the hetero type, arrangement, substituent type, fused position, and the like.

[Patent Document 1]: U.S. Pat. No. 5,843,607
[Patent Document 2]: Japanese Laid-Open Patent Publication No. 1999-162650
[Patent Document 3]: Korean Published Patent Application No. 2008-0085000
[Patent Document 4]: US Patent Publication No. 2010-0187977
[Patent Document 5]: Korean Published Patent Application No. 2011-0018340
[Patent Document 6]: Korean Published Patent Application No. 2009-0057711

Patent Documents 1 and 2 disclose an embodiment in which the indolecarbazole core in which the hetero atom in the 5-membered cyclic compound is composed only of nitrogen (N) is used, and an aryl group substituted or unsubstituted in N of indolocarbazole is used. However, in the prior invention 1, there exists only a simple aryl group substituted or unsubstituted with an alkyl group, an amino group, an alkoxy group, or the like as a substituent, so that the effect of the substituents of the polycyclic compounds was very poor to prove, and only the use as a hole transport material is described, and the use thereof as a phosphorescent host material is not described.

Patent Documents 3 and 4 disclose a compound in which pyridine, pyrimidine, triazine or the like containing an aryl group and N, respectively, were substituted for an indolecarbazole core having a hetero atom N in the same 5-membered cyclic compound as in the above Patent Documents 1 and 2, however only the use examples for phosphorescent green host materials are described, and the performance for other heterocyclic compounds substituted for indolecarbazole core is not described.

In Patent Documents 5, Nitrogen (N), oxygen (O), sulfur (S), carbon and the like are described as heteroatom in the 5-membered cyclic compound, however there are only examples using the same heteroatom in the performance measurement data, the performance characteristics of a 5-membered cyclic compound containing a different heteroatom could not be confirmed.

Therefore, the patent document does not disclose solutions to low charge carrier mobility and low oxidation stability of a 5-membered cyclic compound containing same heteroatom.

When the 5-membered cyclic compound molecules are generally laminated, as the adjacent $\pi$-electrons increase, they have a strong electronical interaction, and this is closely related to the charge carrier mobility, particularly, the same 5-membered cyclic compound of N—N type has an edge-to-face morphology as an order of arrangement of molecules when molecules are laminated, otherwise a different 5-membered cyclic compound with different heteroatoms has an antiparallel cofacial r-stacking structure in which the packing structure of the molecules is opposite to each other, so that the arrangement order of the molecules becomes face-to-face morphology. It is reported that the steric effect of the substituent substituted on the asymmetrically arranged hetero atom N as the cause of this laminated structure causes relatively high carrier mobility and high oxidation stability (*Org. Lett.* 2008, 10, 1199).

In Patent Document 6, an example of using as a fluorescent host material for various polycyclic compounds having 7 or more membered cyclic compounds has been reported.

As described above, the fused positions, the number of rings, the arrangement of heteroatoms, and characteristic change by type of the polycyclic compounds have not yet been sufficiently developed.

Particularly, in a phosphorescent organic electronic element using a phosphorescent dopant material, the LUMO and HOMO levels of the host material have a great influence on the efficiency and life span of the organic electronic element, this is because the charge balance control in the emitting layer, the quenching of the dopant, and the reduction in efficiency and life span due to light emission at the interface of the hole transport layer can be prevented, depending on whether electron and hole injection in the emitting layer can be efficiently controlled.

For fluorescent and phosphorescent host materials, recently we have been studying the increase of efficiency and life span of organic electronic elements using TADF (thermal activated delayed fluorescent), exciplex, etc., particularly, and many studies have been carried out to identify the energy transfer method from the host material to the dopant material.

Although there are various methods for identifying the energy transfer in the emitting layer for TADF (thermally activated delayed fluorescent) and exciplex, it can be easily confirmed by the PL lifetime (TRTP) measurement method.

The TRTP (Time Resolved Transient PL) measurement method is a method of observing a decay time over time after irradiating the host thin film with a pulsed light source, and therefore it is possible to identify the energy transfer method by observing the energy transfer and the lag time. The TRTP measurement can distinguish between fluorescence and phosphorescence, an energy transfer method in a mixed host material, an exciplex energy transfer method, and a TADF energy transfer method.

There are various factors affecting the efficiency and life span depending on the manner in which the energy is transferred from the host material to the dopant material, and the energy transfer method differs depending on the material, so that the development of stable and efficient host material for organic electronic element has not yet been sufficiently developed. Therefore, development of new materials is continuously required, and especially development of a host material for an emitting layer is urgently required.

DETAILED DESCRIPTION OF THE INVENTION

Summary

The present invention has been proposed in order to solve the problems of the phosphorescent host material, and an object of the present invention is, by controlling the HOMO level of a host material of a phosphorescent emitting organic electronic element including a phosphorescent dopant, to provide a compound capable of controlling charge balance and of improving efficiency and life span in an emitting layer, and an organic electronic element using the same and an electronic device thereof.

Technical Solution

In order to control the efficient hole injection in the emitting layer of the phosphorescence emitting organic electronic element, by containing a specific second host material in combination with a specific first host material as a main component, it is possible to reduce the energy barrier of the emitting layer and the adjacent layer, the charge balance in the emitting layer is maximized, thereby providing high efficiency and high life of the organic electronic device.

The present invention provides an organic electronic element comprising a first electrode, a second electrode, and an organic material layer formed between the first electrode and the second electrode, wherein the organic material layer includes an emitting layer, wherein the emitting layer includes a first host compound represented by the following Formula (1) and a second host compound represented by the following Formula (2).

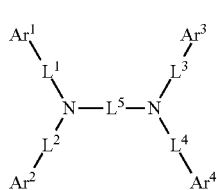

Formula (1)

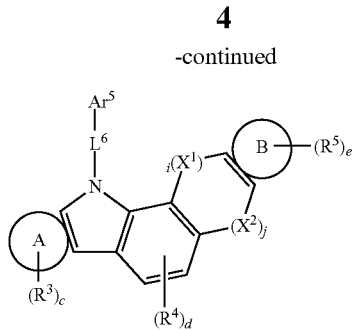

Formula (2)

The present invention also provides an organic electronic element using the compound represented by the above Formulas and an electronic device thereof.

Effects of the Invention

By using the mixture according to the present invention as a phosphorescent host material, it is possible to achieve a high luminous efficiency and a low driving voltage of an organic electric element, and the life span of the device can be greatly improved.

| 100: organic electric element, | 110: substrate |
| 120: the first electrode(anode), | 130: the hole injection layer |
| 140: the hole transport layer, | 141: a buffer layer |
| 150: the emitting layer, | 151: the emitting auxiliary layer |
| 160: the electron transport layer, | 170: the electron injection layer |
| 180: the second electrode(cathode) | |

Figure 2:
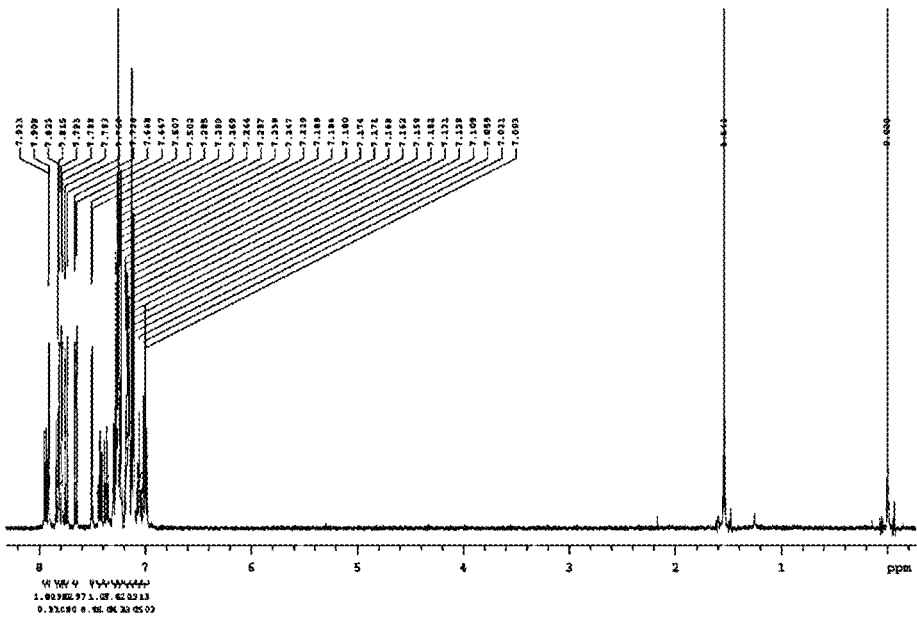
Figure 3:
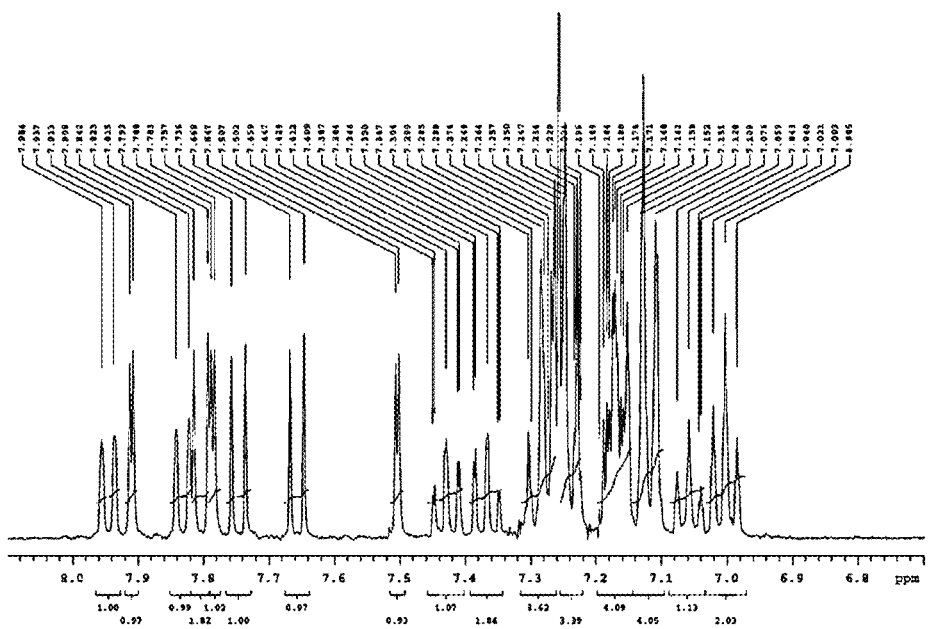

FIG. 2 and FIG. 3 show the 1H NMR analysis result of compound 2-76.

Figure 4:
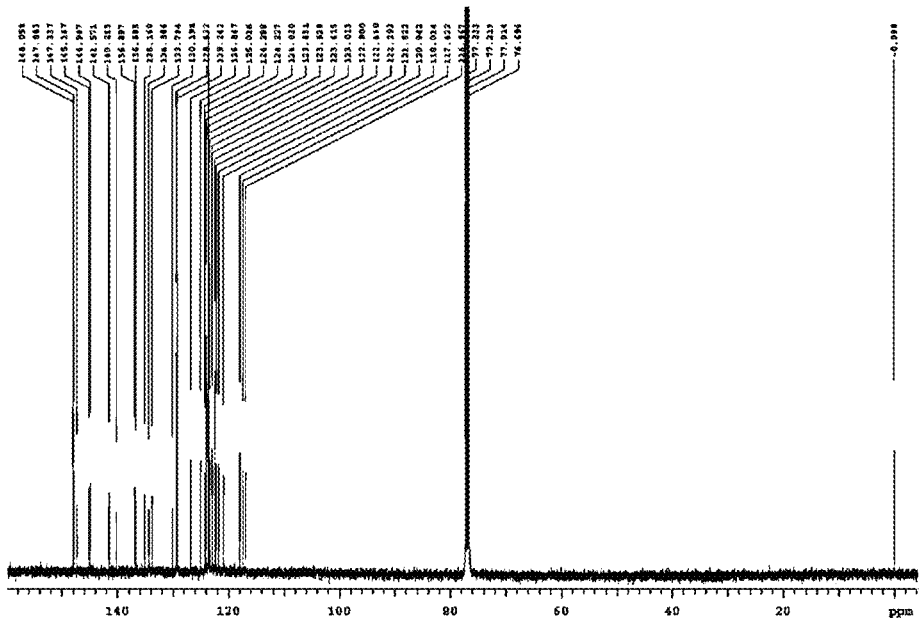
Figure 5:
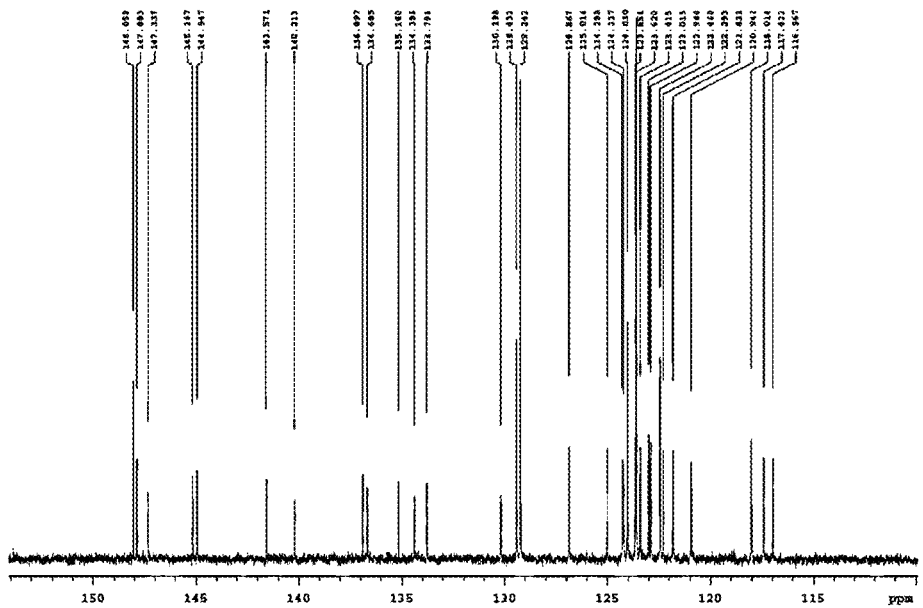

FIG. 4 and FIG. 5 show the 13C NMR analysis result of compound 2-76.

Figure 6:
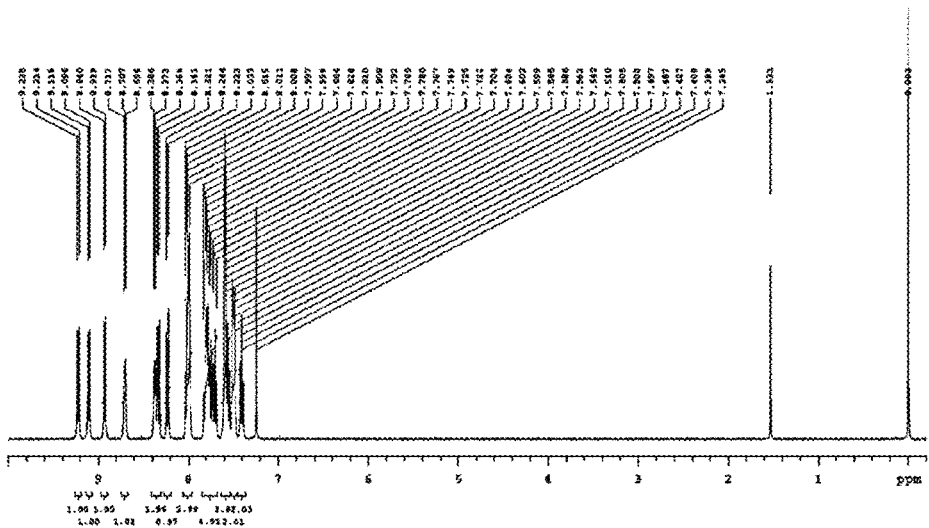

FIG. 6 show the 1H NMR analysis result of compound 2-88.

Figure 7:
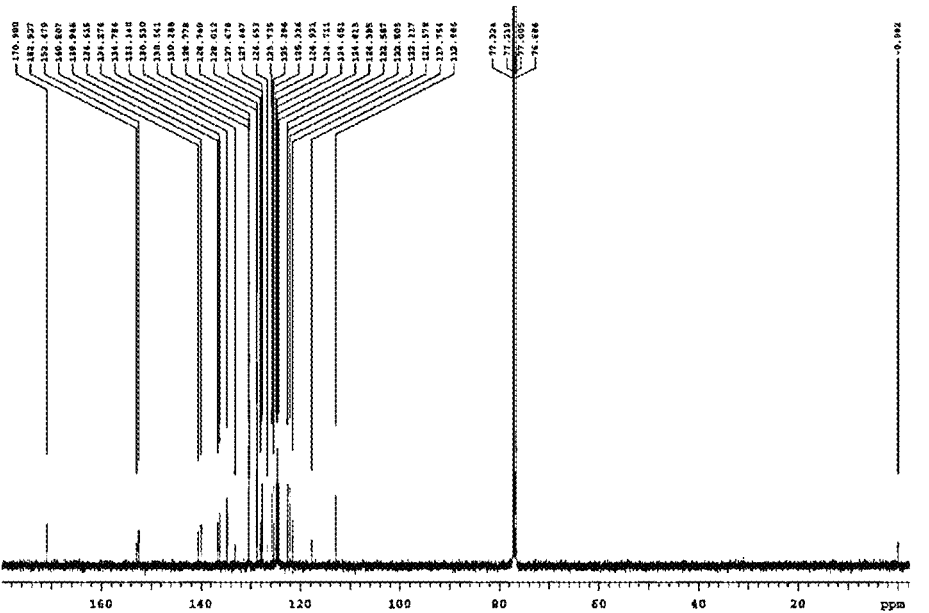

FIG. 7 show the 1H NMR analysis result of compound 3-6.

Figure 8:
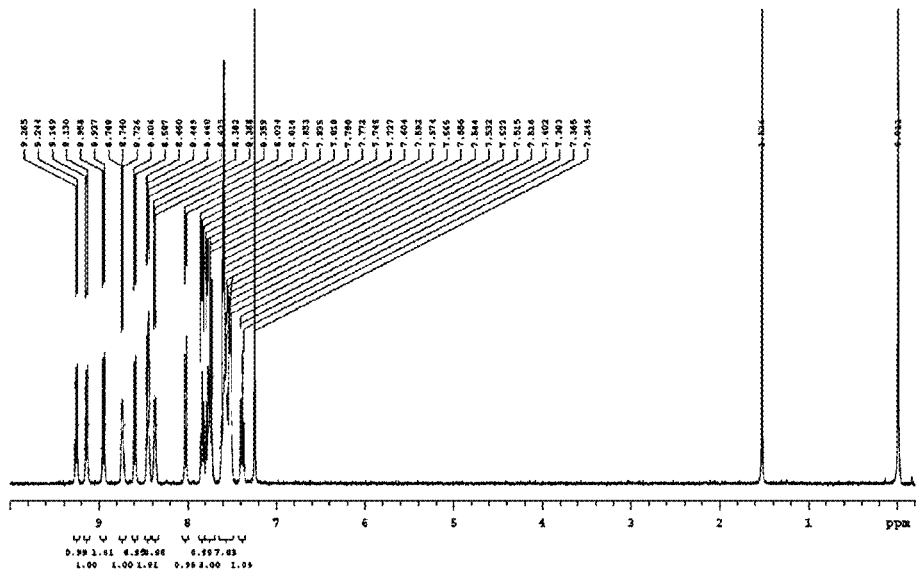

FIG. 8 shows the 13C NMR analysis result of compound 3-6.

Figure 9:
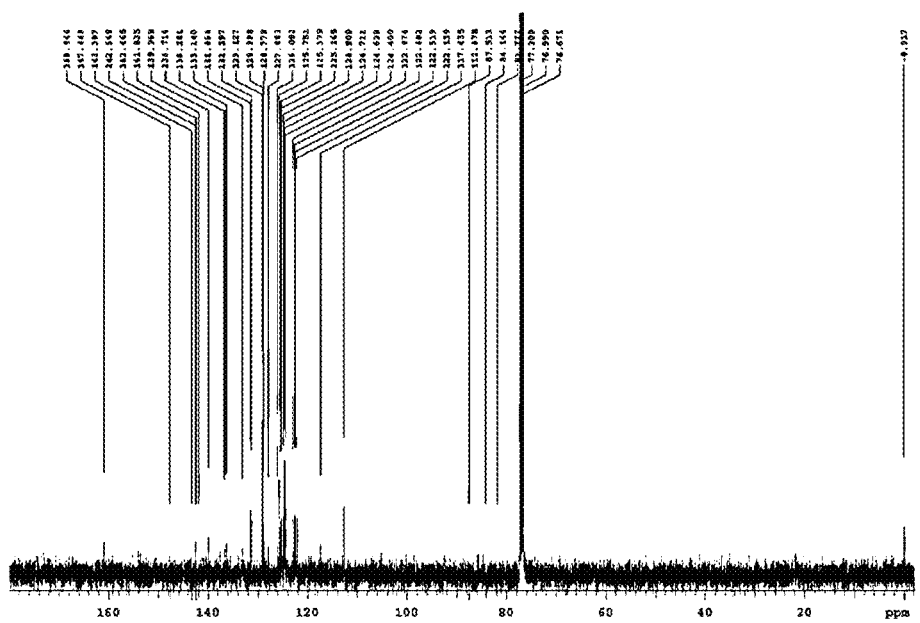

FIG. 9 show the 1H NMR analysis result of compound 3-7.

Figure 10:
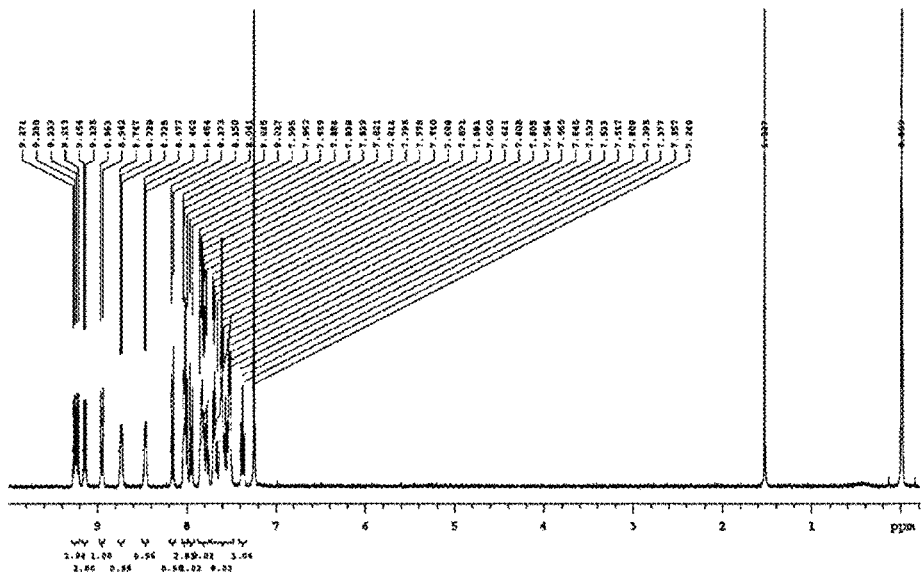

FIG. 10 shows the 13C NMR analysis result of compound 3-7.

Figure 11:
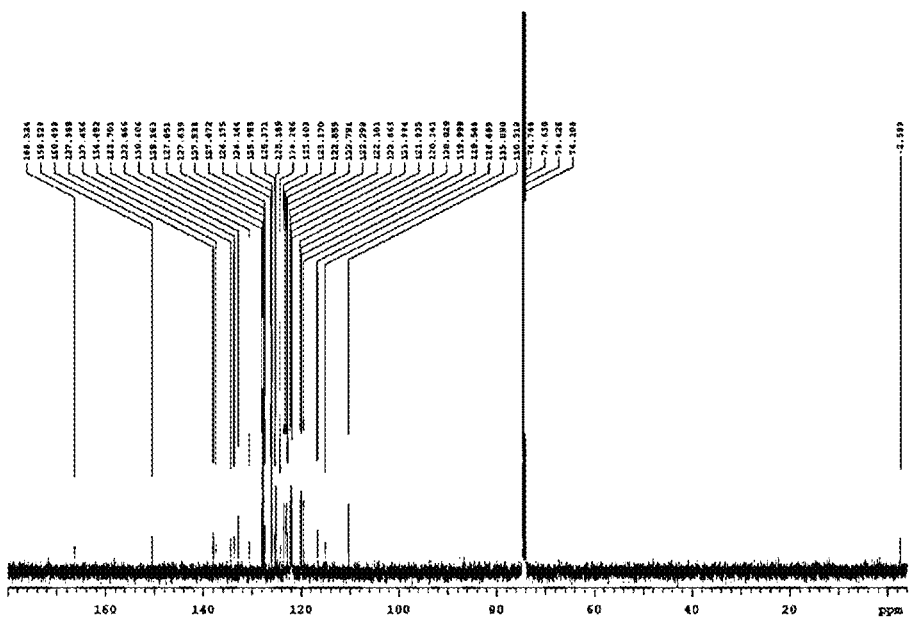

FIG. 11 show the 1H NMR analysis result of compound 3-8.

Figure 12:
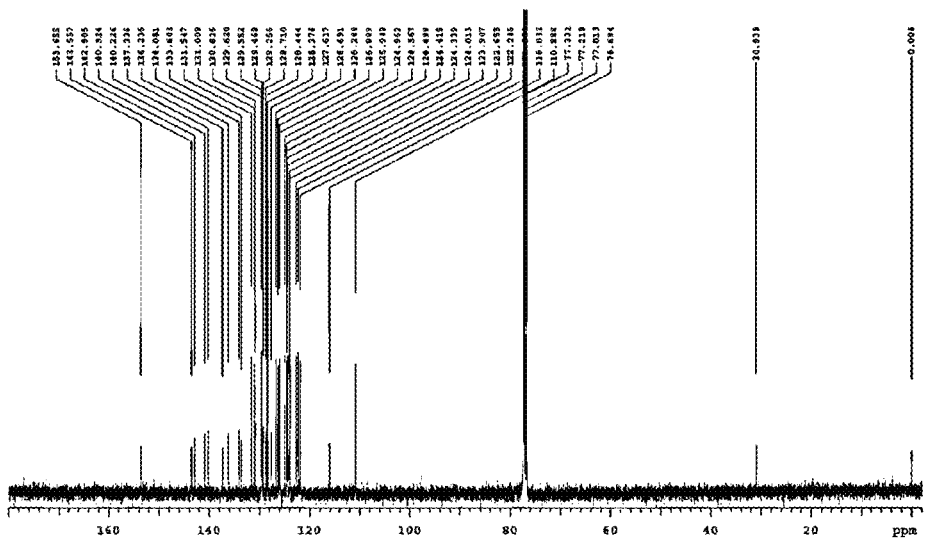

FIG. 12 shows the 13C NMR analysis result of compound 3-8.

Figure 13:
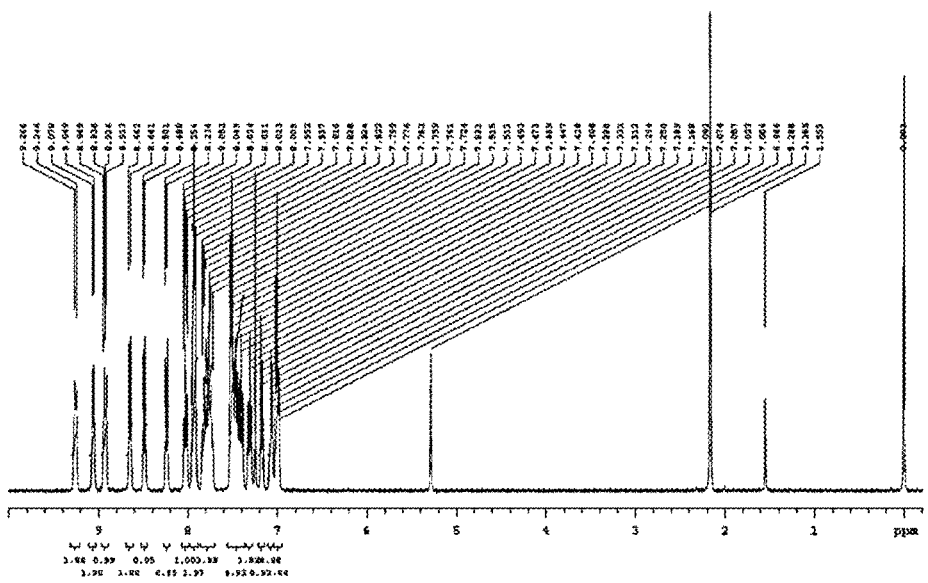

FIG. 13 show the 1H NMR analysis result of compound 3-101.

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "linked" to another component, the component may be directly connected or connected to the other component, but another component may be "connected", "coupled" or "linked" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, includes an alkyl group substituted with a halogen.

Unless otherwise stated, the term "heteroalkyl", as used herein, means alkyl substituted one or more of carbon atoms consisting of an alkyl with hetero atom.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "alkenoxyl group", "alkenoxy group", "alkenyloxyl group" or "alkenyloxy group", as used herein, means an oxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alk-enyl substituted with an arylcarbonyl, wherein the arylcarbonyl may be a carbonyl substituted with an aryl.

Unless otherwise stated, the term "heteroalkyl", as used herein, means alkyl containing one or more of hetero atoms.

Unless otherwise stated, the term "heteroaryl group" or "heteroarylene group", as used herein, means a C2 to C60 aryl containing one or more of hetero atoms or arylene group, but is not limited thereto, and includes at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphatic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring containing $SO_2$ instead of carbon consisting of cycle. For example, "heterocyclic group" includes compound below.

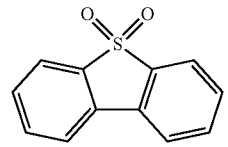 [SMILES: O=S1(=O)c2ccccc2-c2ccccc21]

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "carbonyl", as used herein, is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

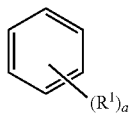

Wherein, when a is an integer of zero, the substituent $R^1$ is absent, that is, when a is 0, it means that hydrogen is bonded to all the carbons forming the benzene ring. In this case, the sign of the hydrogen bonded to the carbon may be omitted and the formula or compound may be described. When a is an integer of 1, the sole substituent $R^1$ is linked to any one of the carbon constituting the benzene ring, and when a is an integer of 2 or 3, they are respectively combined as follows, and when a is an integer from 4 to 6, it is bonded to the carbon of the benzene ring in a similar manner, and when a is an integer of 2 or more, $R^1$ may be the same or different from each other.

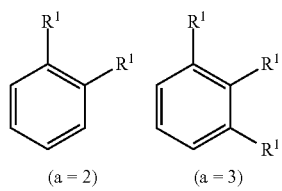

Unless otherwise expressly stated, the terms "ortho", "meta", and "para" used in the present invention refer to the substitution positions of all substituents, and the ortho position indicates the position of the substituent immediately adjacent to the compound, for example, when benzene is used, it means 1 or 2 position, and the meta position is the next substitution position of the neighbor substitution position, when benzene as an example stands for 1 or 3 position, and the para position is the next substitution position of the meta position, which means 1 and 4 position when benzene is taken as an example. A more detailed example of the substitution position is as follows, and it can be confirmed that the ortho-, and meta-position are substituted by non-linear type and para-positions are substituted by linear type.

Example of Ortho-Position

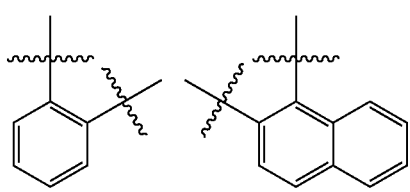

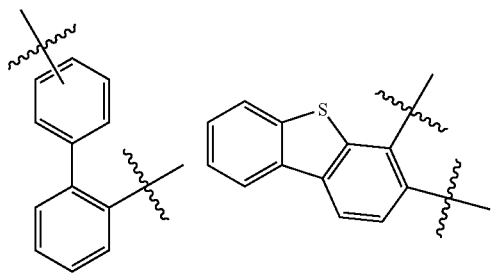

Example of Meta-Position

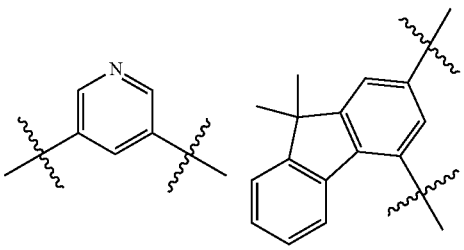

Example of Para-Position

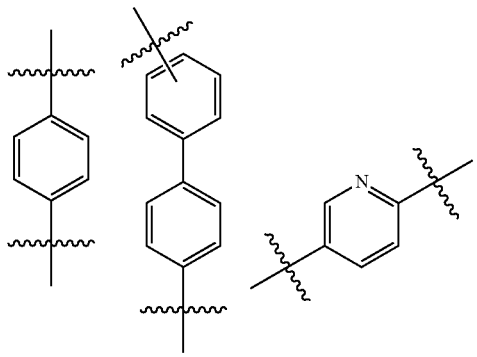

Hereinafter, a compound according to an aspect of the present invention and an organic electric element comprising the same will be described.

The present invention provides an organic electric element comprising a first electrode, a second electrode, and an organic material layer formed between the first electrode and the second electrode, wherein the organic material layer comprises an emitting layer, wherein the emitting layer comprises a first host compound represented by Formula (1) and a second host compound represented by Formula (2) as a phosphorescent light emitting layer.

Formula (1)

Formula (2)

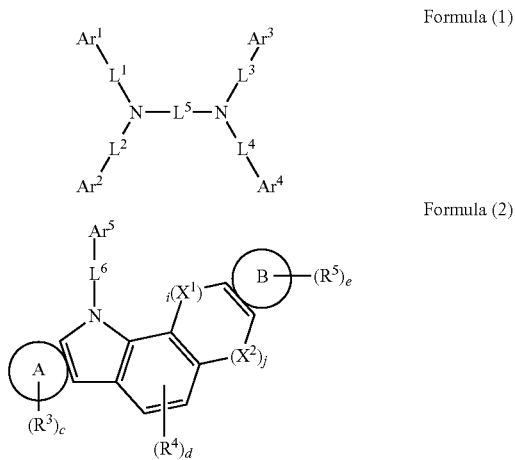

{In Formulas (1) and (2),

1) $Ar^1$, $Ar^2$, $Ar^3$, $Ar^4$ and $Ar^5$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); wherein, L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic; and $R_a$ and $R_b$ are each independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, or P, wherein $Ar^1$ and $Ar^2$ or $Ar^3$ and $Ar^4$ may be bonded to each other to form a ring, 2) c and e are an integer of 0 to 10, and d is an integer of 0 to 2, 3) $R^3$, $R^4$ and $R^5$ are the same or different from each other, and are each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); or in case c, d and e are 2 or more, and $R^3$, $R^4$ and $R^5$ are each in plural being the same or different, and a plurality of $R^3$ or a plurality of $R^4$ or a plurality of $R^5$ may be bonded to each other to form a ring.

4) $L^1$, $L^2$, $L^3$, $L^4$, $L^5$ and $L^6$ are each independently selected from the group consisting of a single bond; a $C_6$-$C_{60}$ arylene group; and a fluorenylene group; a fused ring group of a $C_3$-$C_{60}$ aliphatic ring and a $C_6$-$C_{60}$ aromatic ring; and a $C_2$-$C_{60}$ heterocyclic group; provided that except when $L^5$ is a single bond, 5) A and B are each independently a $C_6$-$C_{60}$ aryl group or a $C_2$-$C_{20}$ heterocyclic group, wherein both A and B are a substituted or unsubstituted $C_6$ aryl group (phenyl group), d is 2, and $R^4$s are bonded to each other to form an aromatic ring or heterocycle, 6) i and j are 0 or 1, with the proviso that i+j is 1 or more, and when i or j is 0, it means a direct bond, 7) $X^1$ and $X^2$ are each independently N-$L^7$-$Ar^6$, O, S, or $CR^6R^7$;

wherein $L^7$ is the same as $L^1$ to $L^4$ or $L^6$, wherein $Ar^6$ is the same as $Ar^1$ to $Ar^5$, wherein $R^6$ and $R^7$ are each independently hydrogen; a $C_6$-$C_{60}$ aryl group; a fluorenyl group; a $C_2$-$C_{60}$ heterocyclic group; or a $C_1$-$C_{50}$ alkyl group; wherein $R^6$ and $R^7$ may combine to each other to form a spiro, wherein, the aryl group, fluorenyl group, arylene group, heterocyclic group, fluorenylene group, fused ring group, alkyl group, alkenyl group, alkoxy group and aryloxy group may be substituted with one or more substituents selected from the group consisting of deuterium; halogen; a silane group substituted or unsubstituted with $C_1$-$C_{20}$ alkyl group or $C_6$-$C_{20}$ aryl group; siloxane group; boron group; germanium group; cyano group; nitro group; -L'-N($R_a$)($R_b$); a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; wherein the substituents may combine each other and form a saturated or unsaturated ring, wherein the term 'ring' means $C_3$-$C_{60}$ aliphatic ring or $C_6$-$C_{60}$ aromatic ring or a $C_2$-$C_{60}$ heterocyclic group or a fused ring formed by the combination of thereof and includes a saturated or unsaturated ring.}

In addition, the present invention provides the compounds represented by Formulas (1) and (2).

The present invention also provides an organic electric element comprising a compound represented by the following Formula (3) when $Ar^1$ and $Ar^2$ in Formula (1) form a ring.

Formula (3)

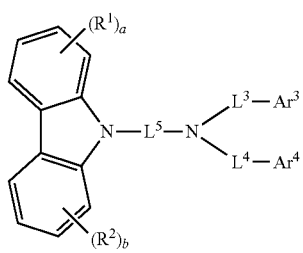

{In Formula (3),
1) $L^3$, $L^4$, $L^5$, $Ar^3$ and $Ar^4$ are the same as defined above,
2) a and b are each independently an integer of 0 to 4,
3) $R^1$ and $R^2$ are the same or different from each other, and are each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{20}$ aliphatic ring and a $C_6$-$C_{20}$ aromatic ring; a $C_1$-$C_{20}$ alkyl group; a $C_2$-$C_{20}$ alkenyl group; a $C_2$-$C_{20}$ alkynyl group; a $C_1$-$C_{20}$ alkoxyl group; a $C_6$-$C_{30}$ aryloxy group; and -L'-N($R_a$)($R_b$); or in case a and b are 2 or more, $R^1$ and $R^2$ are each in plural being the same or different, and a plurality of $R^1$ or a plurality of $R^2$ may be bonded to each other to form a ring.}

In Formula (1) of the present invention, $L^1$, $L^2$, $L^3$, $L^4$ and $L^5$ are each independently any one of the following Formulas (A-1) to (A-13).

(A-1)

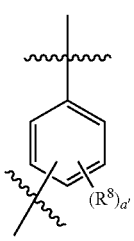

(A-2)

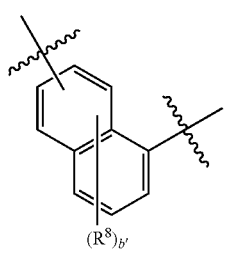

(A-3)

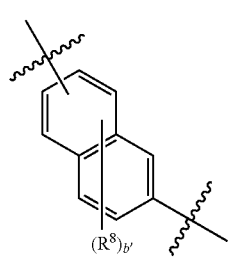

(A-4)

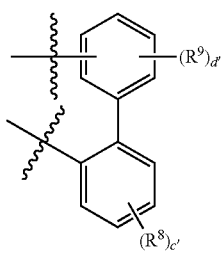

(A-5)

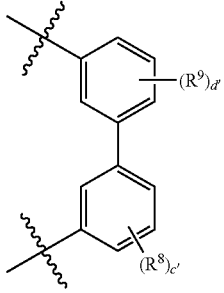

(A-6)

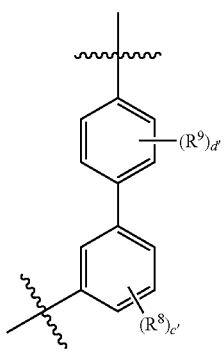

(A-7)

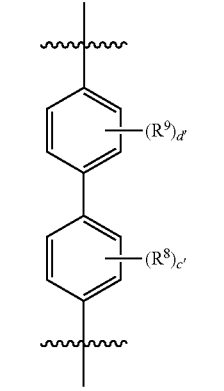

(A-8)

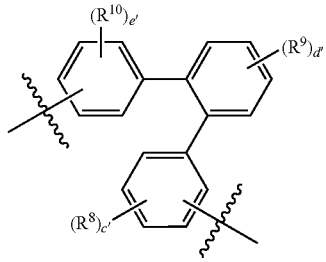

-continued (A-9)
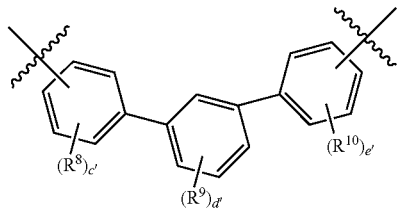

(A-10)
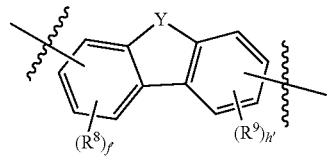

(A-11)
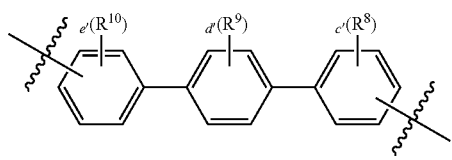

(A-12)
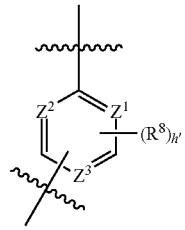

(A-13)
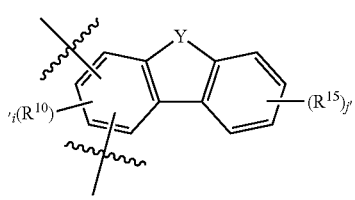

{In Formulas (A-1) to (A-13),
1) a', c', d' and e' are an integer of 0 to 4; and b' is an integer of 0 to 6; and f and g' are an integer of 0 to 3; and h' is an integer of 0 or 1; and i' is an integer of 0 to 2, and j' is an integer of 0 to 4,
2) $R^8$, $R^9$, $R^{10}$ and $R^{15}$ are the same or different from each other, and are each independently selected from the group consisting of hydrogen; deuterium; halogen; a $C_6$-$C_{20}$ aryl group; a fluorenyl group; a $C_2$-$C_{20}$ heterocyclic group including at least one heteroatom of O, N, S, Si or P; a fused ring group of a $C_3$-$C_{20}$ aliphatic ring and a $C_6$-$C_{20}$ aromatic ring; a $C_1$-$C_{20}$ alkyl group; a $C_2$-$C_{20}$ alkenyl group; a $C_2$-$C_{20}$ alkynyl group; a $C_1$-$C_{20}$ alkoxyl group; a $C_6$-$C_{30}$ aryloxy group; and -L'-N($R_a$)($R_b$);
wherein e', f', g', i' and j' are 2 or more, $R^8$, $R^9$, $R^{10}$ and $R^{15}$ are the same or different from each other, and a plurality of $R^8$ or a plurality of $R^9$ or a plurality of $R^{10}$ or a plurality of $R^{15}$, two adjacent $R^8$ and $R^9$, or $R^9$ and $R^{10}$, or $R^{10}$ and $R^{15}$ may be bonded to form an aromatic ring or heteroaromatic ring,
3) Y is N-L-$Ar^7$, O, S or $CR^{11}R^{12}$,
Wherein $L^8$ is the same as $L^1$ to $L^6$ defined above, wherein $Ar^7$ is the same as $Ar^1$ to $Ar^5$ defined above,
Wherein $R^{11}$ and $R^{12}$ are the same as $R^6$ and $R^7$ defined above,
4) $Z^1$, $Z^2$ and $Z^3$ are $CR^{13}$ or N and at least one is N, and $R^{13}$ is the same as $R^8$ and $R^{10}$ defined above.}

In Formula (1), $L^5$ preferably comprises a compound represented by Formula (A-10), and the present invention also provides an organic electric device comprising the same. Formula (A-10) may be represented by the following Formulas C-1 to C-10, preferably Formulas C-2, C-3, C-4, C-6, C-7, C-9.

C-1
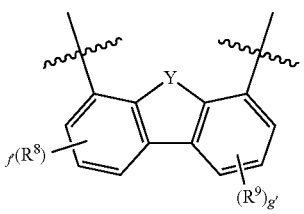

C-2
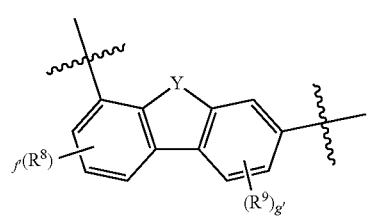

C-3
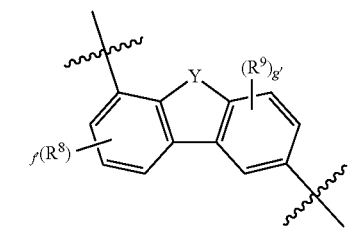

C-4
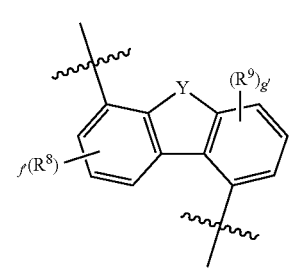

C-5
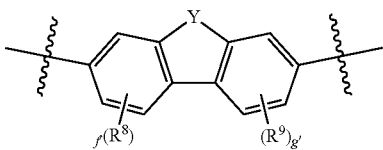

C-6
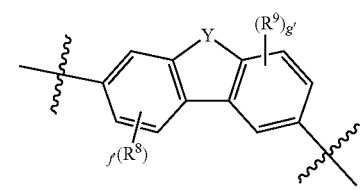

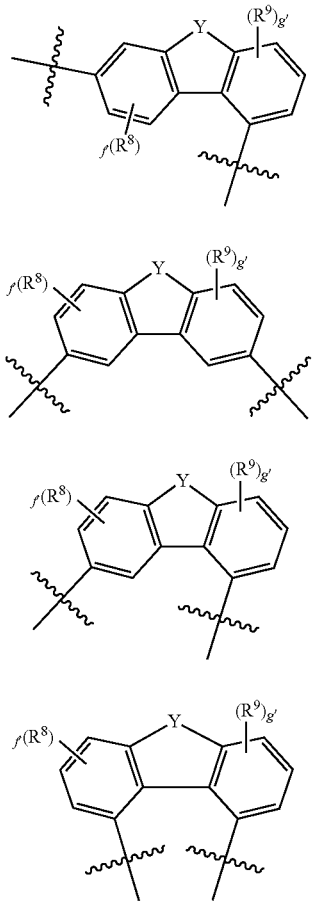

C-7

C-8

C-9

C-10

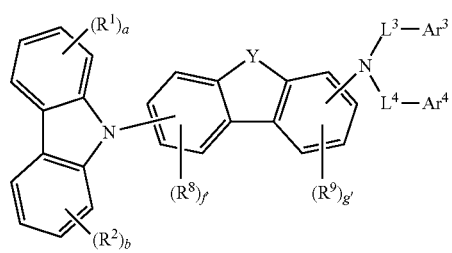

Formula (3-3)

{In Formulas (3-1) to (3-3),
R¹, R², R⁸, R⁹, a, b, a', d', f', g', L³, L⁴, Ar³, Ar⁴ and Y are the same as defined above.}

The compound represented by Formula (1) of the present invention comprises a compound represented by the following Formula (3-4) or (3-5).

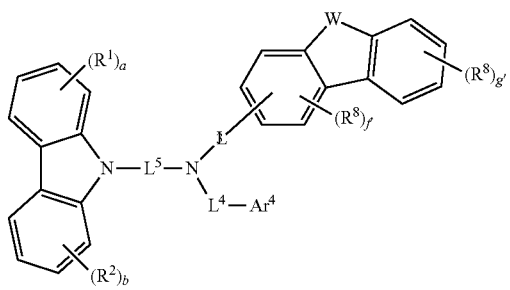

Formula (3-4)

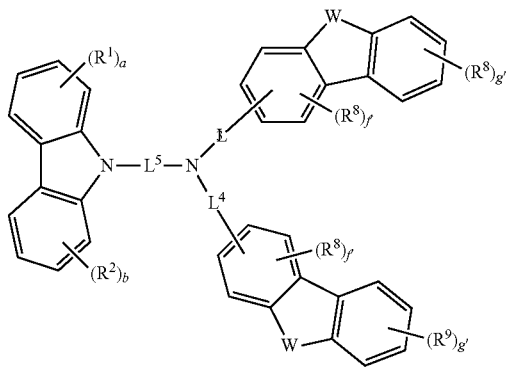

Formula (3-5)

{In Formulas (3-4) and (3-5),
1) Ar⁴, L³, L⁴, L⁵, R¹, R², R₈, R⁹, a, b, f' and g' are the same as defined above,
2) W is as the definition of Y above.}

In one embodiment of the present invention, Ar³ and Ar⁴ in Formula (1) are all C₆-C₂₄ aryl groups, and more specifically, at least one of Ar³ and Ar⁴ of Formula (1) is dibenzothiophene or dibenzofuran.

In one embodiment of the present invention, the first host compound represented by Formula (1) is represented by any one of the following Formulas (3-6) to (3-19).

The first host compound represented by Formula (1) is represented by any one of the following Formulas (3-1) to (3-3).

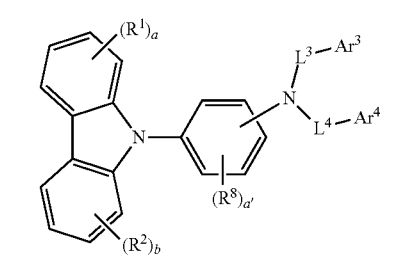

Formula (3-1)

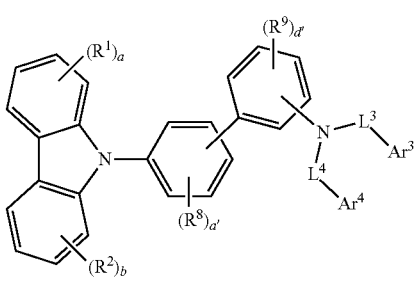

Formula (3-2)

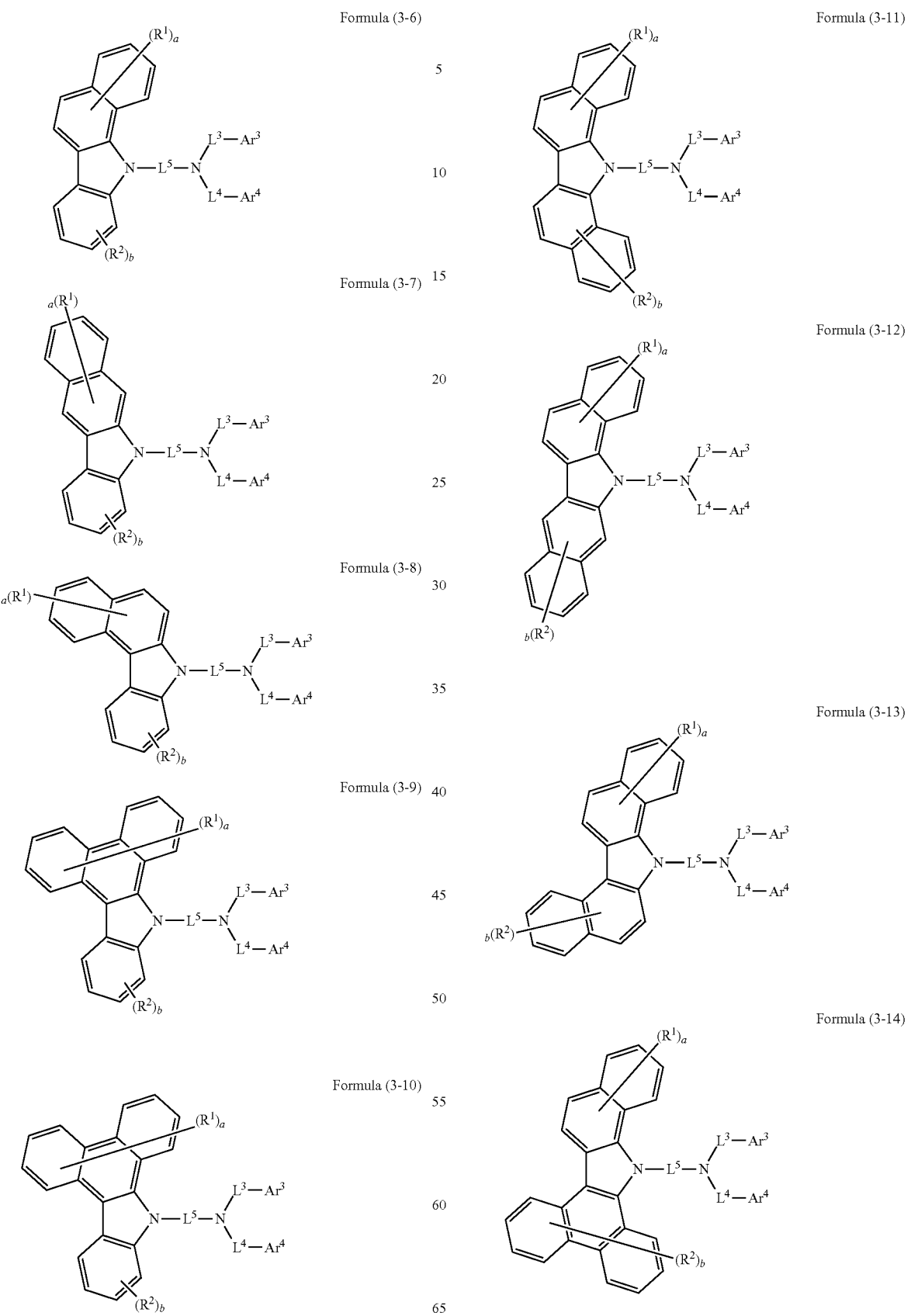

Formula (3-15)

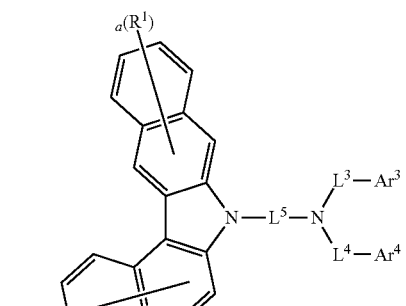

Formula (3-16)

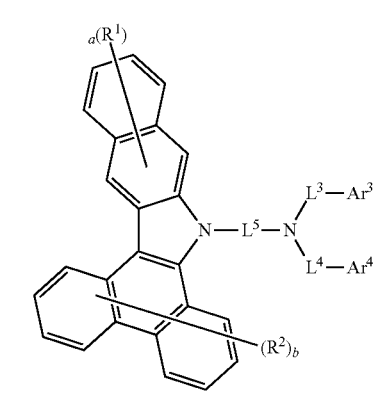

Formula (3-17)

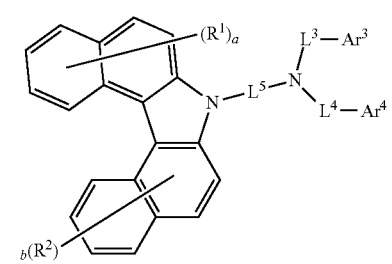

Formula (3-18)

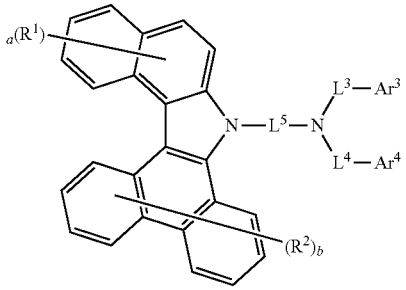

Formula (3-19)

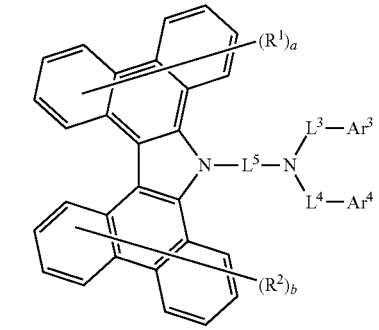

{In Formulas (3-6) to (3-19), $L^3, L^4, L^5, Ar^3, Ar^4, R^1$ and $R^2$ are the same as defined above, and a and b are any one of integers of 0 to 8.}

In another embodiment of the present invention, the first host compound represented by Formula (1) is represented by Formulas (3-20).

Formula (3-20)

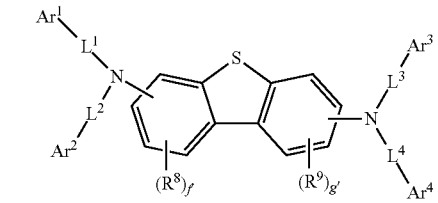

{In Formula (3-20), $Ar^1, Ar^2, Ar^3, Ar^4, L^1, L^2, L^3, L^4, R^8, R^9$, f' and g' are the same as defined above.}

Preferably, at least one of $Ar^1, Ar^2, Ar^3$ and $Ar^4$ in Formula (3-20) is dibenzothiophene or dibenzofuran.

In one embodiment of the present invention, at least one of $L^1, L^2, L^3, L^4$ and $L^5$ in Formula (1) is substituted with a meta position.

In another aspect, the present invention includes a compound wherein the second host compound represented by Formula (2) is represented by the following Formula (4) or (5).

Formula (4)

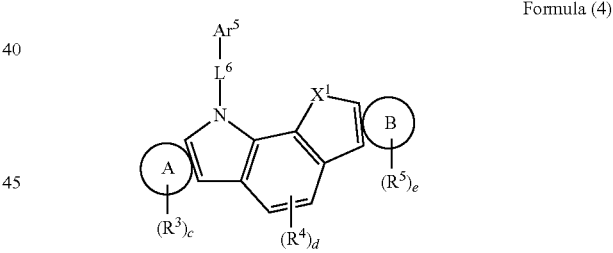

Formula (5)

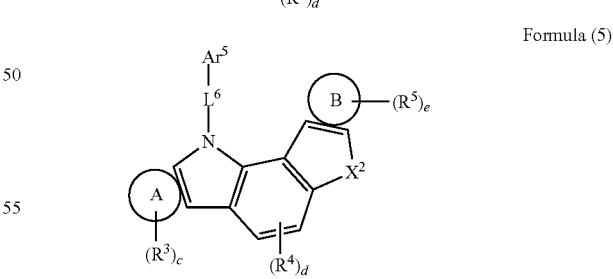

{In Formulas (4) and (5), $R^3, R^4, R^5, L^6, Ar^5, X^1, X^2$, A, B, c, d, and e are the same as defined in Formula (2).}

The present invention also provides an organic electric element comprising a compound wherein A and B in Formula (2) are selected from the group consisting of the following Formulas (B-1) to (B-7).

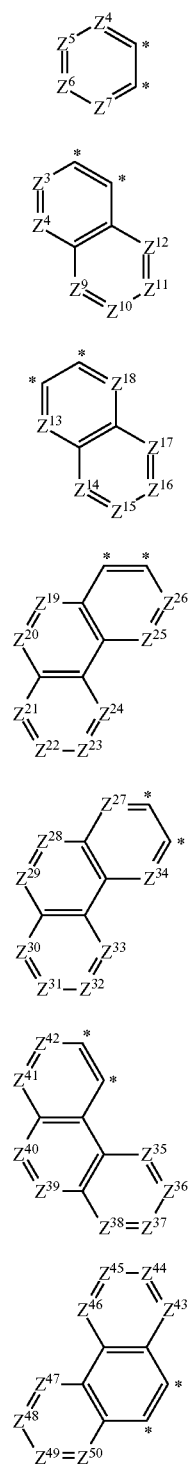

(B-1)
(B-2)
(B-3)
(B-4)
(B-5)
(B-6)
(B-7)

{In Formulas (B-1) to (B-7),
1) $Z^4$ to $Z^{50}$ are $CR^{14}$ or N,
2) $R^{14}$ is the same as $R^3$ to $R^5$ defined above,
3) * indicates the position to be condensed.}

As another example, the present invention provides a compound wherein the second host compound represented by Formula (2) includes a compound represented by any of the following Formulas (4-1) to (4-36).

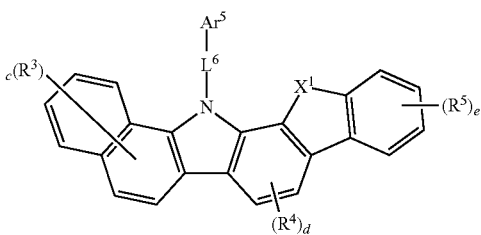

Formula (4-1)

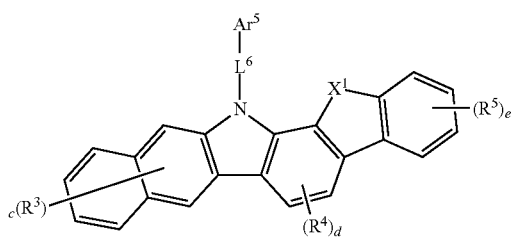

Formula (4-2)

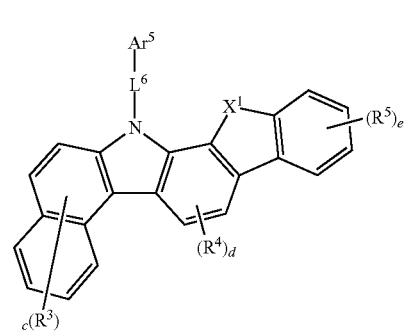

Formula (4-3)

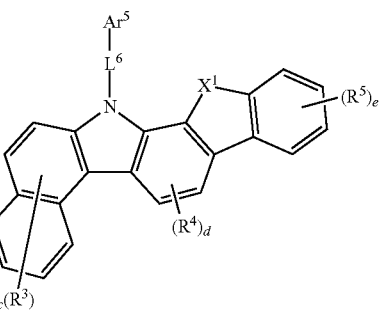

Formula (4-4)

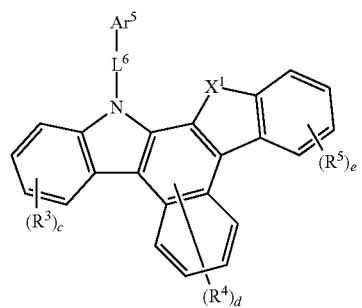

Formula (4-5)

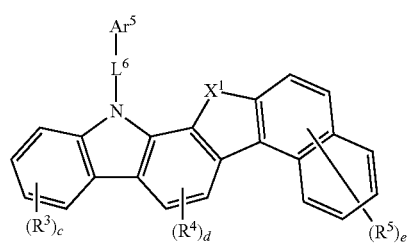

Formula (4-6)
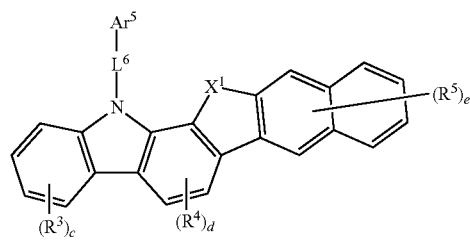
Formula (4-7)
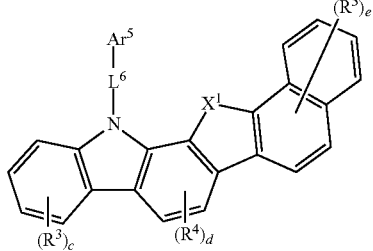
Formula (4-8)
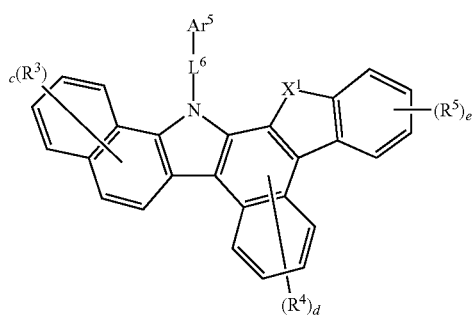
Formula (4-9)
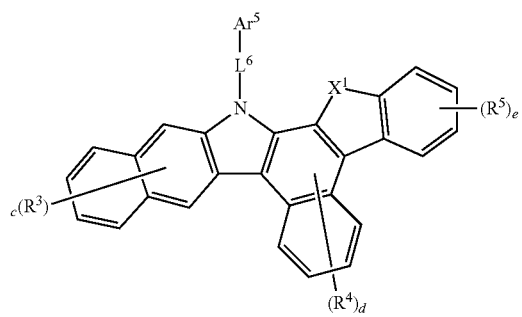
Formula (4-10)
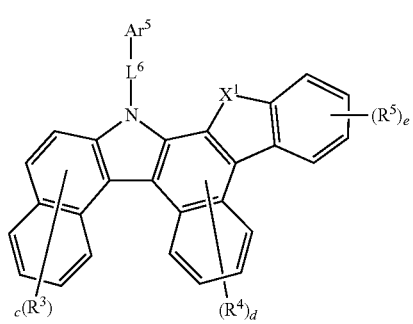
Formula (4-11)
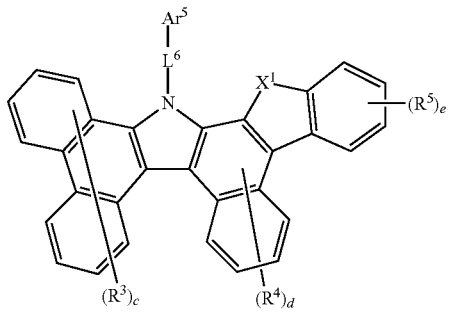
Formula (4-12)
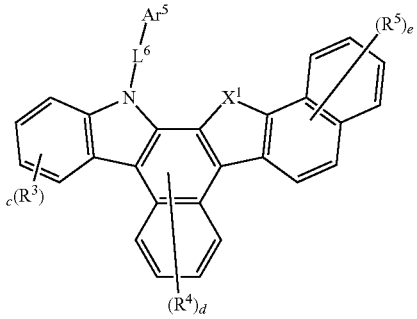
Formula (4-13)
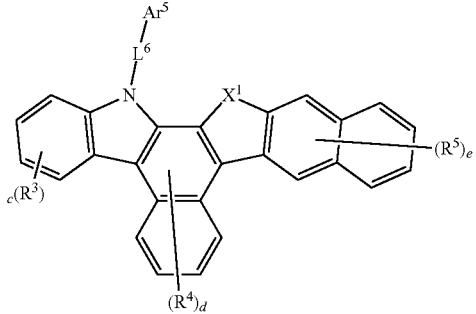
Formula (4-14)
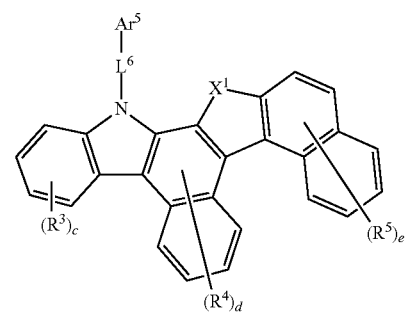
Formula (4-15)
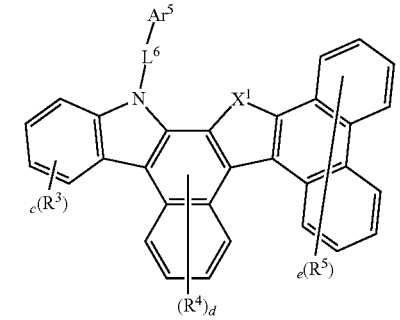

Formula (4-16)
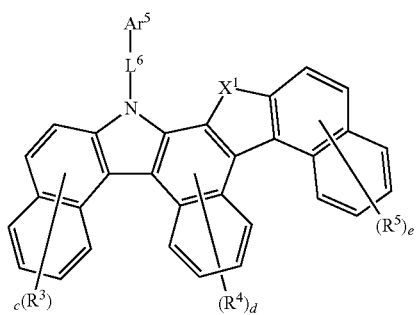
Formula (4-17)
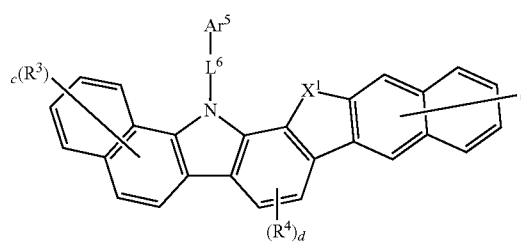
Formula (4-18)
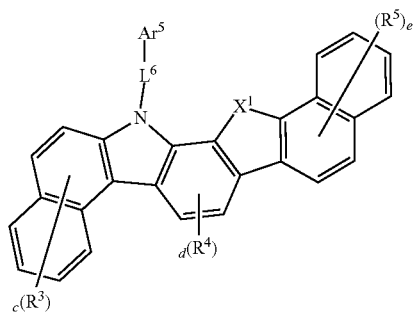
Formula (4-19)
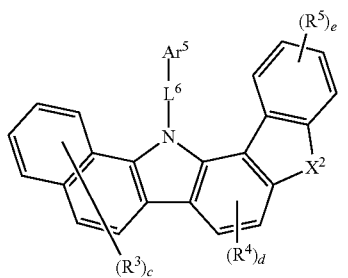
Formula (4-20)
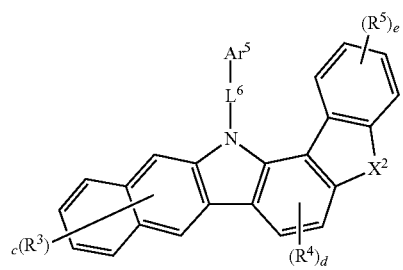
Formula (4-21)
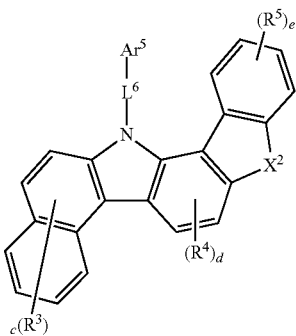
Formula (4-22)
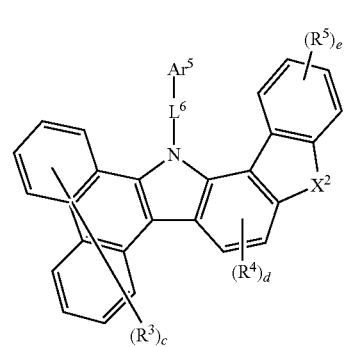
Formula (4-23)
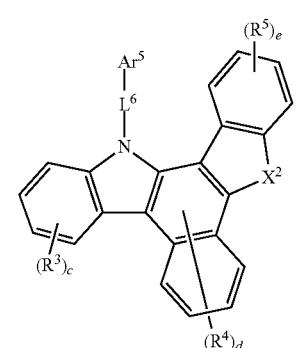
Formula (4-24)
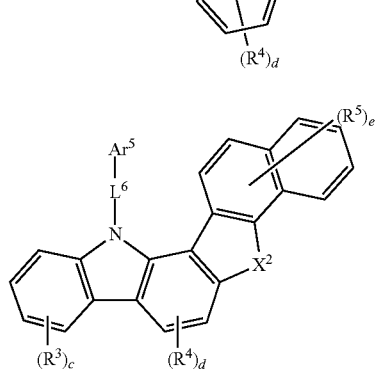
Formula (4-25)
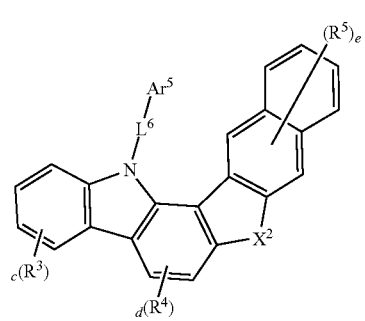

Formula (4-26)
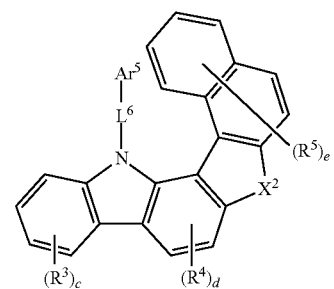
Formula (4-27)
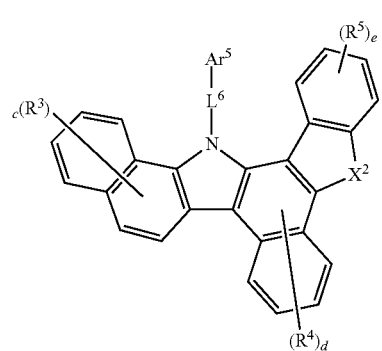
Formula (4-28)
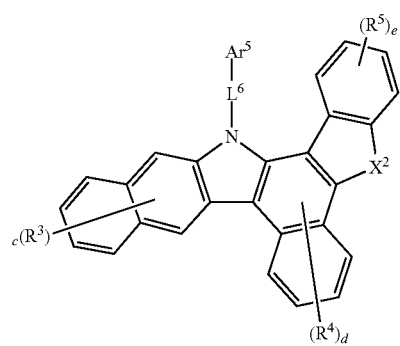
Formula (4-29)
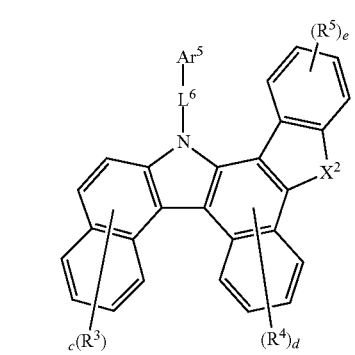
Formula (4-30)
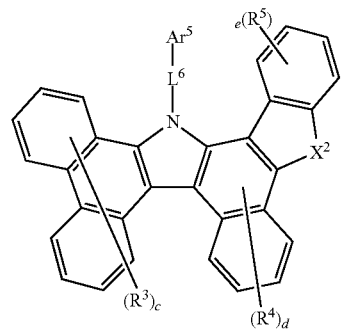
Formula (4-31)
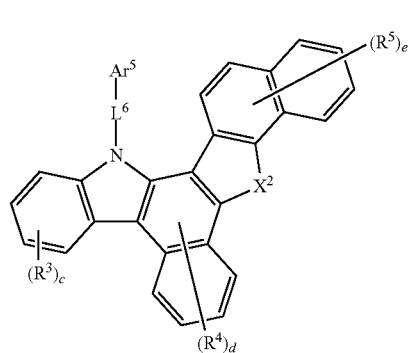
Formula (4-32)
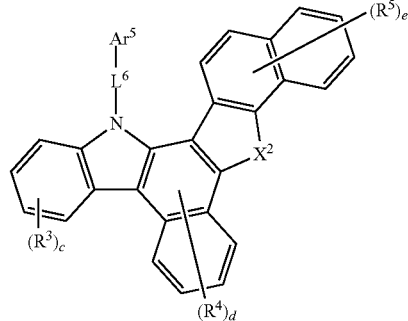
Formula (4-33)
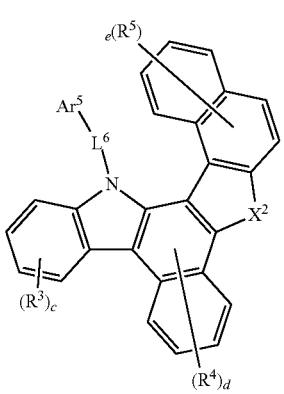

-continued
Formula (4-34)
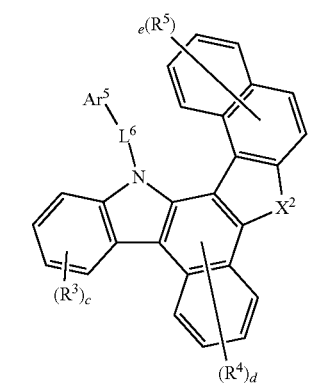
Formula (4-35)
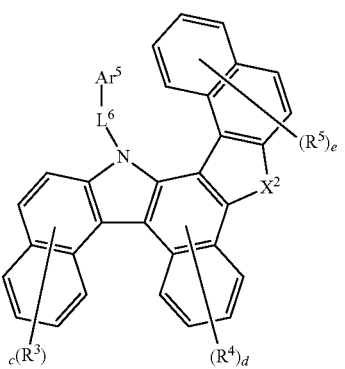
Formula (4-36)
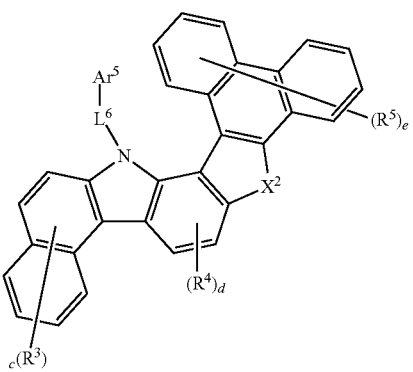
{In Formulas (4-1) to (4-36),
Ar$^5$, L$^6$, X$^1$, X$^2$, R$^3$, R$^4$, R$^5$, c and e are the same as defined above, and d is any one of integer of 0 to 4.}
The second host compound represented by Formula (2) comprises compounds represented by the following Formulas (6-1) to (6-8).
Formula (6-1)
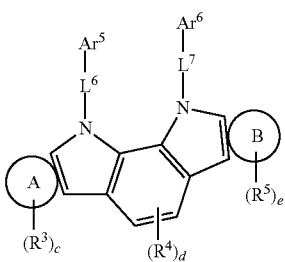
Formula (6-2)
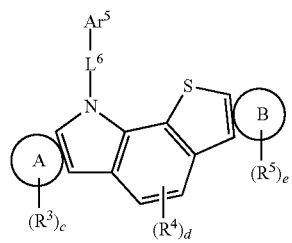
Formula (6-3)
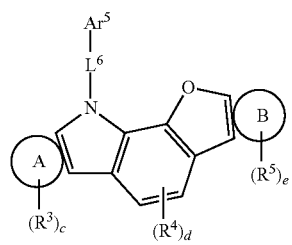
Formula (6-4)
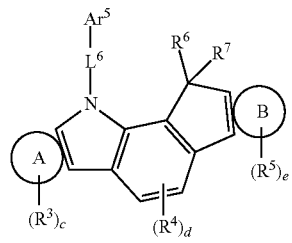
Formula (6-5)
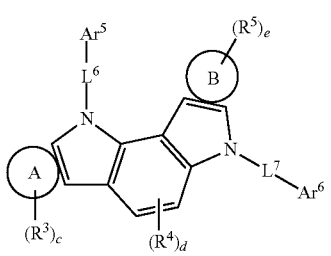
Formula (6-6)
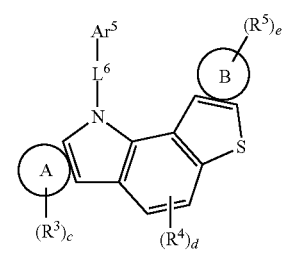
Formula (6-7)
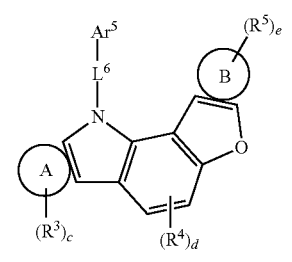

-continued

Formula (6-8)

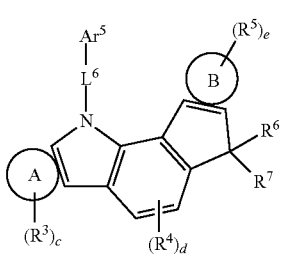

{In Formulas (6-1) to (6-8),
$R^3$, $R^4$, $R^5$, $R^6$, $R^7$, $L^6$, $L^7$, $Ar^5$, $Ar^6$, c, d, e, A and B are the same as defined above.}

In the above Formulas of the present invention, when $Ar^1$, $Ar^2$, $Ar^3$, $Ar^4$, $Ar^5$, $Ar^6$, $Ar^7$ and $R^1$, $R^2$, $R^3$, $R^4$ and $R^5$ are aryl groups, it is preferably $C_6$-$C_{30}$ aryl group, more preferably $C_6$-$C_{24}$ aryl group, and when $Ar^1$, $Ar^2$, $Ar^3$, $Ar^4$, $Ar^5$, $Ar^6$, $Ar^7$ and $R^1$, $R^2$, $R^3$, $R^4$, $R^5$, $R^6$, $R^7$, $R^8$, $R^9$, $R^{10}$ are heterocyclic groups, it is preferably a $C_2$-$C_{40}$ heterocyclic group, more preferably a $C_2$-$C_{30}$ heterocyclic group, still more preferably a $C_2$-$C_{24}$ heterocyclic group.

when $Ar^1$, $Ar^2$, $Ar^3$, $Ar^4$, $Ar^5$, $Ar^6$, $Ar^7$ and $R^1$, $R^2$, $R^3$, $R^4$, $R^5$, $R^6$, $R^7$, $R_8$, $R^9$, R are aryl groups, specific examples thereof include phenyl, biphenyl, terphenyl, quaterphenyl, stylbenyl, naphthyl, anthracenyl, phenanthryl, pyrenyl, perylenyl, klycenyl group, and the like. When $Ar^1$, $Ar^2$, $Ar^3$, $Ar^4$, $Ar^5$, $Ar^6$, $Ar^7$ and $R^1$, $R^2$, $R^3$, $R^4$, $R^5$, $R^6$, $R^7$, $R^8$, $R^9$, $R^{10}$ are heterocyclic groups, specific examples thereof include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a pyrazine group, a triazole group, an acridyl group, a pyridazine group, a pyrazinyl group, a quinolinyl group, a quinazolinyl group, a quinoxalinyl group, a benzoquinoxaline, a dibenzoquinoxaline, a phthalazinyl group, a pyridopyrimidinyl group, a pyridopyrazinyl group, a pyrazinopyrazinyl group, an isoquinoline group, an indole group, a carbazole group, indolocarbazole, acridine, phenoxazine, benzopyridazine0, benzopyrimidine, carboline, benzocarboline, benzoxazole group, a benzoimidazole group, a benzothiazole group, a benzocarbazole group, a benzothiophene group, dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group and dibenzofuranyl group, thienothiophene, benzothienopyridine, benzothienopyrimidine, benzofuropyrimidine, dimethylbenzoindenopyrimidine, phenanthrofuropyrimidine, naphthofuropyrimidine, naphthothienopyrimidine, dibenzothiophene group, thianthrene, dihydrobenzothiophenopyrazine, dihydrobenzofuropyrazine, and the like, but are not limited thereto.

Also, when $L^1$, $L^2$, $L^3$, $L^4$, $L^5$ and $L^6$ in Formula of the present invention are an arylene group, it may preferably be an $C_6$-$C_{30}$ arylene group, more preferably an $C_6$-$C_{18}$ arylene group, illustratively, it may be phenylene, biphenyl, terphenyl, naphthalene, anthracene, phenanthrene, and the like. Preferably, $L^1$ is a heterocyclic group, it is preferably a $C_2$-$C_{30}$ heterocyclic group, more preferably a $C_2$-$C_{18}$ heterocyclic group, illustratively, it can be dibenzofuran, dibenzothiophene, carbazole, and the like, and when $L^1$ is a fluorenylene group, it can be exemplarily 9,9-dimethyl-9H-fluorene.

In the present invention, the first host compound represented by Formula (1) comprises the following Compounds 1-1 to 1-60 and 2-1 to 2-106.

1-1

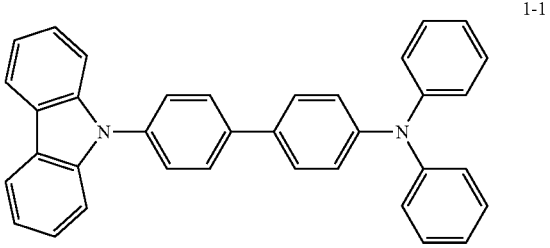

1-2

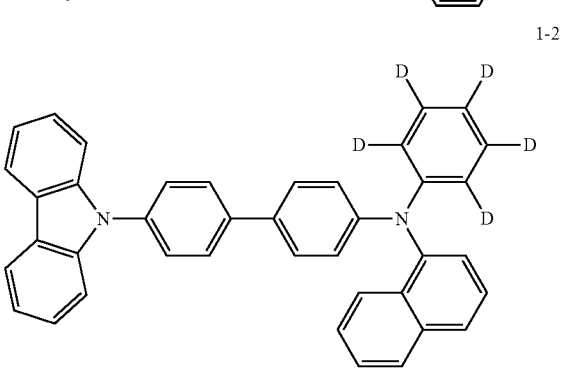

1-3

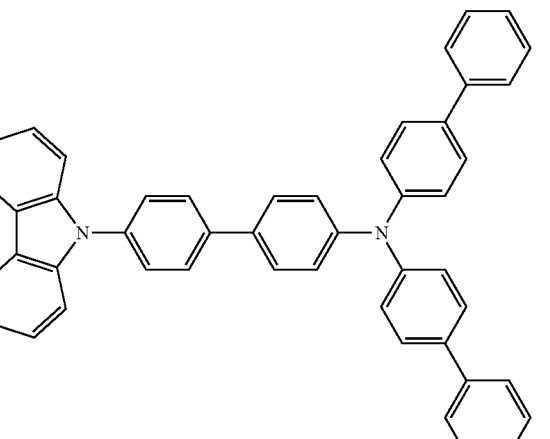

1-4

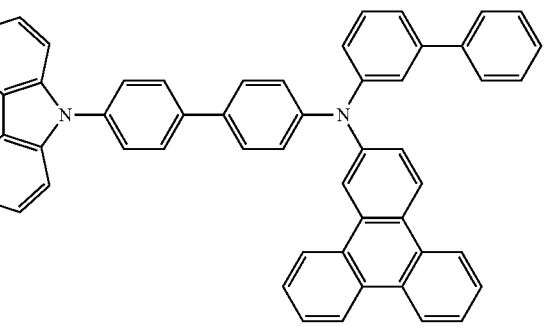

1-5
1-6
1-7
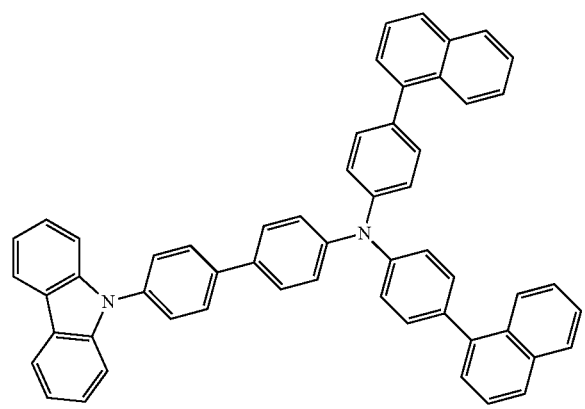
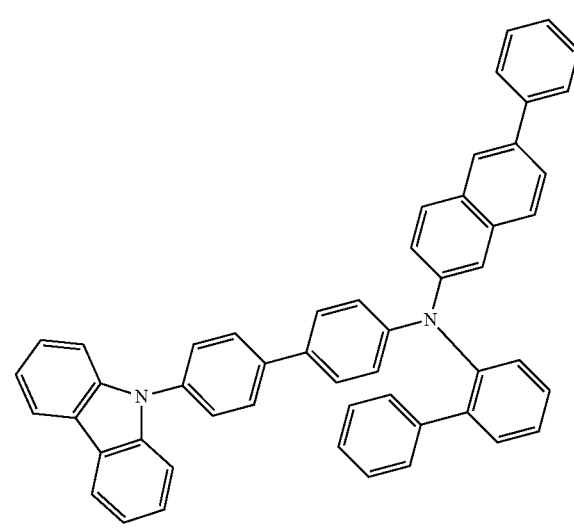
1-8
1-9
1-10
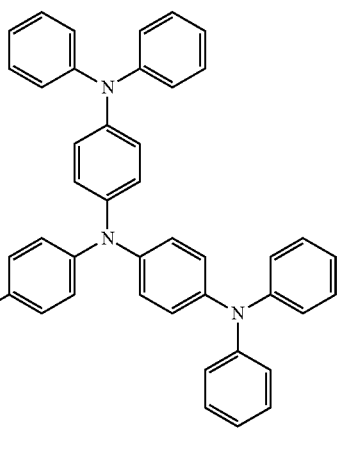
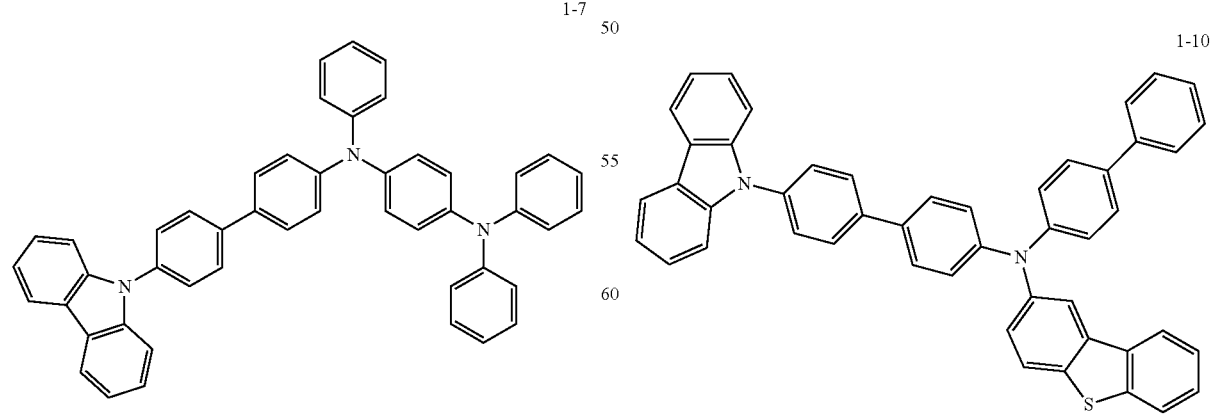

-continued
1-11
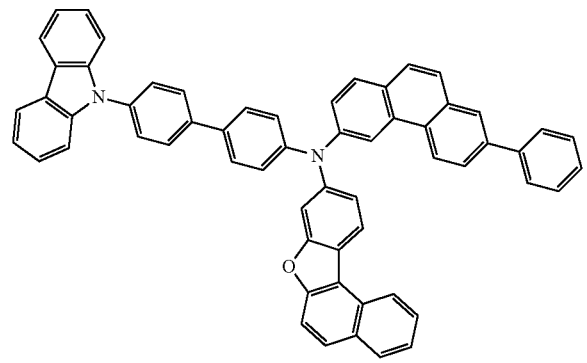
1-12
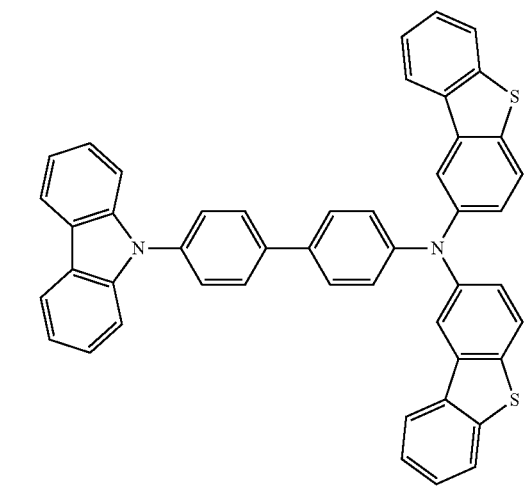
1-13
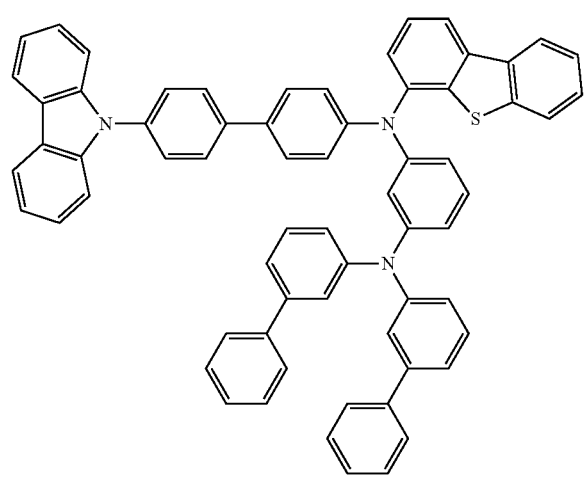
1-14
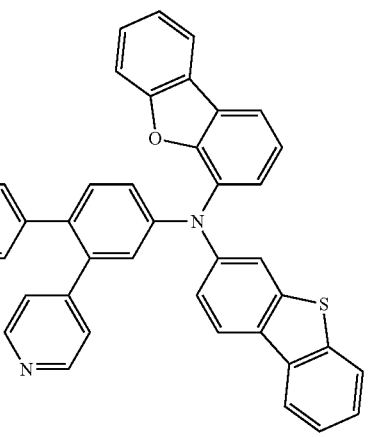
1-15
1-16
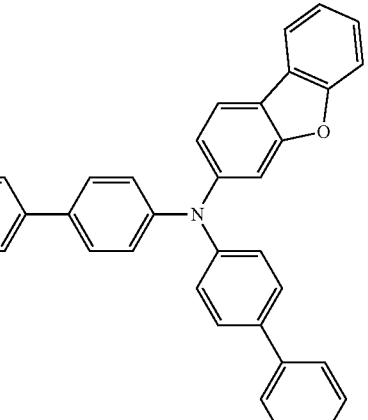

1-17
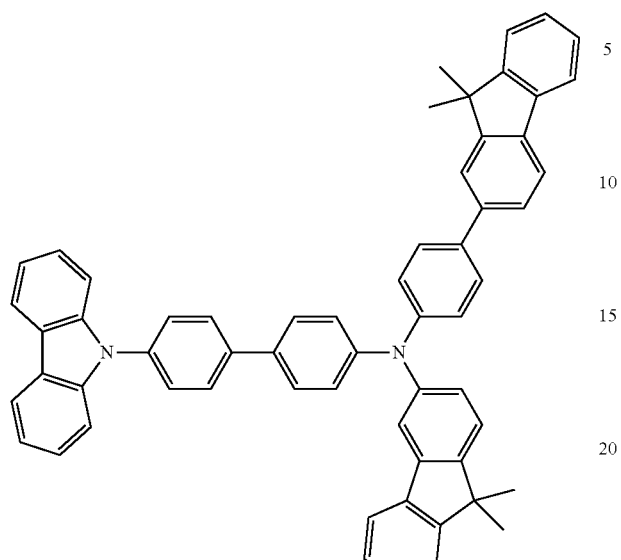
1-18
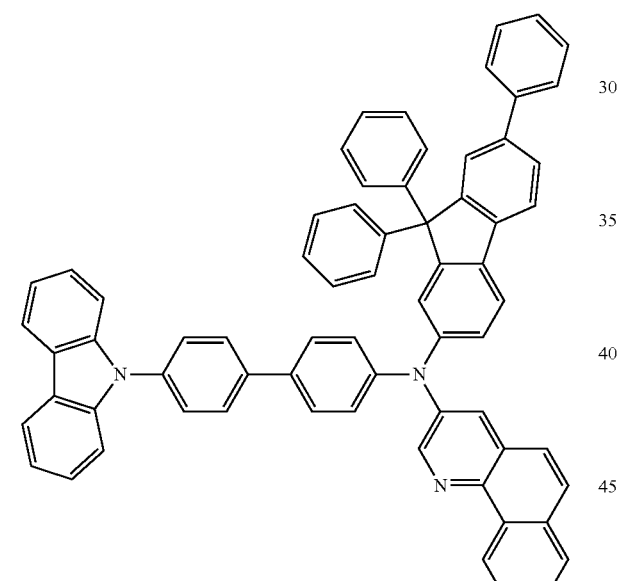
1-19
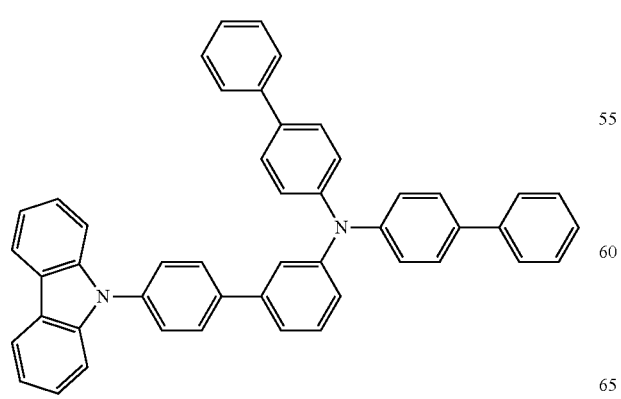
1-20
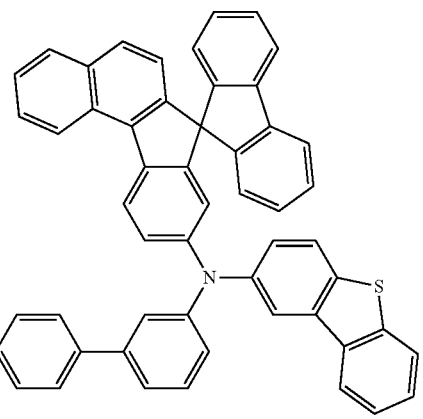
1-21
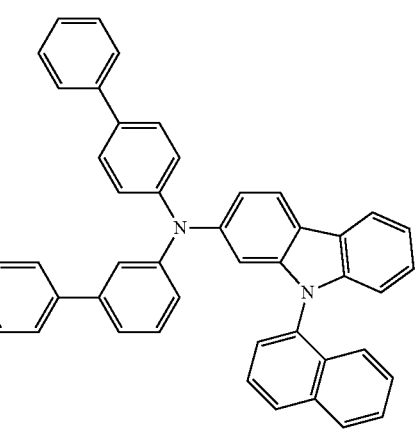
1-22
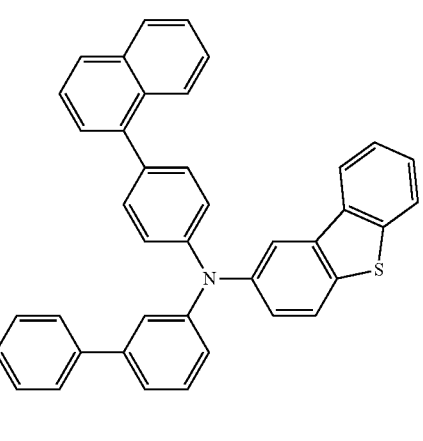

-continued
1-23
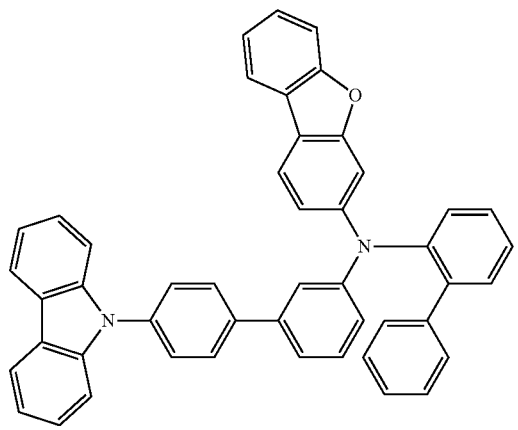
1-24
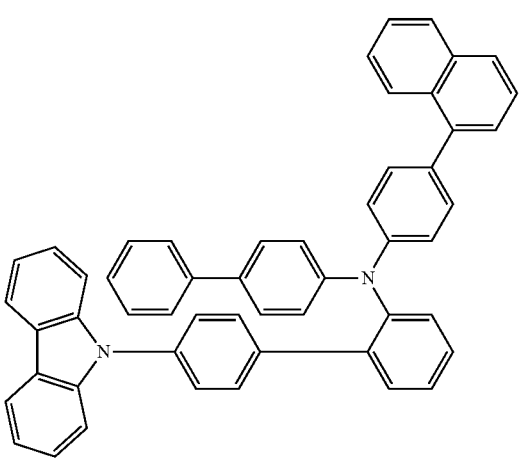
1-25
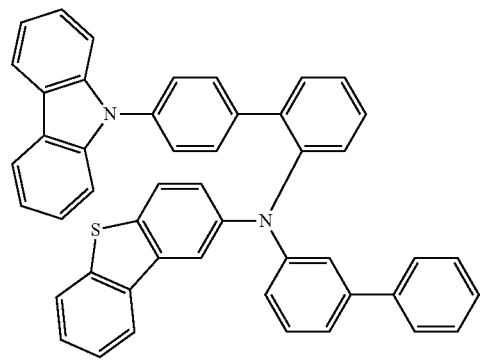
1-26
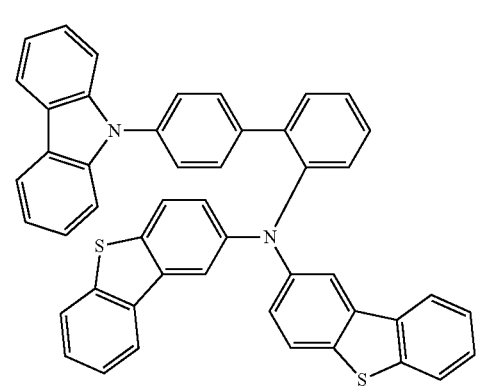
-continued
1-27
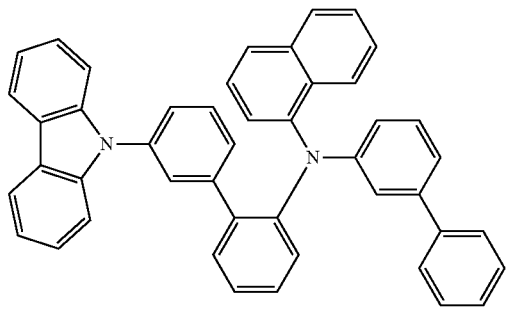
1-28
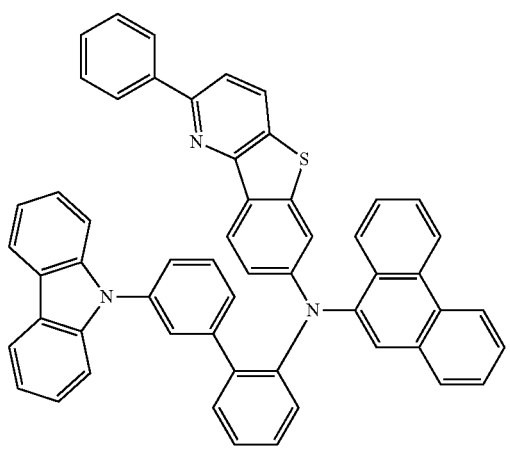
1-29
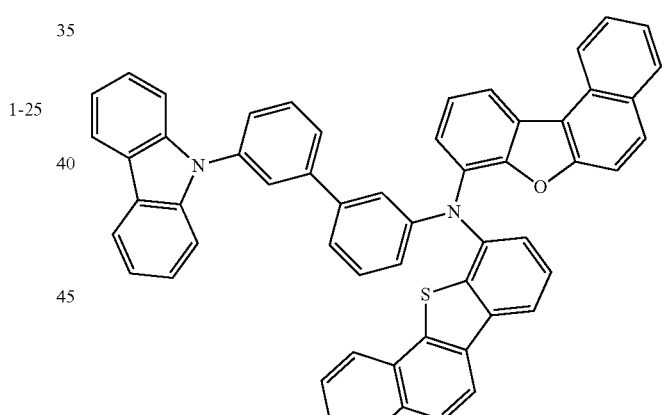
1-30
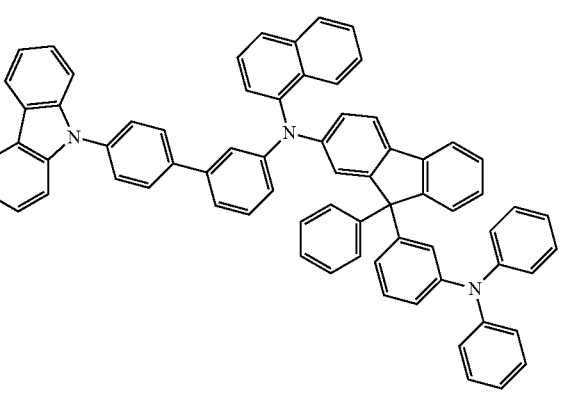

1-31
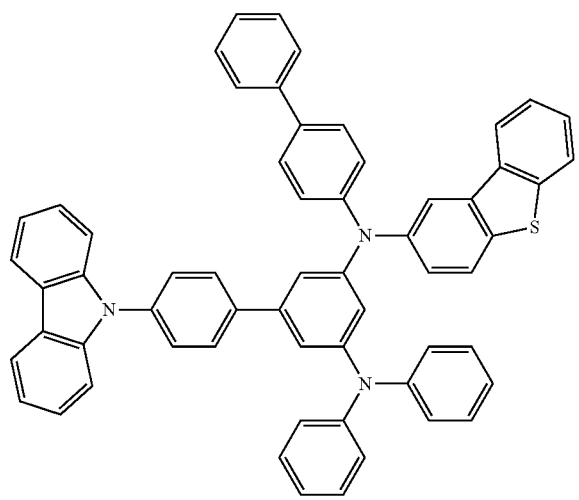
1-32
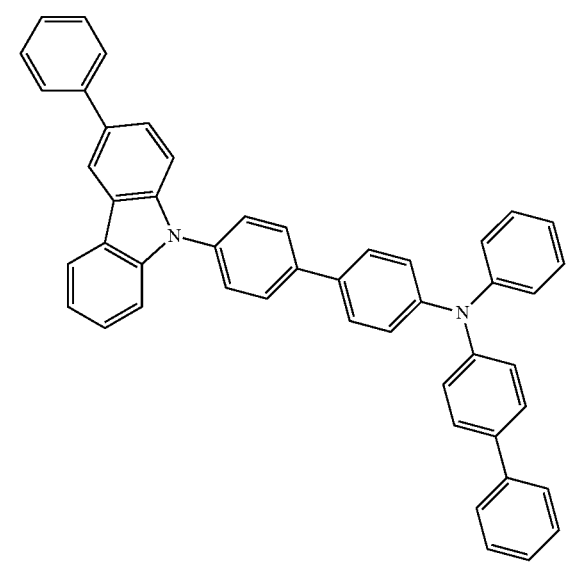
1-33
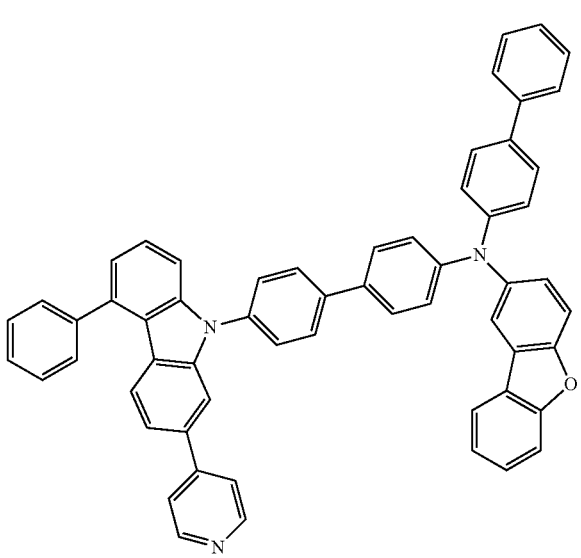
1-34
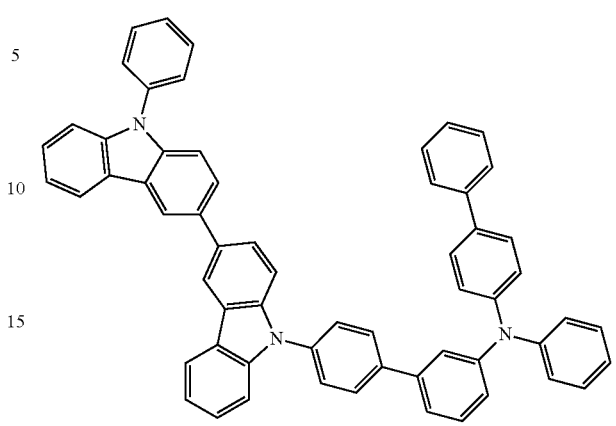
1-35
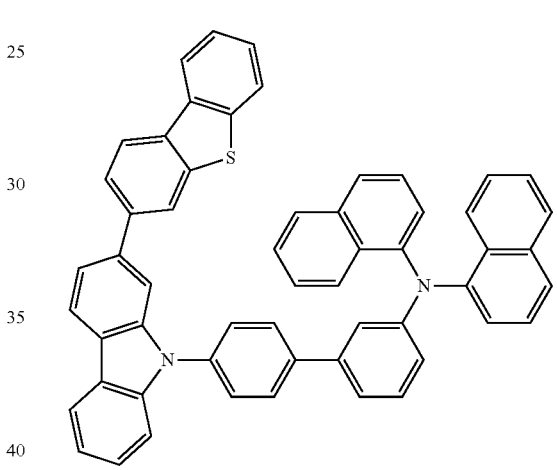
1-36
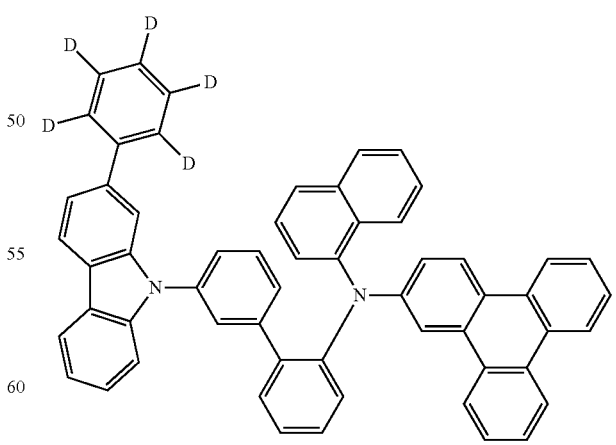

1-37
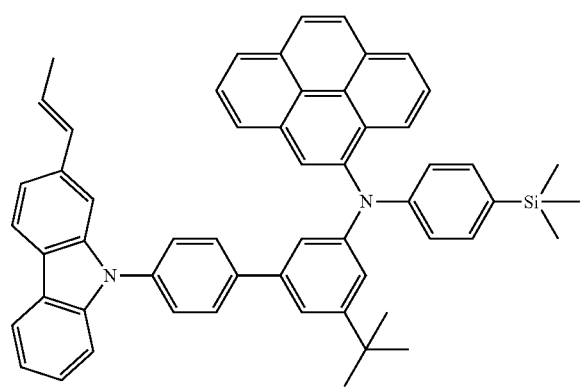
1-38
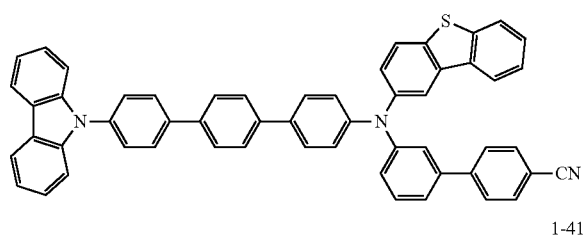
1-39
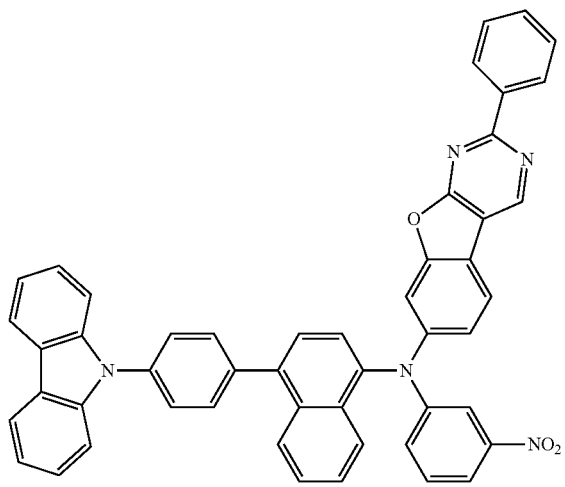
1-40
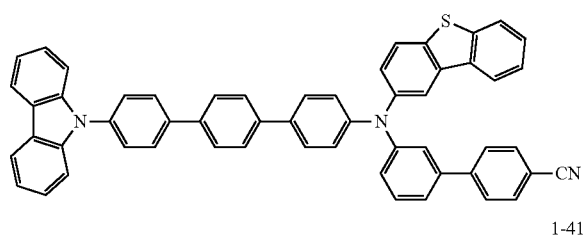
1-41
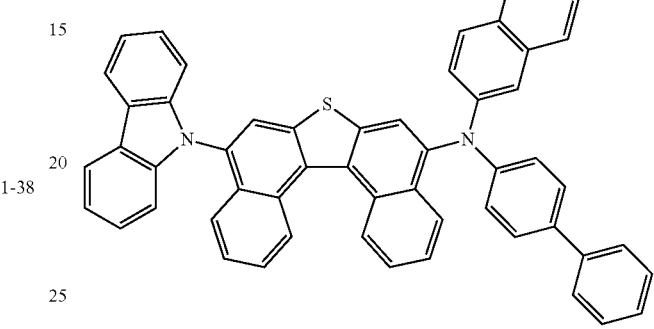
1-42
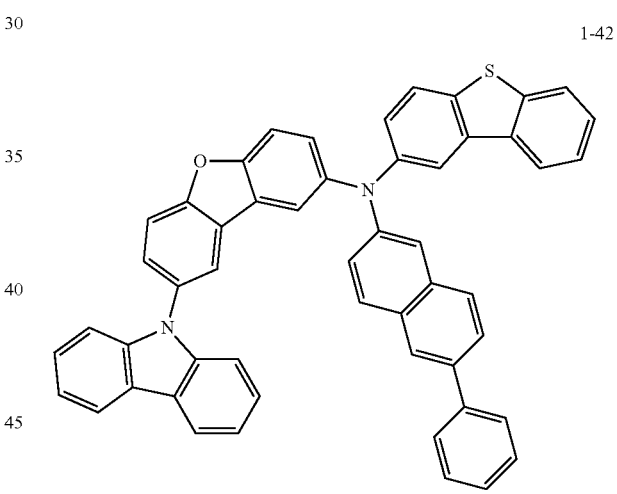
1-43
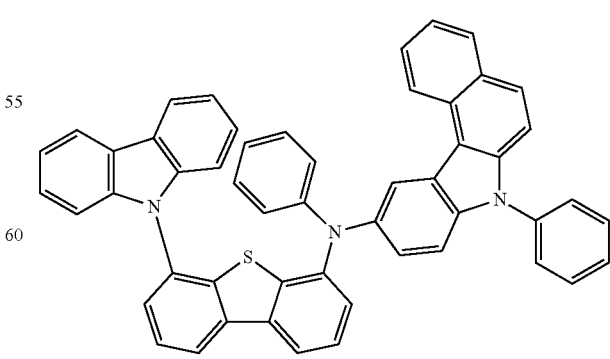

1-44
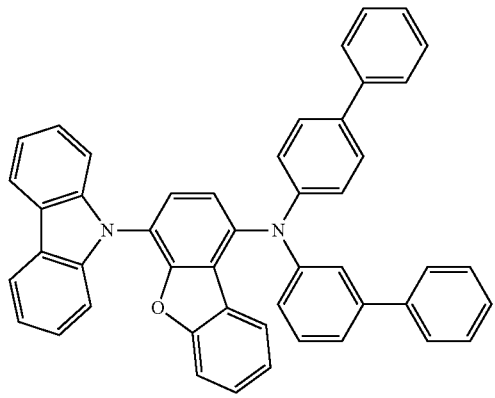
1-45
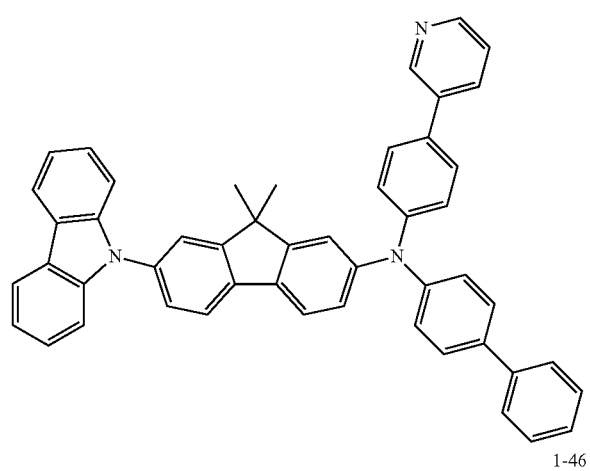
1-46
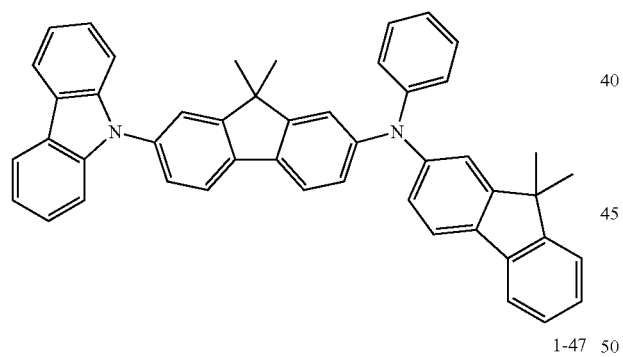
1-47
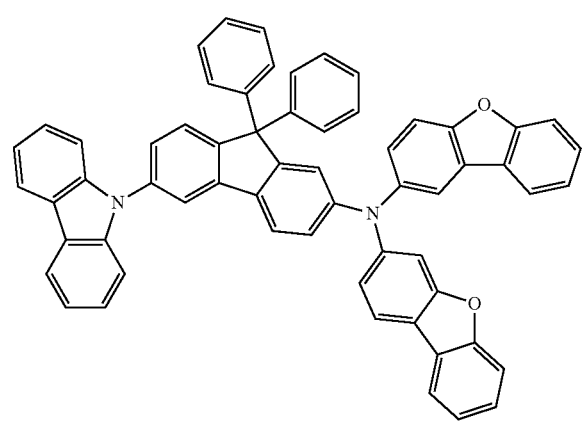
1-48
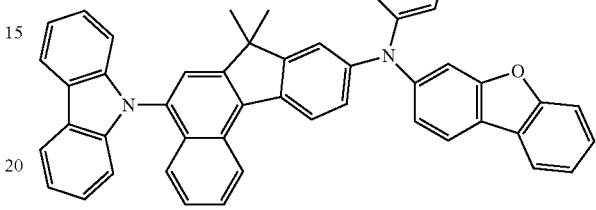
1-49
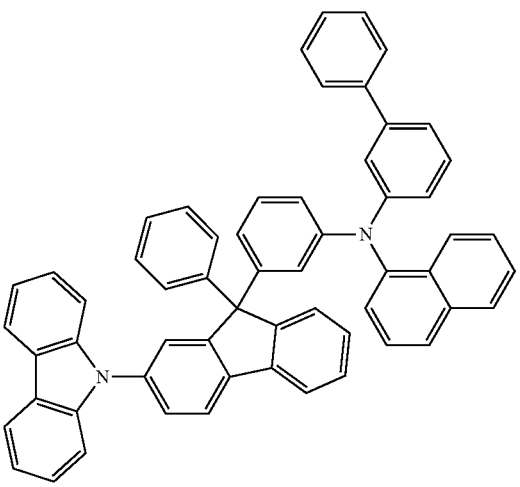
1-50
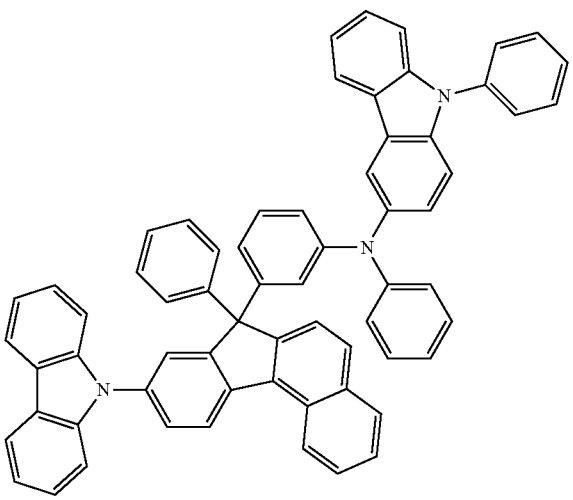

-continued
1-51
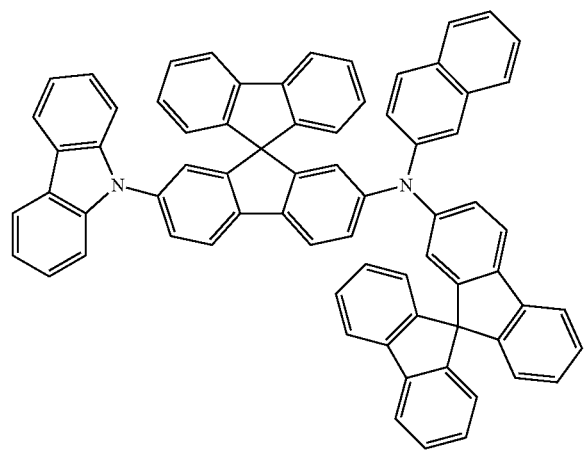
1-52
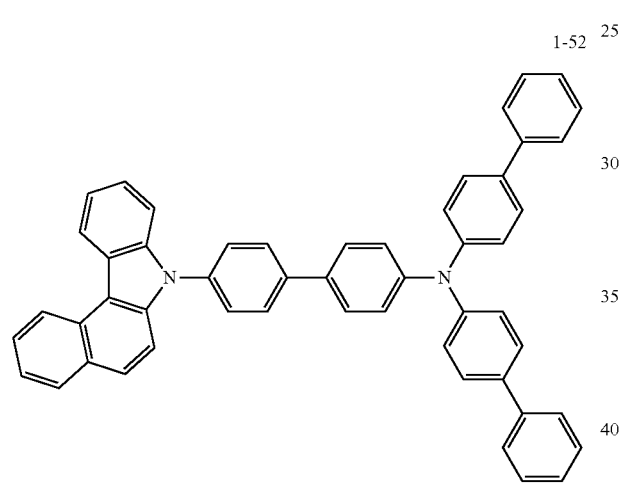
1-53
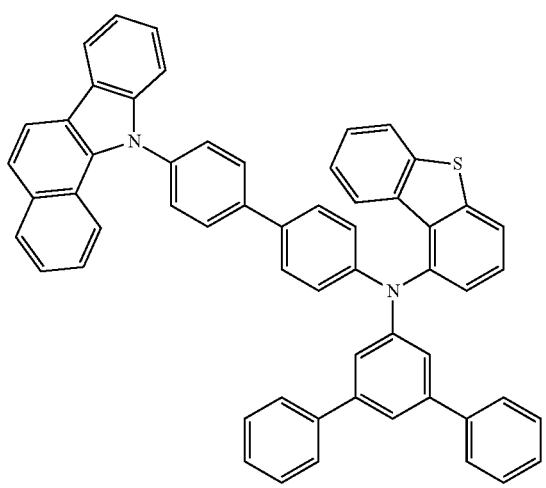
-continued
1-54
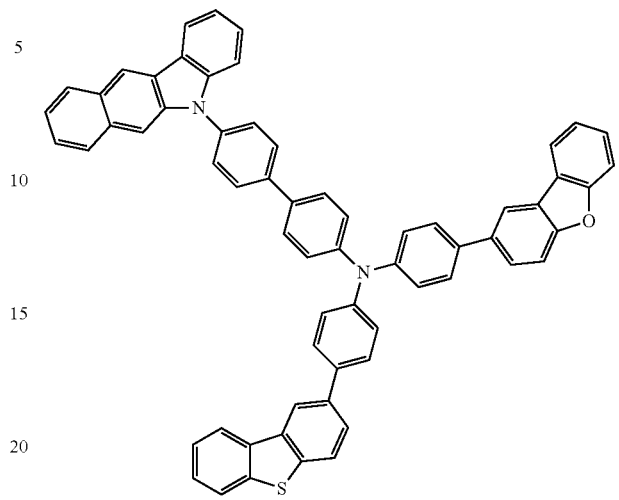
1-55
1-56
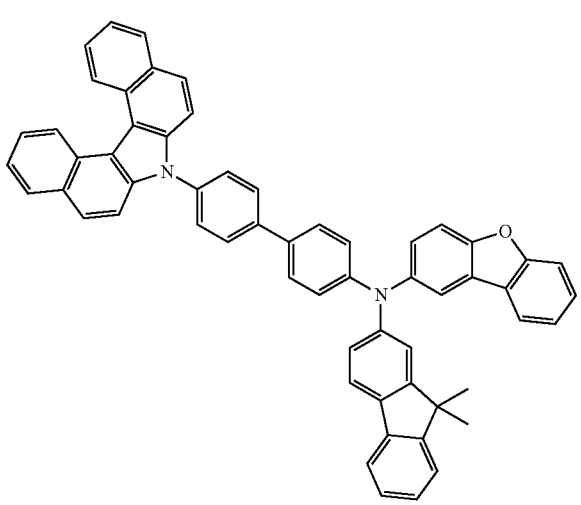

49
-continued
1-57
1-58
1-59
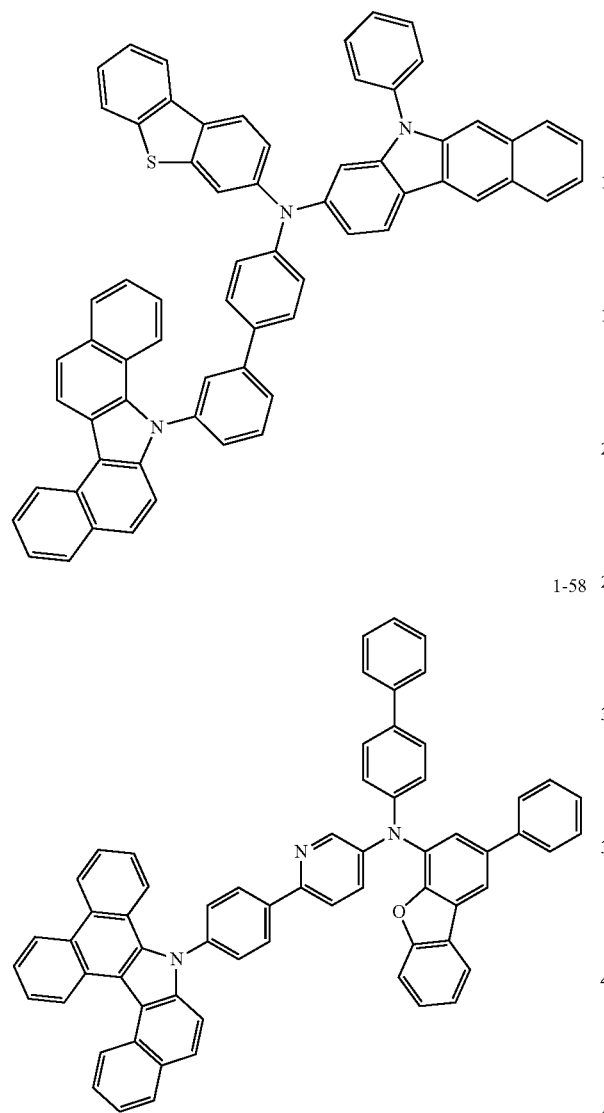
50
-continued
1-60
2-1
2-2
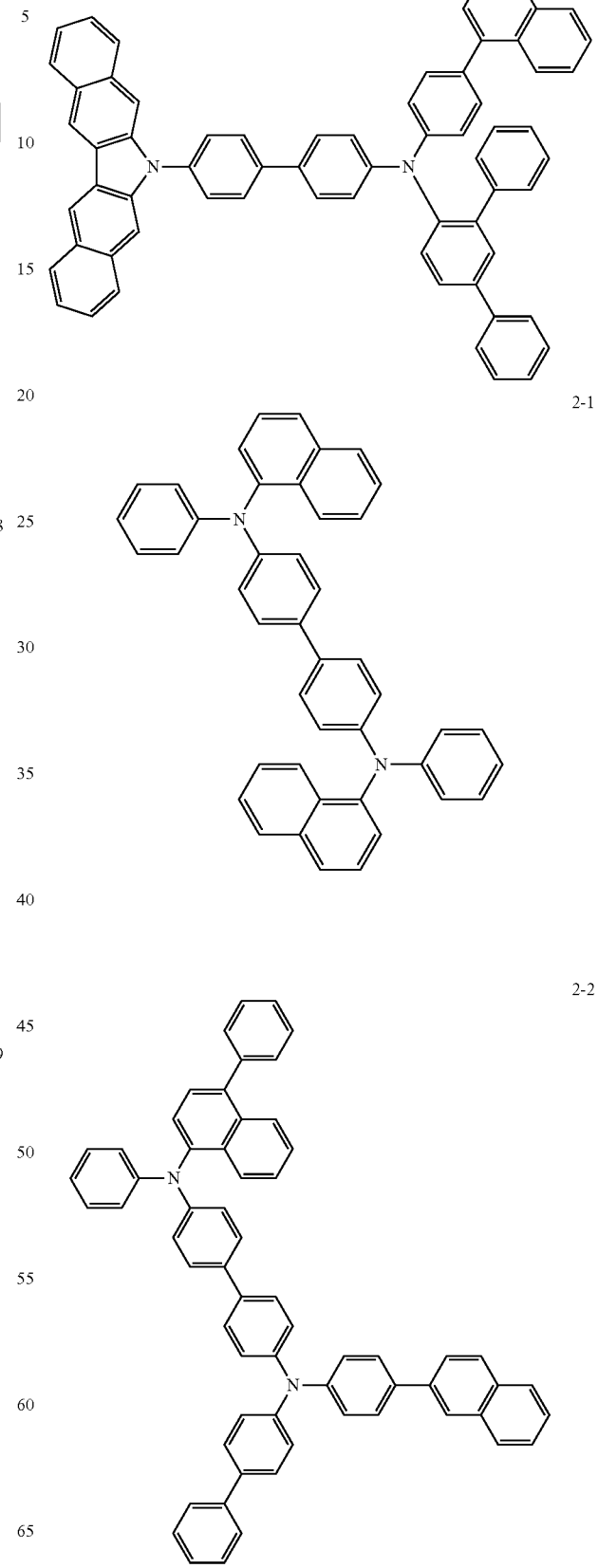

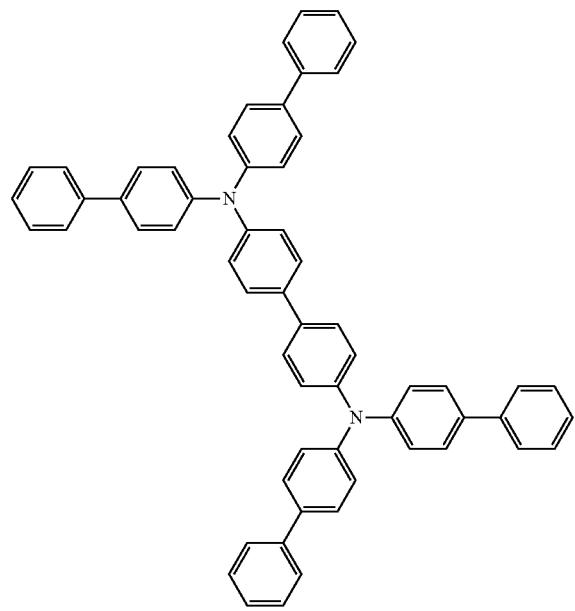
2-3
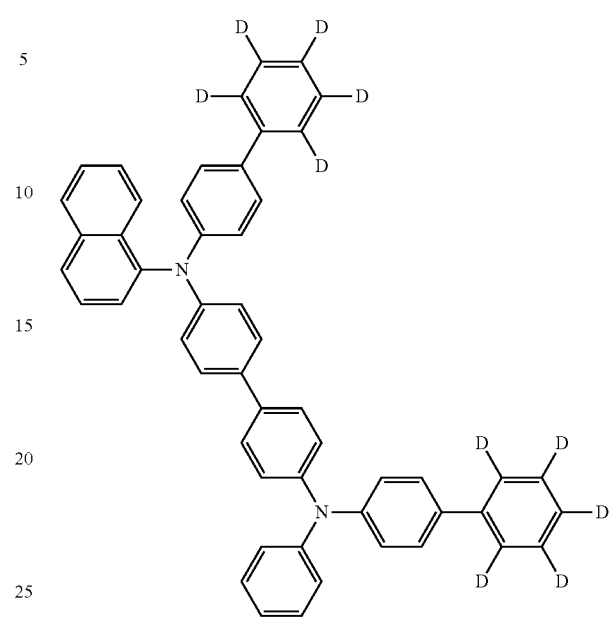
2-5
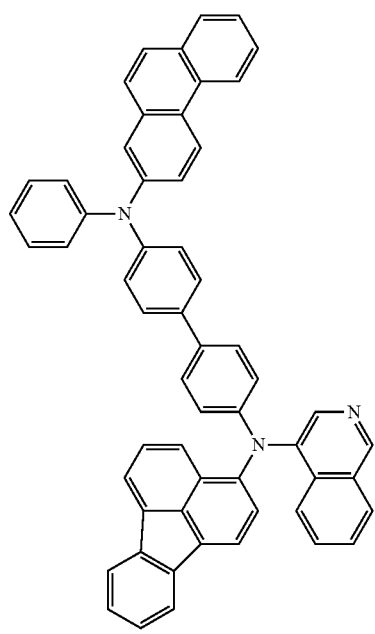
2-4
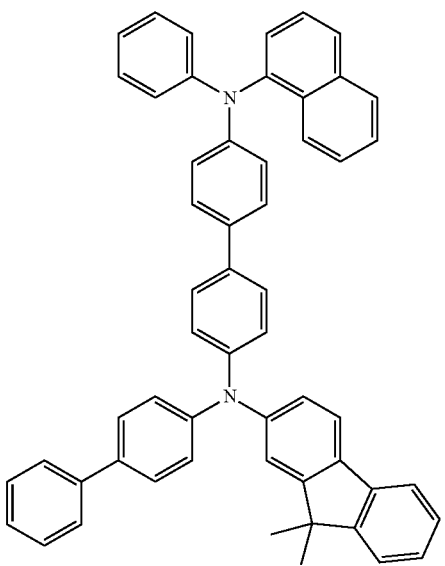
2-6

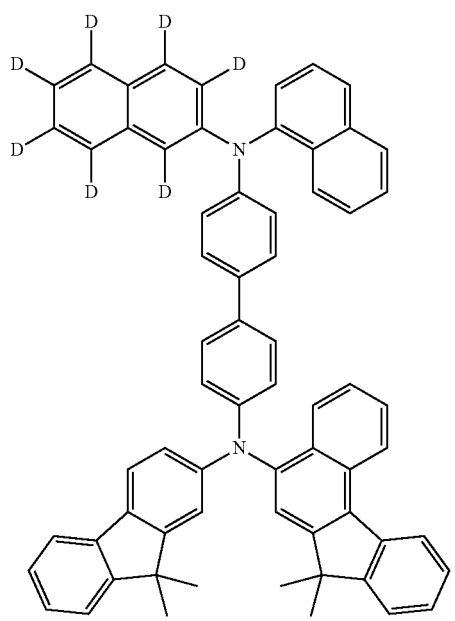
2-7
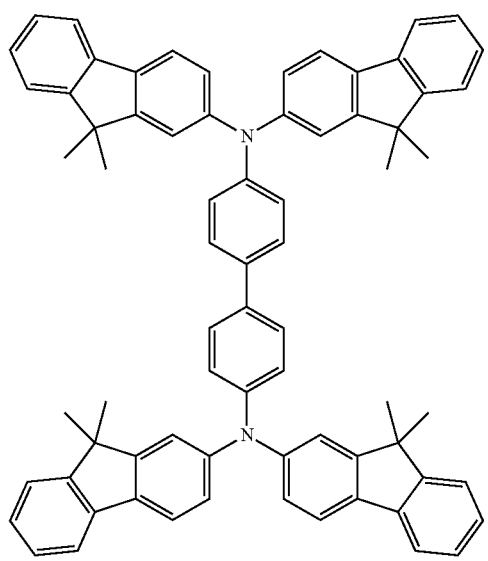
2-9
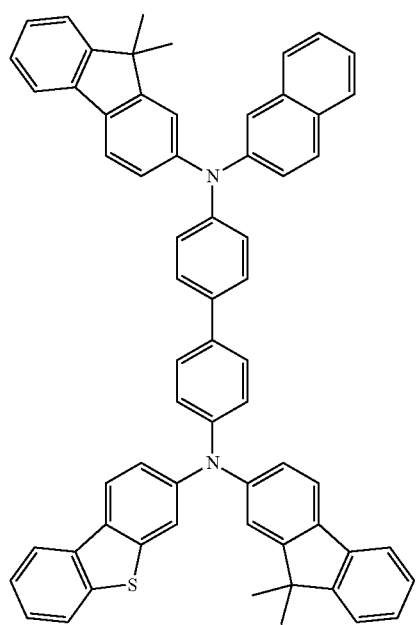
2-8
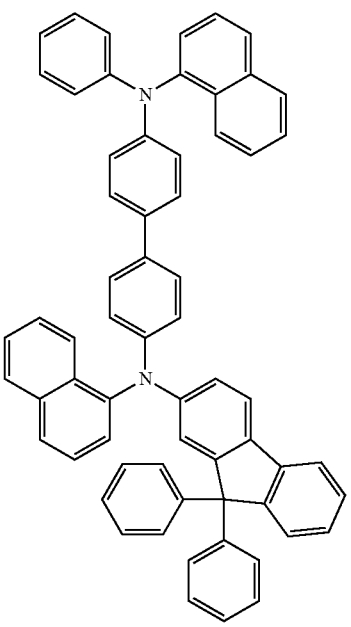
2-10

2-11
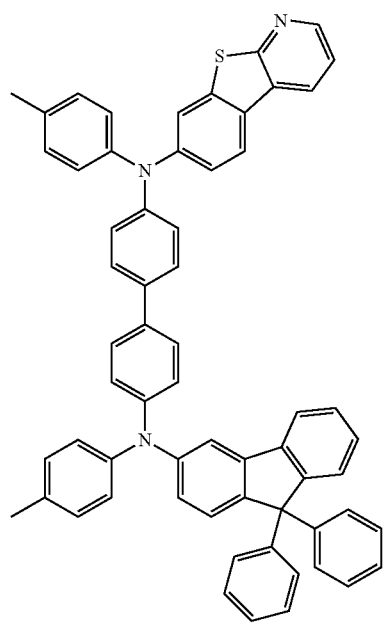
2-12
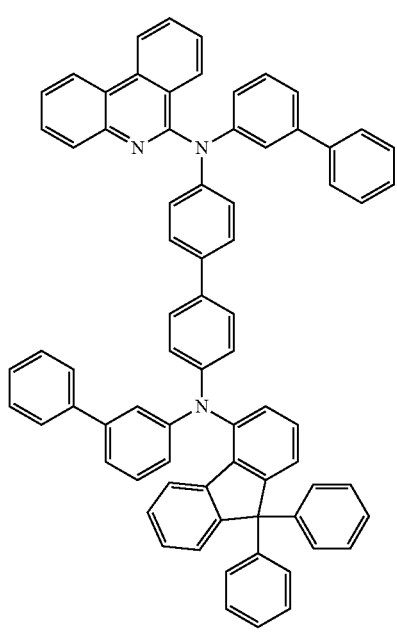
2-13
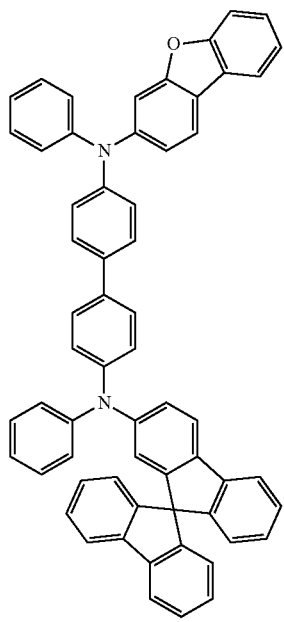
2-14
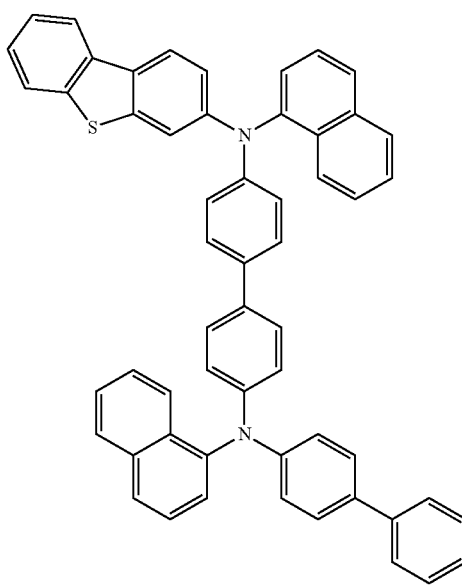

2-15
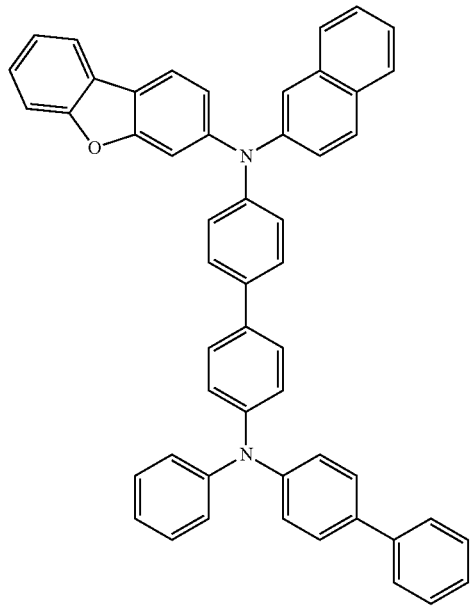
2-17
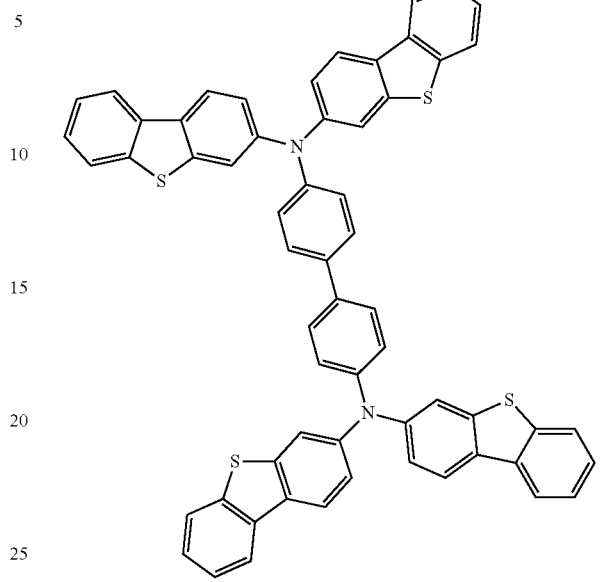
2-16
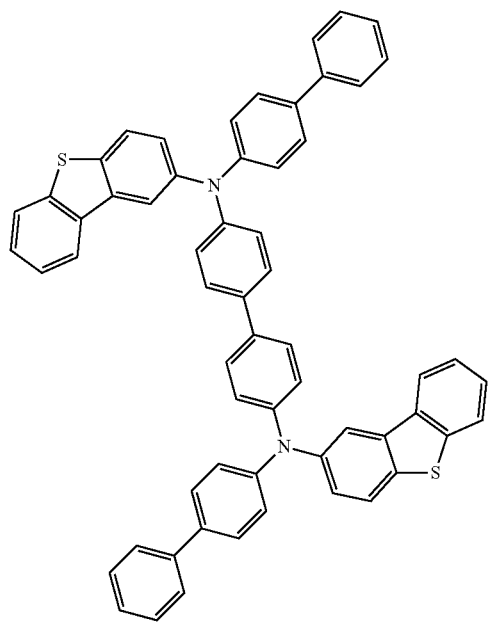
2-18
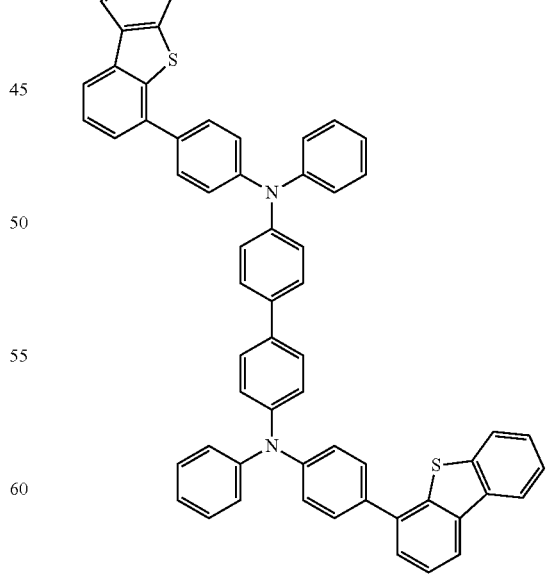

2-19
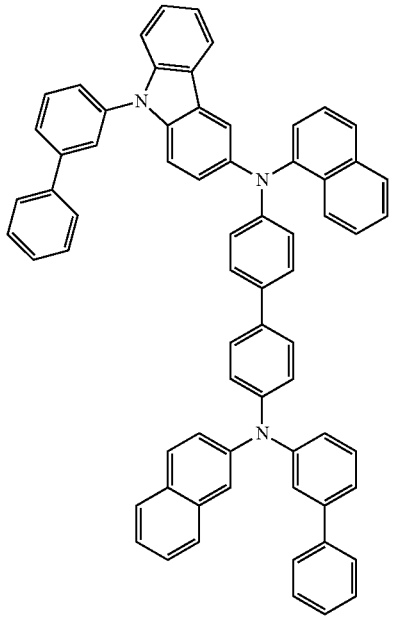
2-20
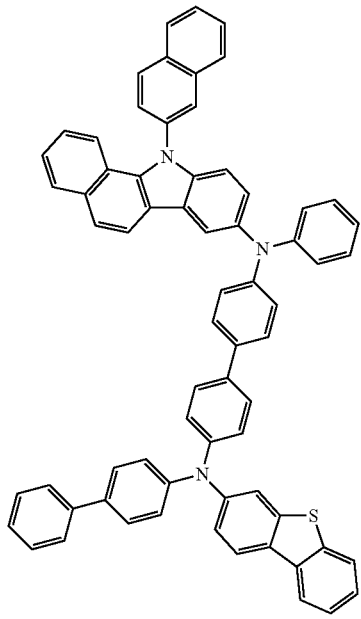
2-21
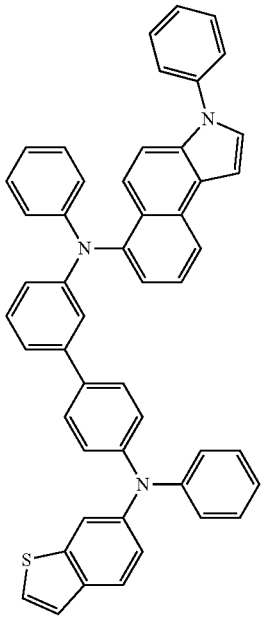
2-22
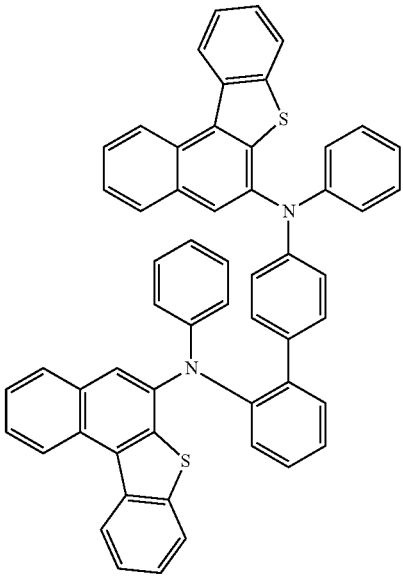

2-23
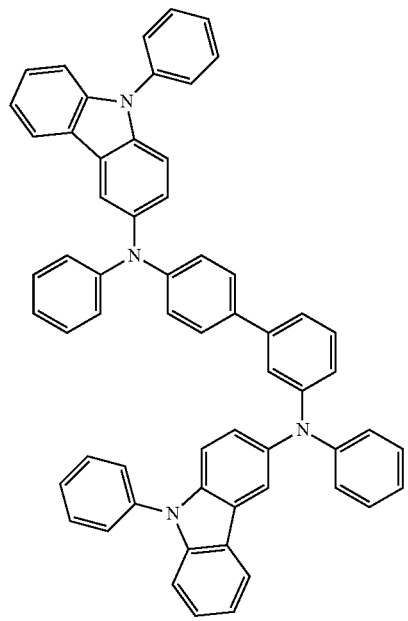
2-24
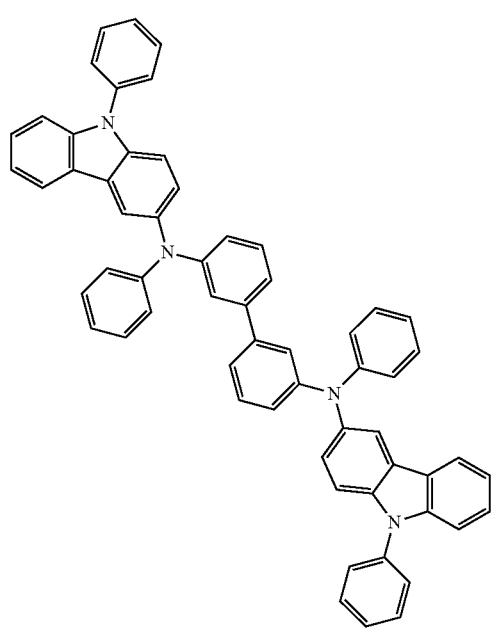
2-25
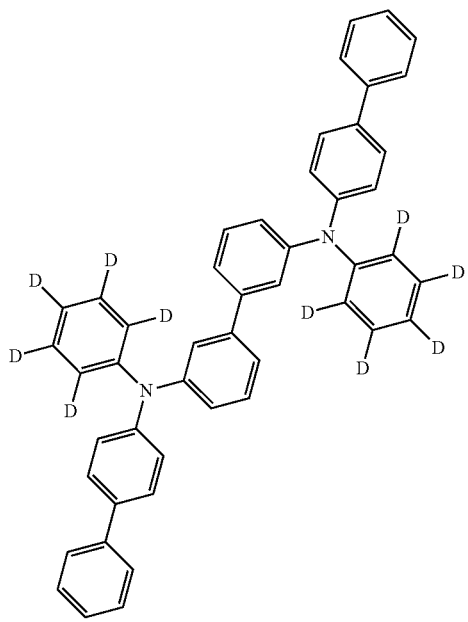
2-26
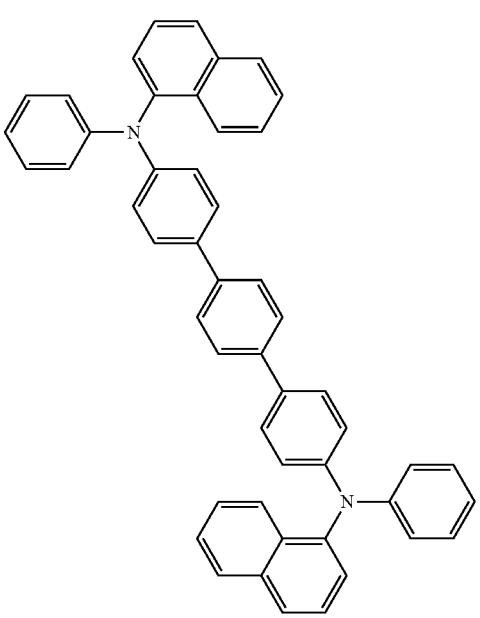

2-27
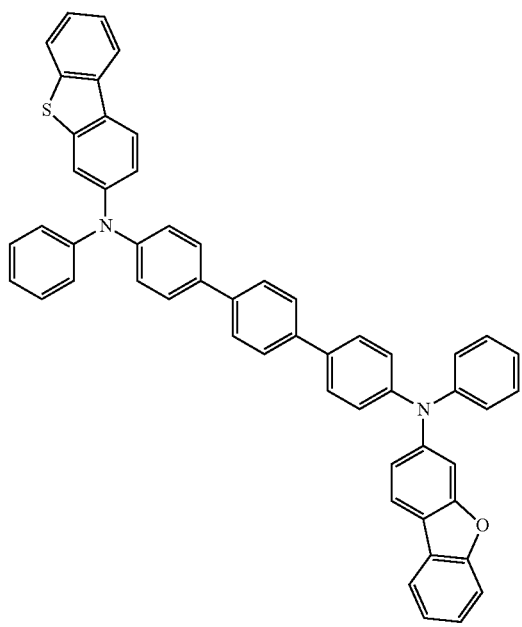
2-29
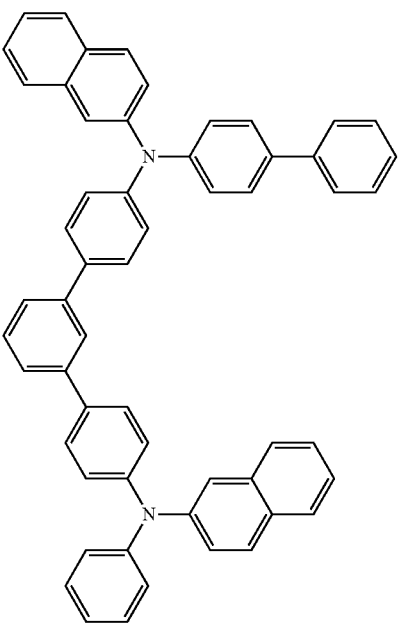
2-28
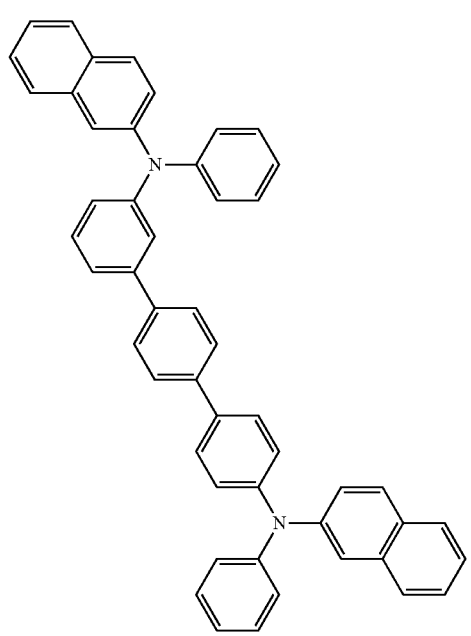
2-30
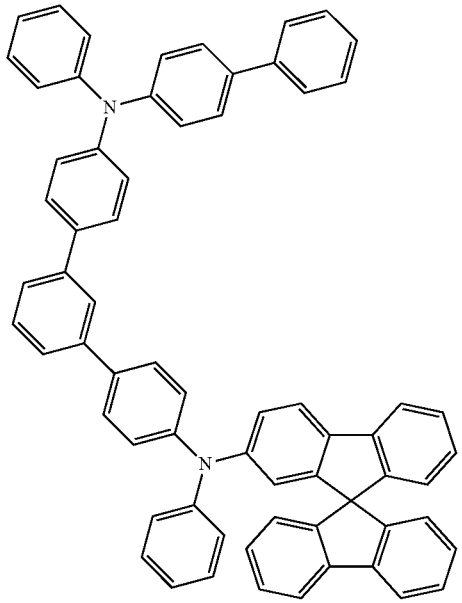

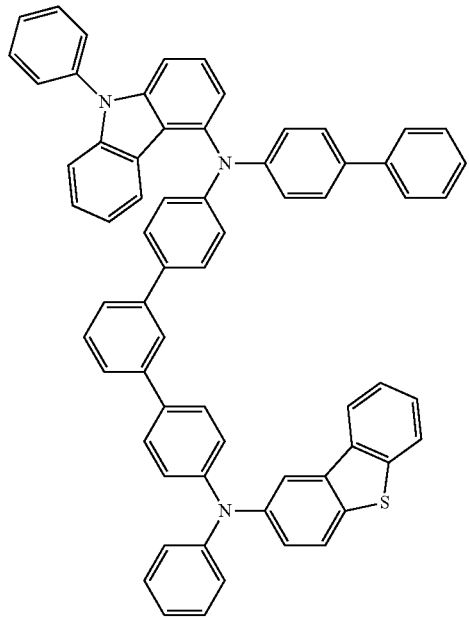
2-31
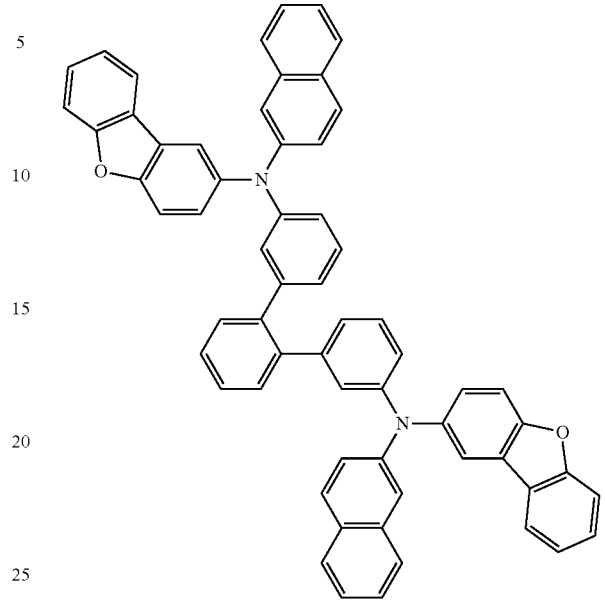
2-33
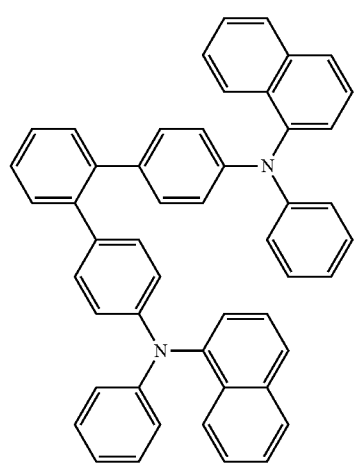
2-32
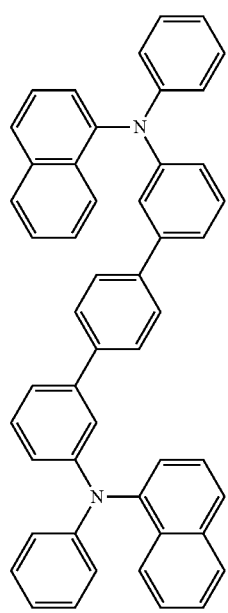
2-34

-continued
2-35
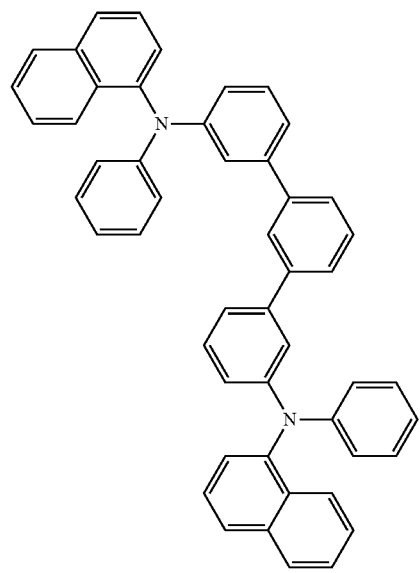
2-36
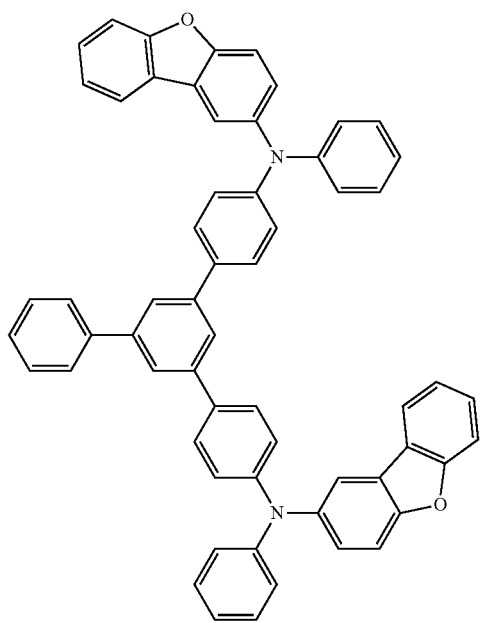
2-37
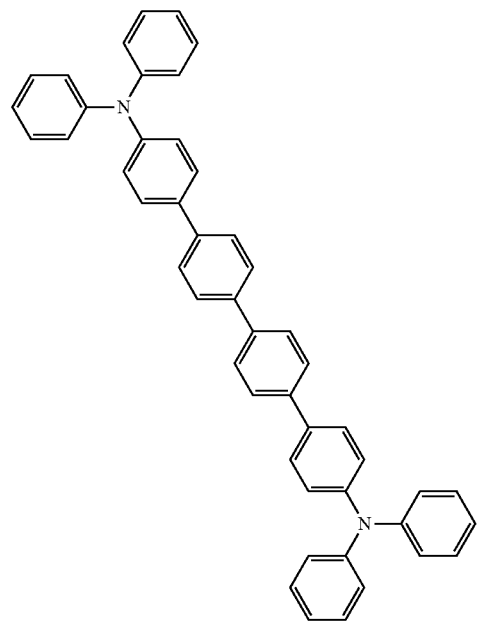
2-38
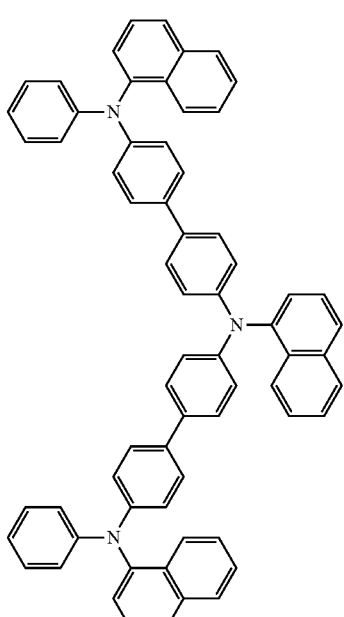

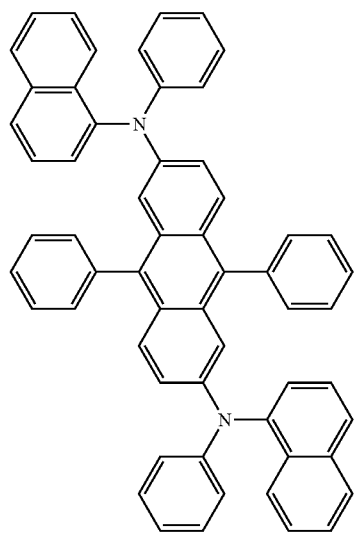
2-39
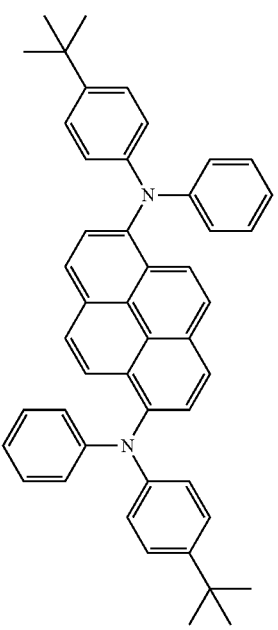
2-40
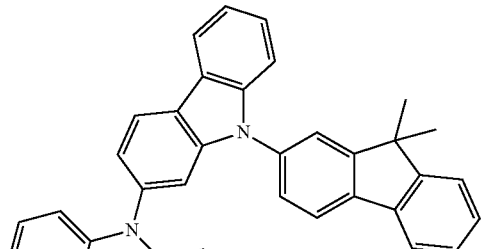
2-41
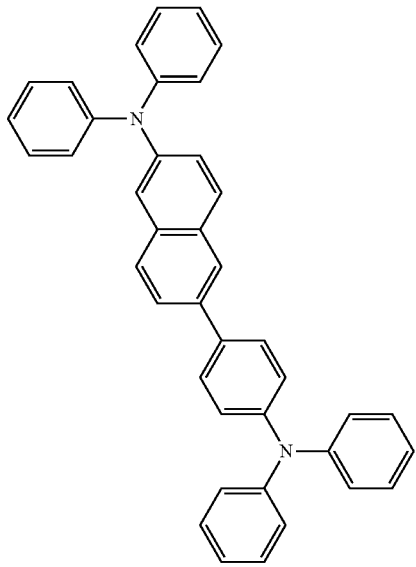
2-42
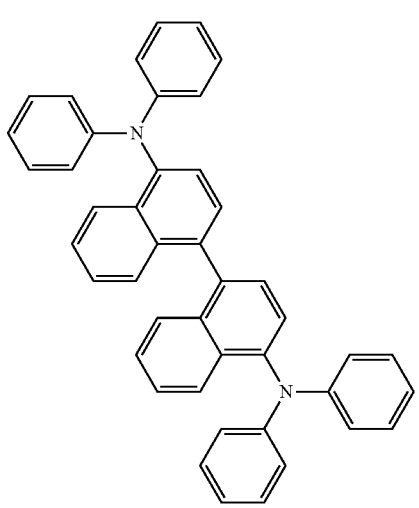
2-43

2-44
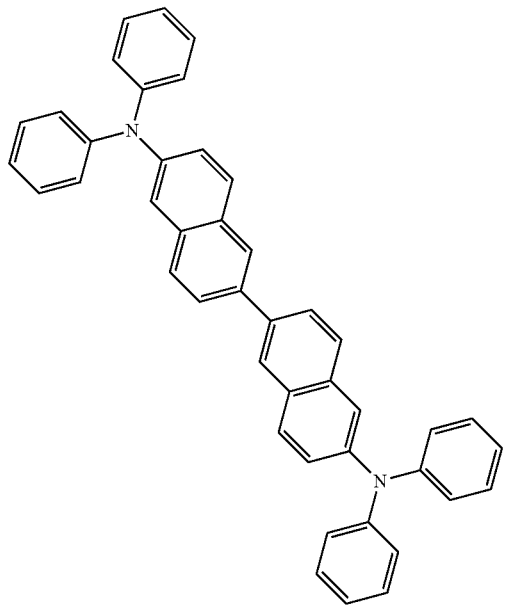
2-45
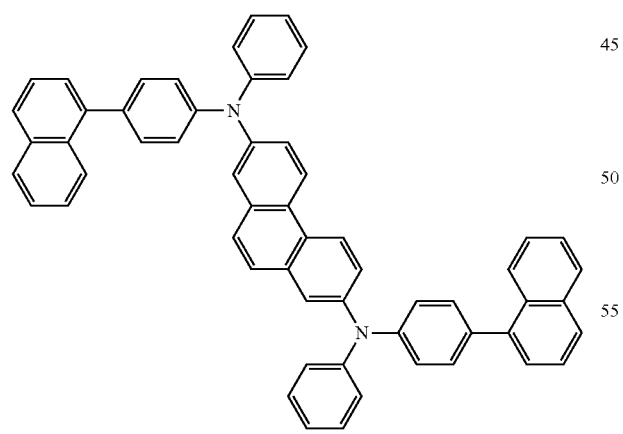
2-46
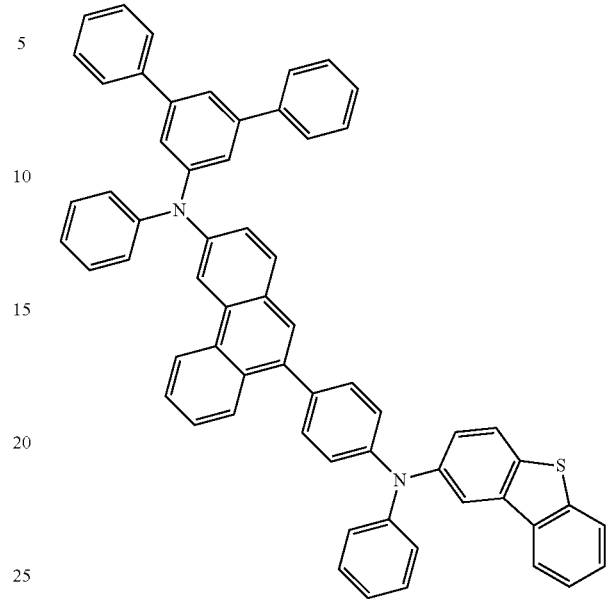
2-47
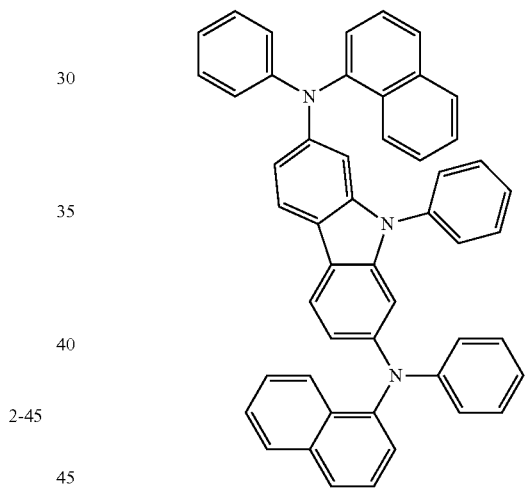
2-48
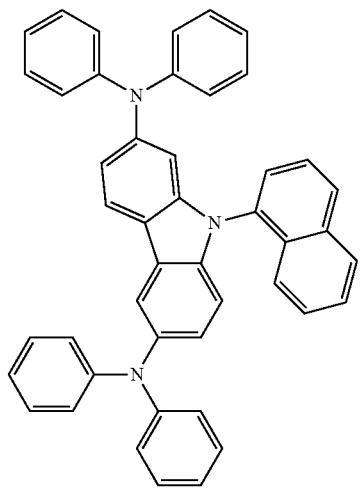

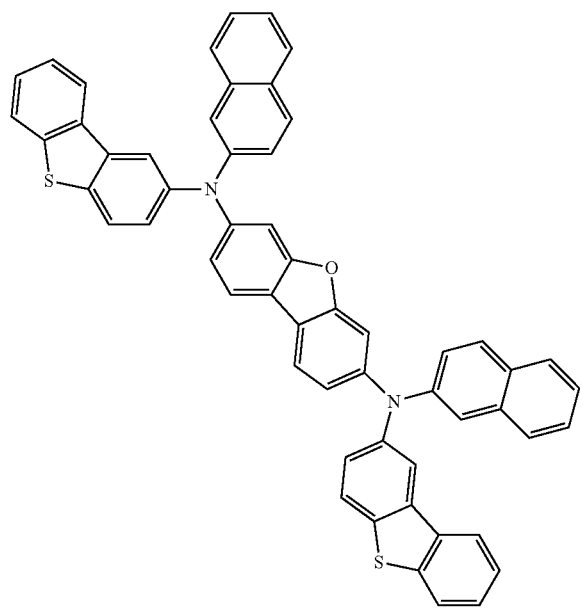
2-49
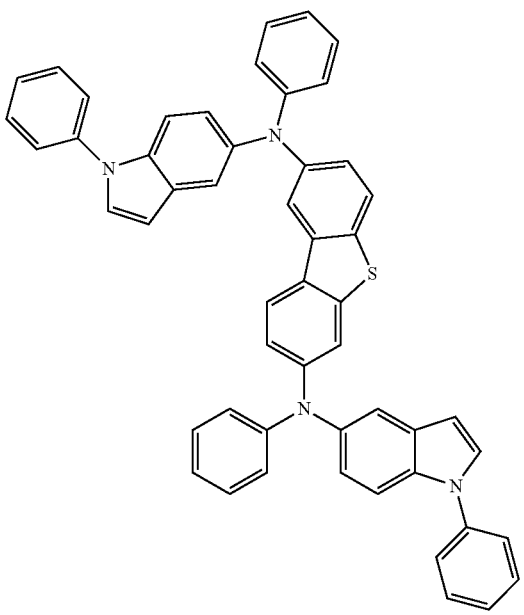
2-51
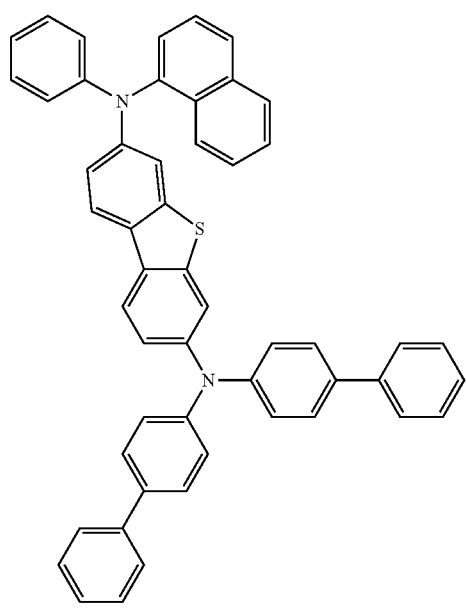
2-50
2-52

2-53
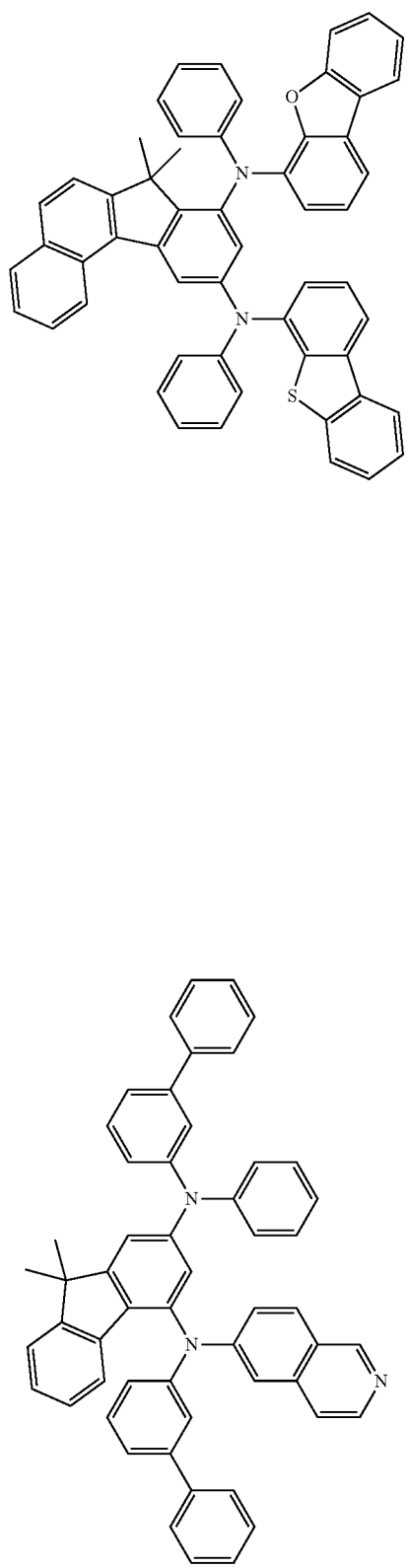
2-54
2-55
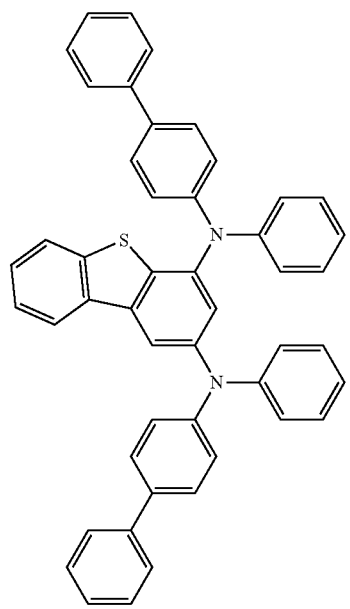
2-56
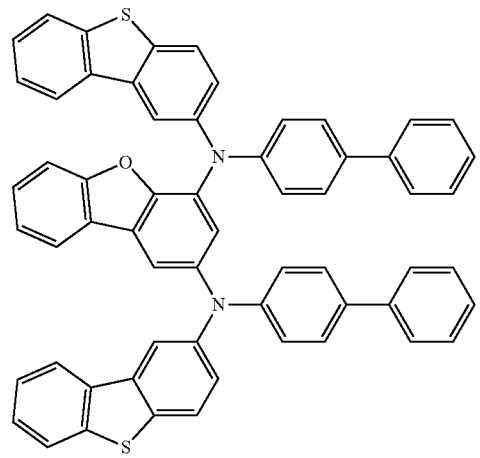
2-57
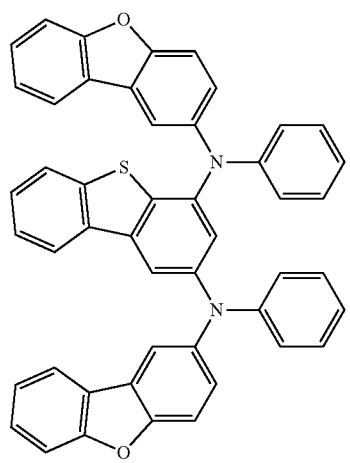

2-58
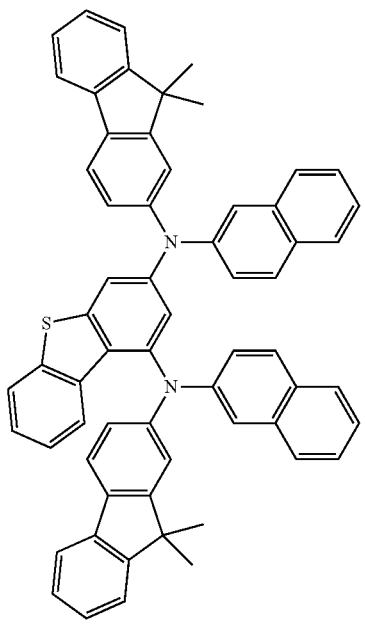
2-60
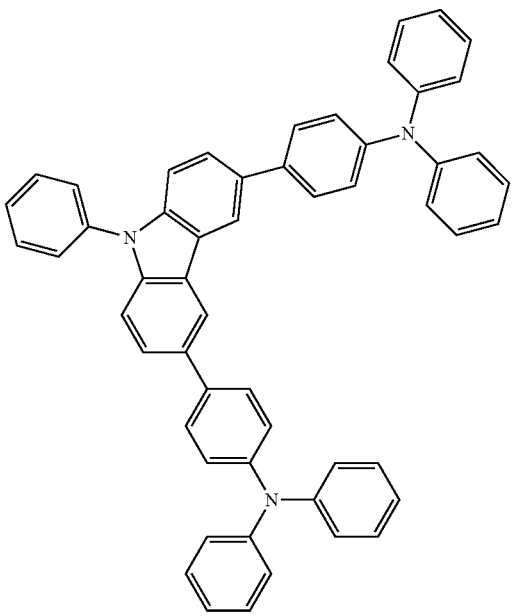
2-59
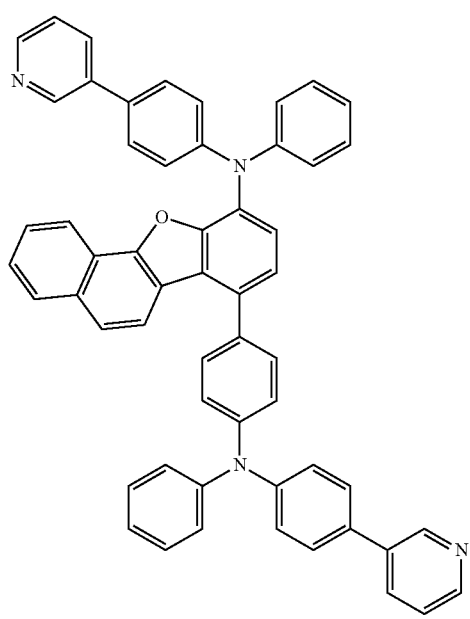
2-61
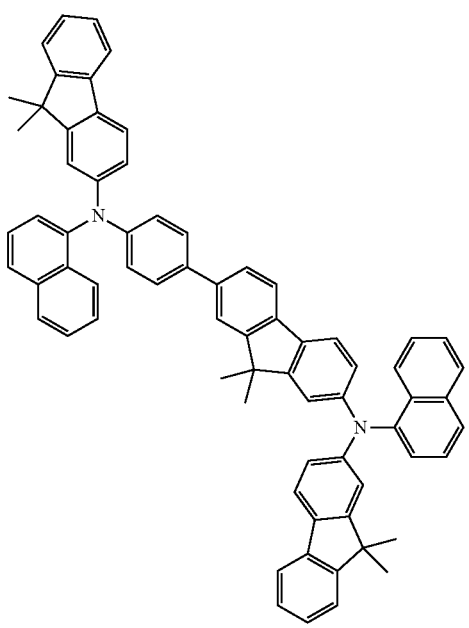

2-62
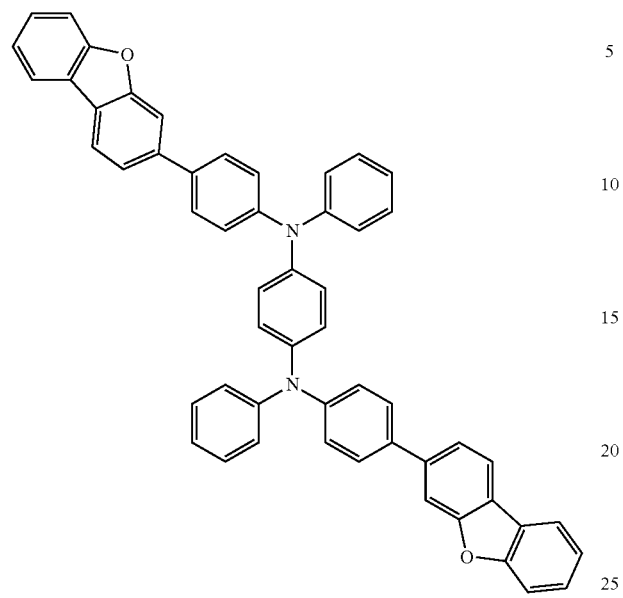
2-63
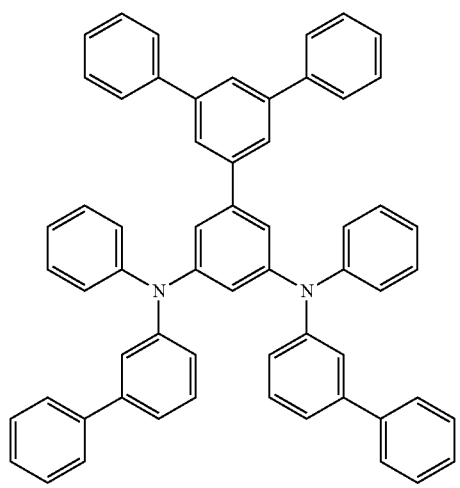
2-64
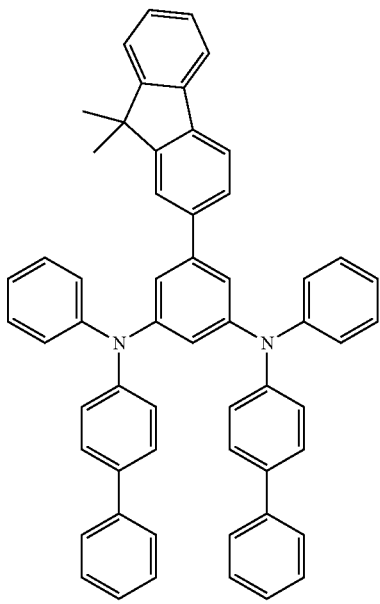
2-65
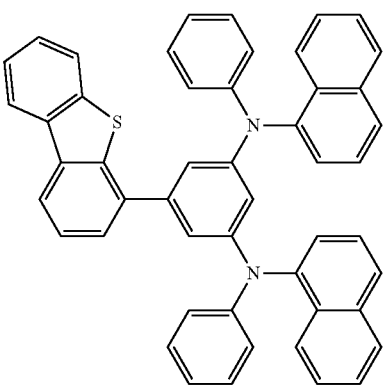
2-66
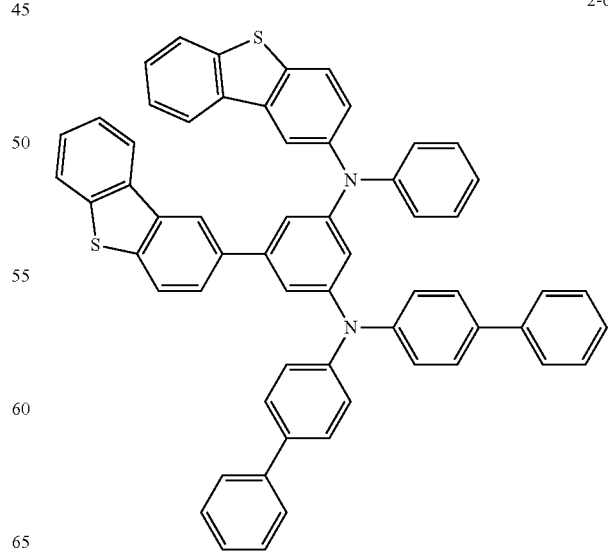

2-67
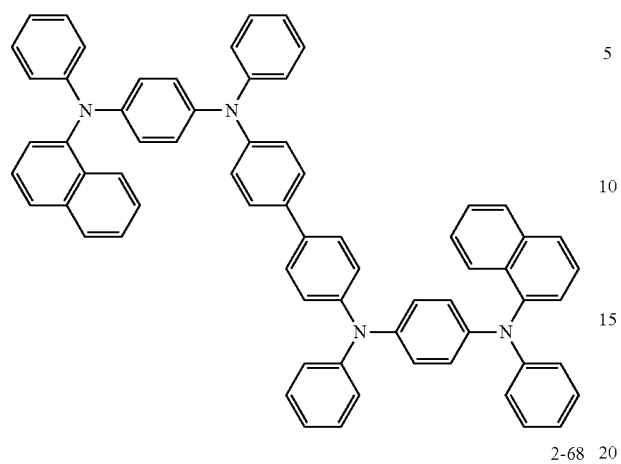
2-68
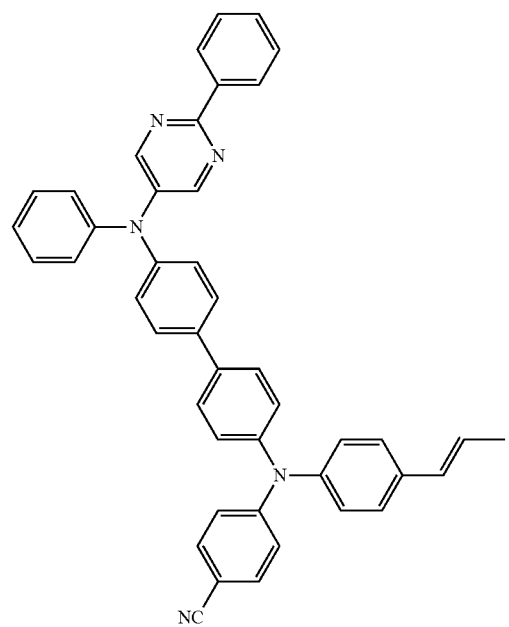
2-69
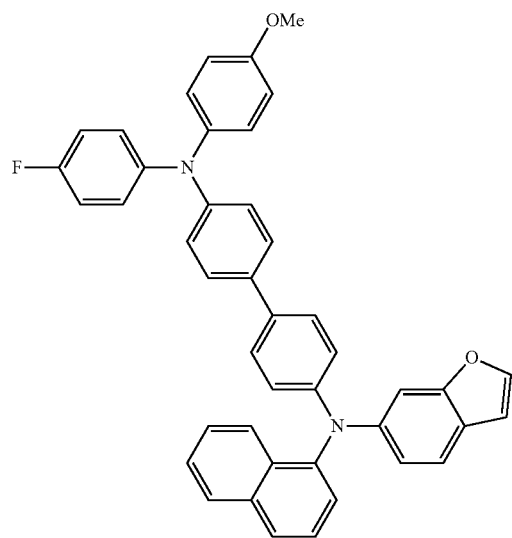
2-70
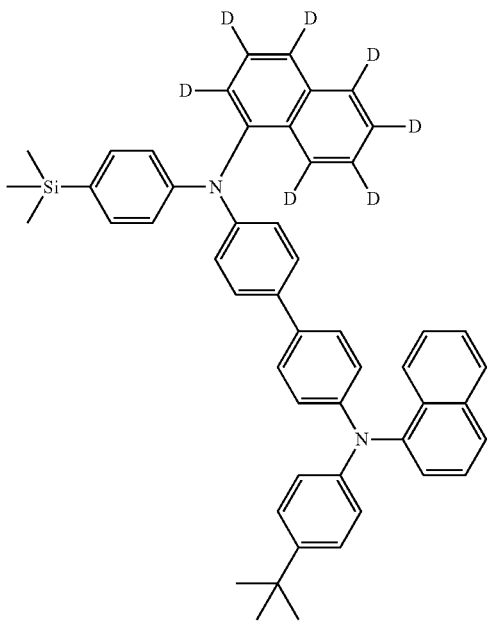
2-71
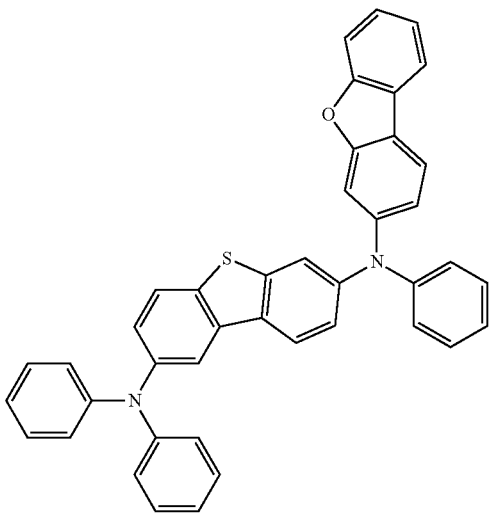
2-72

2-73
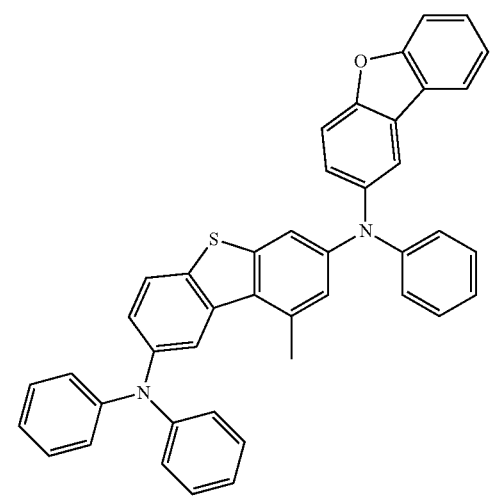
2-74
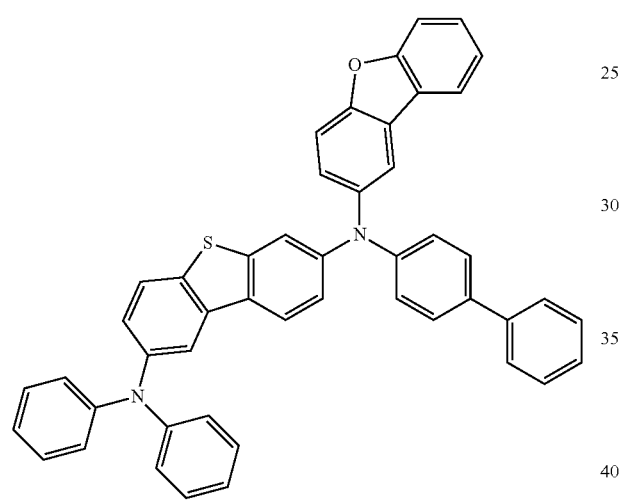
2-75
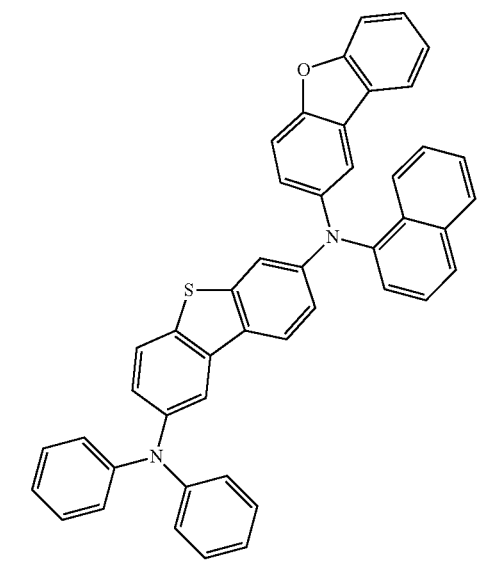
2-76
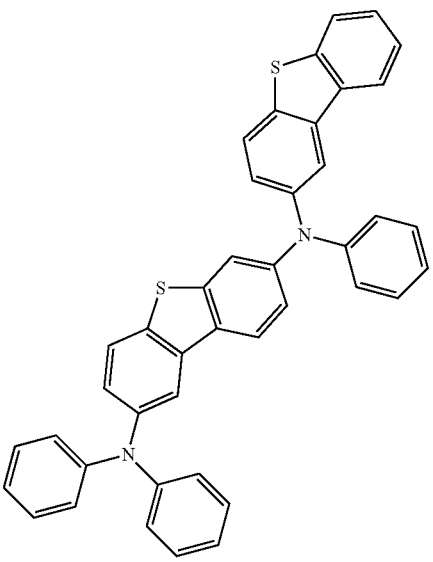
2-77
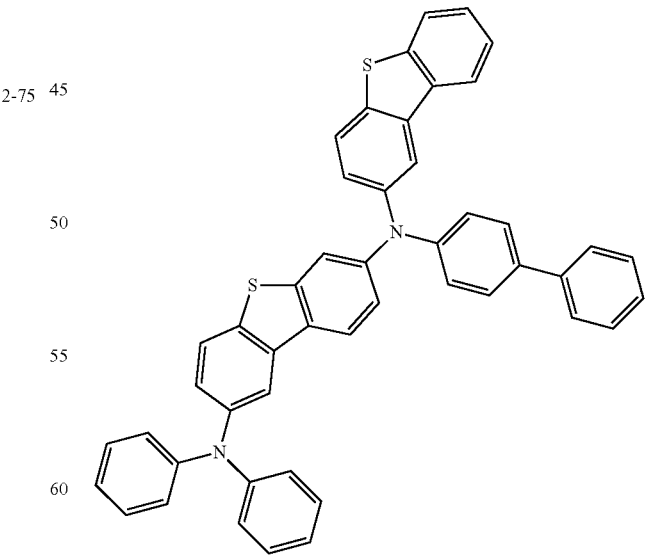

2-78
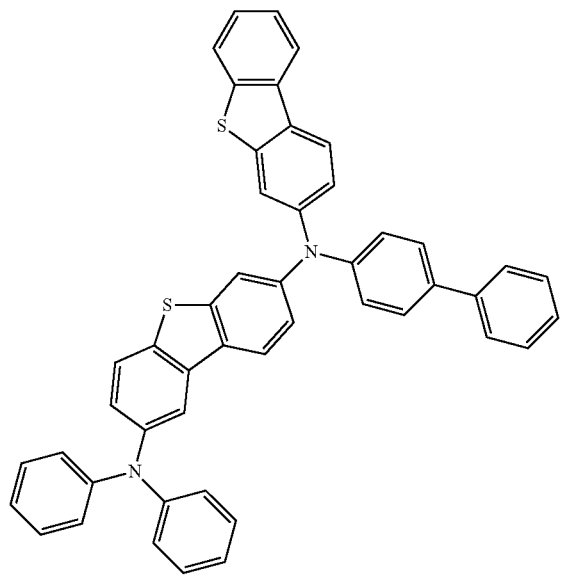
2-79
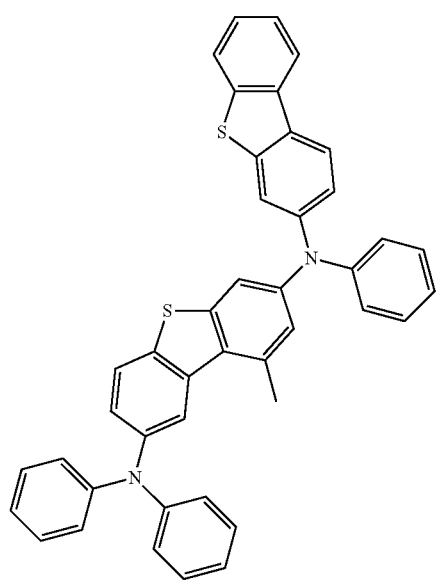
2-80
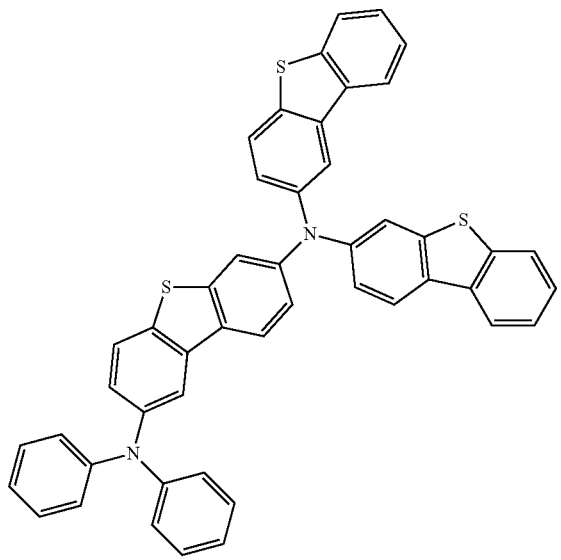
2-81
2-82
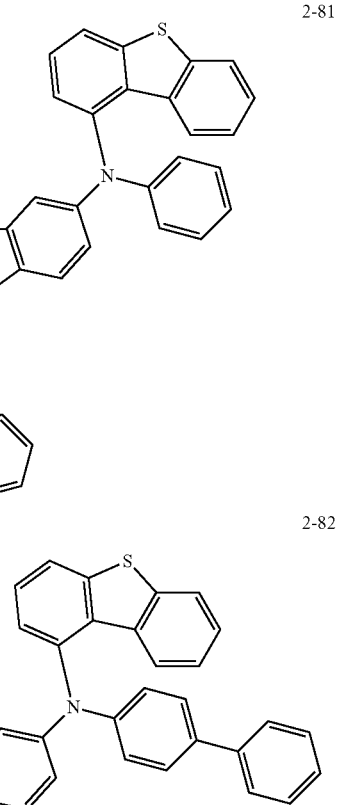

-continued
2-83
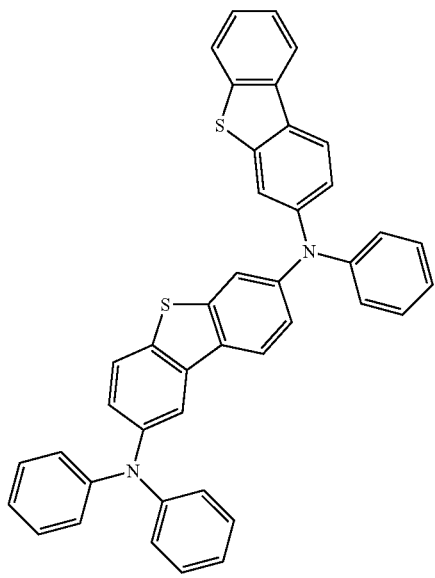
2-84
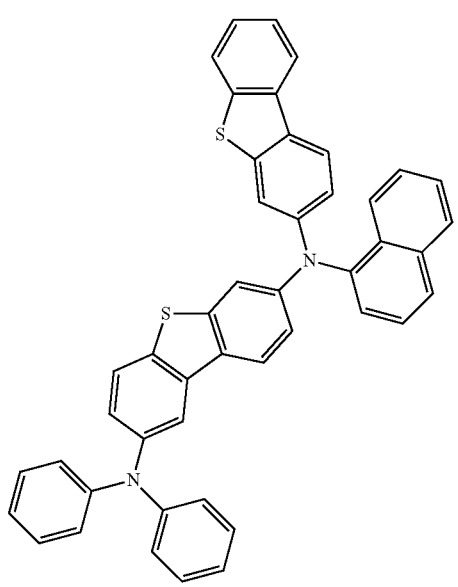
2-85
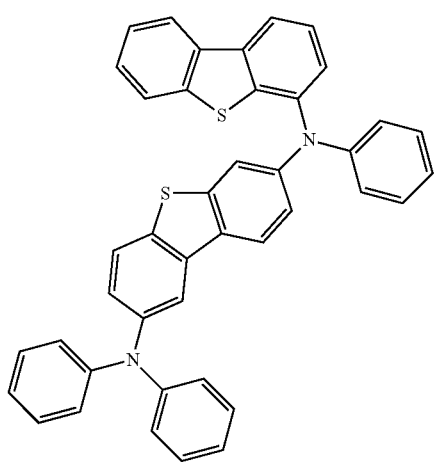
-continued
2-86
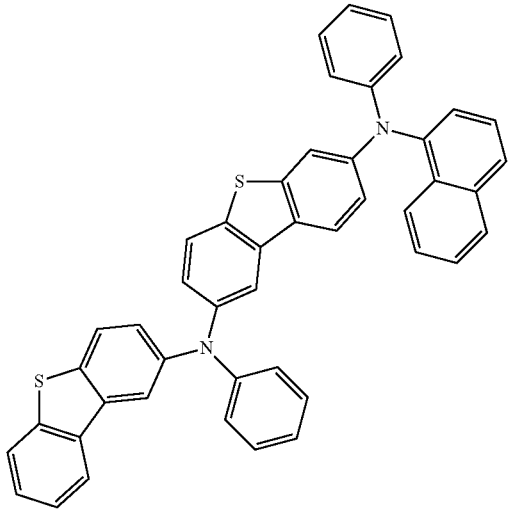
2-87
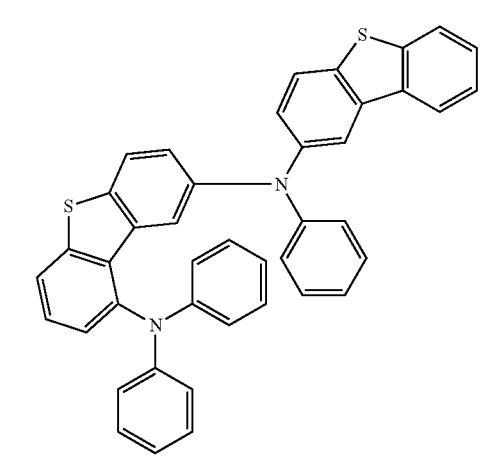
2-88
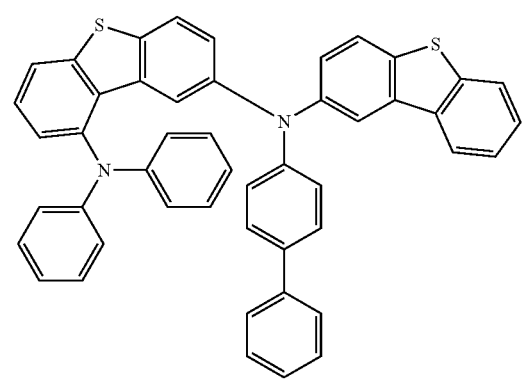

2-89
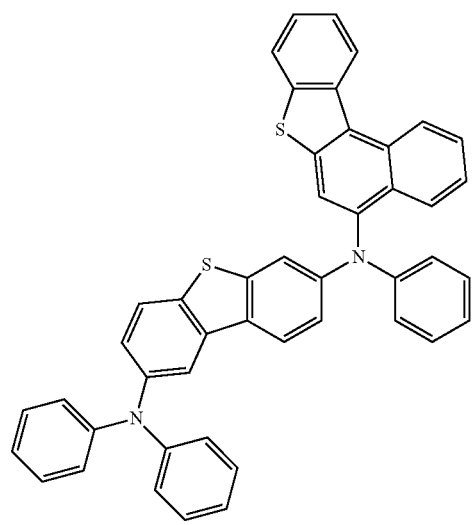
2-92
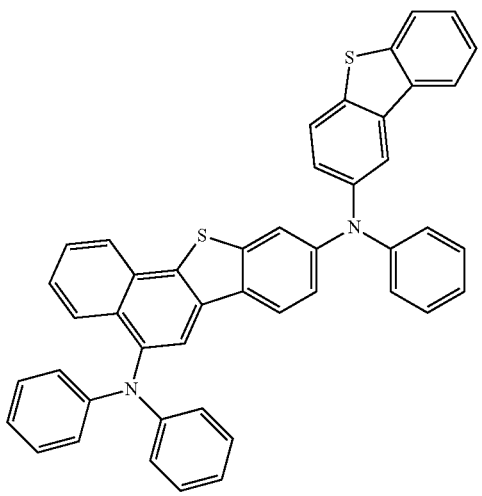
2-90
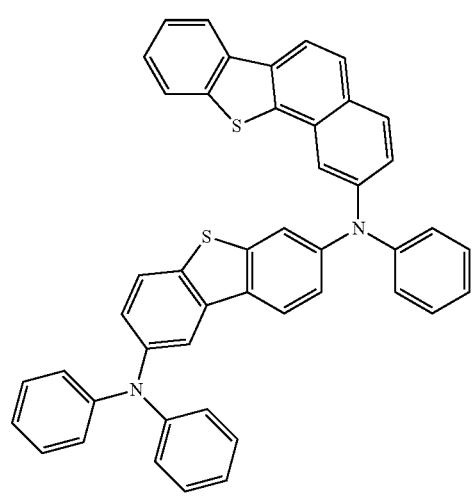
2-93
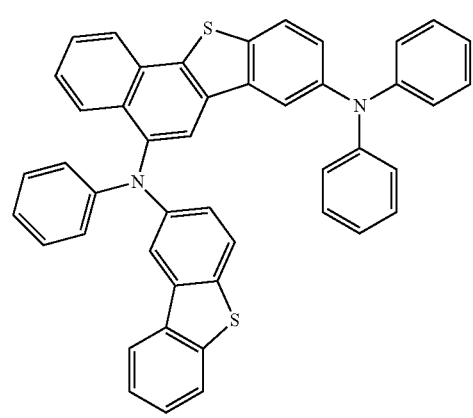
2-91
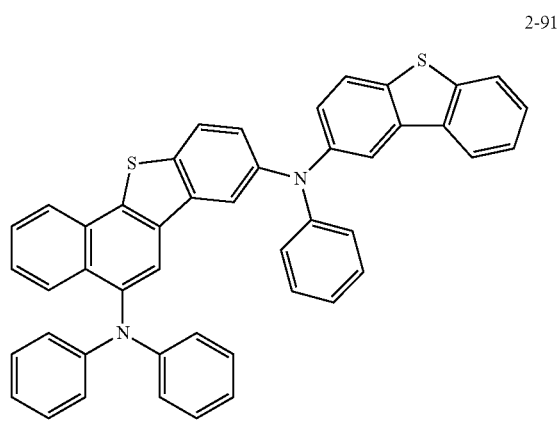
2-94
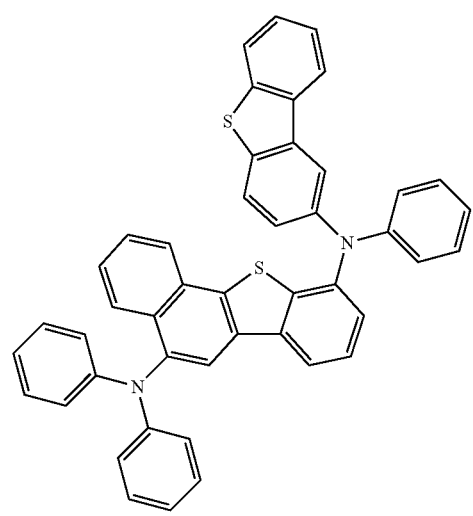

2-95
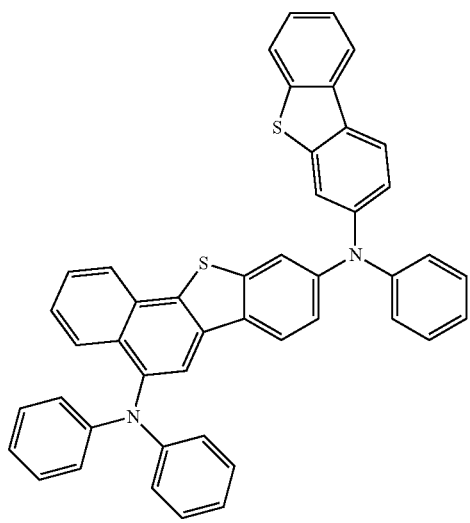
2-96
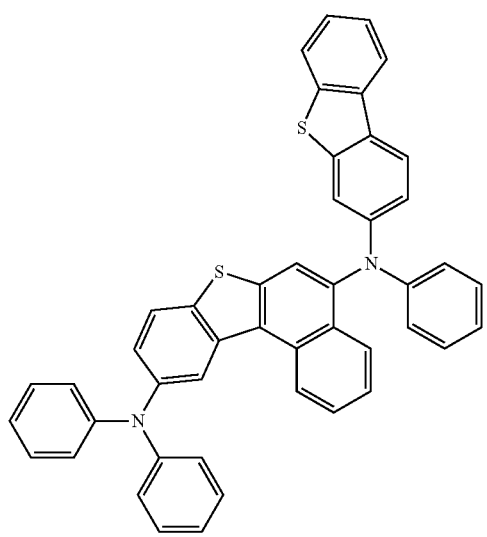
2-97
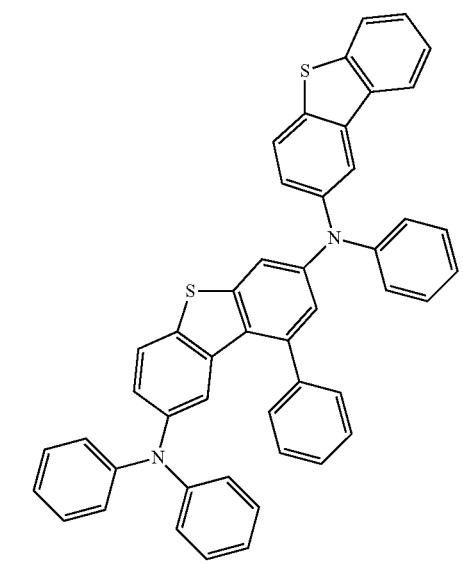
2-98
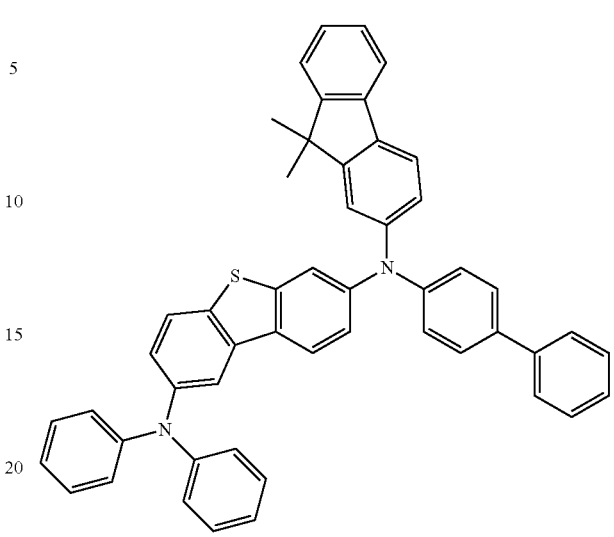
2-99
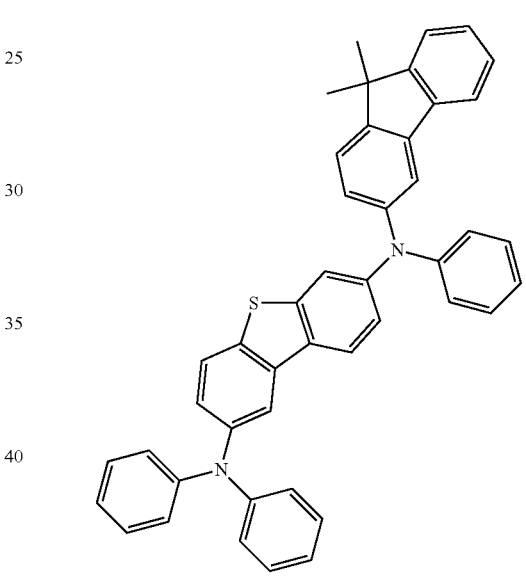
2-100
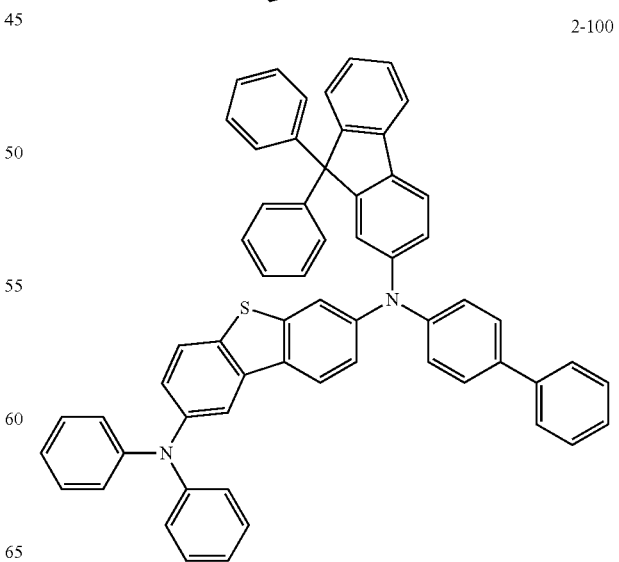

2-101
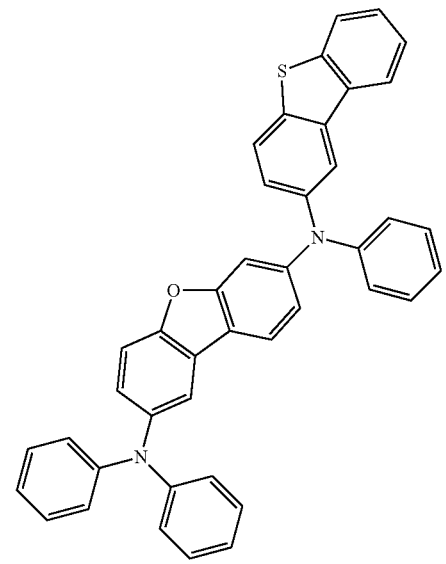
2-102
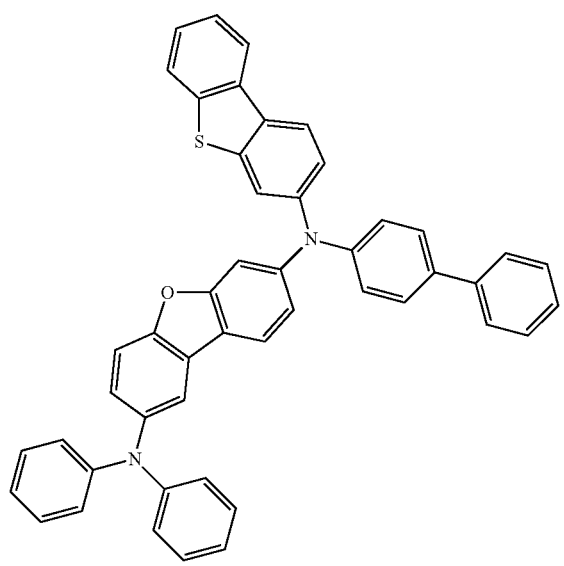
2-103
2-104
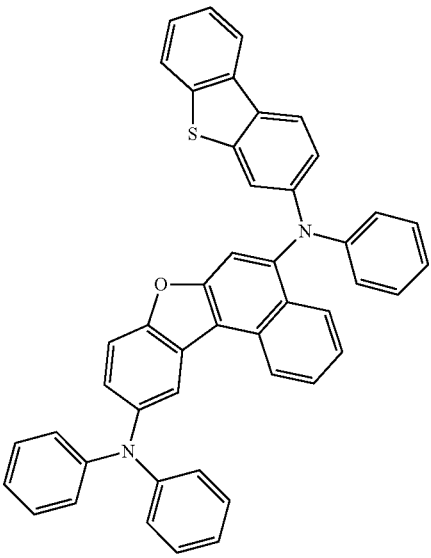
2-105
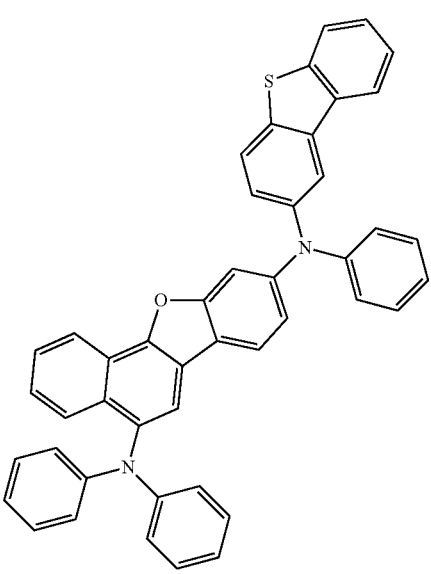
2-106
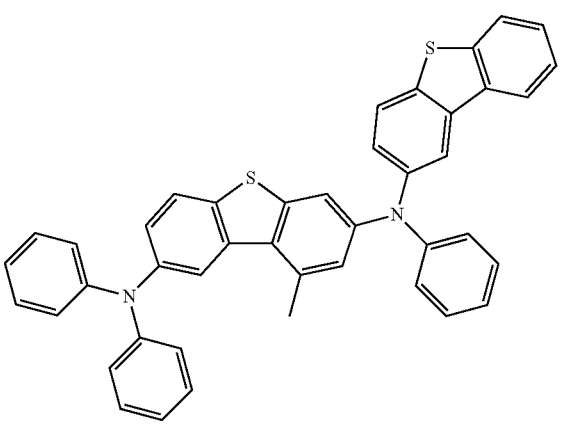
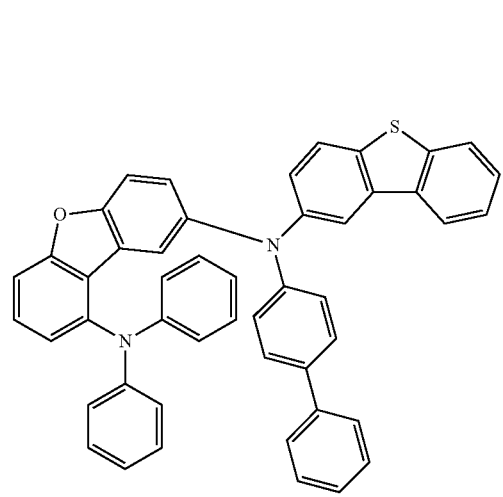
Also, in the present invention, the second host compound represented by Formula (2) comprises the following Compounds 3-1 to 3-124.

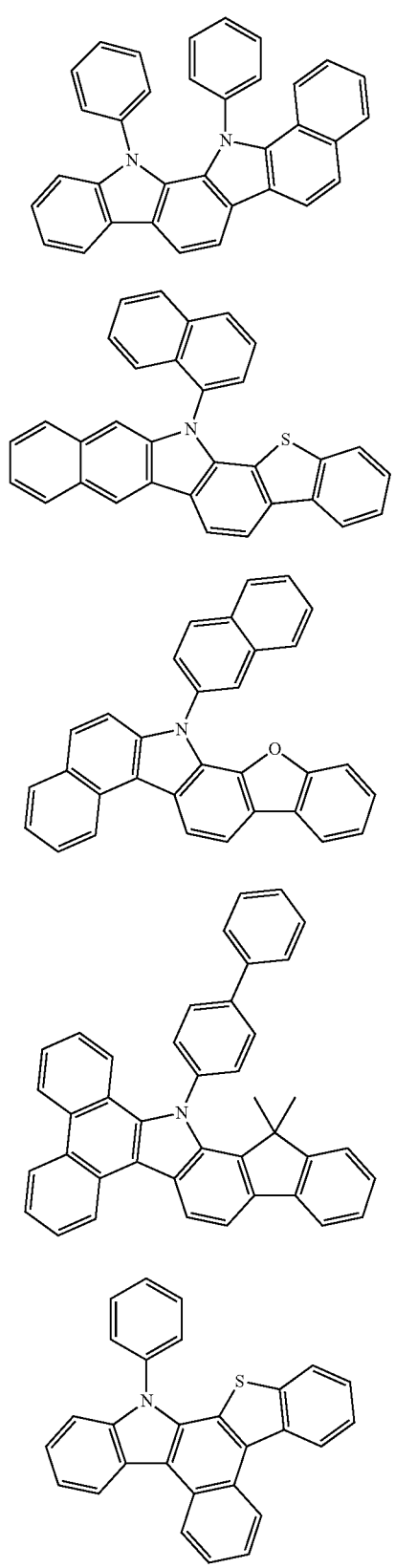
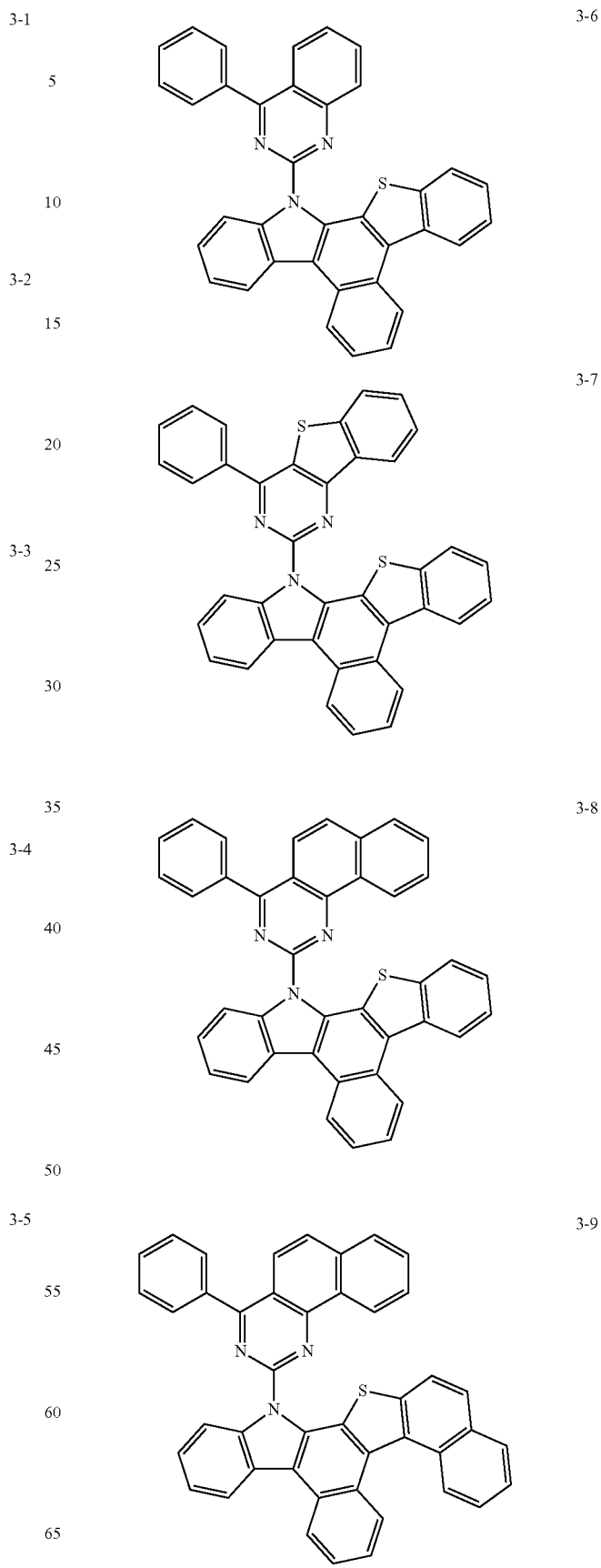

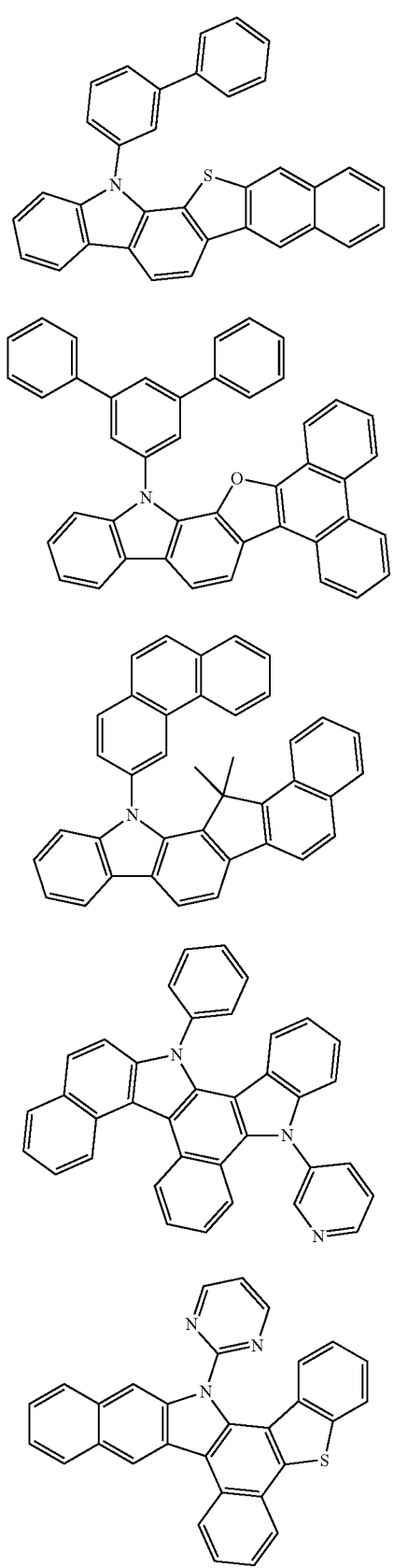
3-10
3-11
3-12
3-13
3-14
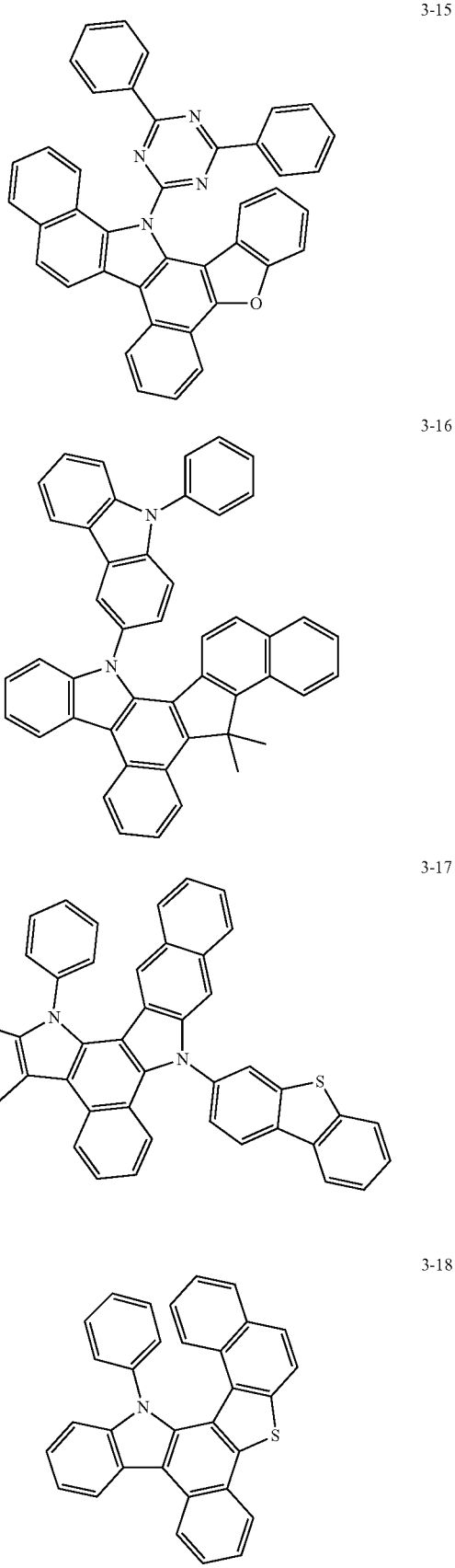
3-15
3-16
3-17
3-18

3-19
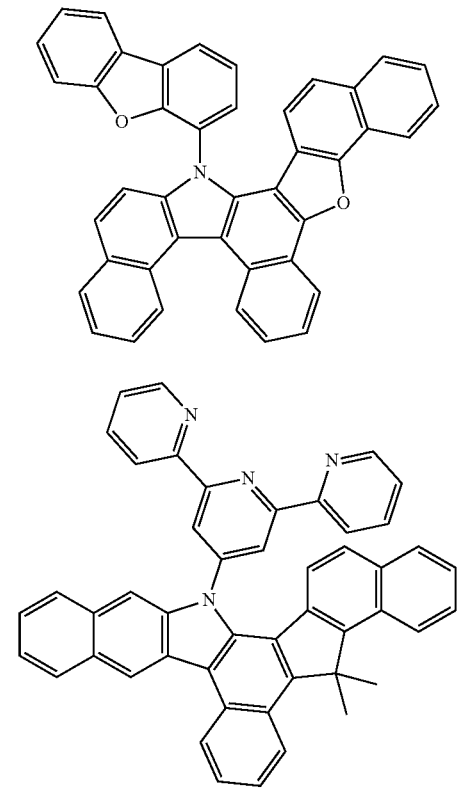
3-20
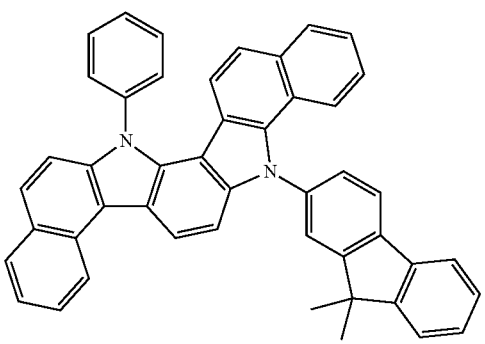
3-21
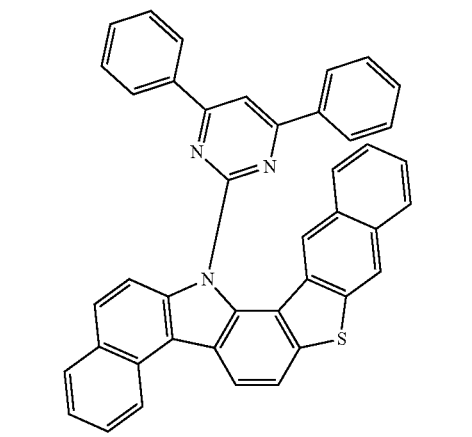
3-22
3-23
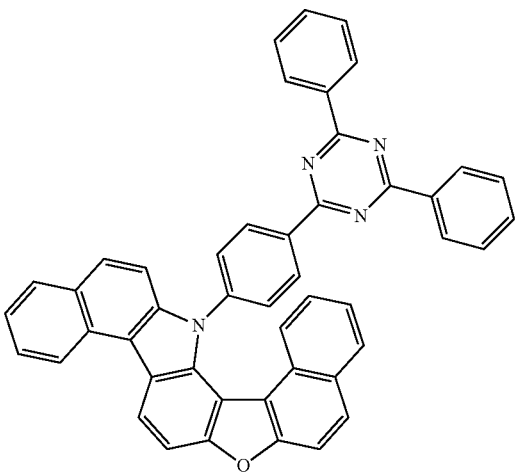
3-24
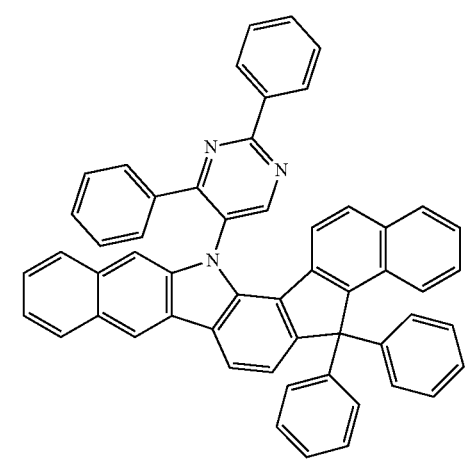
3-25
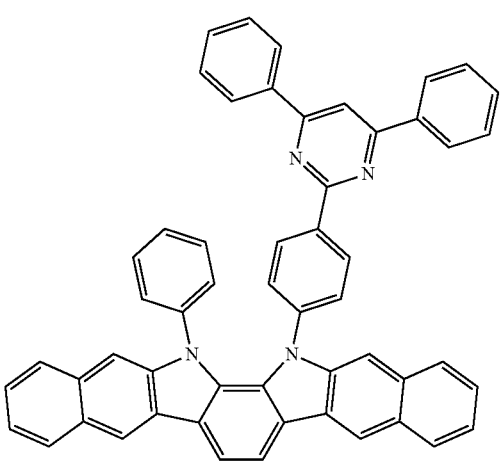

101
-continued
3-26
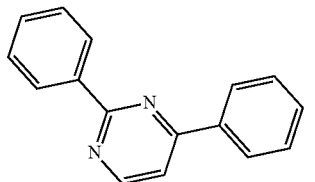
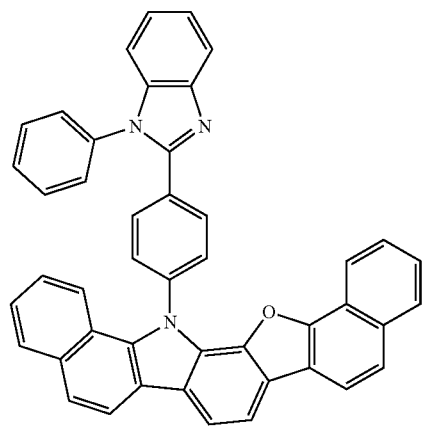
3-27
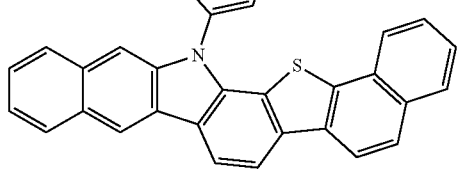
3-28
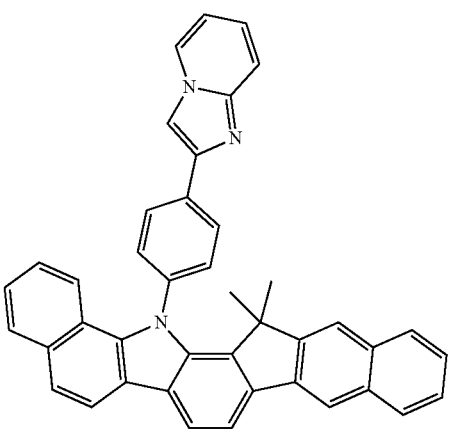
3-29
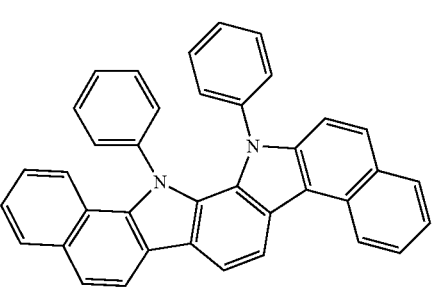
102
-continued
3-30
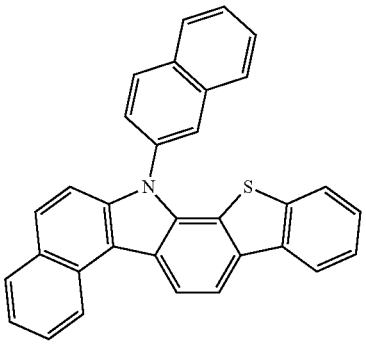
3-31
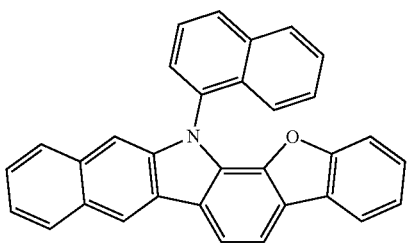
3-32
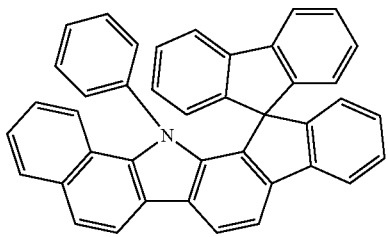
3-33
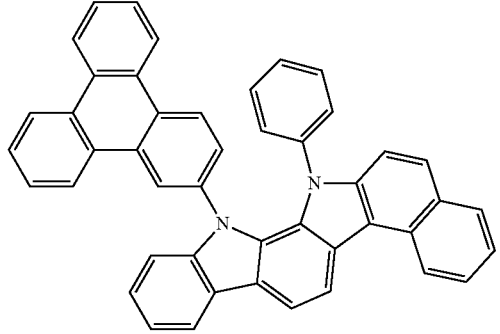
3-34
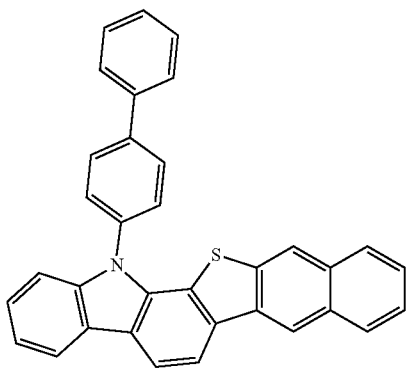

103
-continued
3-35
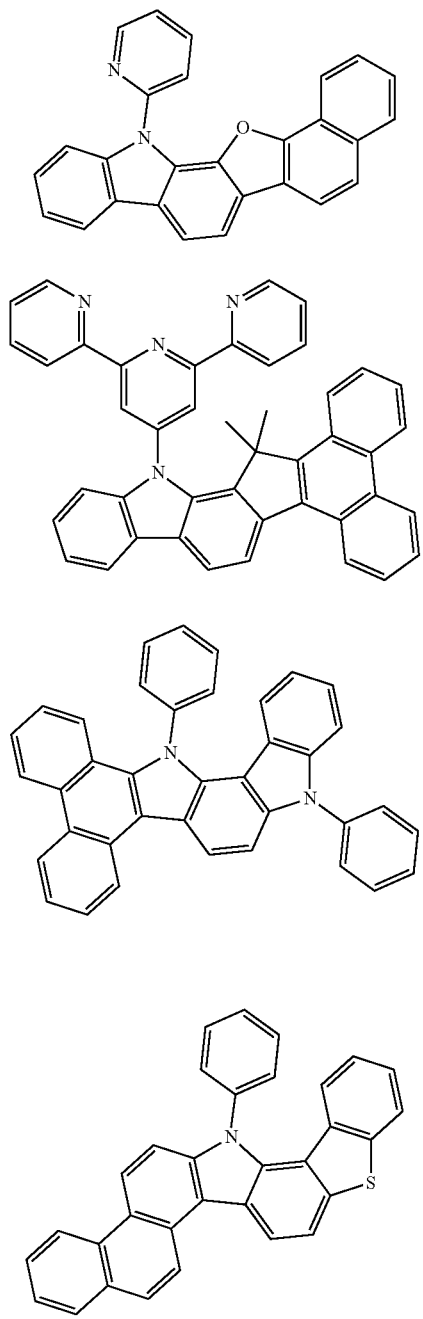
3-36
3-37
3-38
3-39
104
-continued
3-40
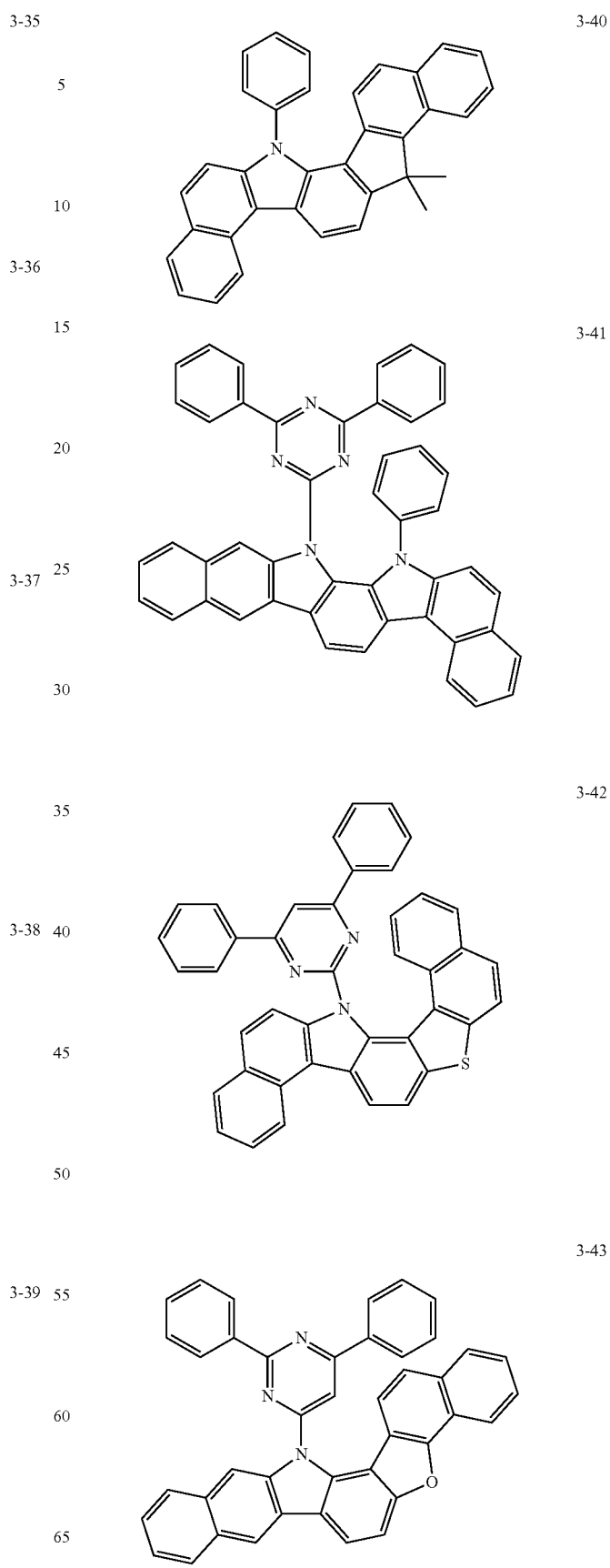
3-41
3-42
3-43

3-44
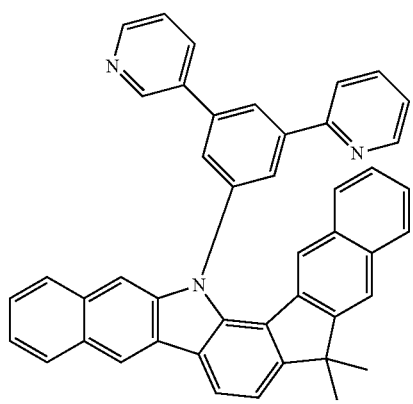
3-45
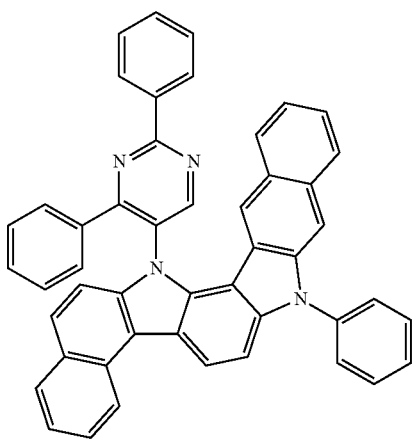
3-46
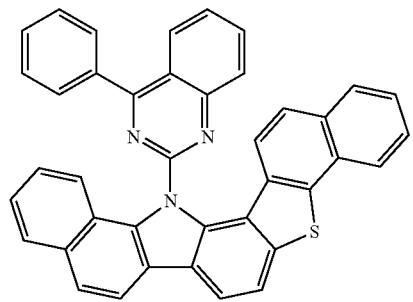
3-47
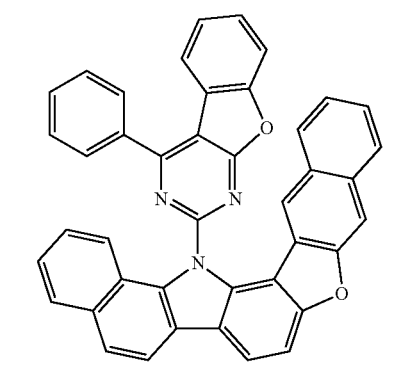
3-48
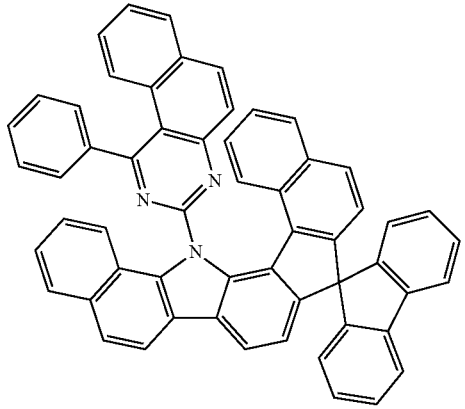
3-49
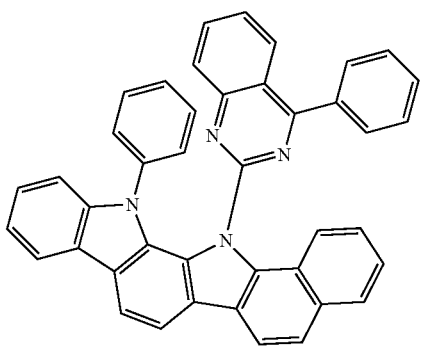
3-50
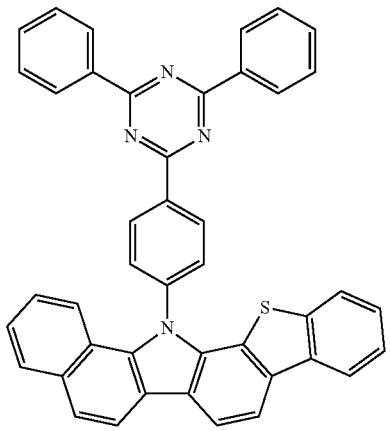
3-51
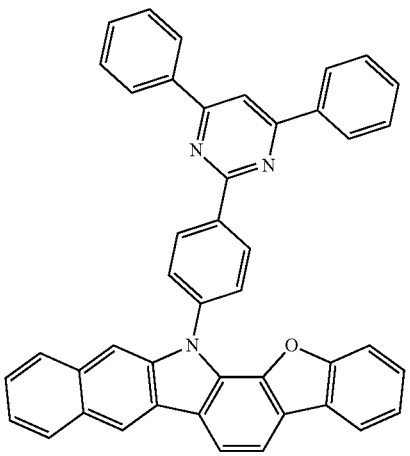

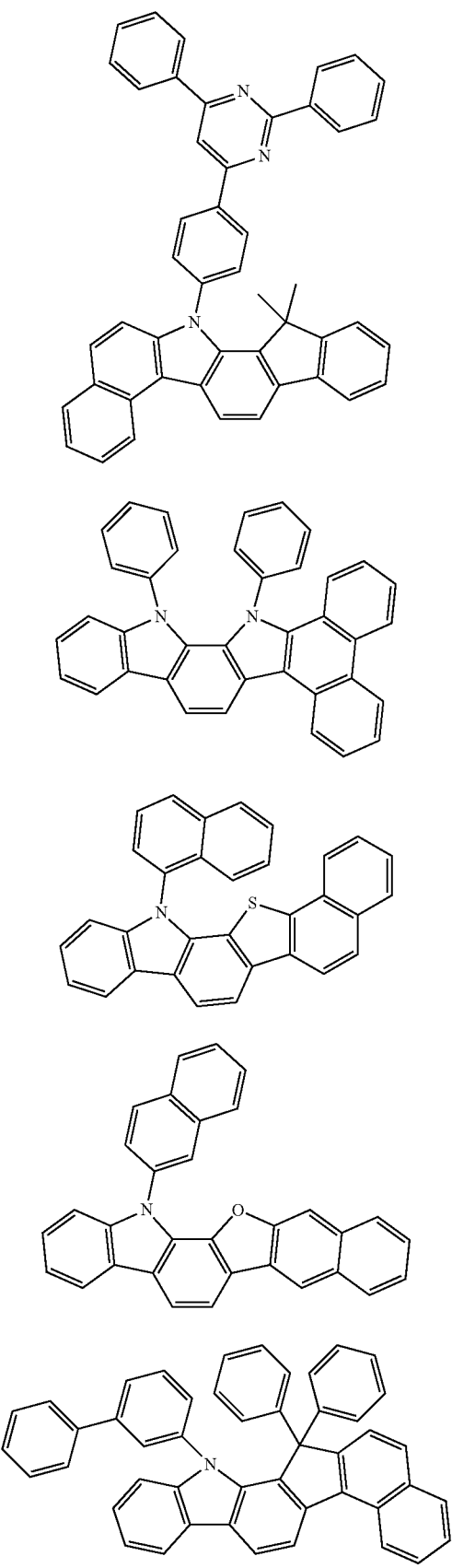
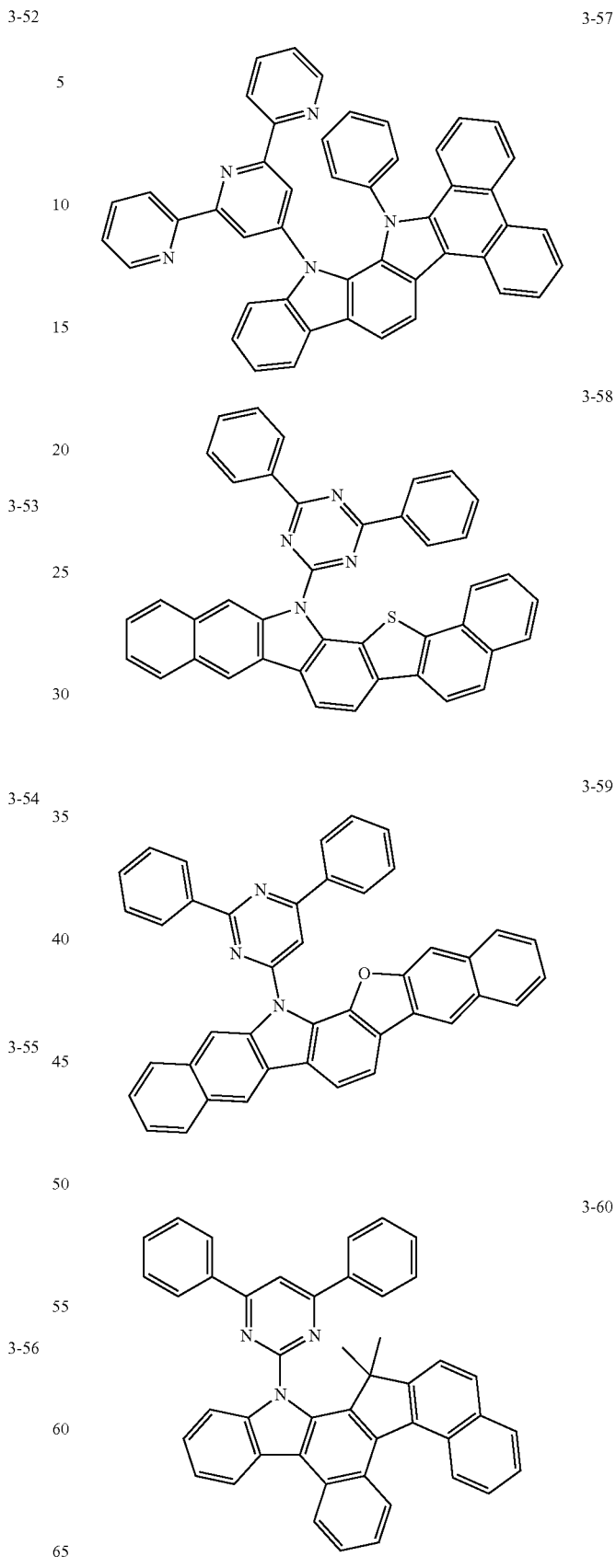

-continued
3-61
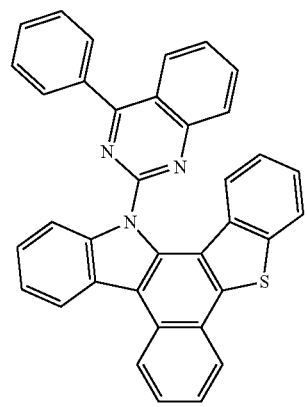
3-62
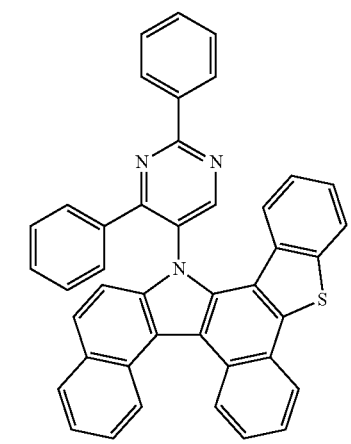
3-63
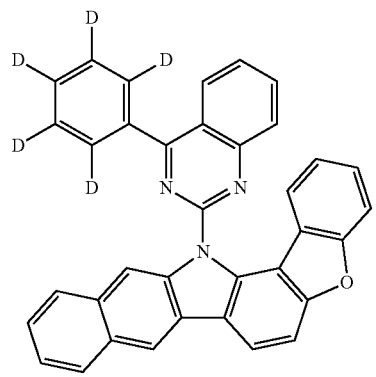
3-64
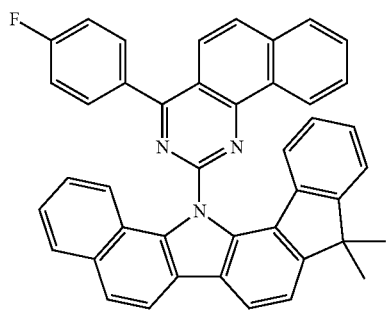
-continued
3-65
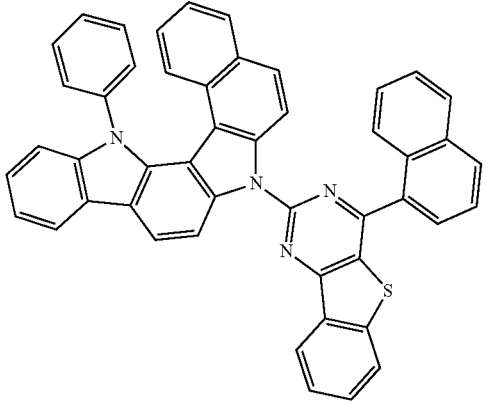
3-66
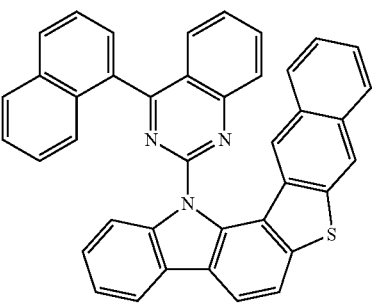
3-67
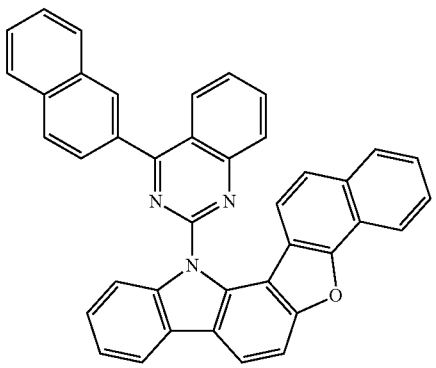
3-68
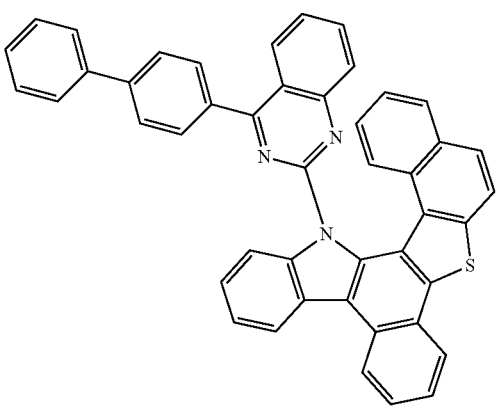

-continued
3-69
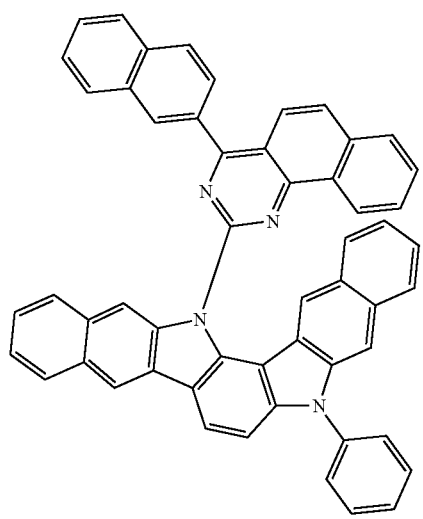
3-70
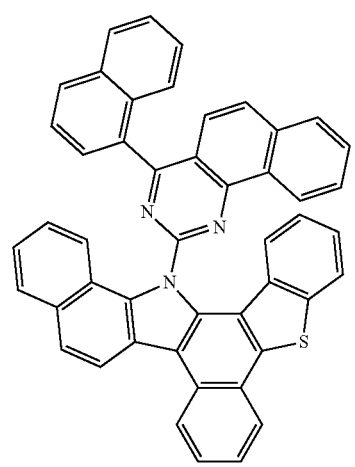
3-71
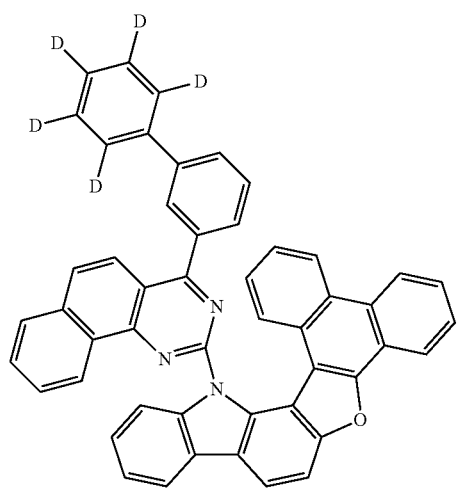
3-72
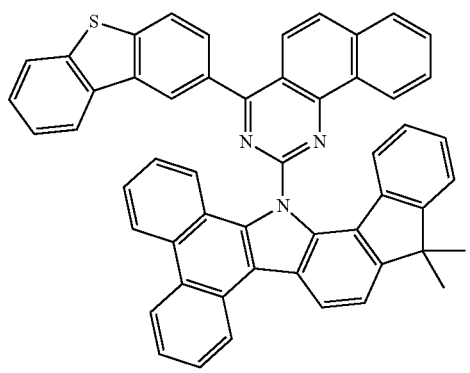
3-73
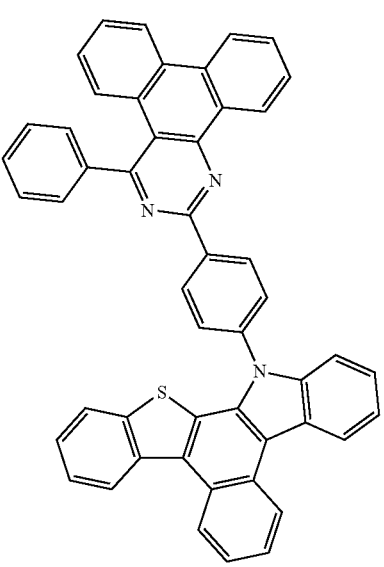
3-74
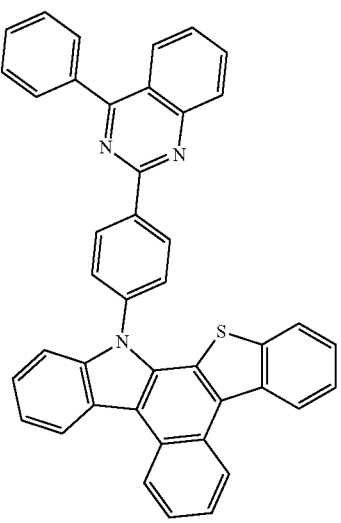

3-75
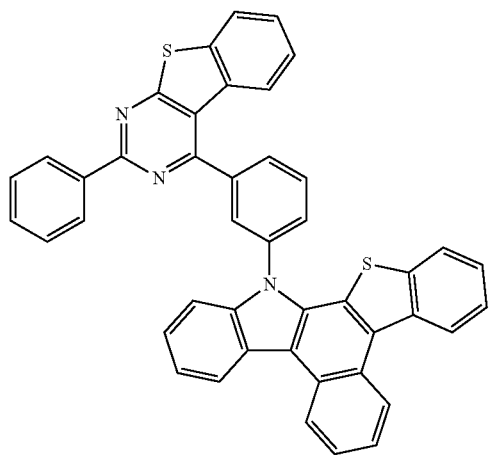
3-76
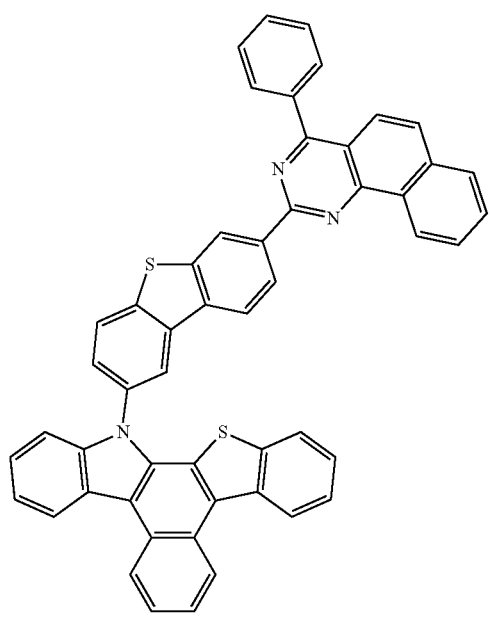
3-77
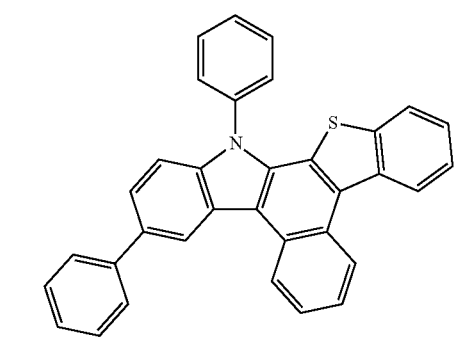
3-78
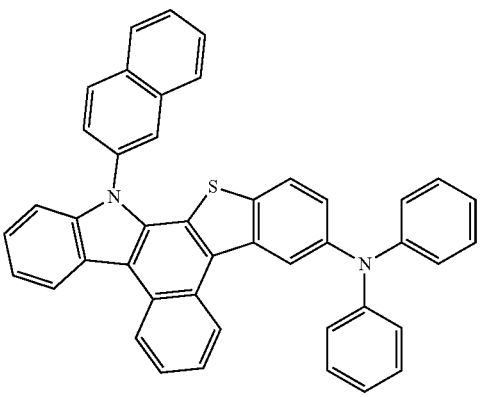
3-79
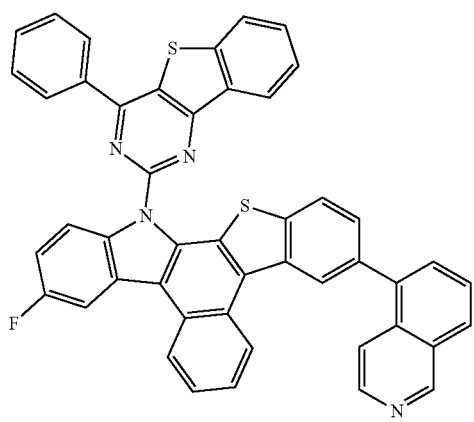
3-80
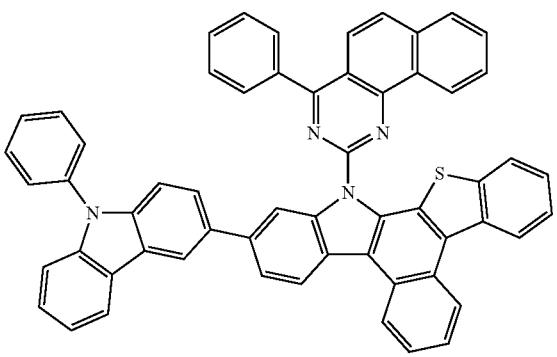
3-81
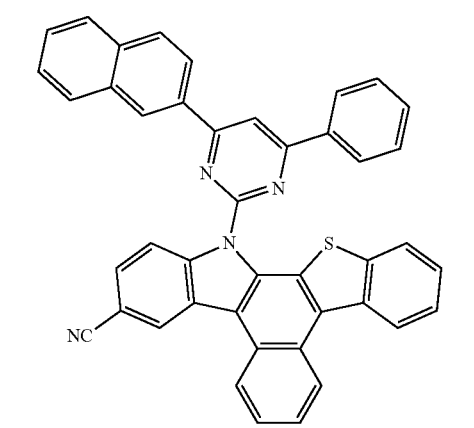

-continued
3-82
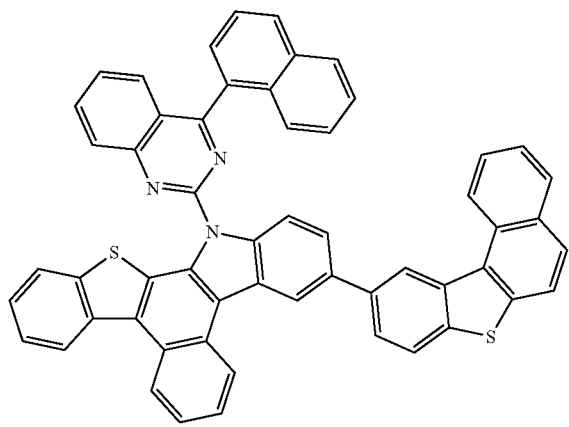
3-83
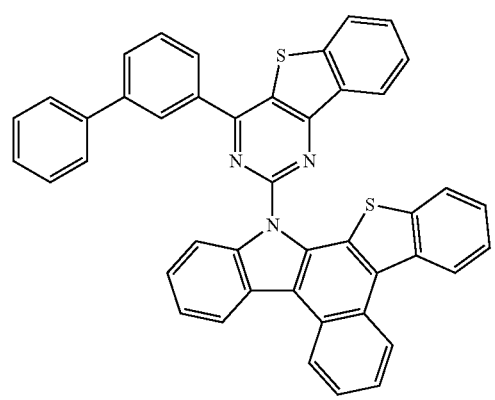
3-84
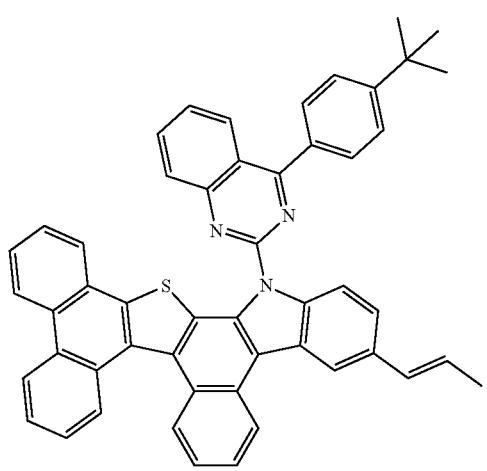
3-85
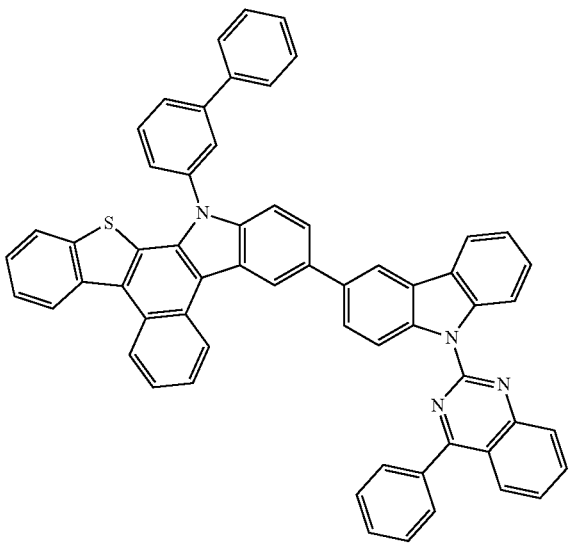
3-86
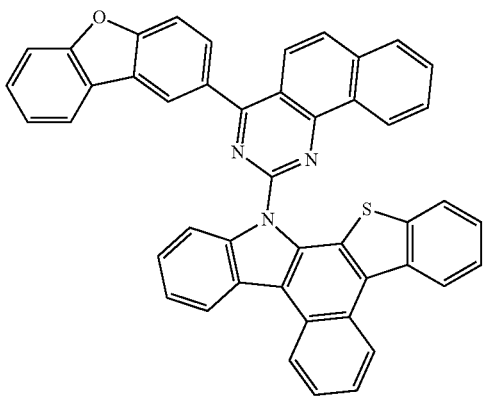
3-87
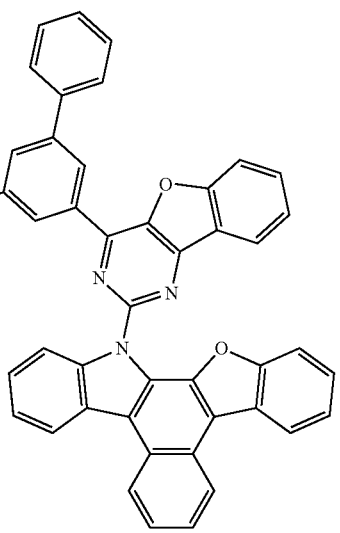

117
-continued
3-88
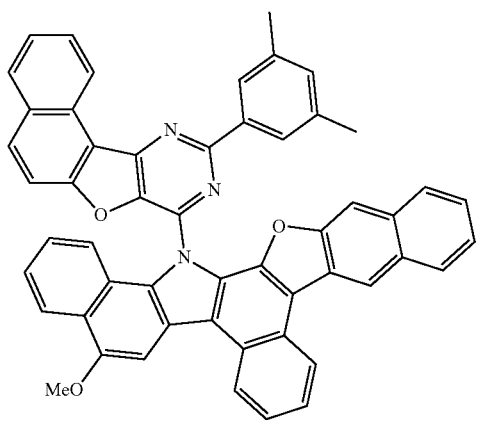
3-89
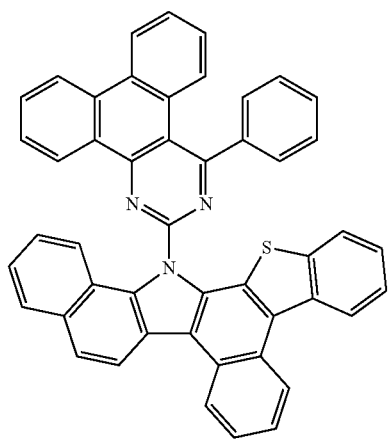
3-90
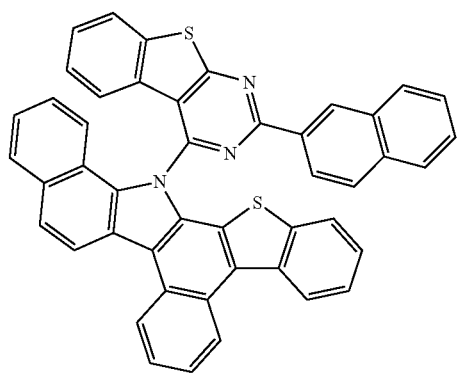
118
-continued
3-91
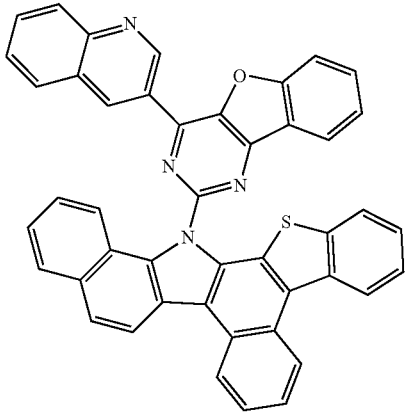
3-92
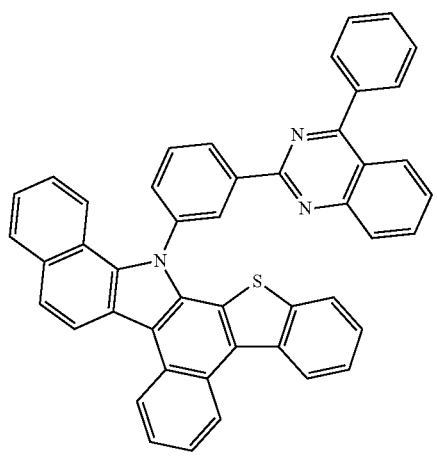
3-93
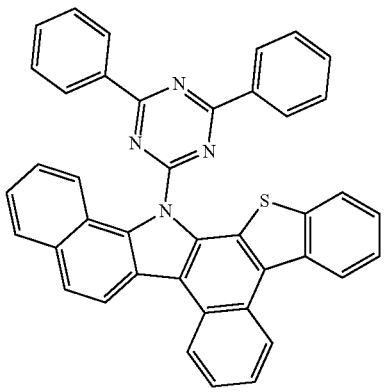

3-94
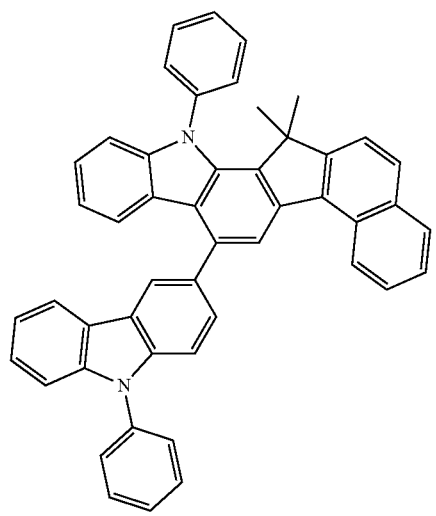
3-95
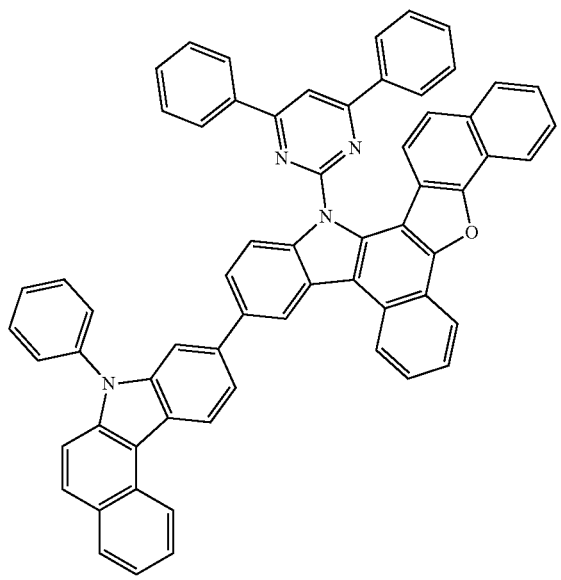
3-96
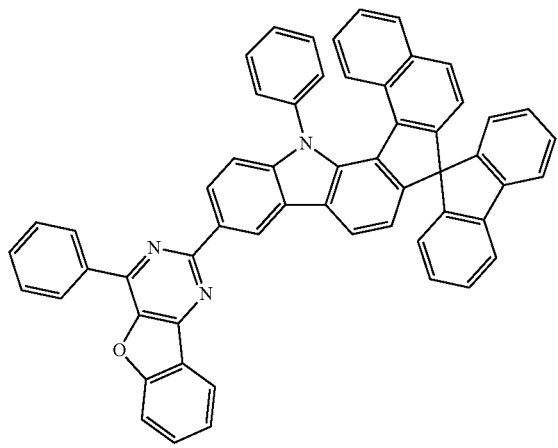
3-97
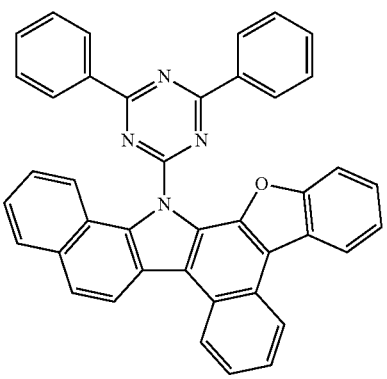
3-98
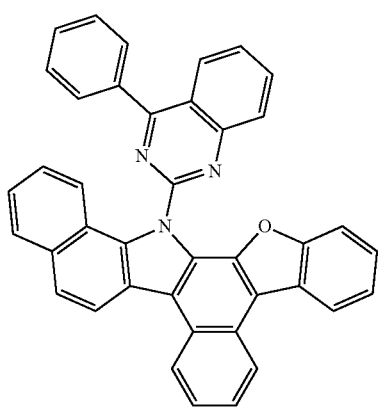
3-99
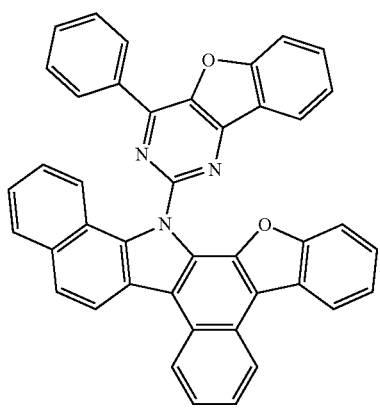

3-100
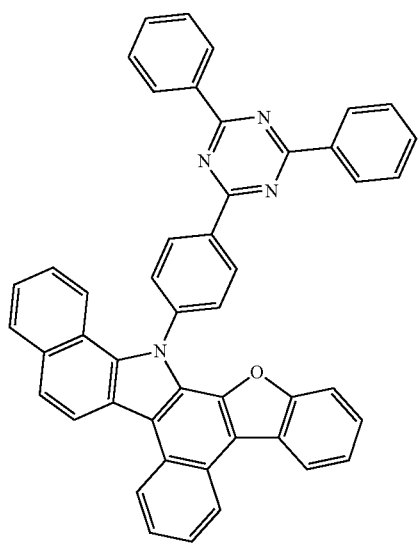
3-101
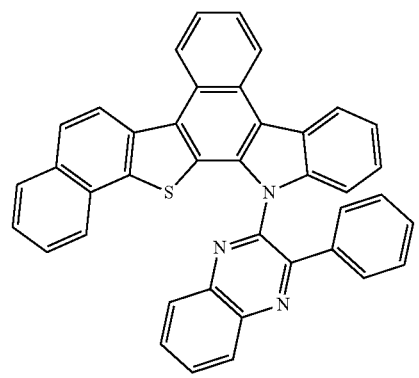
3-102
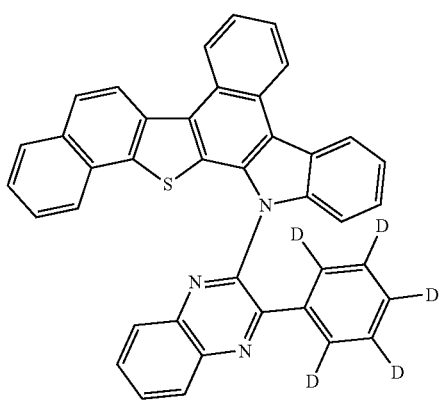
3-103
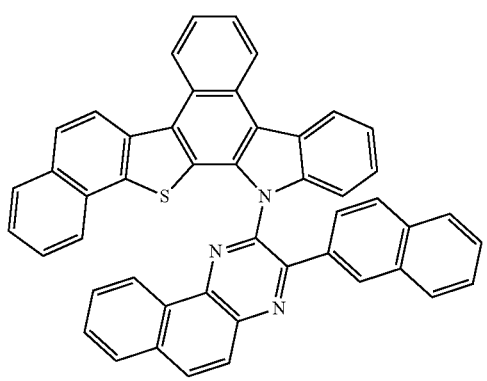
3-104
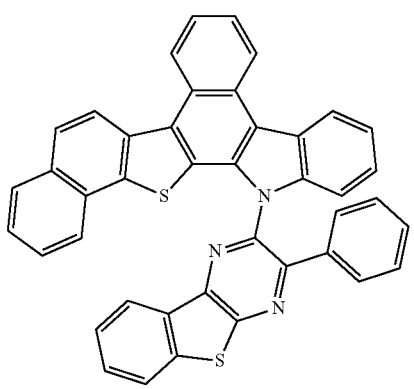
3-105
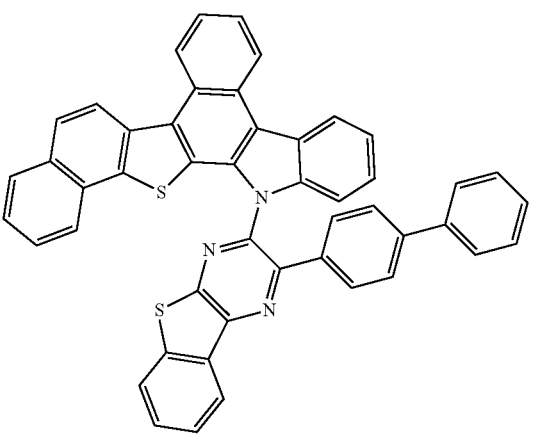
3-106
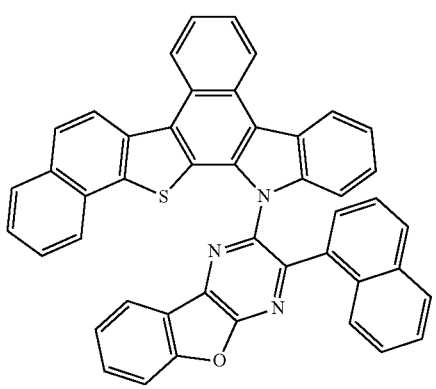

3-107
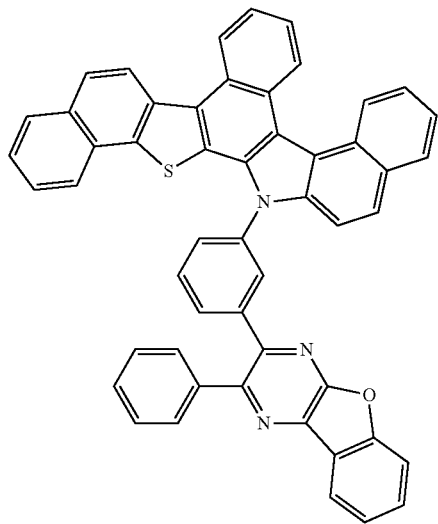
3-108
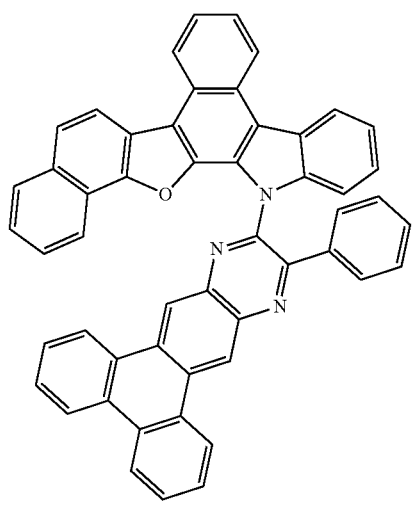
3-109
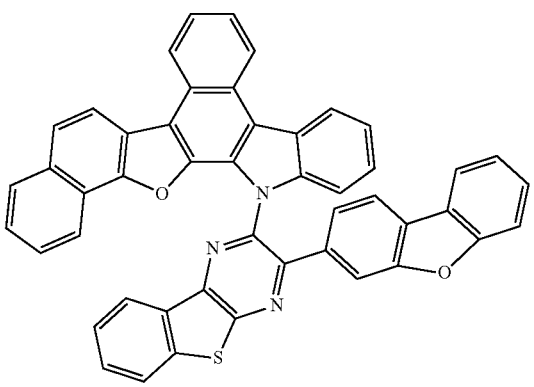
3-110
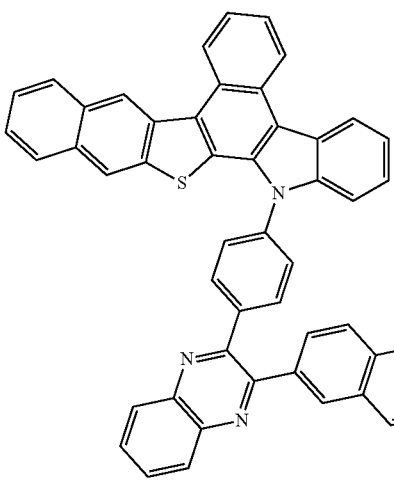
3-111
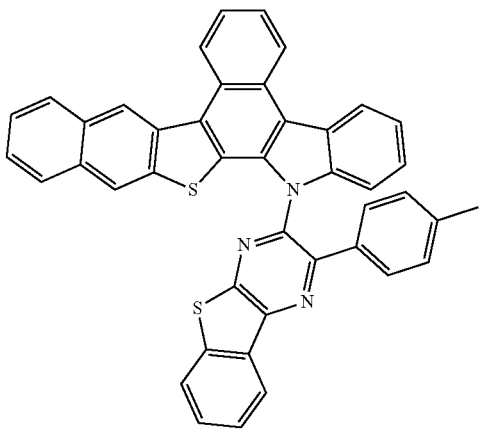
3-112
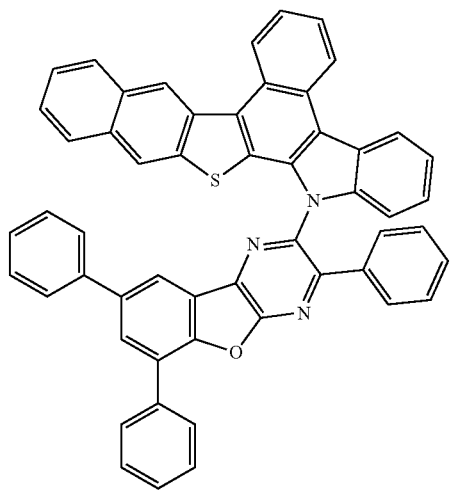

3-113
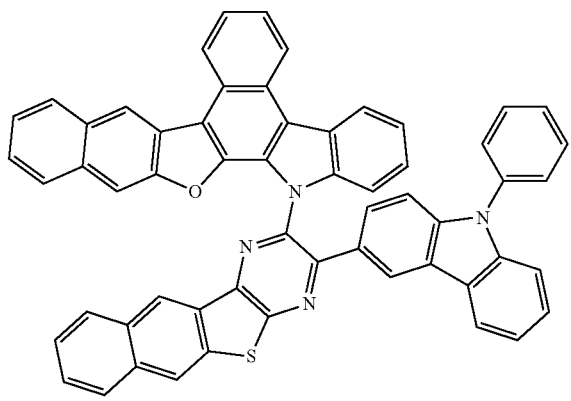
3-114
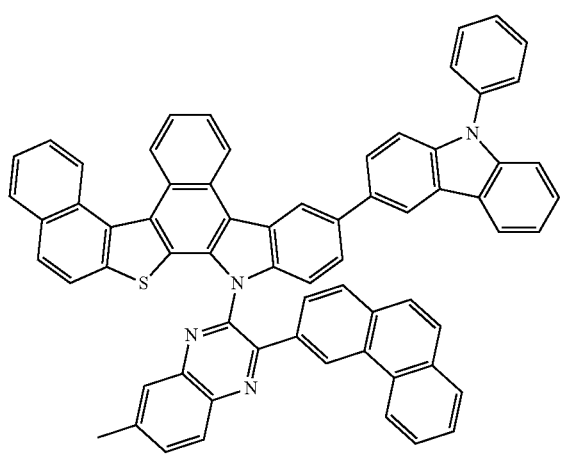
3-115
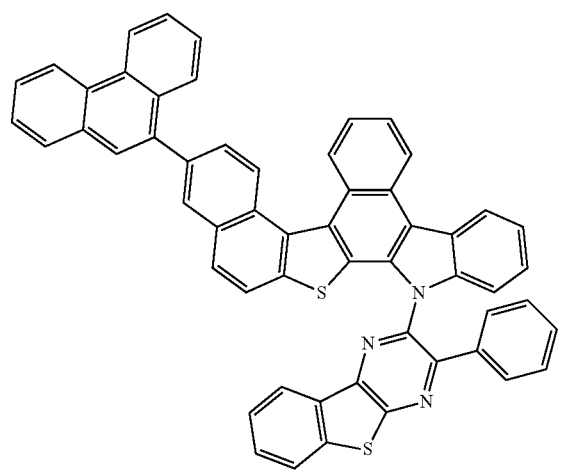
3-116
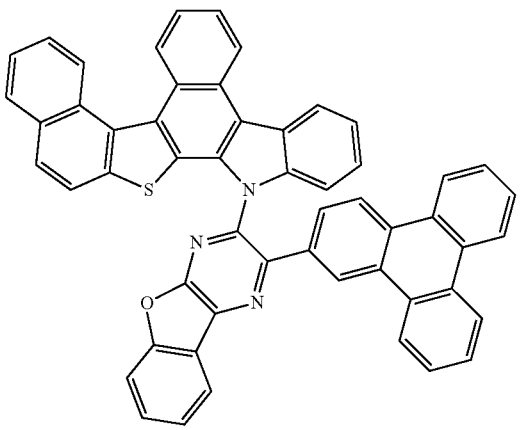
3-117
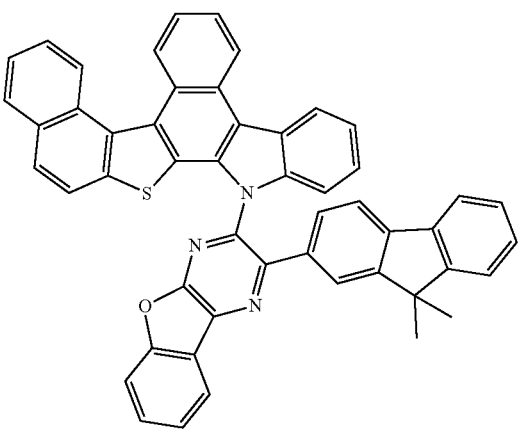
3-118
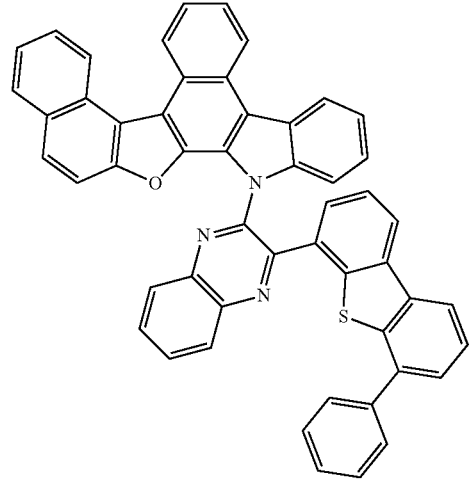

3-119

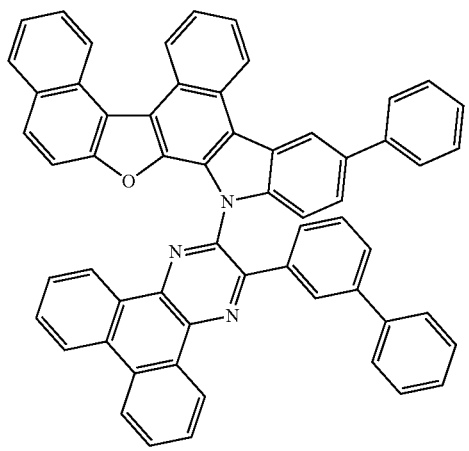

3-120

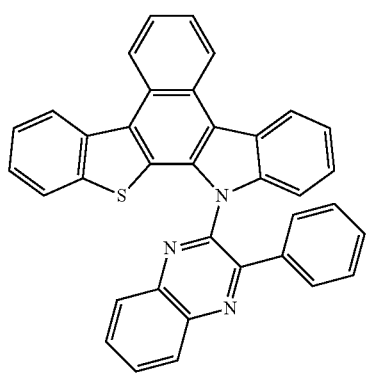

3-121

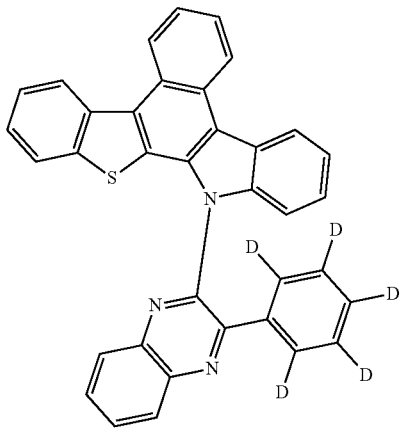

3-122

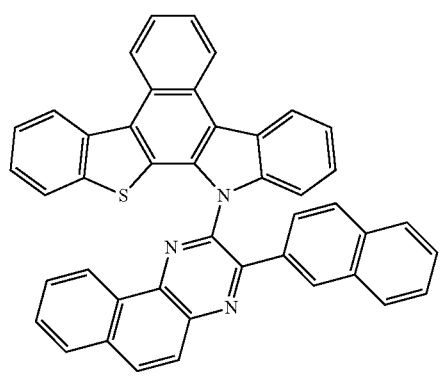

3-123

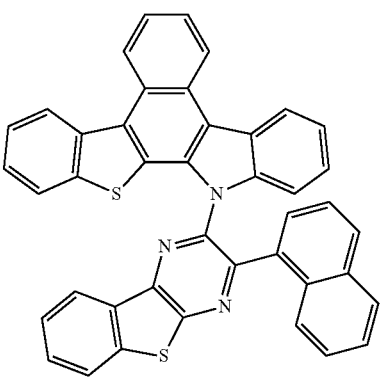

3-124

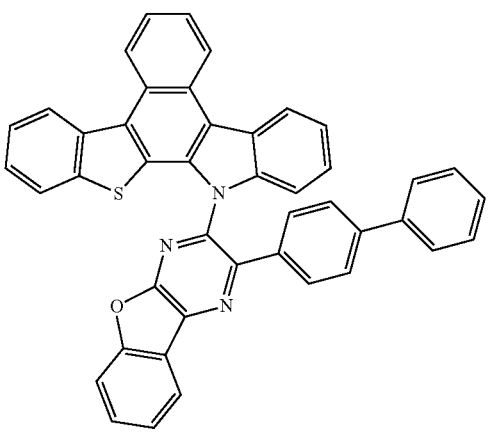

Figure 1:
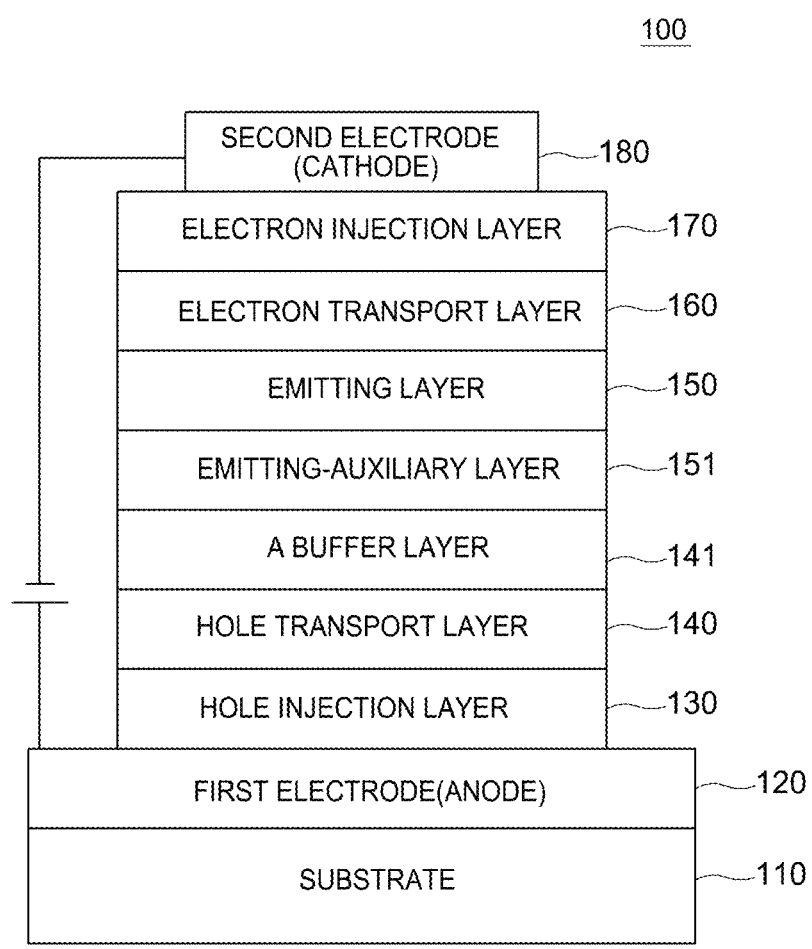
FIG. 1 is an illustration of an organic electroluminescent device according to the present invention.

Referring to FIG. 1, the organic electric element (100) according to the present invention includes a first electrode (120) formed on a substrate (110), a second electrode (180), and an organic material layer including the compound represented by Formula (1) between the first electrode (120) and the second electrode (180). Here, the first electrode (120) may be an anode (positive electrode), and the second electrode (180) may be a cathode (negative electrode). In the case of an inverted organic electric element, the first electrode may be a cathode, and the second electrode may be an anode.

The organic material layer may include a hole injection layer (130), a hole transport layer (140), an emitting layer (150), an electron transport layer (160), and an electron injection layer (170) formed in sequence on the first electrode (120). Here, the remaining layers except the emitting layer (150) may not be formed. The organic material layer may further include a hole blocking layer, an electron blocking layer, an emitting-auxiliary layer (151), an electron transport auxiliary layer, a buffer layer (141), etc., and the electron transport layer (160) and the like may serve as a hole blocking layer.

Although not shown, the organic electric element according to the present invention may further include a protective layer formed on at least one side of the first and second electrodes, which is a side opposite to the organic material layer.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and Ti values and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (130), the hole transport layer (140), the emitting layer (150), the electron transport layer (160), and the electron injection layer (170) is formed thereon, and then depositing a material usable as a cathode thereon can manufacture an organic electroluminescent device according to an embodiment of the present invention.

In addition, an emission auxiliary layer (151) may be further formed between the hole transport layer (140) and the emitting layer (150), and an electron transport auxiliary layer may be further formed between the emitting layer (150) and the electron transport layer (160).

In addition, at least one hole transporting band layer is provided between the first electrode and the emitting layer, wherein the hole transporting band layer may include a hole transport layer, an emitting auxiliary layer or both, wherein the hole transporting band layer includes an organic electronic element comprising the compound represented by Formula (1).

The present invention may further include a light efficiency enhancing layer formed on at least one of the opposite side to the organic material layer among one side of the first electrode, or one of the opposite side to the organic material layer among one side of the second electrode.

Also, the present invention provides the organic electric element wherein the organic material layer is formed by one of a spin coating process, a nozzle printing process, an inkjet printing process, a slot coating process, a dip coating process or a roll-to-roll process, and since the organic material layer according to the present invention can be formed by various methods, the scope of the present invention is not limited by the method of forming the organic material layer.

As another specific example, the present invention provides an organic electric element wherein the emitting layer in the organic material layer is a phosphorescent light emitting layer.

The compounds represented by Formula (1) and (2) are mixed in a ratio of any one of 1:9 to 9:1 to be included in the emitting layer of the organic material layer.

The compound represented by Formula (1) and (2) are mixed in a ratio of any one of 1:9 to 5:5 to be included in the emitting. Preferably, the mixing ratio of the compound represented by Formula (1) and the compound represented by Formula (2) is mixed at a ratio of 1:9 or 5:5, to be included as the emitting layer, or the mixture ratio is mixed in a ratio of 2:8 to 3:7, to be used in the emitting layer. More preferably, the mixing ratio of the compound represented by Formula (1) and the compound represented by Formula (2) is mixed at a ratio of 2:8 or 3:7, to be included in the emitting layer.

In another aspect, in one embodiment of the present invention, the present invention provides a first electrode; a second electrode; and an organic material layer disposed between the first electrode and the second electrode and including at least an hole transport layer, an emitting auxiliary layer and an emitting layer, wherein the hole transport layer or the emitting auxiliary layer comprise a compound represented by Formula (1), wherein the emitting layer comprises a compound represented by Formula (2). That is, the compound represented by Formula (1) can be used as the material of the hole transport layer and/or the emitting auxiliary layer.

In another aspect, in one embodiment of the present invention, the present invention provides a first electrode; a second electrode; and an organic material layer disposed between the first electrode and the second electrode and including at least an emitting auxiliary layer and an emitting layer, wherein at least one emitting auxiliary layer material of the organic material layers comprises a compound represented by Formula (1), wherein at least one host material in the emitting layer comprises a compound represented by Formula (2).

The organic electric element according to an embodiment of the present invention may be a front emission type, a back emission type, or a both-sided emission type, depending on the material used.

WOLED (White Organic Light Emitting Device) has advantages of high resolution realization and excellent fairness, and can be manufactured using conventional LCD color filter technology. Various structures for a white organic light emitting device mainly used as a backlight device have been proposed and patented. Representatively, there are side-by-side arrangement of the radiation part of the R (red), G (green) and B (blue), a stacking method in which R, G, and B emitting layers are laminated on top and bottom, electroluminescence by the blue (B) organic emitting layer and, by using the light from this, a color conversion material (CCM) method using a photo-luminescence of an inorganic phosphor, etc., and the present invention may be applied to such WOLED.

The present invention also provides an electronic device comprising a display device including the organic electric element; and a control unit for driving the display device.

According to another aspect, the present invention provides an display device wherein the organic electric element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis Examples of the compound represented by Formula (1) and (2) of the present invention and preparation examples of the organic electric element of the present invention will be described in detail by way of example, but are not limited to the following examples.

Synthesis Example 1

I. Synthesis of Formula (1)

The final products 1 represented by Formula (1) of the present invention can be synthesized by reaction between Sub 1 and Sub 2 as illustrated in the following Reaction Scheme 1 or Reaction Scheme 2.

131

<Reaction Scheme 1>

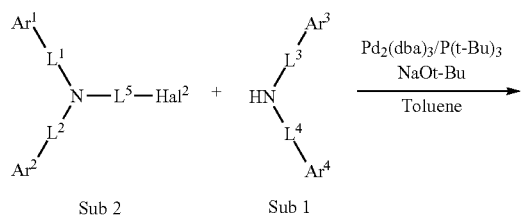

(Hal² = Br, Cl)

When $L^5$ of the Final Products of Reaction Scheme 1 is

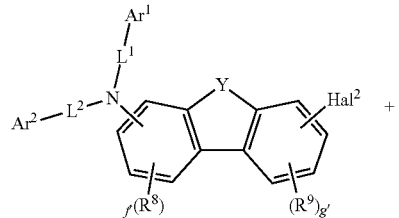

C-10

Final Products 1' can be synthesized by the following reaction path, but not limited thereto.

<Reaction Scheme 1'>

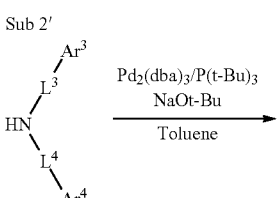

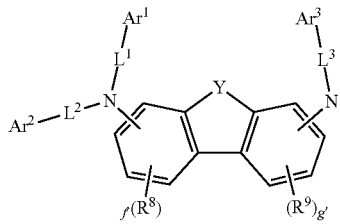

Final Product 1'

132

$Ar^1, Ar^2, Ar^3, Ar^4, L^1, L^2, L^3, L^4, Y, R^8, R^9$, f' and g' are the same as defined above.

In the reaction scheme 1', the synthesis method disclosed in Korean Patent No. 10-1668448 filed by the present applicant was used in the case of Final Products 1'. (See Reaction Scheme 1)

<Reaction Scheme 2> $L^1$ and $L^2$ are single bonds, and $Ar^1$ and $Ar^2$ form a ring.

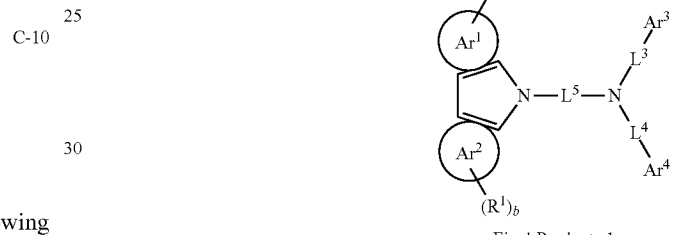

1. Synthesis Example of Sub 1

Sub 1 of reaction scheme 1 can be synthesized by the reaction path of the following reaction scheme 3, but is not limited thereto.

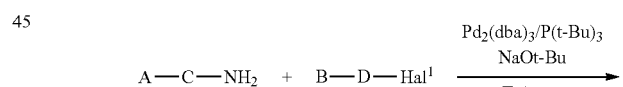

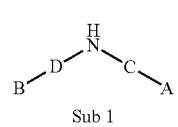

(Hal¹ = Br, Cl)

A is $Ar^1, Ar^3$; B is $Ar^2, Ar^3$; C is $L^1, L^3$; D is $L^2, L^4$;

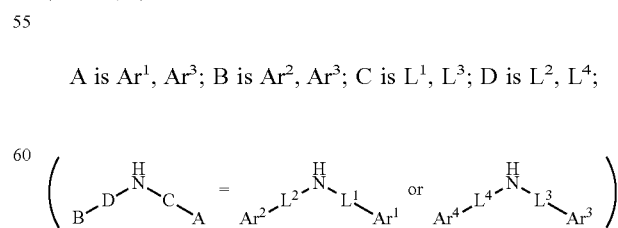

The synthesis examples of specific compounds belonging to Sub 1 are as follows.

(1) Synthesis of Sub 1-1

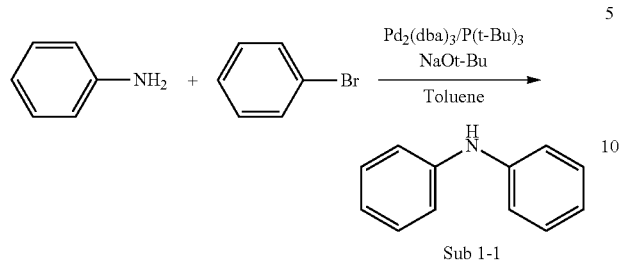

Sub 1-1

Aniline (40 g, 429.5 mmol) was dissolved in toluene (3000 ml) in a round bottom flask, and bromobenzene (74.18 g, 472.5 mmol), Pd$_2$(dba)$_3$ (19.66 g, 21.5 mmol), 50% P(t-Bu)$_3$ (20.9 ml, 43 mmol), NaOt-Bu (136.22 g, 1417.4 mmol) were added and stirred at 100° C. After the reaction was completed, the reaction mixture was extracted with CH$_2$Cl$_2$ and water. The organic layer was dried over MgSO$_4$ and concentrated.

The resulting compound was separated by silicagel column chromatography and recrystallized to obtain 54.51 g of the product. (Yield: 75%)

(2) Synthesis of Sub 1-11

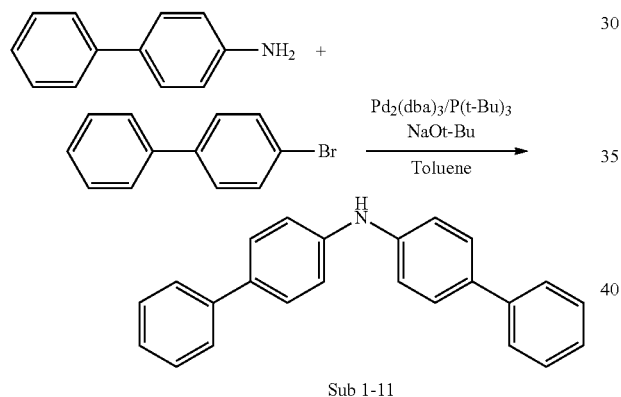

Sub 1-11

[1,1'-biphenyl]-4-amine (30 g, 177.3 mmol), 4-bromo-1,1'-biphenyl (45.46 g, 195 mmol), Pd$_2$(dba)$_3$ (8.12 g, 8.9 mmol), 50% P(t-Bu)$_3$ (8.6 ml, 17.7 mmol), NaOt-Bu (56.23 g, 585 mmol), toluene (1860 ml) were carried out in the same manner as in Sub 1-1 to give the product (45.01 g, 79%).

(3) Synthesis of Sub 1-22

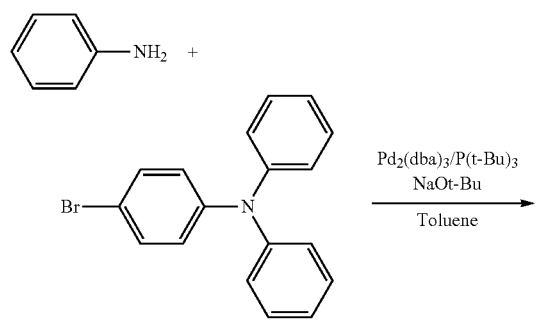

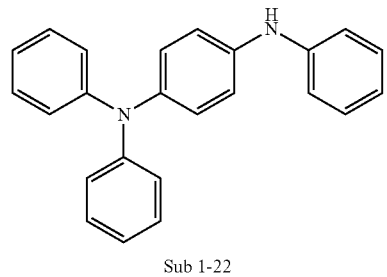

Sub 1-22 aniline (12.12 g, 130.16 mmol), 4-bromo-N,N-diphenylaniline (42.2 g 130.16 mmol), Pd$_2$(dba)$_3$ (3.58 g, 3.90 mmol), P(t-Bu)$_3$ (1.58 g, 7.81 mmol), NaOt-Bu (37.52 g, 390.48 mmol), toluene (1367 ml) were carried out in the same manner as in Sub 1-1 to give the product (34.16 g, 78%).

(4) Synthesis of Sub 1-40

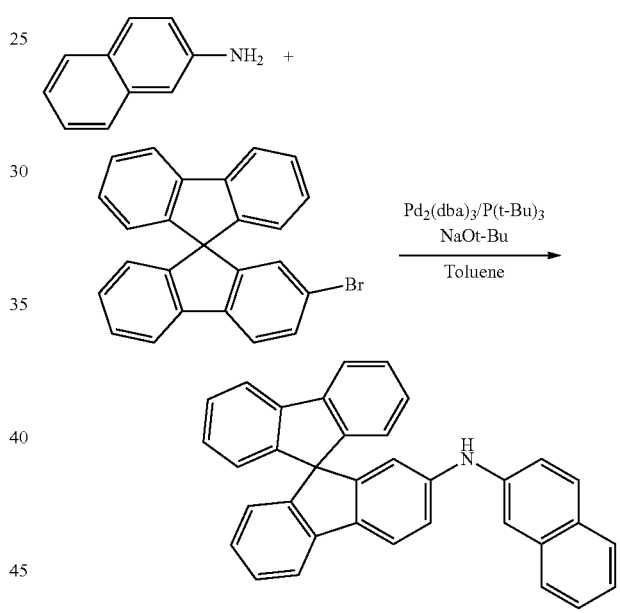

Sub 1-40 naphthalen-2-amine (14.85 g, 103.72 mmol), 2-bromo-9,9'-spirobi[fluorene] (41 g, 103.72 mmol), Pd$_2$(dba)$_3$ (2.85 g, 3.11 mmol), P(t-Bu)$_3$ (1.26 g, 6.22 mmol), NaOt-Bu (29.90 g, 311.16 mmol), toluene (1089 ml) were carried out in the same manner as in Sub 1-1 to give the product (34.17 g, 72%).

(5) Synthesis of Sub 1-46

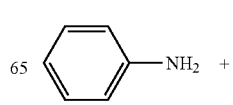

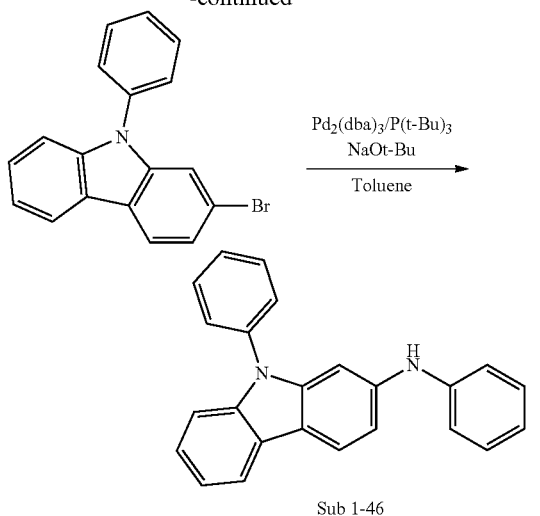

Sub 1-46 aniline (15 g, 161.1 mmol), 2-bromo-9-phenyl-9H-carbazole (57.08 g, 177.2 mmol), Pd₂(dba)₃ (7.37 g, 8.1 mmol), 50% P(t-Bu)₃ (7.9 ml, 16.1 mmol), NaOt-Bu (51.08 g, 531.5 mmol), toluene (1690 ml) were carried out in the same manner as in Sub 1-1 to give the product (36.63 g, 68%).

(6) Synthesis of Sub 1-57

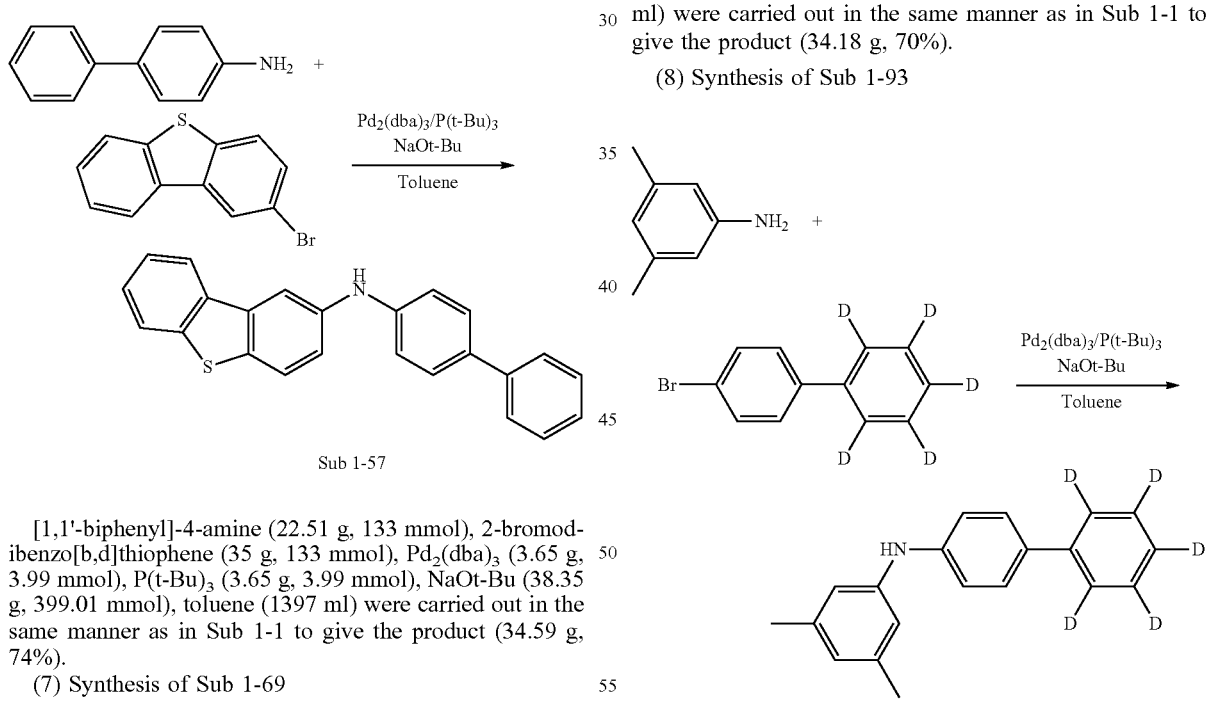

Sub 1-57

[1,1'-biphenyl]-4-amine (22.51 g, 133 mmol), 2-bromodibenzo[b,d]thiophene (35 g, 133 mmol), Pd₂(dba)₃ (3.65 g, 3.99 mmol), P(t-Bu)₃ (3.65 g, 3.99 mmol), NaOt-Bu (38.35 g, 399.01 mmol), toluene (1397 ml) were carried out in the same manner as in Sub 1-1 to give the product (34.59 g, 74%).

(7) Synthesis of Sub 1-69

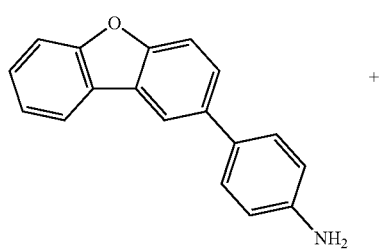

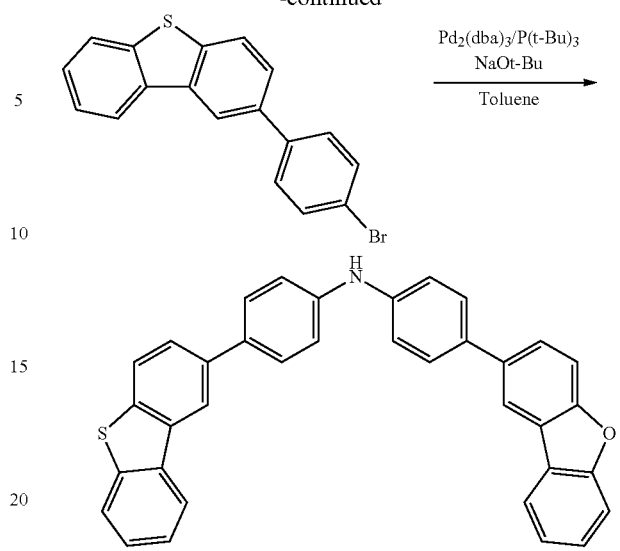

Sub 1-69

4-(dibenzo[b,d]furan-2-yl)aniline (24.46 g, 94.33 mmol), 2-(4-bromophenyl)dibenzo[b,d]thiophene (32 g, 94.33 mmol), Pd₂(dba)₃ (2.59 g, 2.83 mmol), P(t-Bu)₃ (1.15 g, 5.66 mmol), NaOt-Bu (27.19 g, 282.98 mmol), toluene (990 ml) were carried out in the same manner as in Sub 1-1 to give the product (34.18 g, 70%).

(8) Synthesis of Sub 1-93

Sub 1-93

3,5-dimethylaniline (21.88 g, 180.57 mmol), 4-bromo-1,1'-biphenyl-2',3',4',5',6'-d₅ (43 g, 180.57 mmol), Pd₂(dba)₃ (4.96 g, 5.42 mmol), P(t-Bu)₃ (2.19 g, 10.83 mmol), NaOt-Bu (52.06 g, 541.70 mmol), toluene (1896 ml) were carried out in the same manner as in Sub 1-1 to give the product (34.18 g, 68%).

Examples of Sub 1 are as follows, but are not limited thereto

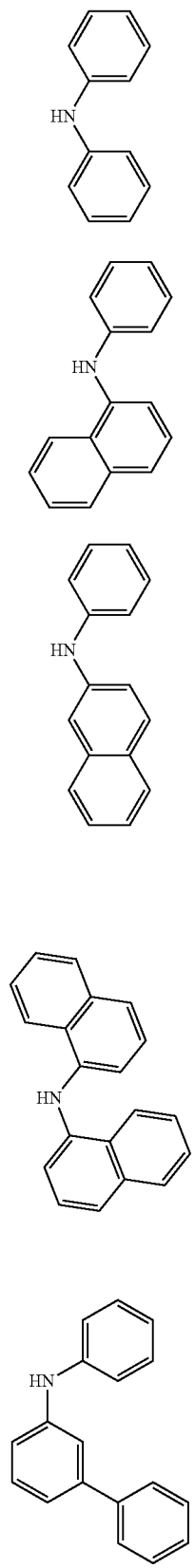
Sub 1-1
Sub 1-2
Sub 1-3
Sub 1-4
Sub 1-5
Sub 1-6
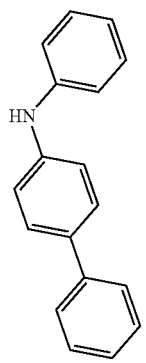
Sub 1-7
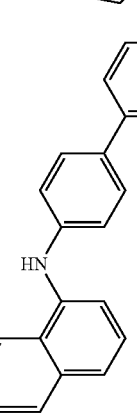
Sub 1-8
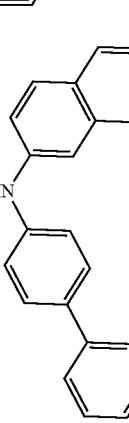
Sub 1-9
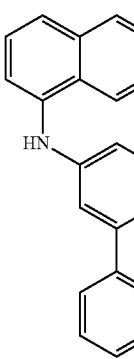

Sub 1-10 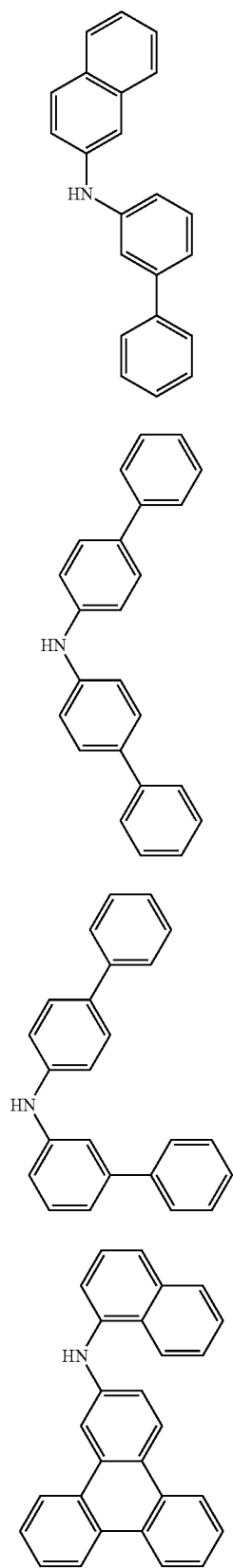
Sub 1-11
Sub 1-12
Sub 1-13
Sub 1-14 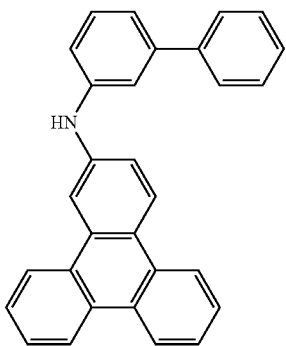
Sub 1-15 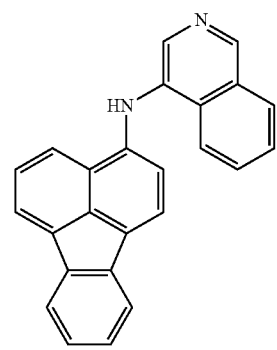
Sub 1-16 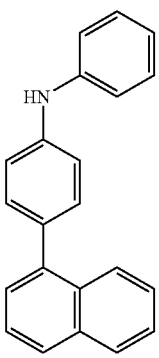
Sub 1-17 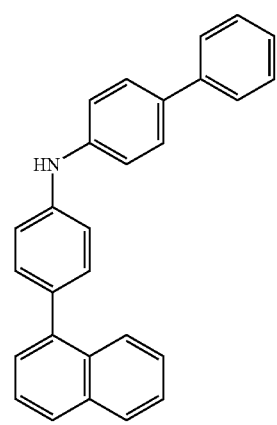

Sub 1-18
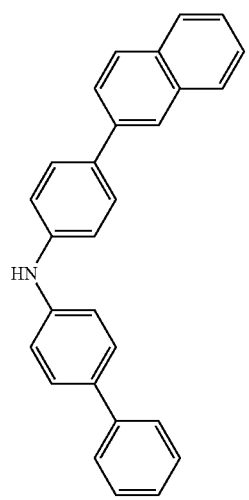
Sub 1-19
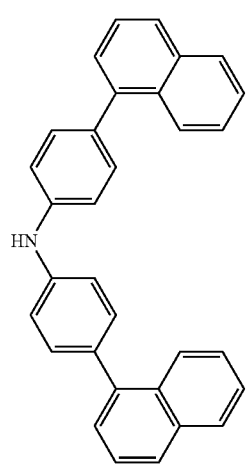
Sub 1-20
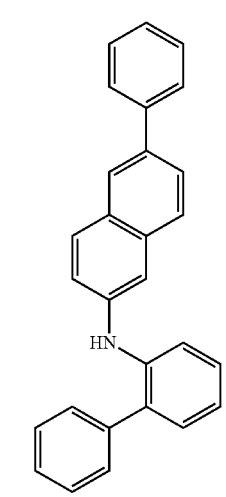
Sub 1-21
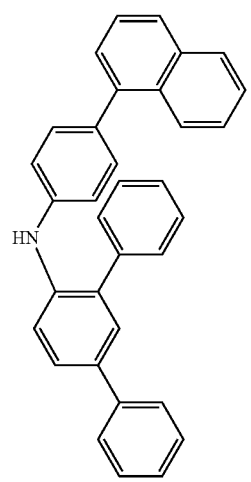
Sub 1-22
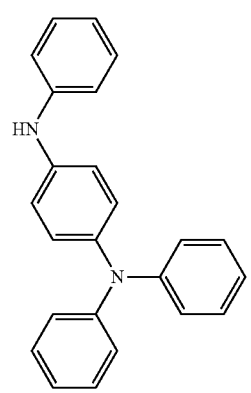
Sub 1-23
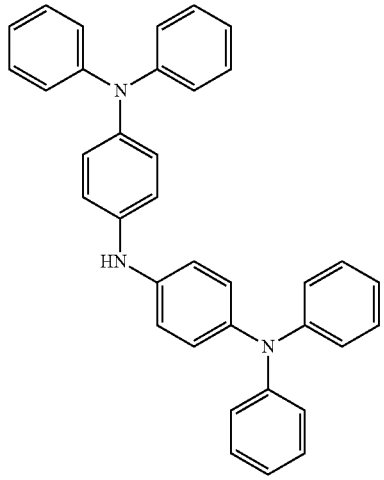

Sub 1-24
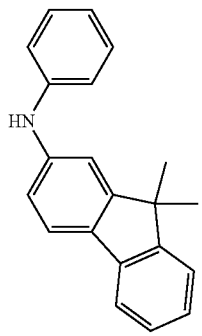
Sub 1-25
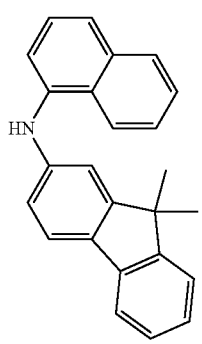
Sub 1-26
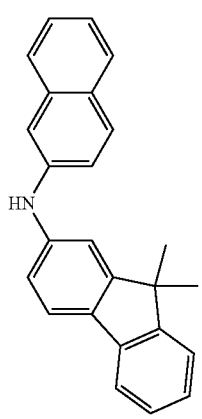
Sub 1-27
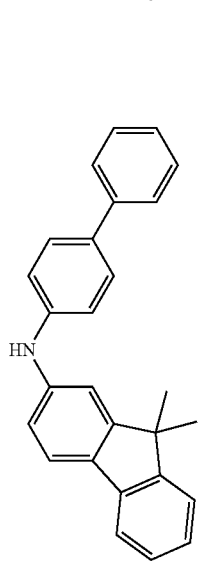
Sub 1-28
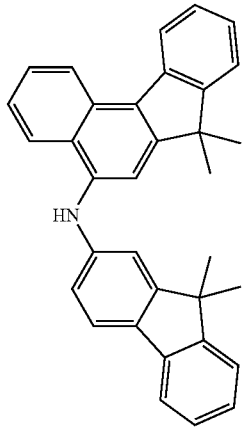
Sub 1-29
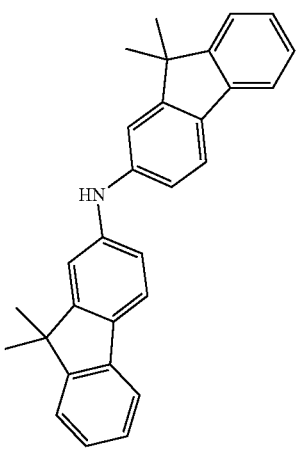
Sub 1-30
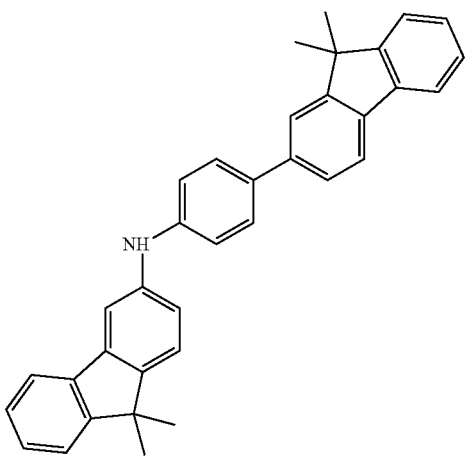

Sub 1-31
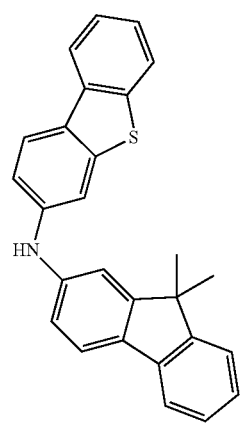
Sub 1-32
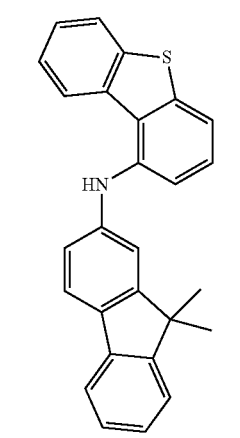
Sub 1-33
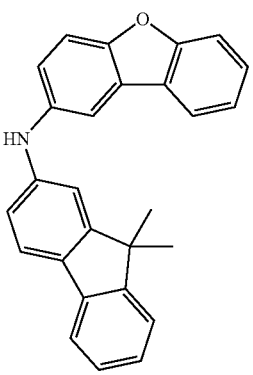
Sub 1-34
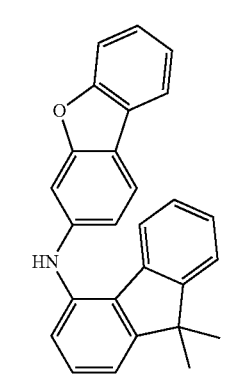
Sub 1-35
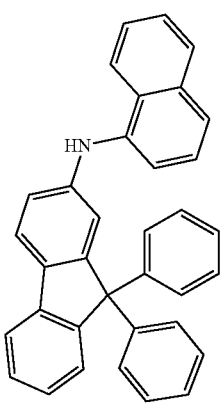
Sub 1-36
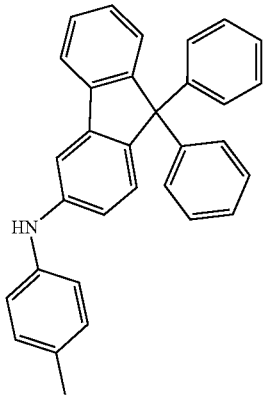
Sub 1-37
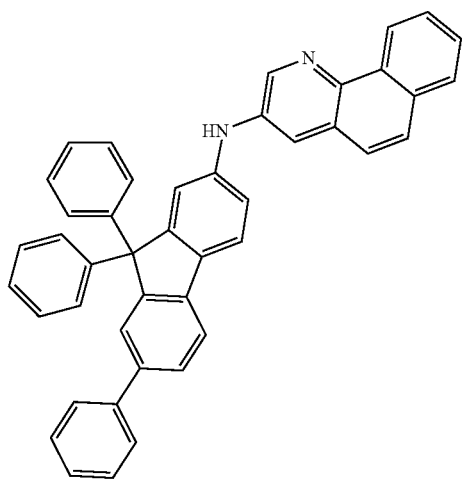

Sub 1-38
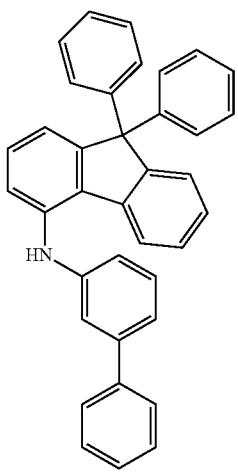
Sub 1-39
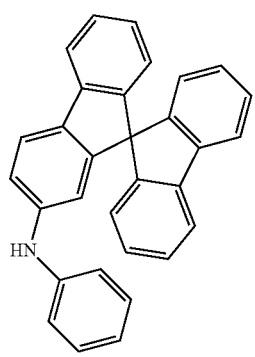
Sub 1-40
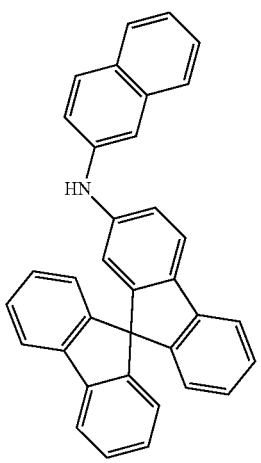
Sub 1-41
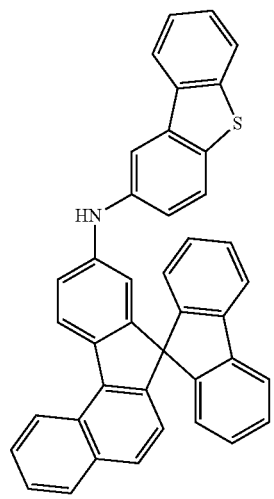
Sub 1-42
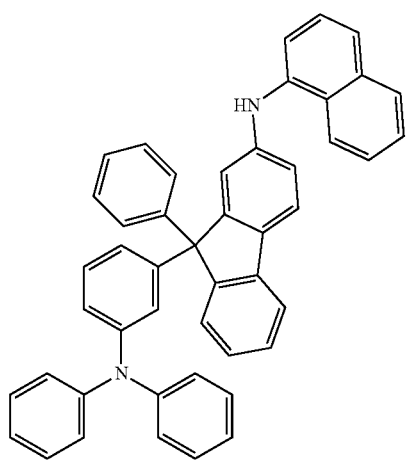
Sub 1-43
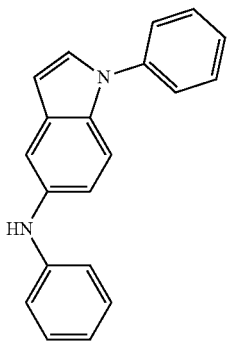
Sub 1-44
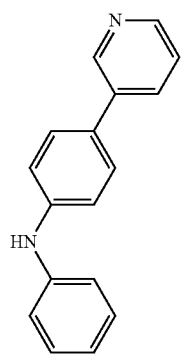

-continued
Sub 1-45
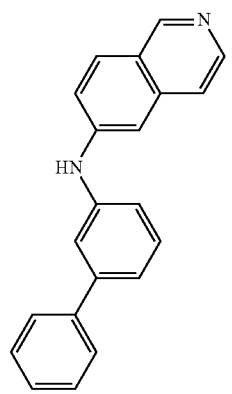
Sub 1-46
Sub 1-47
Sub 1-48
-continued
Sub 1-49
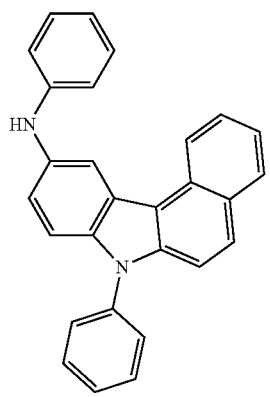
Sub 1-50
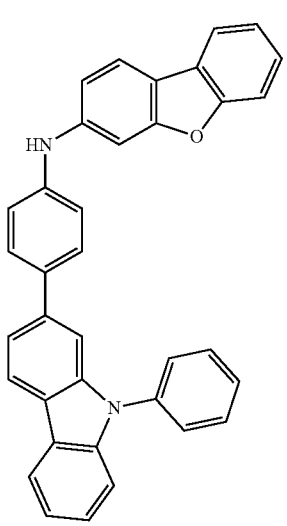
Sub 1-51
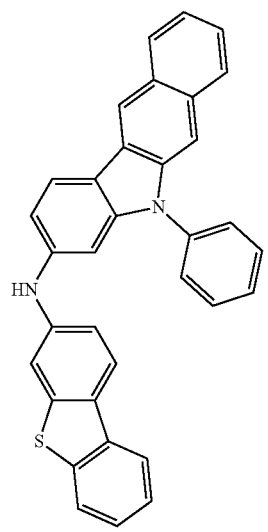

Sub 1-52
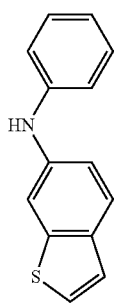
Sub 1-53
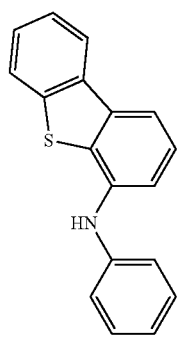
Sub 1-54
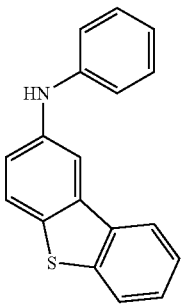
Sub 1-55
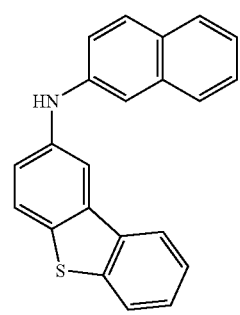
Sub 1-56
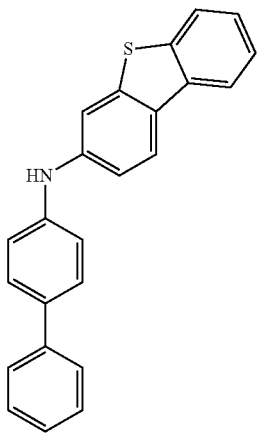
Sub 1-57
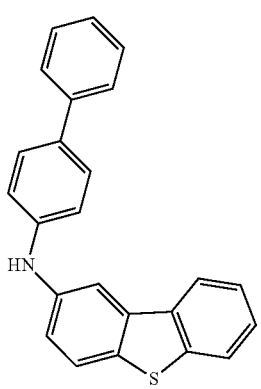
Sub 1-58
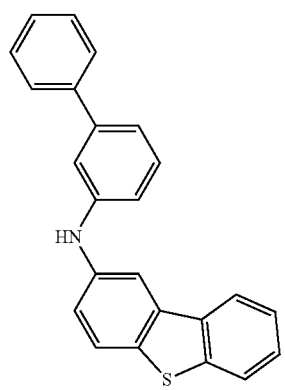
Sub 1-59
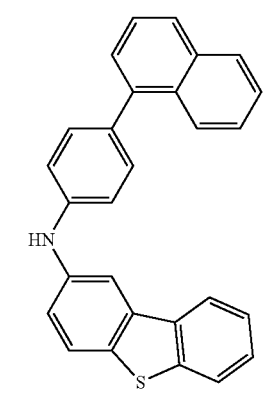

-continued
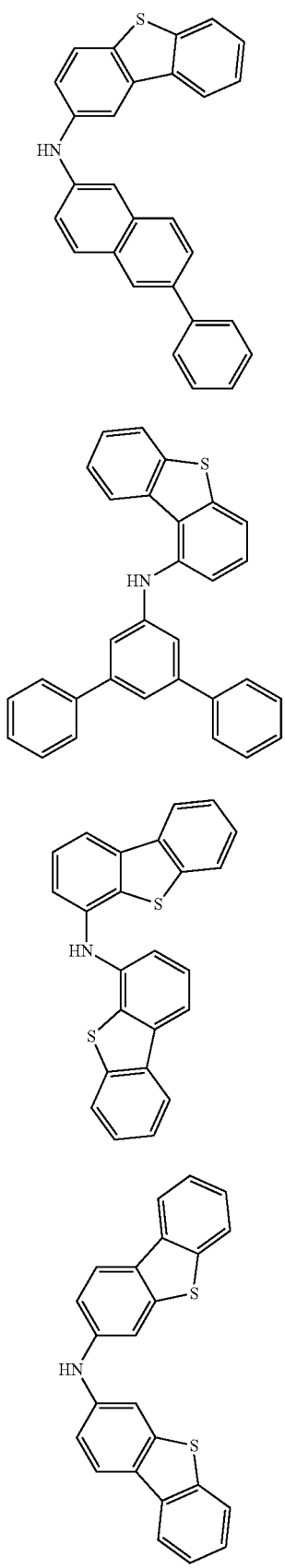
Sub 1-60
Sub 1-61
Sub 1-62
Sub 1-63
-continued
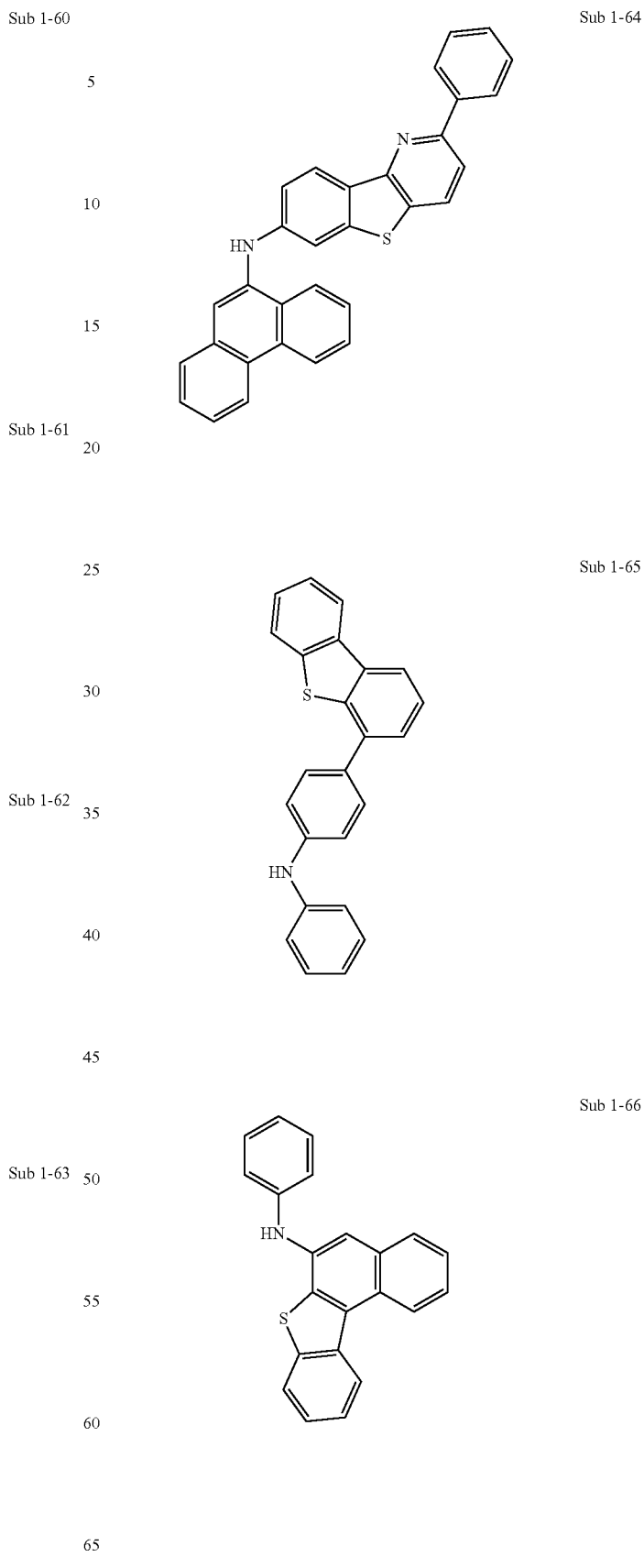
Sub 1-64
Sub 1-65
Sub 1-66

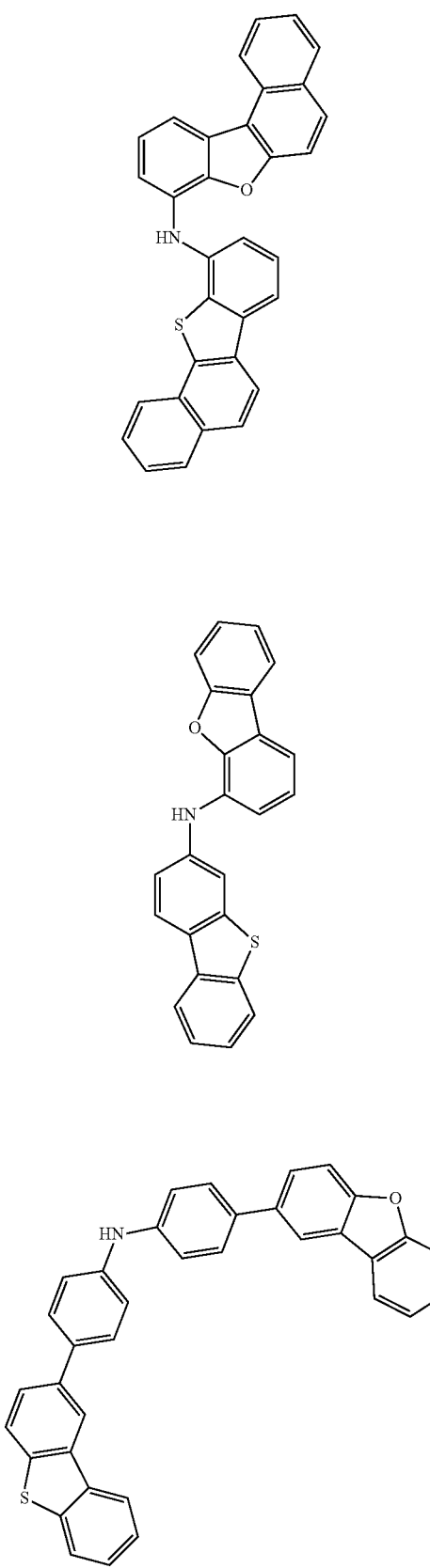
Sub 1-67
Sub 1-68
Sub 1-69
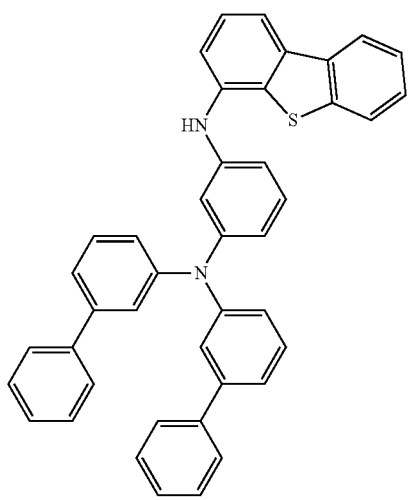
Sub 1-70
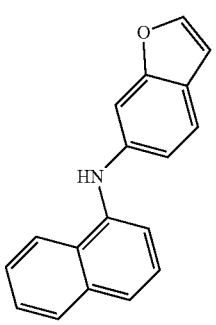
Sub 1-71
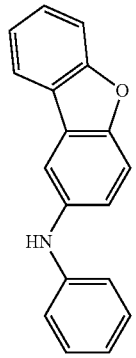
Sub 1-72
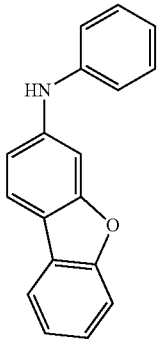
Sub 1-73

157
-continued
158
-continued
Sub 1-74
Sub 1-75
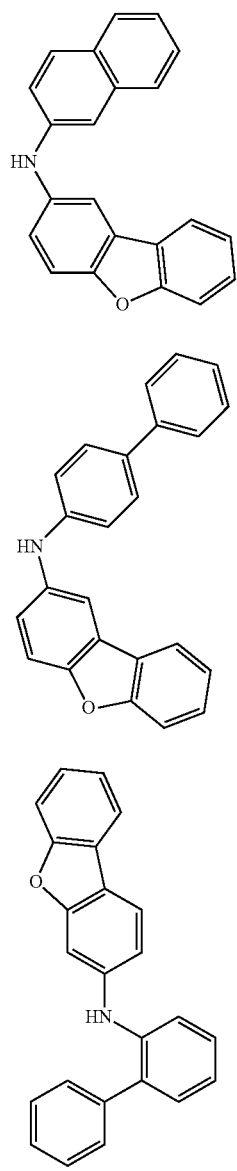
Sub 1-76
Sub 1-77
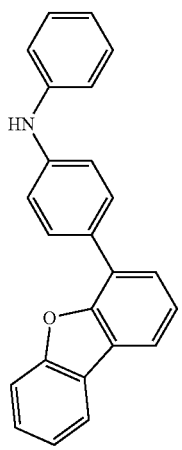
Sub 1-78
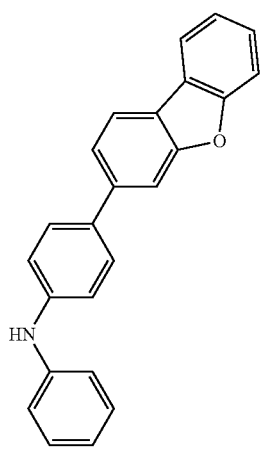
Sub 1-79
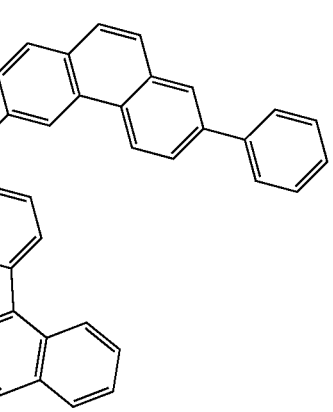
Sub 1-80
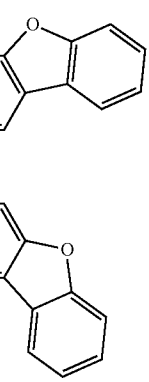

Sub 1-81
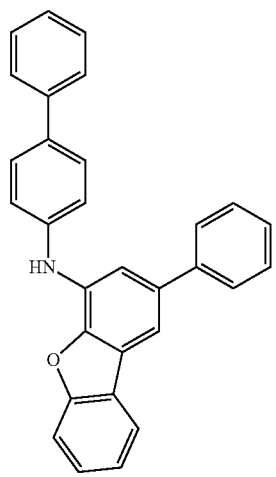
Sub 1-82
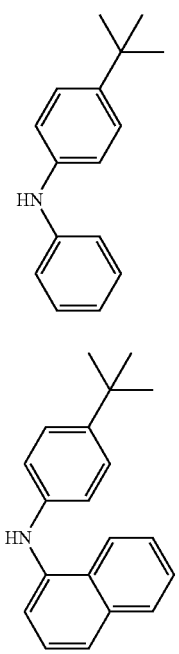
Sub 1-83
Sub 1-84
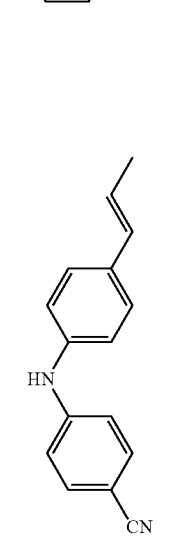
Sub 1-85
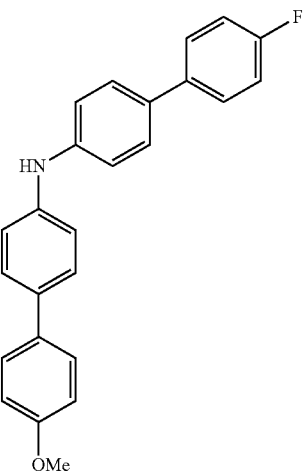
Sub 1-86
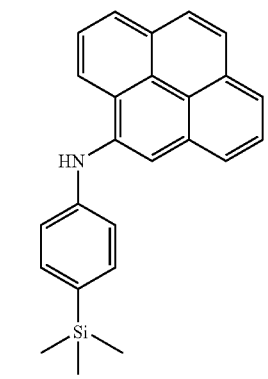
Sub 1-87
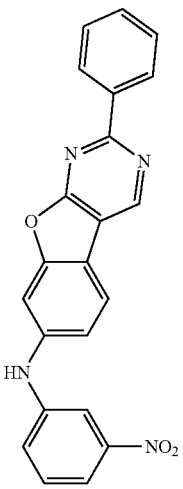

-continued
Sub 1-88
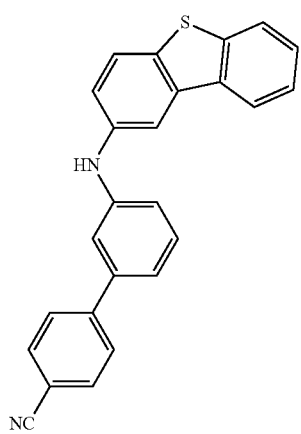
Sub 1-89
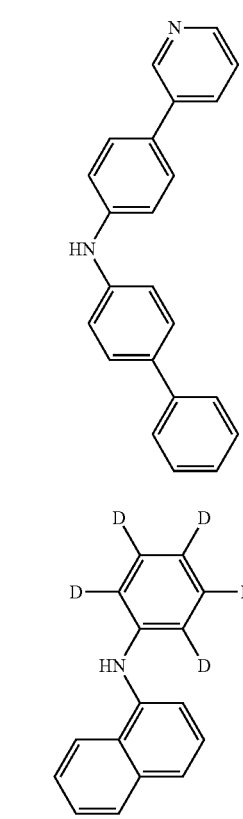
Sub 1-90
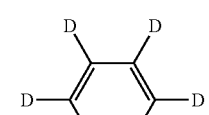
Sub 1-91
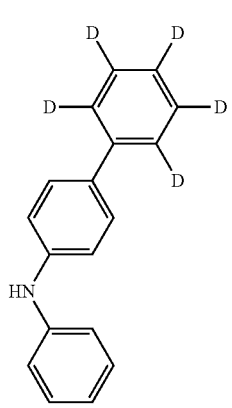
-continued
Sub 1-92
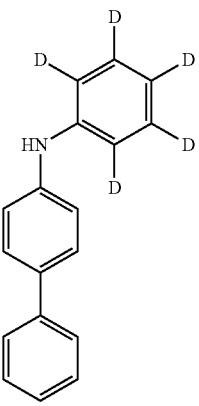
Sub 1-93
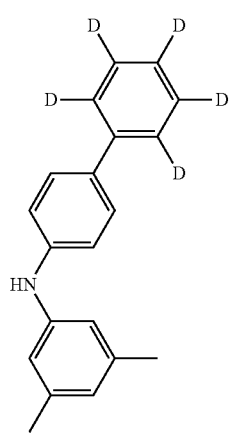
Sub 1-94
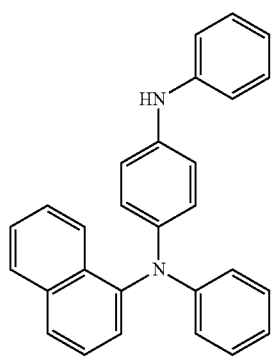

Sub 1-95
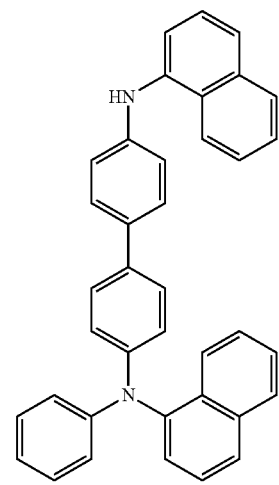
Sub 1-96
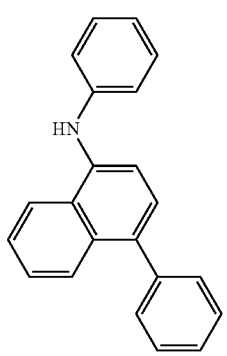
Sub 1-97
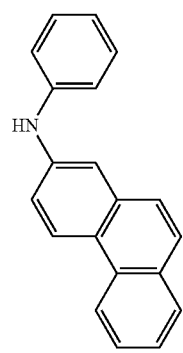
Sub 1-98
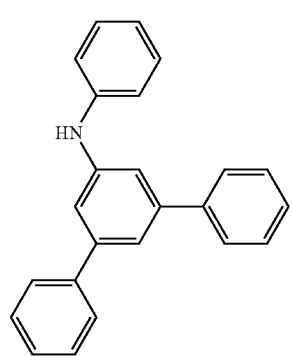
Sub 1-99
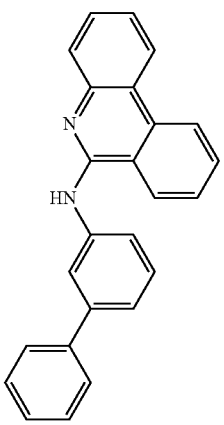
Sub 1-100
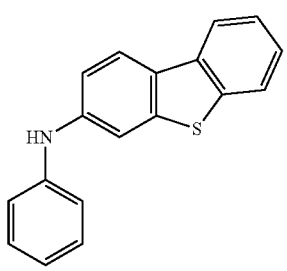
Sub 1-101
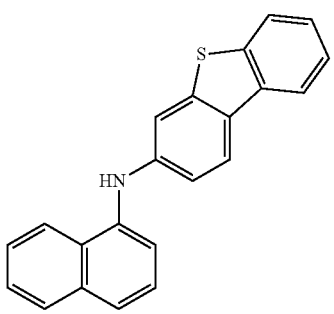
Sub 1-102
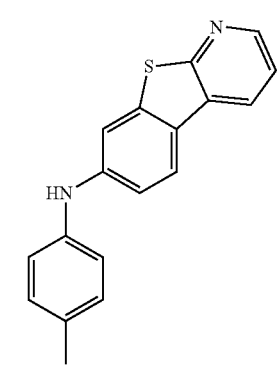

Sub 1-103
Sub 1-104
Sub 1-105
Sub 1-106
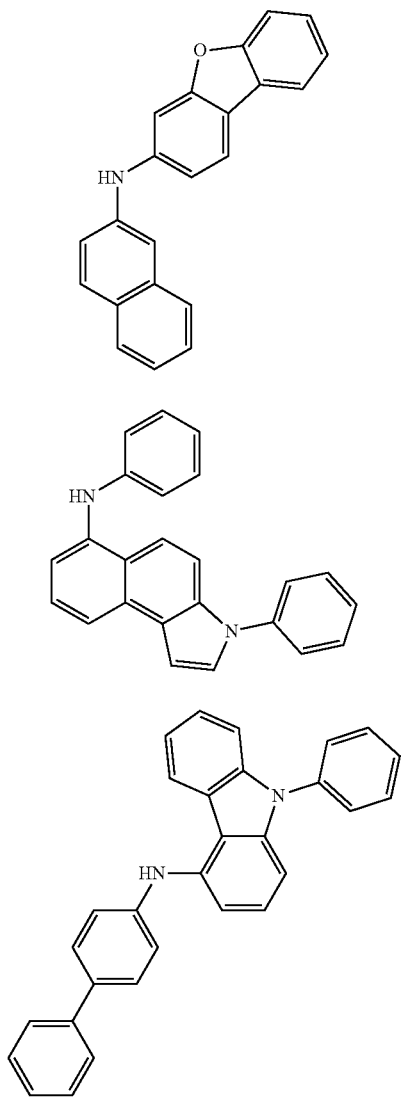
Sub 1-107
Sub 1-108
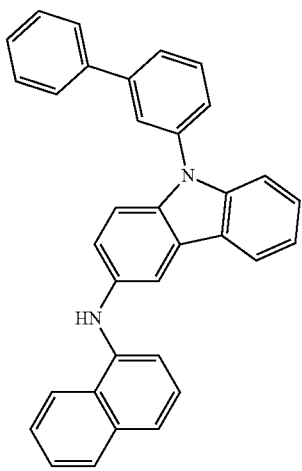
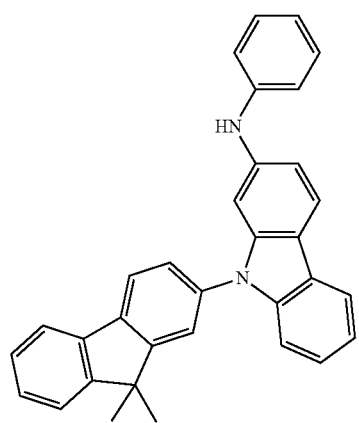
Sub 1-109

Sub 1-110

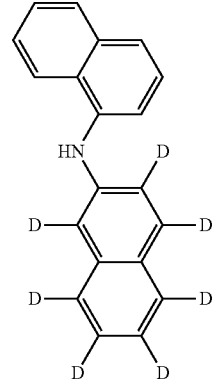

Sub 1-111

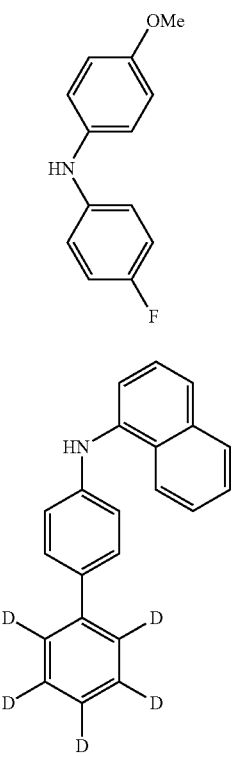

Sub 1-112

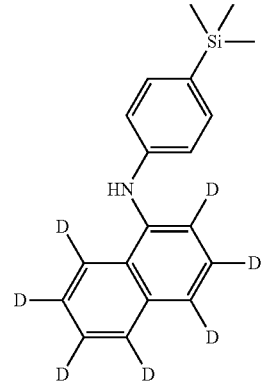

Sub 1-113

TABLE 1

| compound | FD-MS | compound | FD-MS |
|---|---|---|---|
| Sub 1-1 | m/z = 169.09 ($C_{12}H_{11}N$ = 169.22) | Sub 1-2 | m/z = 219.10 ($C_{16}H_{13}N$ = 219.28) |
| Sub 1-3 | m/z = 245.12 ($C_{18}H_{15}N$ = 245.32) | Sub 1-4 | m/z = 269.12 ($C_{20}H_{15}N$ = 269.34) |
| Sub 1-5 | m/z = 245.12 ($C_{18}H_{15}N$ = 245.32) | Sub 1-6 | m/z = 245.12 ($C_{18}H_{15}N$ = 245.32) |
| Sub 1-7 | m/z = 295.14 ($C_{22}H_{17}N$ = 295.38) | Sub 1-8 | m/z = 295.14 ($C_{22}H_{17}N$ = 295.38) |
| Sub 1-9 | m/z = 295.14 ($C_{22}H_{17}N$ = 295.38) | Sub 1-10 | m/z = 295.14 ($C_{22}H_{17}N$ = 295.38) |
| Sub 1-11 | m/z = 321.15 ($C_{24}H_{19}N$ = 321.41) | Sub 1-12 | m/z = 321.15 ($C_{24}H_{19}N$ = 321.41) |
| Sub 1-13 | m/z = 369.15 ($C_{28}H_{19}N$ = 369.47) | Sub 1-14 | m/z = 395.17 ($C_{30}H_{21}N$ = 395.51) |
| Sub 1-15 | m/z = 295.14 ($C_{22}H_{17}N$ = 295.38) | Sub 1-16 | m/z = 652.25 ($C_{48}H_{32}N_2O$ = 652.80) |
| Sub 1-17 | m/z = 371.17 ($C_{28}H_{21}N$ = 371.48) | Sub 1-18 | m/z = 371.17 ($C_{28}H_{21}N$ = 371.48) |
| Sub 1-19 | m/z = 421.18 ($C_{32}H_{23}N$ = 421.54) | Sub 1-20 | m/z = 371.17 ($C_{28}H_{21}N$ = 371.48) |
| Sub 1-21 | m/z = 447.20 ($C_{34}H_{25}N$ = 447.58) | Sub 1-22 | m/z = 336.16 ($C_{24}H_{20}N_2$ = 336.43) |
| Sub 1-23 | m/z = 503.24 ($C_{36}H_{29}N_3$ = 503.64) | Sub 1-24 | m/z = 285.15 ($C_{21}H_{19}N$ = 285.38) |
| Sub 1-25 | m/z = 335.17 ($C_{25}H_{21}N$ = 335.44) | Sub 1-26 | m/z = 335.17 ($C_{25}H_{21}N$ = 335.44) |
| Sub 1-27 | m/z = 361.18 ($C_{27}H_{23}N$ = 361.48) | Sub 1-28 | m/z = 451.23 ($C_{34}H_{29}N$ = 451.61) |
| Sub 1-29 | m/z = 401.21 ($C_{30}H_{27}N$ = 401.55) | Sub 1-30 | m/z = 477.25 ($C_{36}H_{31}N$ = 477.65) |
| Sub 1-31 | m/z = 391.14 ($C_{27}H_{21}NS$ = 391.53) | Sub 1-32 | m/z = 391.14 ($C_{27}H_{21}NS$ = 391.53) |
| Sub 1-33 | m/z = 375.16 ($C_{27}H_{21}NO$ = 375.46) | Sub 1-34 | m/z = 375.16 ($C_{27}H_{21}NO$ = 375.46) |
| Sub 1-35 | m/z = 459.20 ($C_{35}H_{25}N$ = 459.58) | Sub 1-36 | m/z = 423.20 ($C_{32}H_{25}N$ = 423.56) |
| Sub 1-37 | m/z = 586.24 ($C_{44}H_{30}N_2$ = 586.74) | Sub 1-38 | m/z = 485.21 ($C_{37}H_{27}N$ = 485.63) |
| Sub 1-39 | m/z = 407.17 ($C_{31}H_{21}N$ = 407.52) | Sub 1-40 | m/z = 457.18 ($C_{35}H_{23}N$ = 457.58) |
| Sub 1-41 | m/z = 563.17 ($C_{41}H_{25}NS$ = 563.72) | Sub 1-42 | m/z = 626.27 ($C_{47}H_{34}N_2$ = 626.80) |
| Sub 1-43 | m/z = 284.13 ($C_{20}H_{16}N_2$ = 284.36) | Sub 1-44 | m/z = 246.12 ($C_{17}H_{14}N_2$ = 246.31) |
| Sub 1-45 | m/z = 296.13 ($C_{21}H_{16}N_2$ = 296.37) | Sub 1-46 | m/z = 334.15 ($C_{24}H_{18}N_2$ = 334.42) |
| Sub 1-47 | m/z = 334.15 ($C_{24}H_{18}N_2$ = 334.42) | Sub 1-48 | m/z = 460.19 ($C_{34}H_{24}N_2$ = 460.58) |
| Sub 1-49 | m/z = 384.16 ($C_{28}H_{20}N_2$ = 384.48) | Sub 1-50 | m/z = 500.19 ($C_{36}H_{24}N_2O$ = 500.60) |
| Sub 1-51 | m/z = 490.15 ($C_{34}H_{22}N_2S$ = 490.62) | Sub 1-52 | m/z = 225.06 ($C_{14}H_{11}S$ = 225.31) |
| Sub 1-53 | m/z = 275.08 ($C_{18}H_{13}NS$ = 275.37) | Sub 1-54 | m/z = 275.08 ($C_{18}H_{13}NS$ = 275.37) |
| Sub 1-55 | m/z = 325.09 ($C_{22}H_{15}NS$ = 325.43) | Sub 1-56 | m/z = 351.11 ($C_{24}H_{17}NS$ = 351.47) |
| Sub 1-57 | m/z = 351.11 ($C_{24}H_{17}NS$ = 351.47) | Sub 1-58 | m/z = 351.11 ($C_{24}H_{17}NS$ = 351.47) |
| Sub 1-59 | m/z = 401.12 ($C_{28}H_{19}NS$ = 401.53) | Sub 1-60 | m/z = 401.12 ($C_{28}H_{19}NS$ = 401.53) |
| Sub 1-61 | m/z = 427.14 ($C_{30}H_{21}NS$ = 427.57) | Sub 1-62 | m/z = 381.06 ($C_{24}H_{15}NS_2$ = 381.51) |
| Sub 1-63 | m/z = 381.06 ($C_{24}H_{15}NS_2$ = 381.51) | Sub 1-64 | m/z = 452.13 ($C_{31}H_{20}N_2S$ = 452.58) |
| Sub 1-65 | m/z = 351.11 ($C_{24}H_{17}NS$ = 351.47) | Sub 1-66 | m/z = 325.09 ($C_{22}H_{15}NS$ = 325.43) |
| Sub 1-67 | m/z = 465.12 ($C_{32}H_{19}NOS$ = 465.57) | Sub 1-68 | m/z = 365.09 ($C_{24}H_{15}NOS$ = 365.45) |
| Sub 1-69 | m/z = 517.15 ($C_{37}H_{23}NOS$ = 517.65) | Sub 1-70 | m/z = 594.21 ($C_{42}H_{30}N_2S$ = 594.78) |

TABLE 1-continued

| compound | FD-MS | compound | FD-MS |
| --- | --- | --- | --- |
| Sub 1-71 | m/z = 259.10 ($C_{18}H_{13}NO$ = 259.31) | Sub 1-72 | m/z = 259.10 ($C_{18}H_{13}NO$ = 259.31) |
| Sub 1-73 | m/z = 259.10 ($C_{18}H_{13}NO$ = 259.31) | Sub 1-74 | m/z = 309.12 ($C_{22}H_{15}NO$ = 309.36) |
| Sub 1-75 | m/z = 335.13 ($C_{24}H_{17}NO$ = 335.40) | Sub 1-76 | m/z = 335.13 ($C_{24}H_{17}NO$ = 335.40) |
| Sub 1-77 | m/z = 335.13 ($C_{24}H_{17}NO$ = 335.40) | Sub 1-78 | m/z = 335.13 ($C_{24}H_{17}NO$ = 335.40) |
| Sub 1-79 | m/z = 485.18 ($C_{36}H_{23}NO$ = 485.59) | Sub 1-80 | m/z = 349.11 ($C_{24}H_{15}NO_2$ = 349.39) |
| Sub 1-81 | m/z = 411.16 ($C_{30}H_{21}NO$ = 411.49) | Sub 1-82 | m/z = 225.15 ($C_{16}H_{19}N$ = 225.34) |
| Sub 1-83 | m/z = 275.17 ($C_{20}H_{21}N$ = 275.40) | Sub 1-84 | m/z = 234.12 ($C_{16}H_{14}N_2$ = 234.30) |
| Sub 1-85 | m/z = 369.15 ($C_{25}H_{20}FNO$ = 369.44) | Sub 1-86 | m/z = 365.16 ($C_{25}H_{23}NSi$ = 365.55) |
| Sub 1-87 | m/z = 382.38 ($C_{22}H_{14}N_4O_3$ = 382.38) | Sub 1-88 | m/z = 376.10 ($C_{25}H_{16}N_2S$ = 376.48) |
| Sub 1-89 | m/z = 322.15 ($C_{23}H_{18}N_2$ = 322.41) | Sub 1-90 | m/z = 224.14 ($C_{16}H_8D_5N$ = 224.32) |
| Sub 1-91 | m/z = 250.15 ($C_{18}H_{10}D_5N$ = 250.36) | Sub 1-92 | m/z = 250.15 ($C_{18}H_{10}D_5N$ = 250.36) |
| Sub 1-93 | m/z = 278.18 ($C_{20}H_{14}D_5N$ = 278.41) | Sub 1-94 | m/z = 386.18 ($C_{28}H_{22}N_2$ = 386.50) |
| Sub 1-95 | m/z = 512.23 ($C_{38}H_{28}N_2$ = 512.66) | Sub 1-96 | m/z = 295.14 ($C_{22}H_{17}N$ = 295.39) |
| Sub 1-97 | m/z = 269.12 ($C_{20}H_{15}N$ = 269.35) | Sub 1-98 | m/z = 321.15 ($C_{24}H_{19}N$ = 321.42) |
| Sub 1-99 | m/z = 346.15 ($C_{25}H_{18}N_2$ = 346.43) | Sub 1-100 | m/z = 275.08 ($C_{18}H_{13}NS$ = 275.37) |
| Sub 1-101 | m/z = 325.09 ($C_{22}H_{15}NS$ = 325.43) | Sub 1-102 | m/z = 290.09 ($C_{18}H_{14}N_2S$ = 290.38) |
| Sub 1-103 | m/z = 309.12 ($C_{22}H_{15}NO$ = 309.37) | Sub 1-104 | m/z = 334.15 ($C_{24}H_{18}N_2$ = 334.42) |
| Sub 1-105 | m/z = 410.18 ($C_{30}H_{22}N_2$ = 410.52) | Sub 1-106 | m/z = 450.21 ($C_{33}H_{26}N_2$ = 450.59) |
| Sub 1-107 | m/z = 460.19 ($C_{34}H_{24}N_2$ = 460.58) | Sub 1-108 | m/z = 434.18 ($C_{32}H_{22}N_2$ = 434.54) |
| Sub 1-109 | m/z = 247.11 ($C_{16}H_{13}N_3$ = 247.30) | Sub 1-110 | m/z = 217.09 ($C_{13}H_{12}FNO$ = 217.24) |
| Sub 1-111 | m/z = 300.17 ($C_{22}H_{12}D_5N$ = 300.42) | Sub 1-112 | m/z = 276.16 ($C_{20}H_8D_7N$ = 276.39) |
| Sub 1-113 | m/z = 298.19 ($C_{19}H_{14}D_7NSi$ = 298.51) | | |

2. Synthesis of Sub 2

Sub 2 of Reaction Scheme 1 can be synthesized by the reaction path of the following Reaction Scheme 4 or 5, but is not limited thereto.

<Reaction Scheme 4>

($Hal^4$=I, Br; $Hal^2$=Br, Cl)

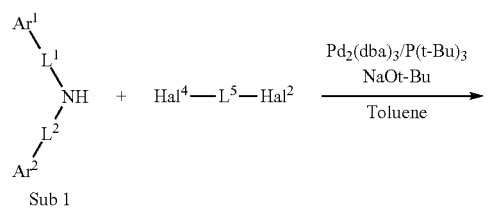

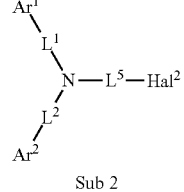

Sub 2

<Reaction Scheme 5> $L^1$ and $L^2$ are single bonds, and $Ar^1$ and $Ar^2$ form a ring.

($Hal^3$=I, Br)

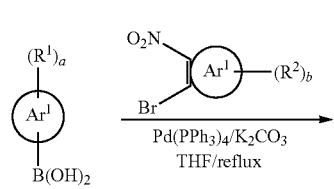

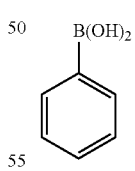

Sub 2A-I

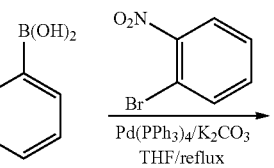

Sub 2A-II    Sub 2A

Examples of synthesis of specific compounds belonging to Sub 2 and Sub 2A are as follows.

Synthesis of Sub 2A-1

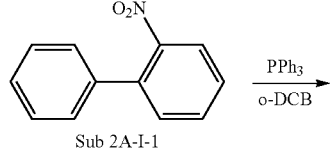

Sub 2A-I-1

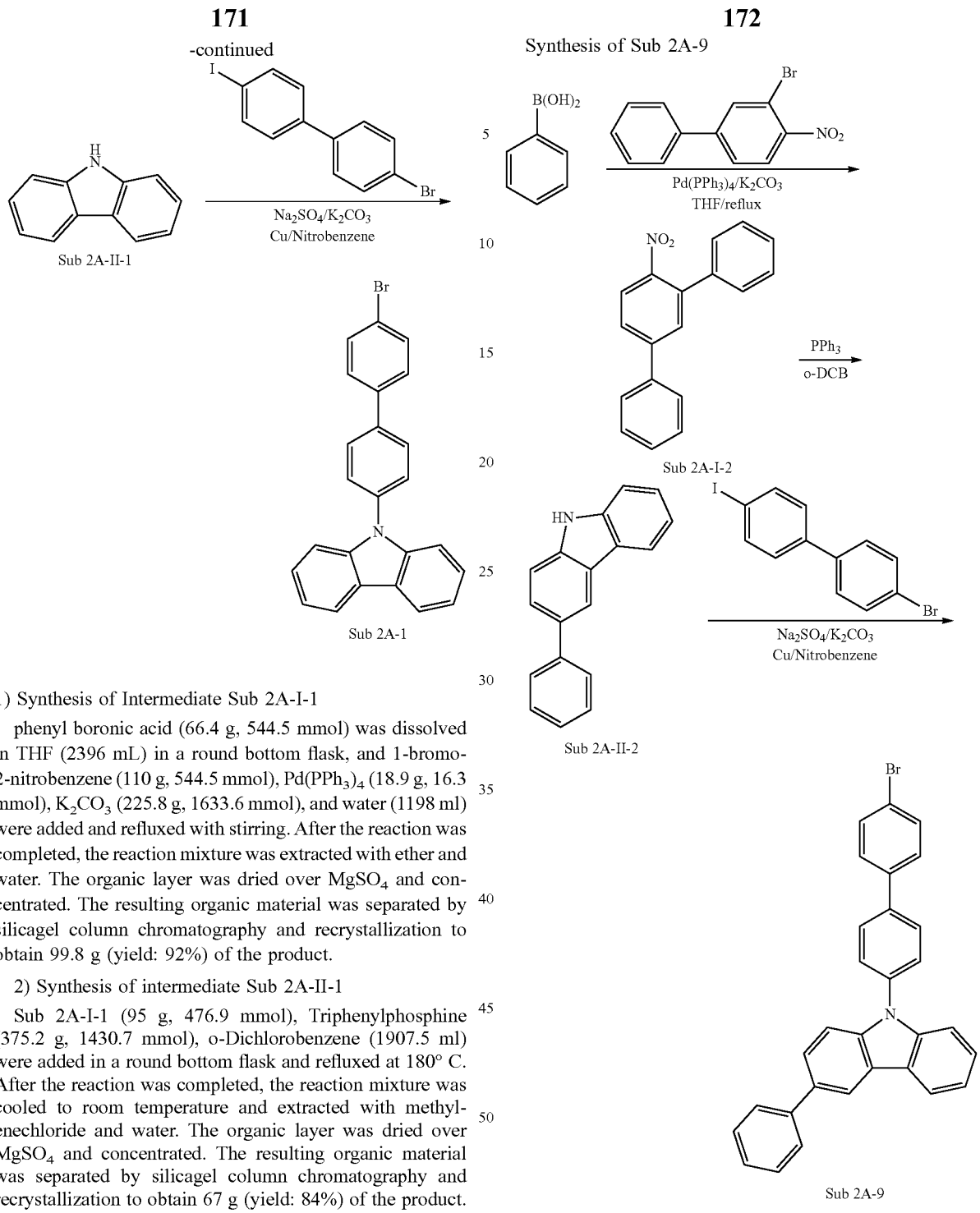

Synthesis of Sub 2A-9

1) Synthesis of Intermediate Sub 2A-I-1 phenyl boronic acid (66.4 g, 544.5 mmol) was dissolved in THF (2396 mL) in a round bottom flask, and 1-bromo-2-nitrobenzene (110 g, 544.5 mmol), Pd(PPh$_3$)$_4$ (18.9 g, 16.3 mmol), K$_2$CO$_3$ (225.8 g, 1633.6 mmol), and water (1198 ml) were added and refluxed with stirring. After the reaction was completed, the reaction mixture was extracted with ether and water. The organic layer was dried over MgSO$_4$ and concentrated. The resulting organic material was separated by silicagel column chromatography and recrystallization to obtain 99.8 g (yield: 92%) of the product.

2) Synthesis of intermediate Sub 2A-II-1

Sub 2A-I-1 (95 g, 476.9 mmol), Triphenylphosphine (375.2 g, 1430.7 mmol), o-Dichlorobenzene (1907.5 ml) were added in a round bottom flask and refluxed at 180° C. After the reaction was completed, the reaction mixture was cooled to room temperature and extracted with methylenechloride and water. The organic layer was dried over MgSO$_4$ and concentrated. The resulting organic material was separated by silicagel column chromatography and recrystallization to obtain 67 g (yield: 84%) of the product.

3) Synthesis of Sub 2A-1

Sub 2A-II-1 (59 g, 352.9 mmol) was dissolved in nitrobenzene (1765 ml) in a round bottom flask, and 4-bromo-4'-iodo-1,1'-biphenyl (139.3 g, 388.1 mmol), Na$_2$SO$_4$ (50.1 g, 352.9 mmol), K$_2$CO$_3$ (48.8 g, 352.9 mmol), Cu (6.7 g, 105.9 mmol) were added and stirred at 200° C. When the reaction was complete, nitrobenzene was removed by distillation and extracted with CH$_2$Cl$_2$ and water. The organic layer was dried over MgSO$_4$ and concentrated. The resulting compound was separated by silicagel column chromatography and recrystallization to obtain 102.6 g (yield: 73%) of the product.

1) Synthesis of Intermediate Sub 2A-I-2 phenylboronic acid (65.8 g, 539.4 mmol), THF(2373 ml), 3-bromo-4-nitro-1,1'-biphenyl (150 g, 539.4 mmol), Pd(PPh$_3$)$_4$ (18.7 g, 16.2 mmol), K$_2$CO$_3$ (223.6 g, 1618 mmol) and water (1187 ml) were carried out in the same manner as Sub 2A-I-1 to obtain 106.9 g of the product. (Yield: 72%)

2) Synthesis of intermediate Sub 2A-II-2

Sub 2A-I-2 (100 g, 363.2 mmol), Triphenylphosphine (285.8 g, 1089.7 mmol), o-Dichlorobenzene (1453 mL) were carried out in the same manner as Sub 2A-II-1 to obtain 54.8 g of the product. (Yield: 62%)

3) Synthesis of Sub 2A-9

Sub 2A-II-2 (40 g, 164.4 mmol), nitrobenzene(822 ml), 4-bromo-4'-iodo-1,1'-biphenyl (64.9 g, 180.8 mmol), Na₂SO₄ (23.4 g, 164.4 mmol), K₂CO₃ (22.7 g, 164.4 mmol), Cu (3.1 g, 49.3 mmol) were carried out in the same manner as Sub 2A-1 to obtain 55.4 g of the product. (Yield: 71%)

Synthesis of Sub 2A-18

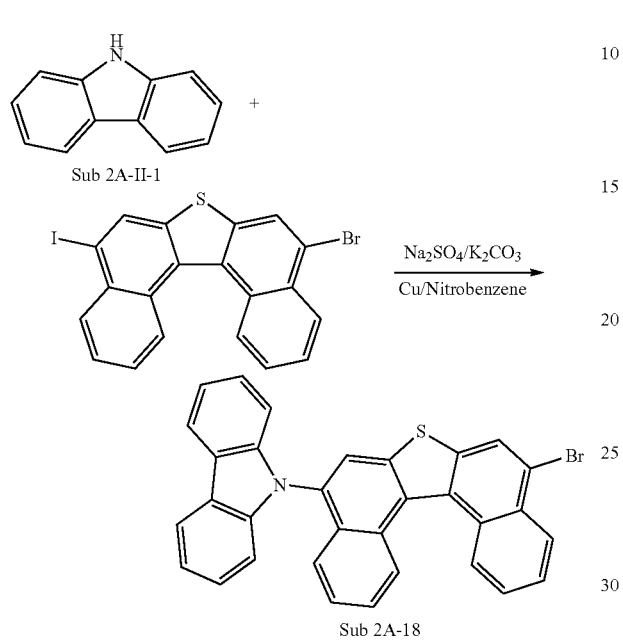

Sub 2A-II-1 (30 g, 179.4 mmol), nitrobenzene(897 ml), 5-bromo-9-iododinaphtho[2,1-b: 1',2'-d]thiophene (96.5 g, 197.4 mmol), Na₂SO₄ (25.5 g, 179.4 mol), K₂CO₃ (24.8 g, 179.4 mmol), Cu (3.4 g, 53.8 mmol) were carried out in the same manner as Sub 2A-1 to obtain 61.6 g of the product. (Yield: 65%)

Synthesis of Sub 2A-20

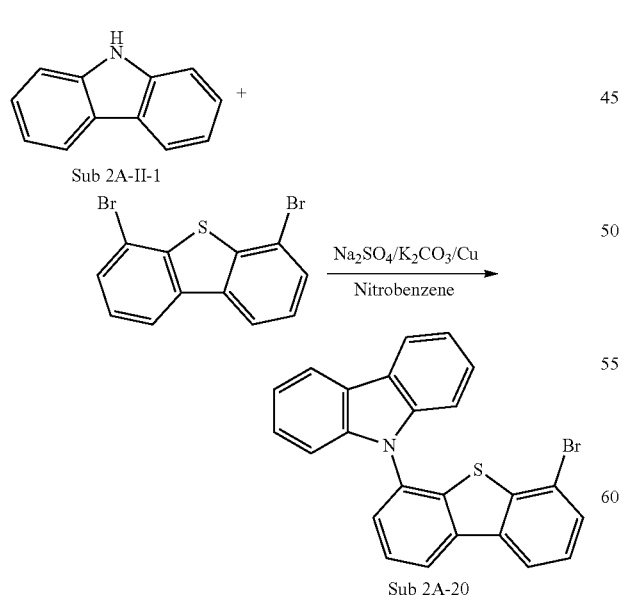

Sub 2A-II-1 (30 g, 179.4 mmol), nitrobenzene(897 ml), 2-bromo-7-iodo-9,9-diphenyl-9H-fluorene (78.8 g, 197.4 mmol), Na₂SO₄ (25.5 g, 179.4 mmol), K₂CO₃ (24.8 g, 179.4 mmol), Cu (3.4 g, 53.8 mmol) were carried out in the same manner as Sub 2A-1 to obtain 53 g of the product. (Yield: 69%)

Synthesis of Sub 2A-19

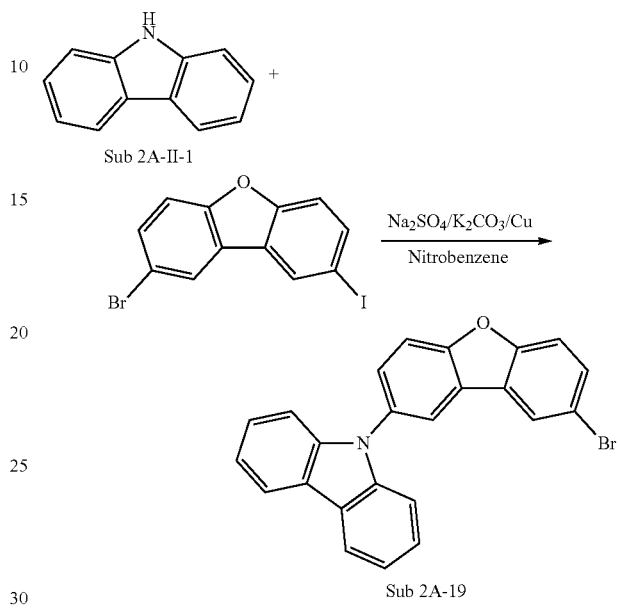

Sub 2A-II-1 (30 g, 179.4 mmol), nitrobenzene(897 ml), 2-bromo-7-iodo-9,9-diphenyl-9H-fluorene (78.8 g, 197.4 mmol), Na₂SO₄ (25.5 g, 179.4 mmol), K₂CO₃ (24.8 g, 179.4 mmol), Cu (3.4 g, 53.8 mmol) were carried out in the same manner as Sub 2A-1 to obtain 49.6 g of the product. (Yield: 67%)

Synthesis of Sub 2A-22

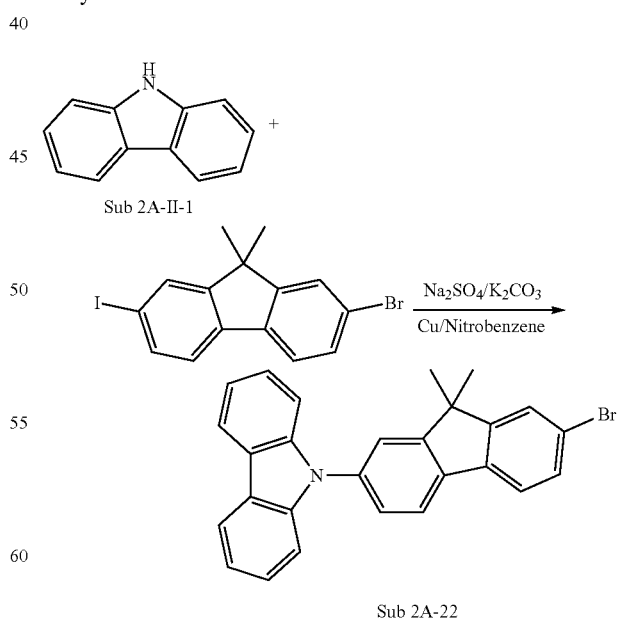

Sub 2A-II-1 (30 g, 179.4 mmol), nitrobenzene(897 ml), 2-bromo-7-iodo-9,9-dimethyl-9H-fluorene (78.8 g, 197.4 mmol), Na₂SO₄ (25.5 g, 179.4 mmol), K₂CO₃ (24.8 g, 179.4

Synthesis of Sub 2A-33

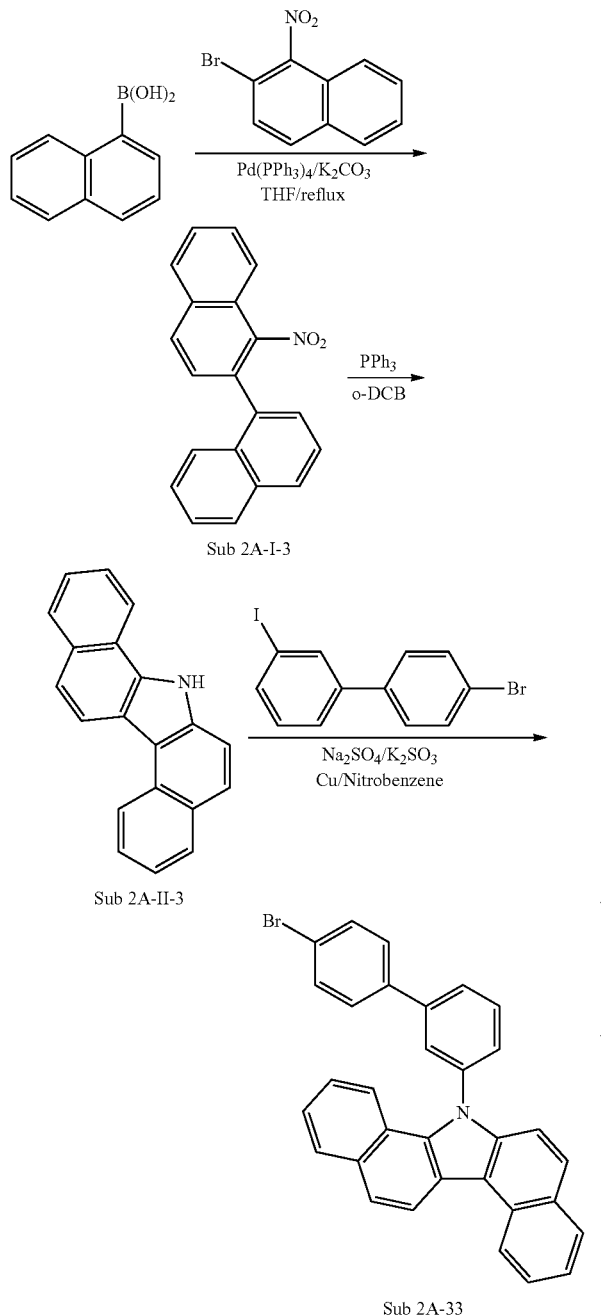

Sub 2A-33

1) Synthesis of intermediate Sub 2A-I-3 naphthalen-1-ylboronic acid (68.2 g, 396.7 mmol), THF (1745 ml), 2-bromo-1-nitronaphthalene (100 g, 396.7 mmol), Pd(PPh₃)₄ (13.8 g, 11.9 mmol), K₂CO₃ (164.5 g, 1190 mmol) and water (873 ml) were carried out in the same manner as Sub 2A-1 to obtain 83.1 g of the product. (Yield: 70%)

2) Synthesis of intermediate Sub 2A-II-3

Sub 2A-I-3 (80 g, 267.3 mmol), Triphenylphosphine (210.3 g, 801.8 mmol), o-Dichlorobenzene (1069 mL) were carried out in the same manner as Sub 2A-II-1 to obtain 45.7 g of the product. (Yield: 64%)

3) Synthesis of Sub 2A-33

Sub 2A-II-3 (45 g, 168.3 mmol), nitrobenzene(842 ml), 4'-bromo-3-iodo-1,1'-biphenyl (66.5 g, 185.2 m mol), Na₂SO₄ (23.9 g, 168.3 mmol), K₂CO₃ (23.3 g, 168.3 mmol), Cu (3.2 g, 50.5 mmol) were carried out in the same manner as Sub 2A-1 to obtain 50.3 g of the product. (Yield: 60%)

Synthesis of Sub 2A-34

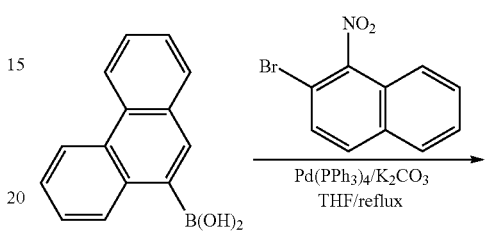

Sub 2A-I-4

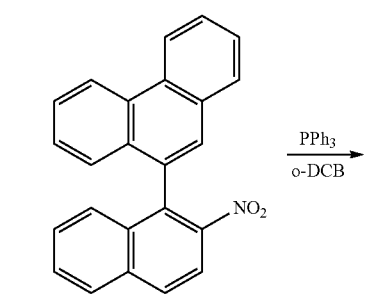

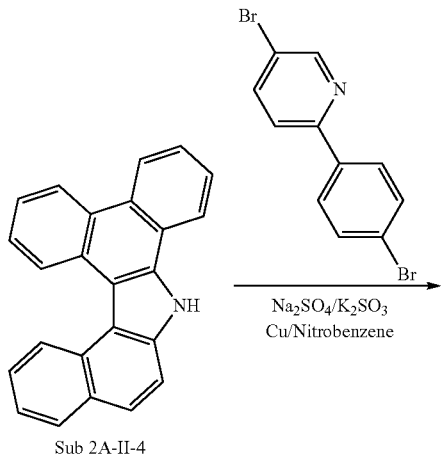

Sub 2A-II-4

-continued

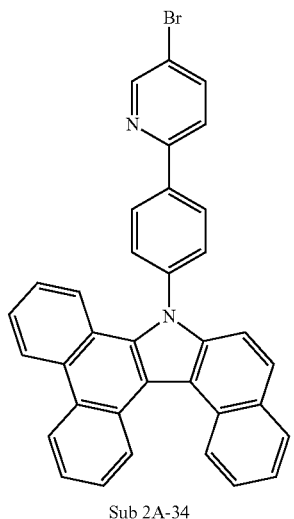

Sub 2A-34

1) Synthesis of Intermediate Sub 2A-I-4 naphthalen-1-ylboronic acid (44.05 g, 198.36 mmol), THF(873 ml), 2-bromo-1-nitronaphthalene (50 g, 198.36 mmol), Pd(PPh$_3$)$_4$ (6.88 g, 5.95 mmol), K$_2$CO$_3$ (82.25 g, 595.07 mmol) and water (436 ml) were carried out in the same manner as Sub 2A-I-1 to obtain 57.52 g of the product. (Yield: 83%)

2) Synthesis of intermediate Sub 2A-II-4

Sub 2A-I-4 (57.52 g, 164.63 mmol), Triphenylphosphine (107.95 g, 411.57 mmol), o-Dichlorobenzene (823 ml) were carried out in the same manner as Sub 2A-II-1 to obtain 22.99 g of the product. (Yield: 44%)

3) Synthesis of Sub 2A-34

Sub 2A-II-4 (22.99 g, 72.44 mmol), nitrobenzene(362 ml), 4'-bromo-3-iodo-1,1'-biphenyl (22.67 g, 72.44 mmol), Na$_2$SO$_4$ (5.14 g, 36.22 mmol), K$_2$CO$_3$ (5.01 g, 36.22 mmol), Cu (0.69 g, 10.87 mmol) were carried out in the same manner as Sub 2A-1 to obtain 26.27 g of the product. (Yield: 66%)

Synthesis of Sub 2-1

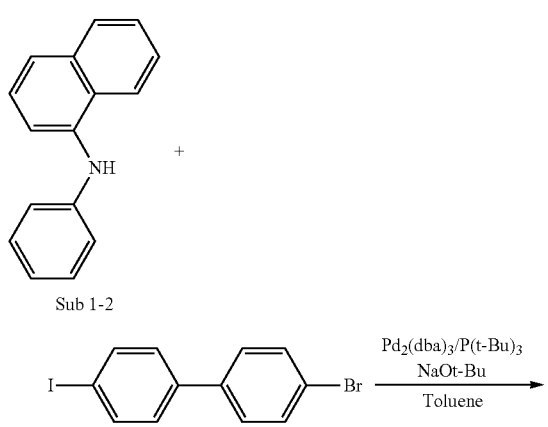

-continued

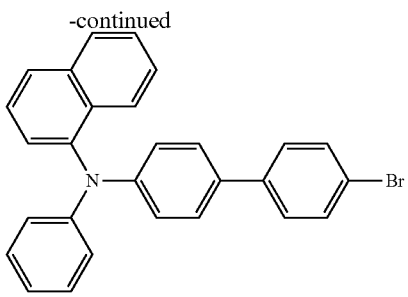

Sub 2-1

Sub 1-2 (20.16 g, 91.92 mmol) was dissolved in toluene (965 ml) in a round bottom flask, and 4-bromo-4'-iodo-1,1'-biphenyl (33 g, 91.92 mmol), Pd$_2$(dba)$_3$ (1.26 g, 1.38 mmol), P(t-Bu)$_3$ (0.56 g, 2.76 mmol), NaOt-Bu (13.25 g, 137.88 mmol) were added and stirred at 70° C. When the reaction was complete, the reaction mixture was extracted with CH$_2$Cl$_2$ and water. The organic layer was dried over MgSO$_4$ and concentrated. The resulting compound was separated by silicagel column chromatography and recrystallization to obtain 28.15 g (yield: 68%) of the product.

Synthesis of Sub 2-7

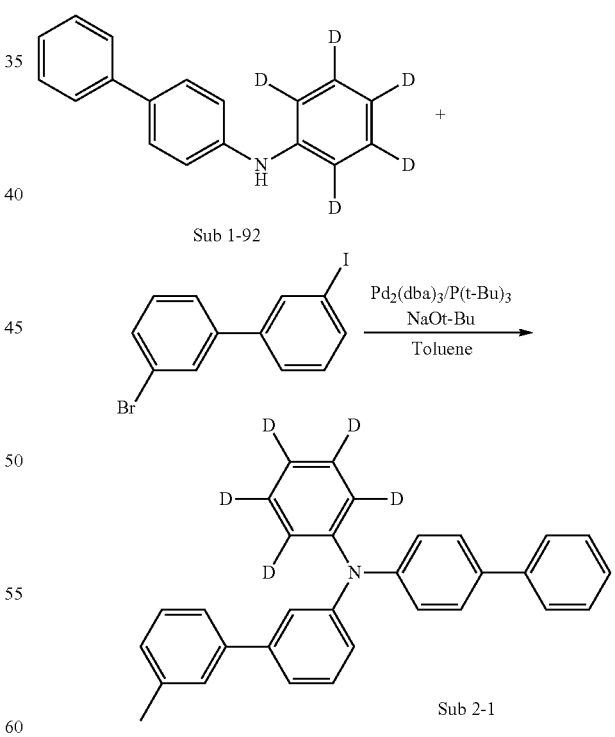

Sub 1-92 (17.43 g, 69.64 mmol), toluene (731 ml), 3-bromo-3'-iodo-1,1'-biphenyl (25 g, 69.64 mmol), Pd$_2$(dba)$_3$ (0.96 g, 1.04 mmol), P(t-Bu)$_3$ (0.42 g, 2.09 mmol), NaOt-Bu (10.04 g, 104.46 mmol) were carried out in the same manner as Sub 2-1 to obtain 23.13 g of the product. (Yield: 69%)

Synthesis of Sub 2-14

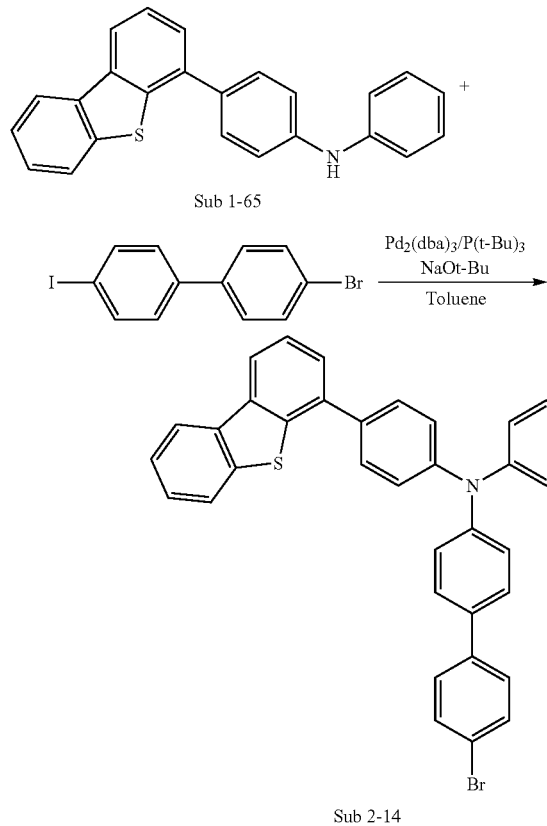

Sub 1-65 (24.48 g, 69.64 mmol), toluene (731 ml), 2-bromo-6-iodonaphthalene (25 g, 69.64 mmol), Pd$_2$(dba)$_3$ (0.96 g, 1.04 mmol), P(t-Bu)$_3$ (0.42 g, 2.09 mmol), NaOt-Bu (10.04 g, 104.46 mmol) were carried out in the same manner as Sub 2-1 to obtain 27.18 g of the product. (Yield: 67%)

Synthesis of Sub 2-28

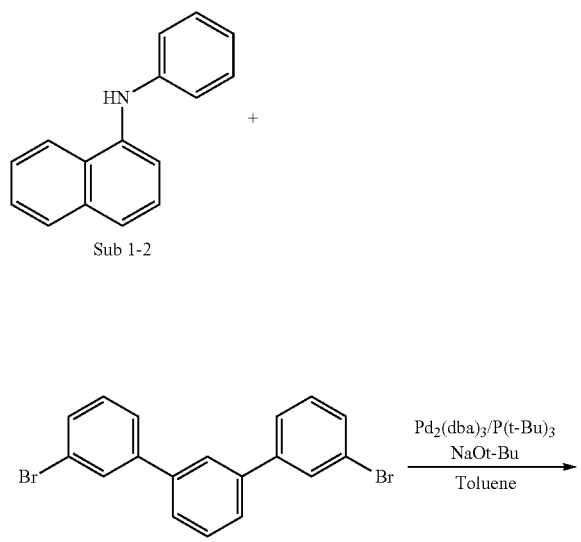

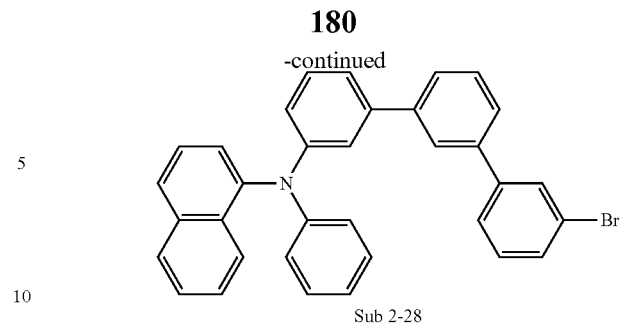

Sub 1-2 (21.87 g, 66.99 mmol), toluene (703 ml), 3,3"-dibromo-1,1':3',1"-terphenyl (26 g, 66.99 mmol), Pd$_2$(dba)$_3$ (0.92 g, 1 mmol), P(t-Bu)$_3$ (0.41 g, 2.01 mmol), NaOt-Bu (9.66 g, 100.49 mmol) were carried out in the same manner as Sub 2-1 to obtain 21.87 g of the product. (Yield: 62%)

Synthesis of Sub 2-29

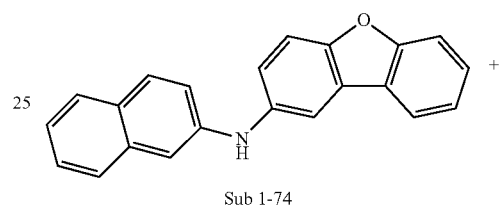

Sub 1-74

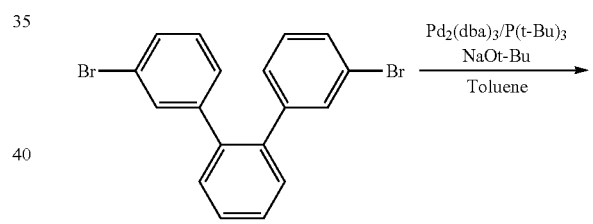

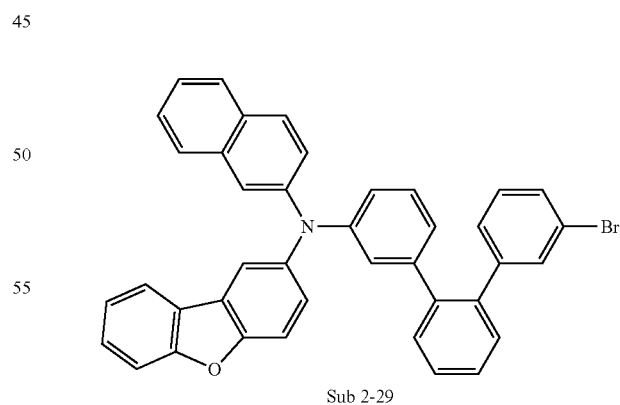

Sub 2-29

Sub 1-74 (20.73 g, 66.99 mmol), toluene (703 ml), 3,3"-dibromo-1,1':2',1"-terphenyl (26 g, 66.99 mmol), Pd$_2$(dba)$_3$ (0.92 g, 1 mmol), P(t-Bu)$_3$ (0.41 g, 2.01 mmol), NaOt-Bu (9.66 g, 100.49 mmol) were carried out in the same manner as Sub 2-1 to obtain 24.78 g of the product. (Yield: 60%)

Synthesis of Sub 2-36

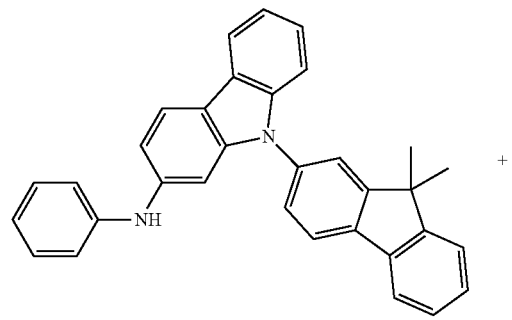

Sub 1-65

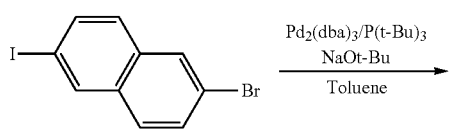

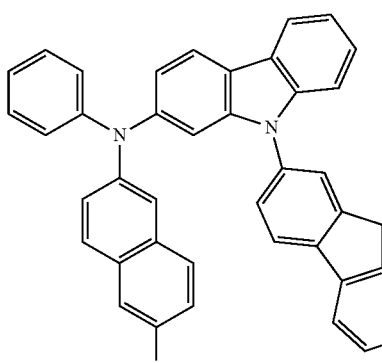

Sub 2-36

Sub 1-106 (31.12 g, 69.08 mmol), toluene (725 ml), 2-bromo-6-iodonaphthalene (23 g, 69.08 mmol), Pd₂(dba)₃ (0.95 g, 1.04 mmol), P(t-Bu)₃ (0.42 g, 2.07 mmol), NaOt-Bu (9.96 g, 103.61 mmol) were carried out in the same manner as Sub 2-1 to obtain 28.98 g of the product. (Yield: 64%)

Synthesis of Sub 2-44

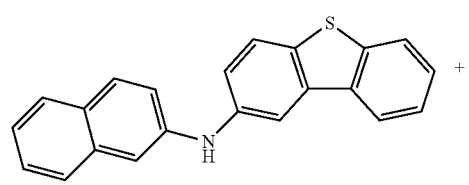

Sub 1-55

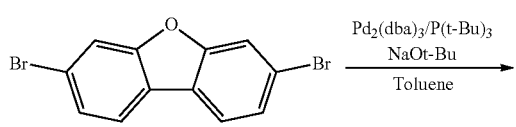

-continued

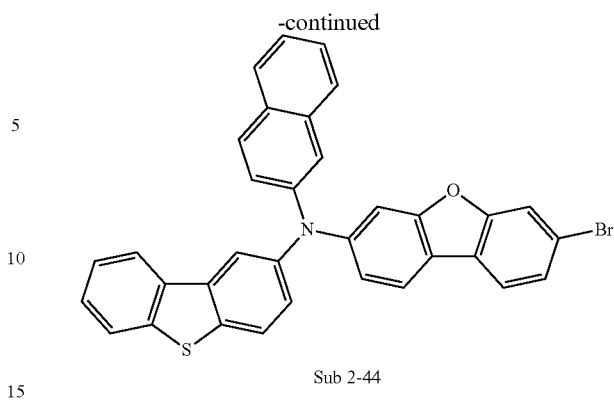

Sub 2-44

Sub 1-55 (25.96 g, 79.76 mmol), toluene (837 ml), 3,7-dibromodibenzo[b,d]furan (26 g, 79.76 mmol), Pd₂(dba)₃ (1.10 g, 1.20 mmol), P(t-Bu)₃ (0.48 g, 2.39 mmol), NaOt-Bu (11.5 g, 119.64 mmol) were carried out in the same manner as Sub 2-1 to obtain 30.94 g of the product. (Yield: 68%)

Synthesis of Sub 2-56

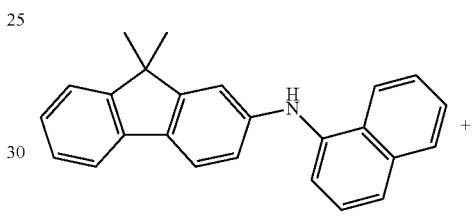

Sub 1-25

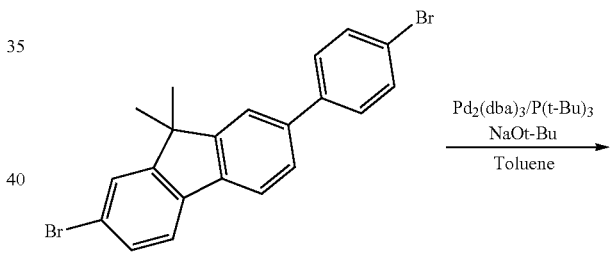

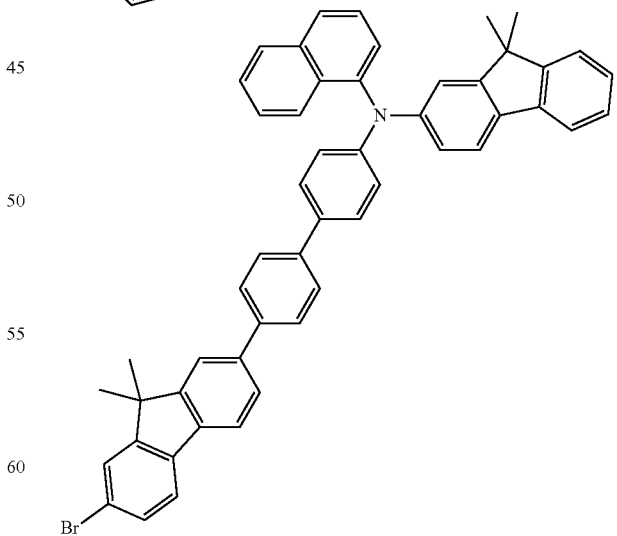

Sub 2-56

Sub 1-25 (20.37 g, 60.72 mmol), toluene (638 ml), 2-bromo-7-(4-bromophenyl)-9,9-dimethyl-9H-fluorene (26 g, 60.72 mmol), Pd₂(dba)₃ (0.83 g, 0.91 mmol), P(t-Bu)₃ (0.37 g, 1.82 mmol), NaOt-Bu (8.75 g, 91.09 mmol) were carried out in the same manner as Sub 2-1 to obtain 25.70 g of the product. (Yield: 62%)

Synthesis of Sub 2-59

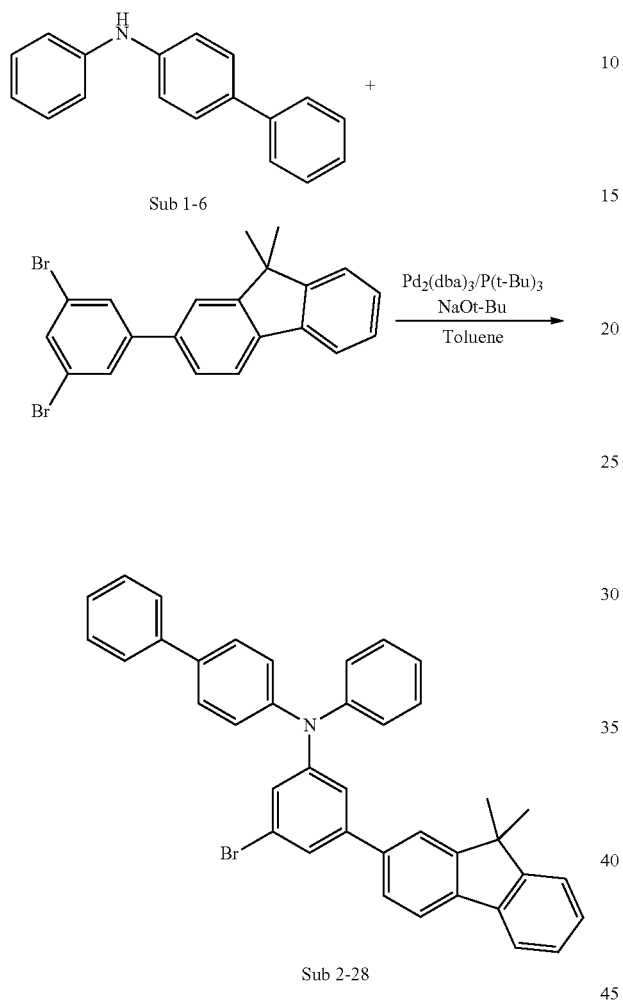

Sub 1-6 (14.90 g, 60.72 mmol), toluene (638 ml), 2-(3, 5-dibromophenyl)-9,9-dimethyl-9H-fluorene (26 g, 60.72 mmol), Pd₂(dba)₃ (0.83 g, 0.91 mmol), P(t-Bu)₃ (0.37 g, 1.82 mmol), NaOt-Bu (8.75 g, 91.09 mmol) were carried out in the same manner as Sub 2-1 to obtain 21.23 g of the product. (Yield: 59%)

Examples of Sub 2 and Sub 2A are as follows, but are not limited thereto.

Sub 2A-1

Sub 2A-2

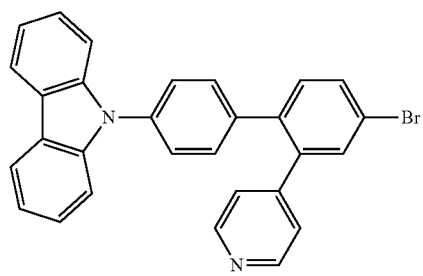

Sub 2A-3

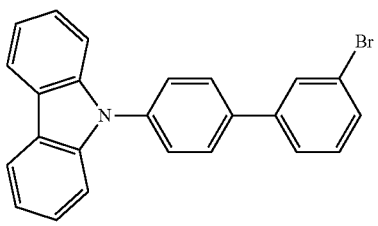

Sub 2A-4

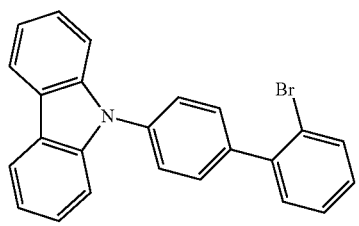

Sub 2A-5

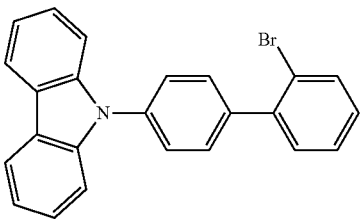

Sub 2A-6

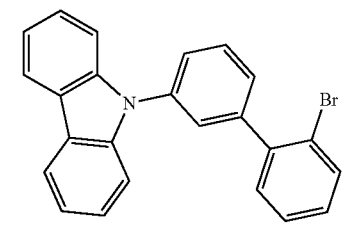

Sub 2A-7

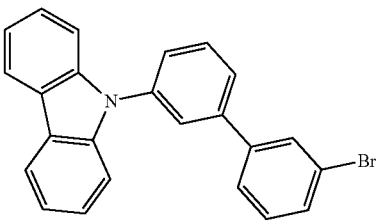

Sub 2A-8
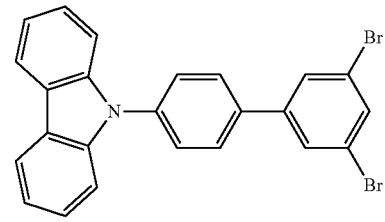
Sub 2A-9
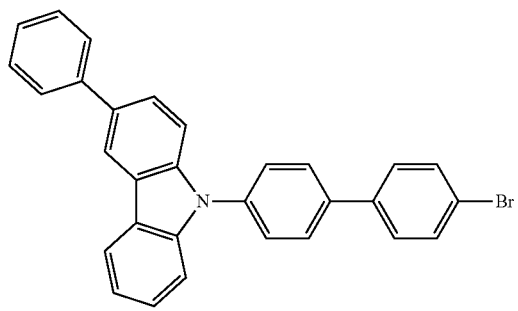
Sub 2A-10
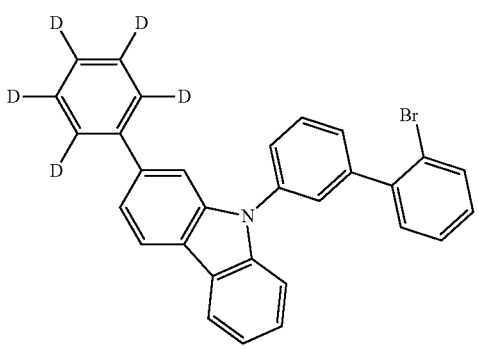
Sub 2A-11
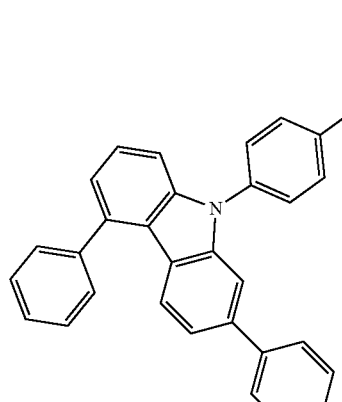
Sub 2A-12
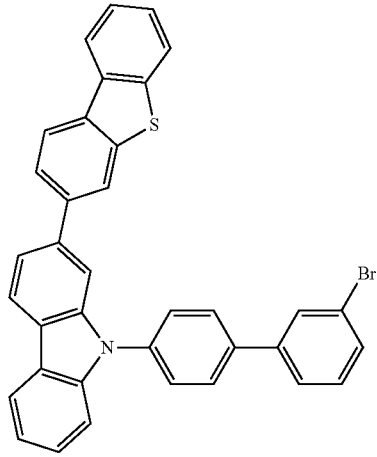
Sub 2A-13
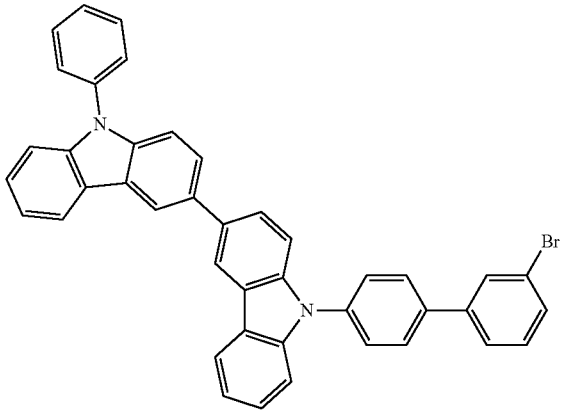
Sub 2A-14
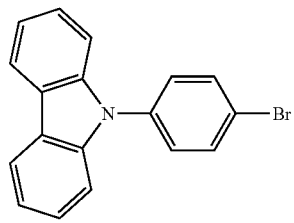
Sub 2A-15
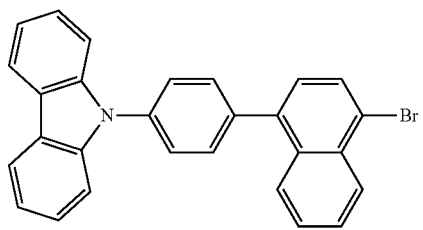
Sub 2A-16
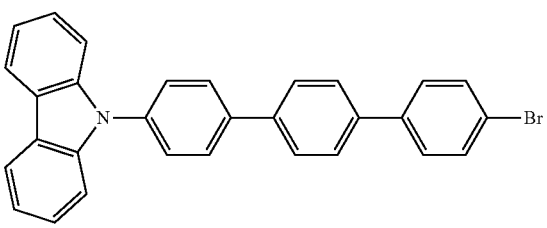

Sub 2A-17
Sub 2A-18
Sub 2A-19
Sub 2A-20
Sub 2A-21
Sub 2A-22
Sub 2A-23
Sub 2A-24
Sub 2A-25
Sub 2A-26
Sub 2A-27
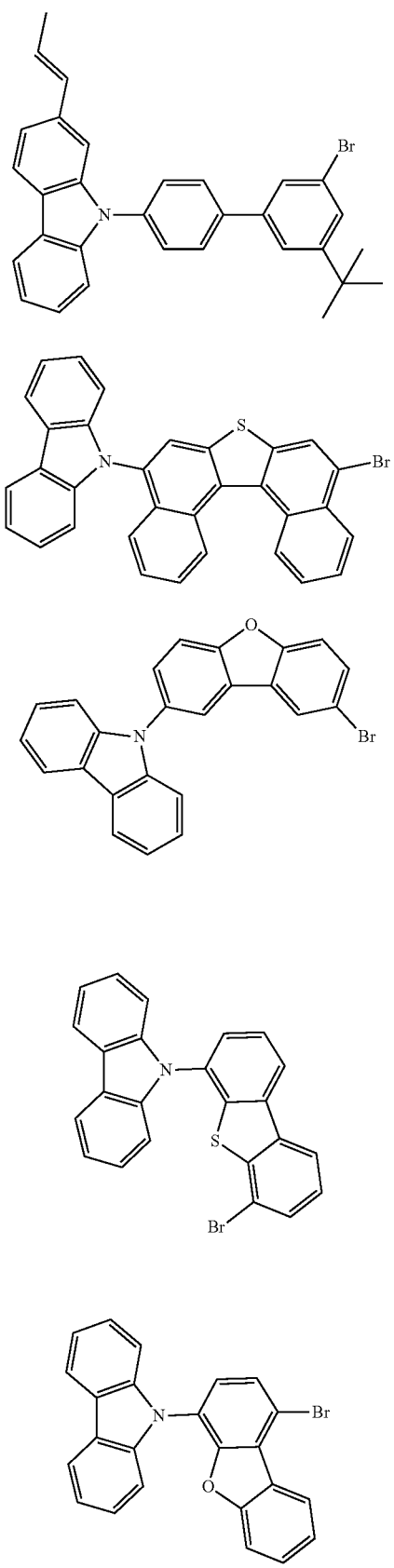
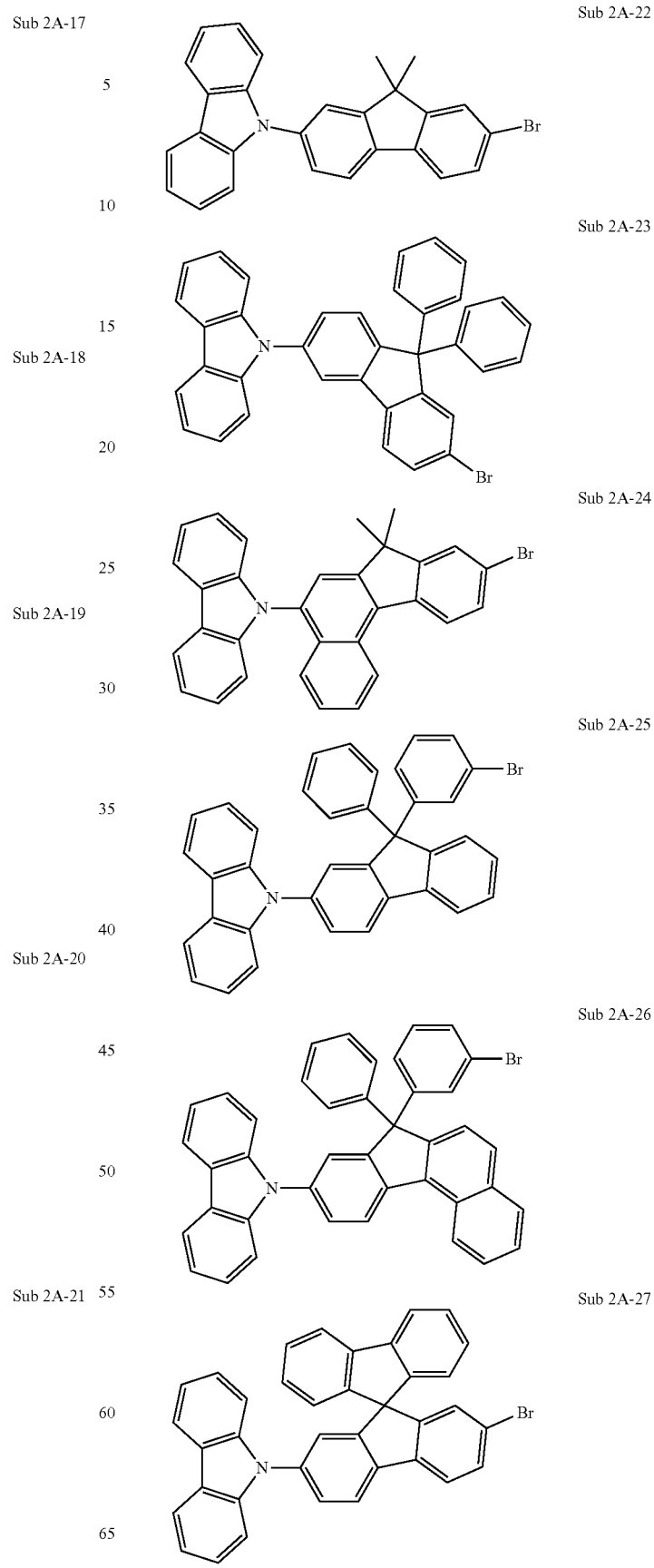

Sub 2A-28
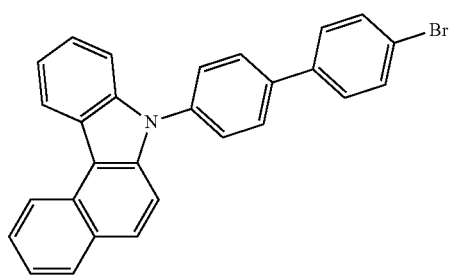
Sub 2A-29
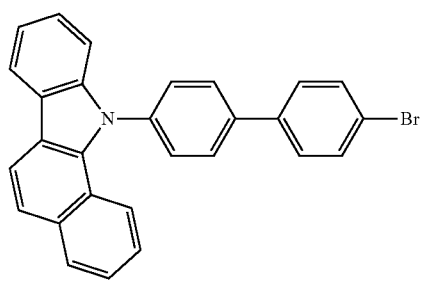
Sub 2A-30
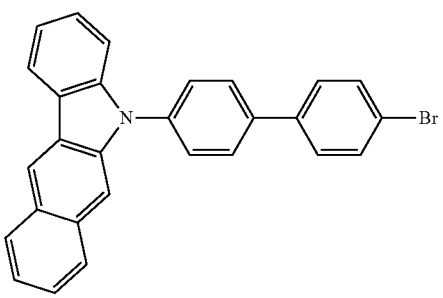
Sub 2A-31
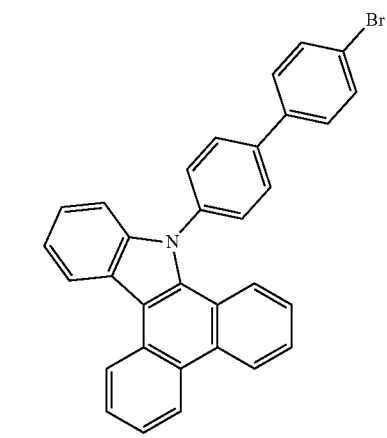
Sub 2A-32
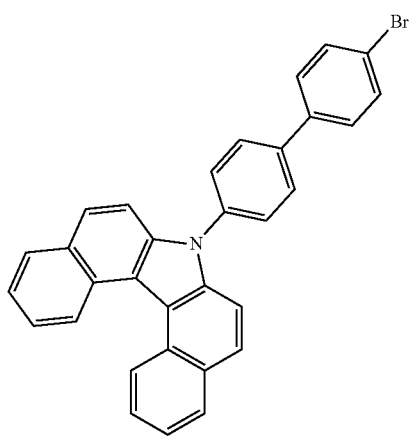
Sub 2A-33
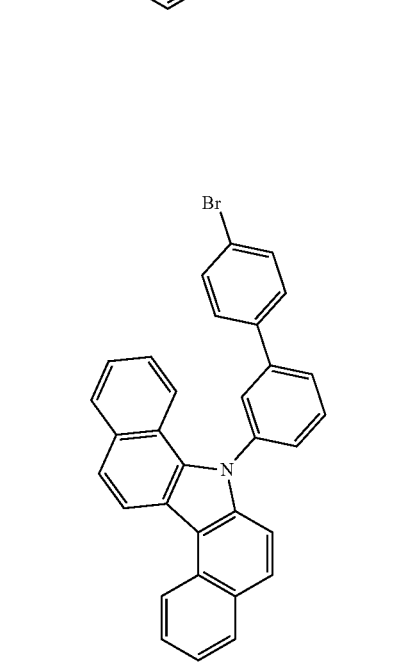
Sub 2A-34
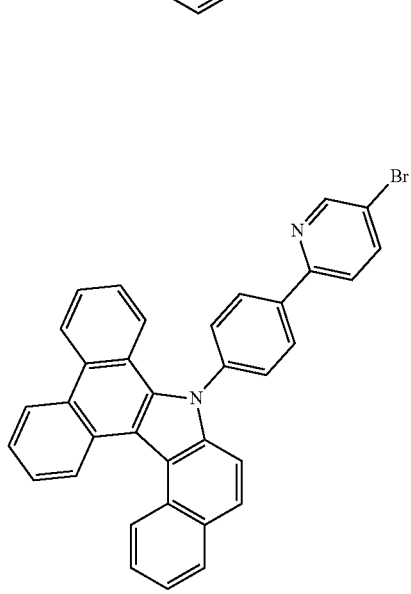

Sub 2A-35
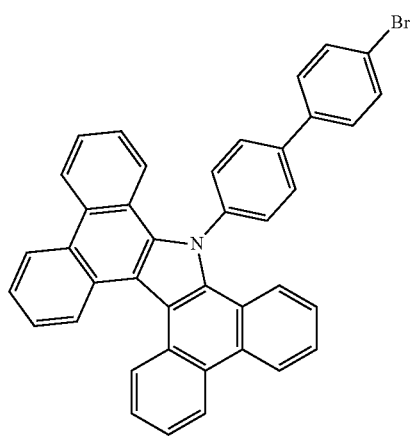
Sub 2A-36
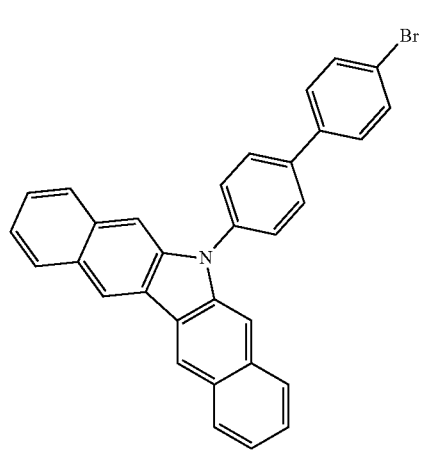
Sub 2-1
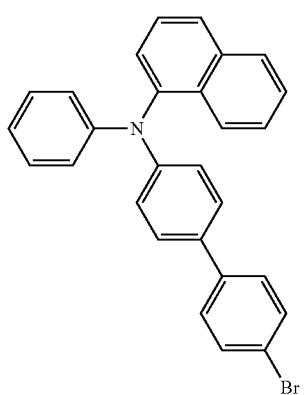
Sub 2-2
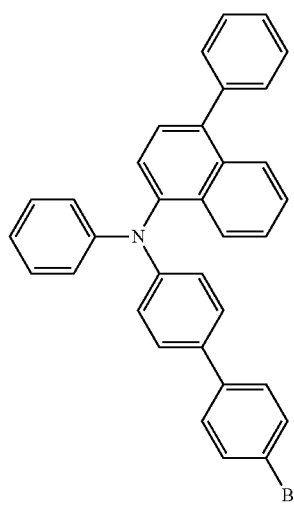
Sub 2-3
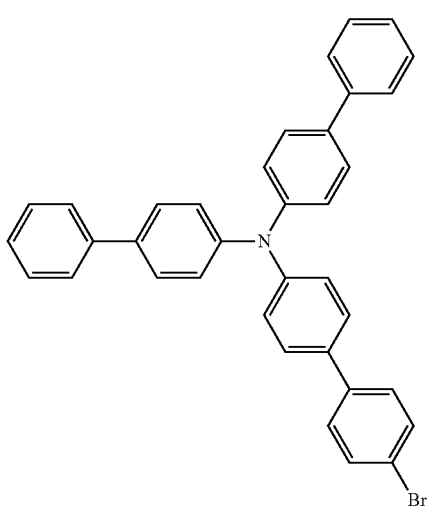
Sub 2-4
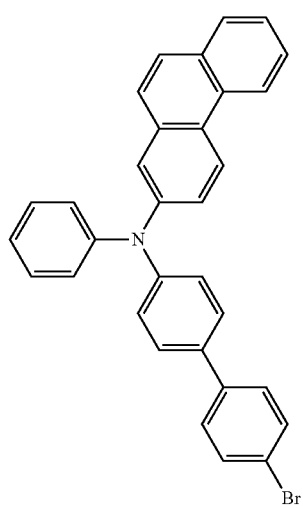

Sub 2-5
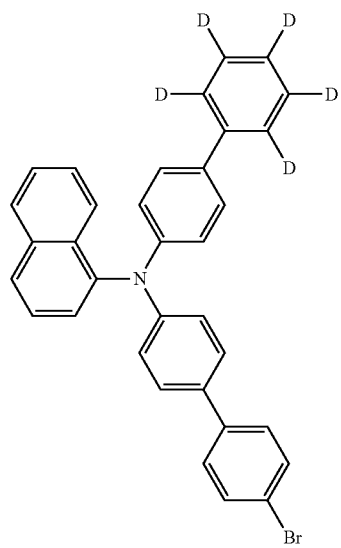
Sub 2-6
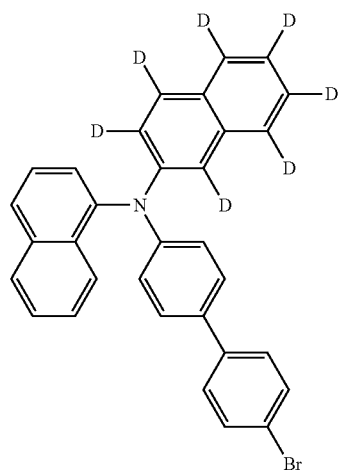
Sub 2-7
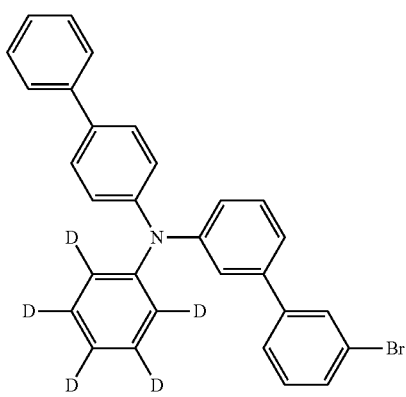
Sub 2-8
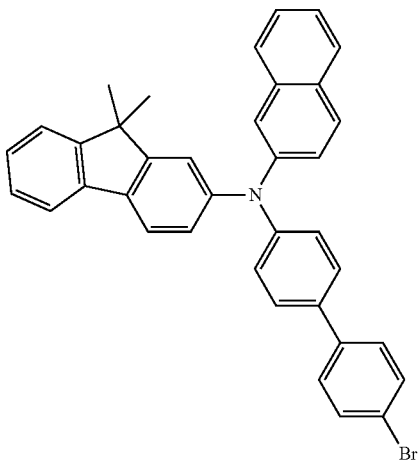
Sub 2-9
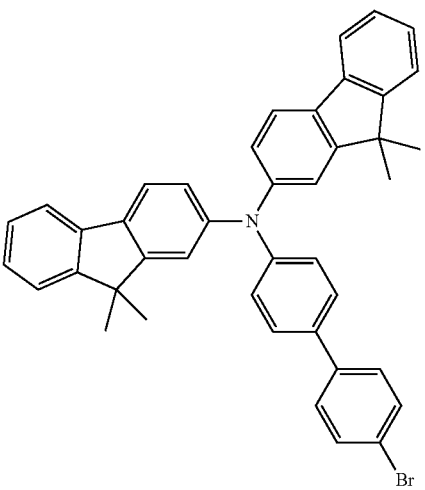
Sub 2-10
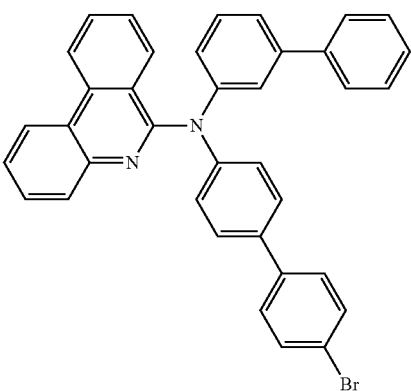

Sub 2-11
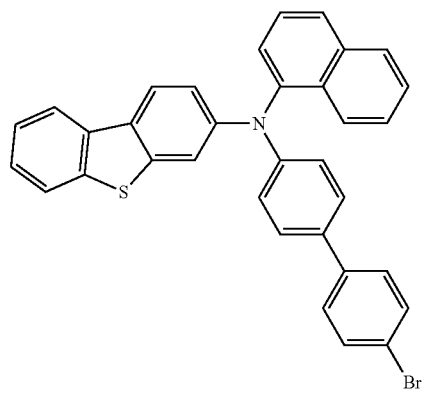
Sub 2-12
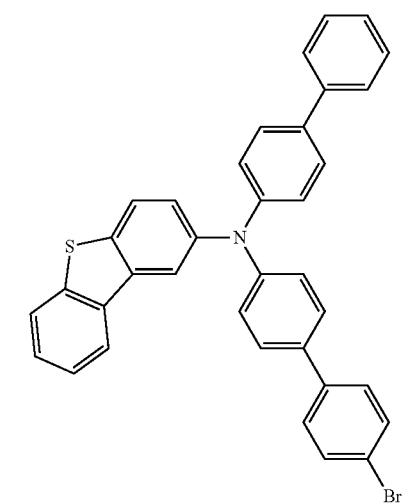
Sub 2-13
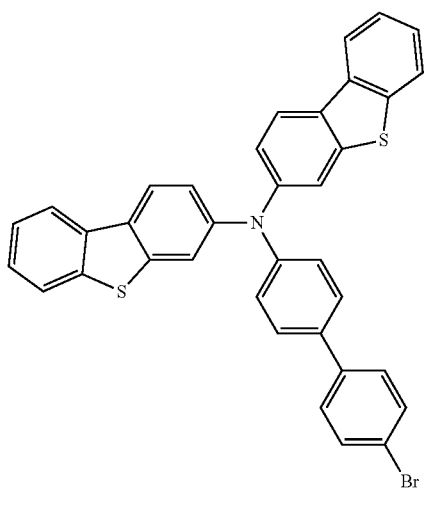
Sub 2-14
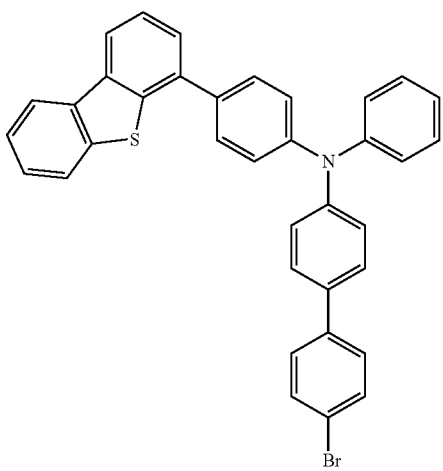
Sub 2-15
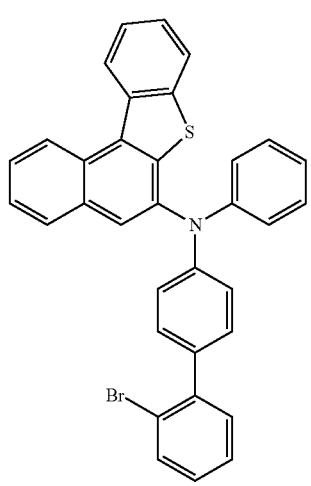
Sub 2-16
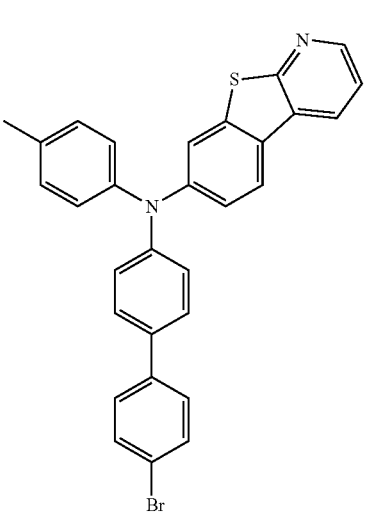

Sub 2-17
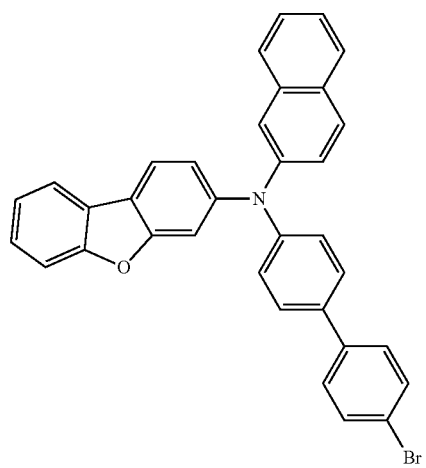
Sub 2-18
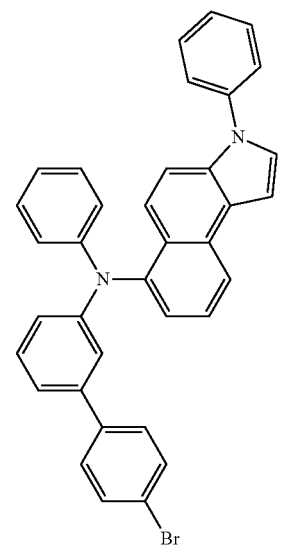
Sub 2-19
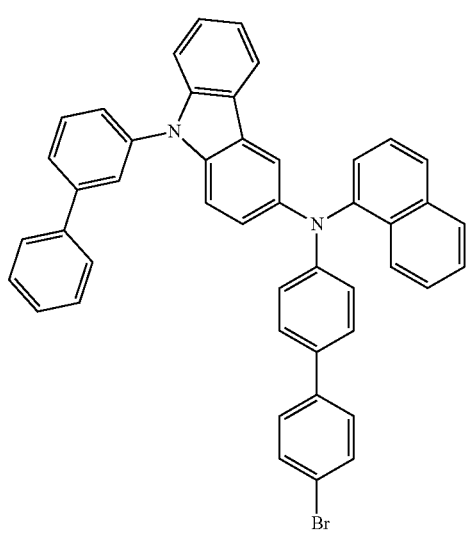
Sub 2-20
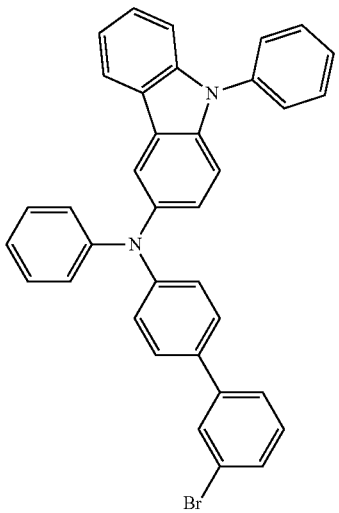
Sub 2-21
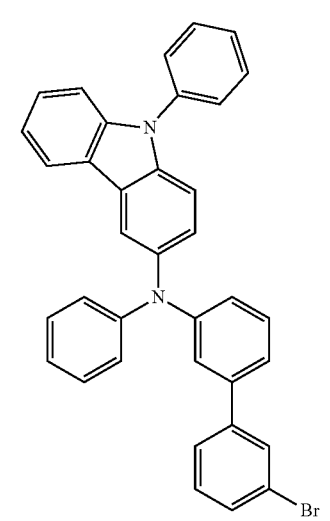
Sub 2-22
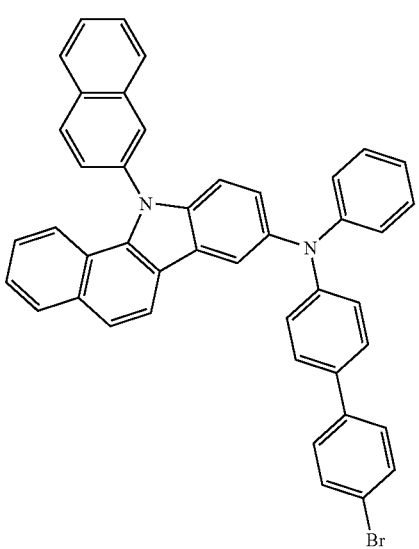

-continued
Sub 2-23
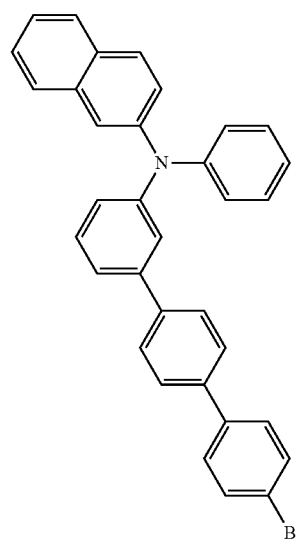
Sub 2-24
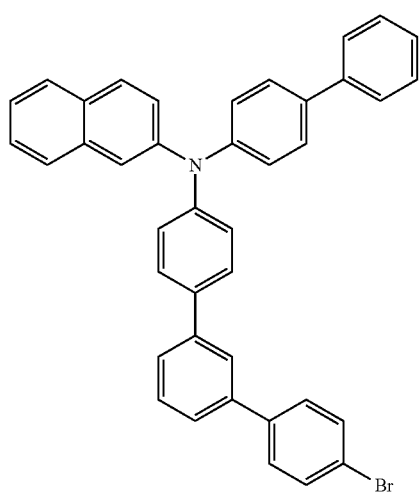
Sub 2-25
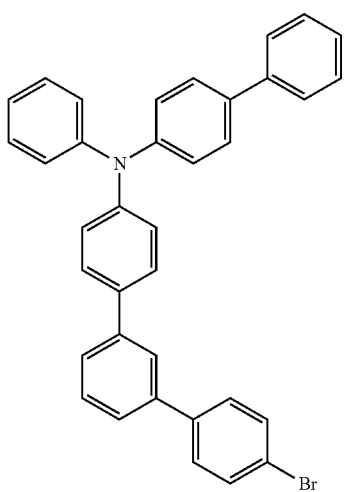
Sub 2-26
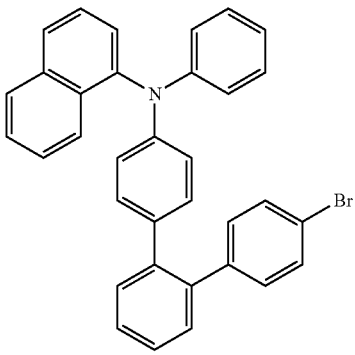
Sub 2-27
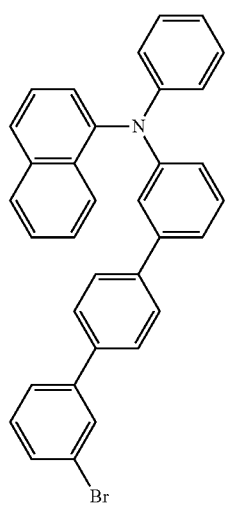
Sub 2-28
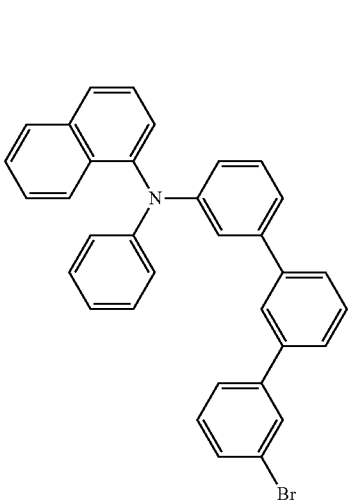

Sub 2-29
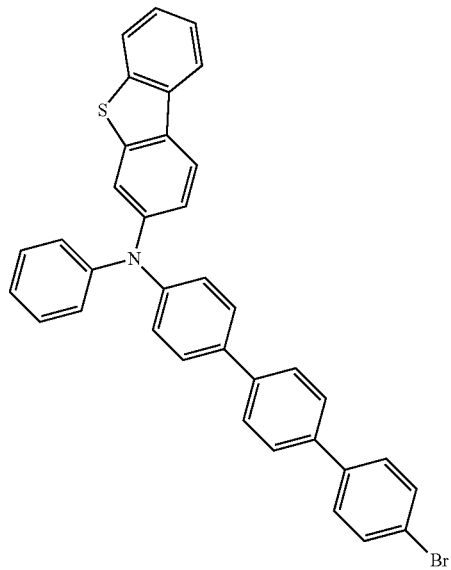
Sub 2-30
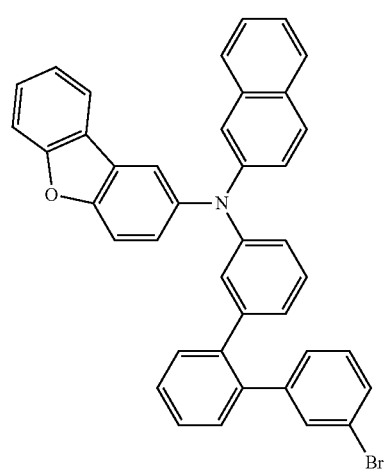
Sub 2-31
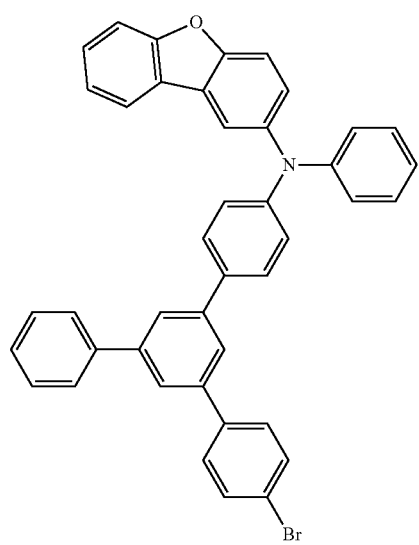
Sub 2-32
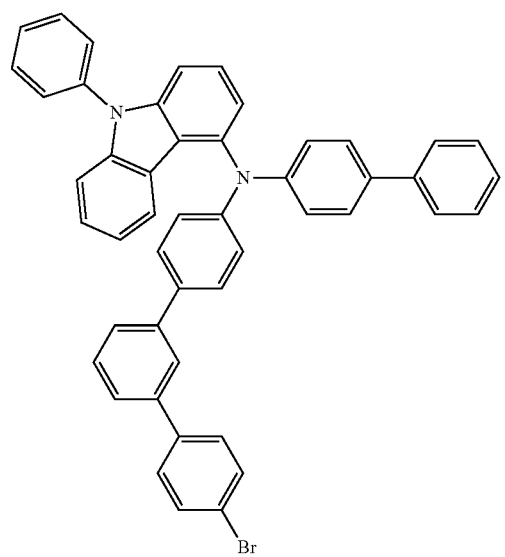
Sub 2-33
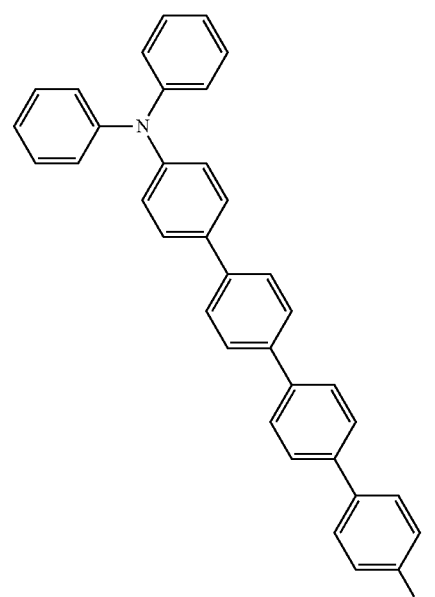
Sub 2-34
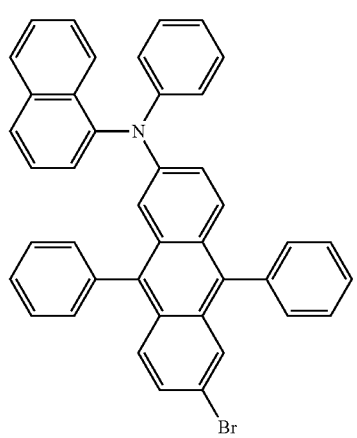

Sub 2-35
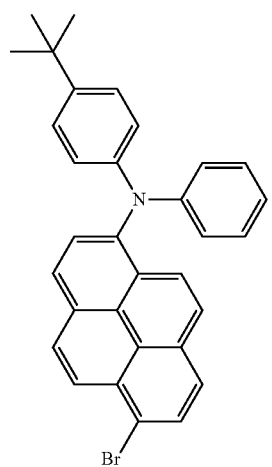
Sub 2-36
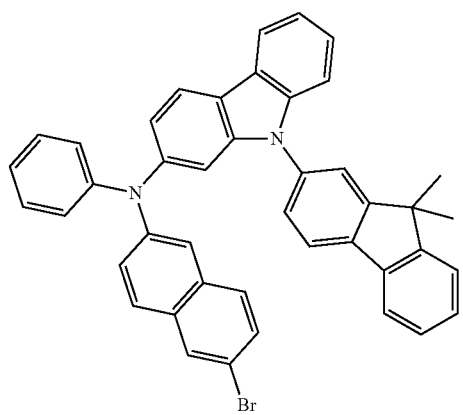
Sub 2-37
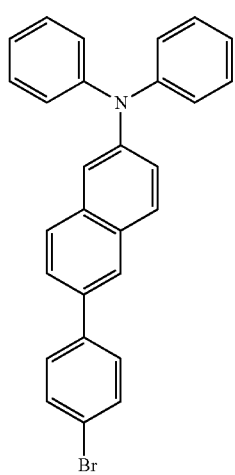
Sub 2-38
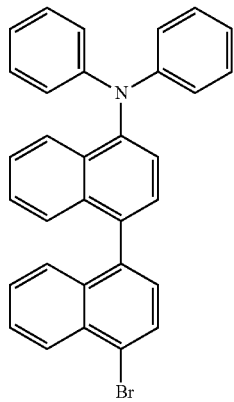
Sub 2-39
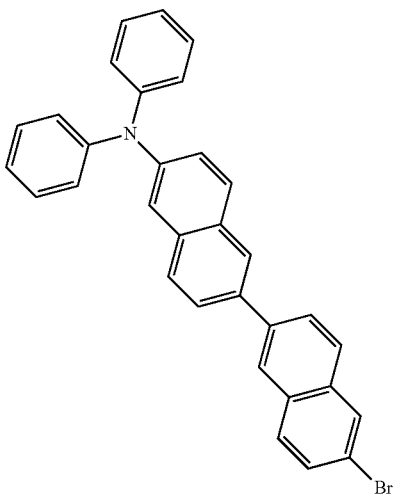
Sub 2-40
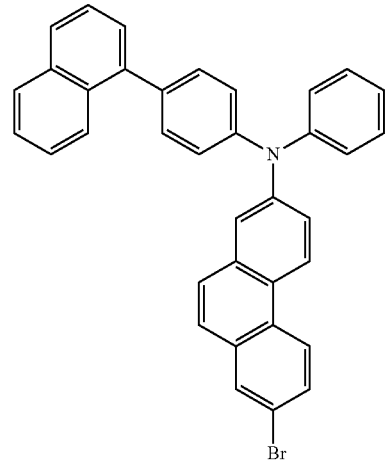

205
-continued
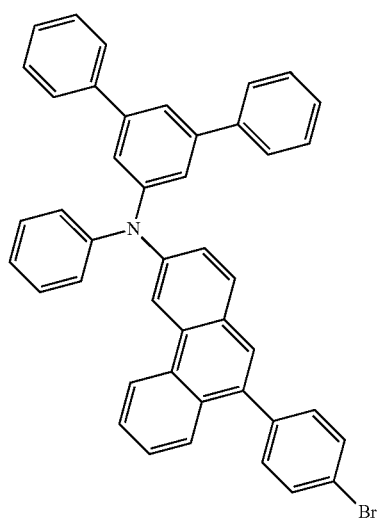
Sub 2-41
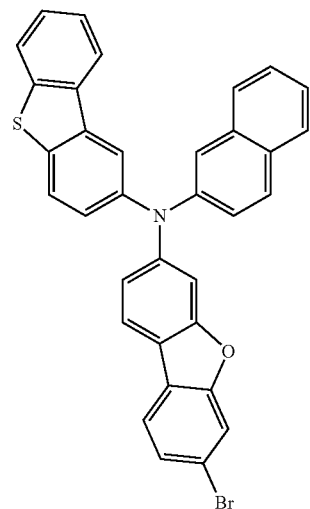
Sub 2-44
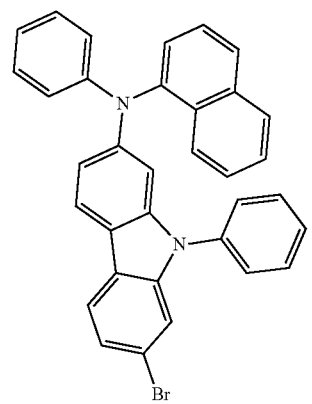
Sub 2-42
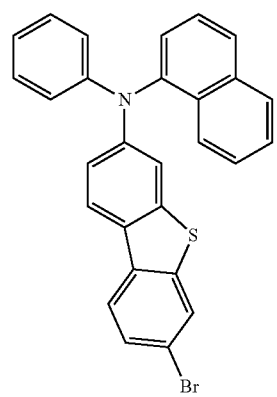
Sub 2-45
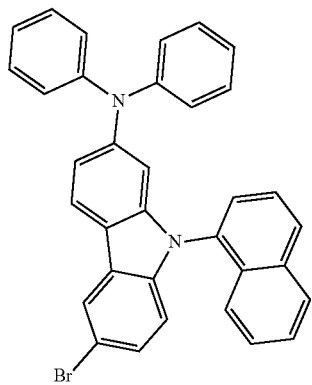
Sub 2-43
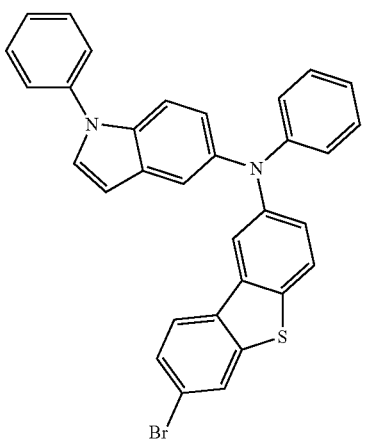
Sub 2-46
206
-continued Sub 2-47
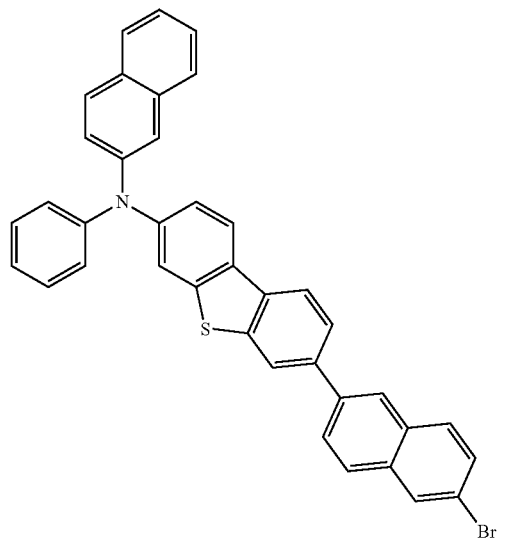
Sub 2-48
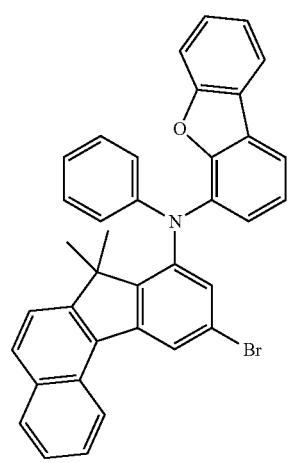
Sub 2-49
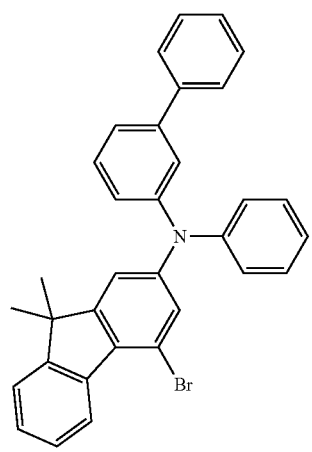
Sub 2-50
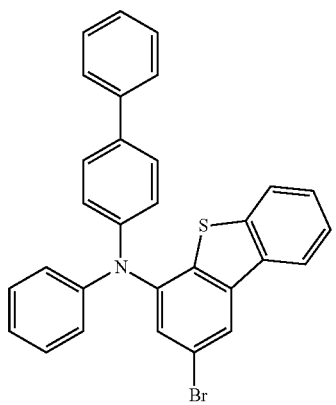
Sub 2-51
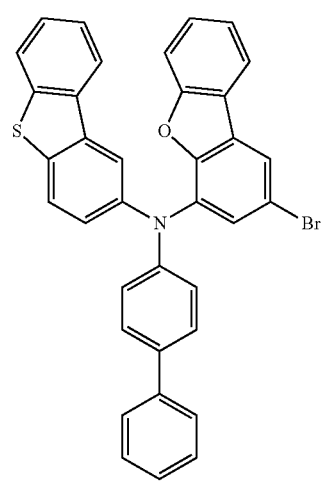
Sub 2-52
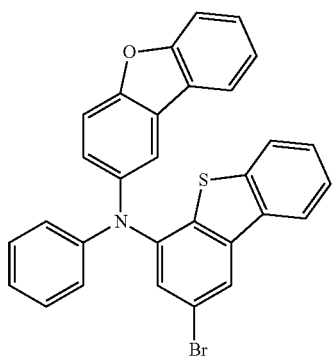

-continued
Sub 2-53
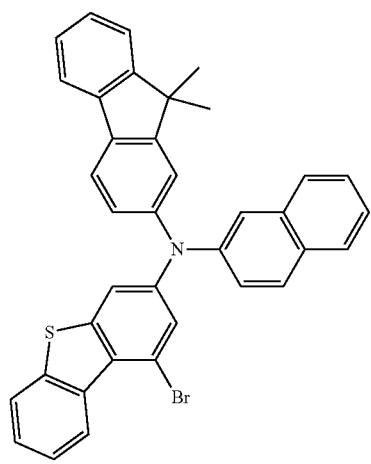
Sub 2-54
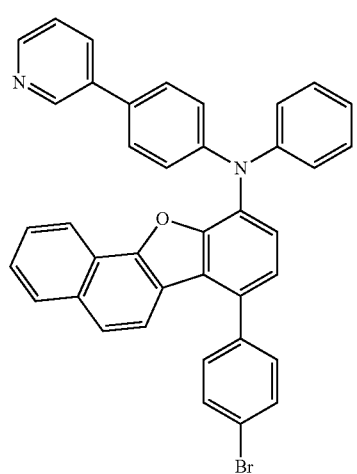
Sub 2-55
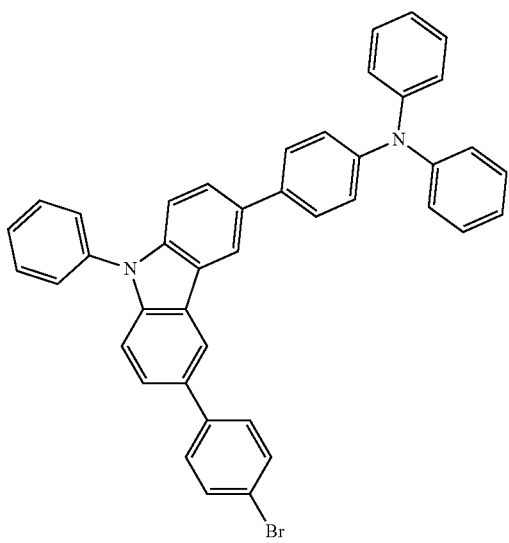
-continued
Sub 2-56
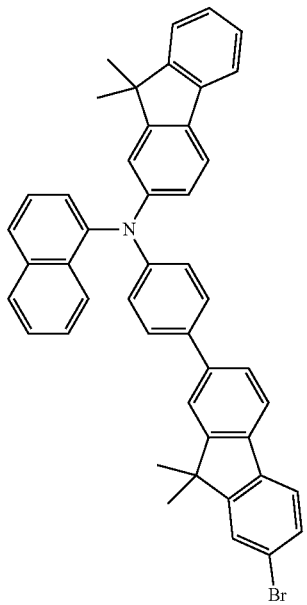
Sub 2-57
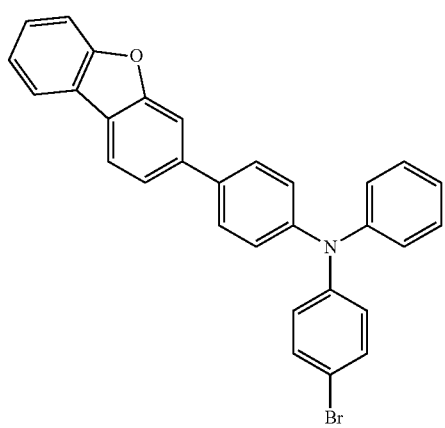
Sub 2-58
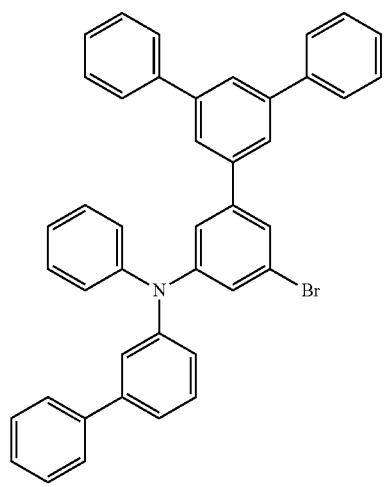

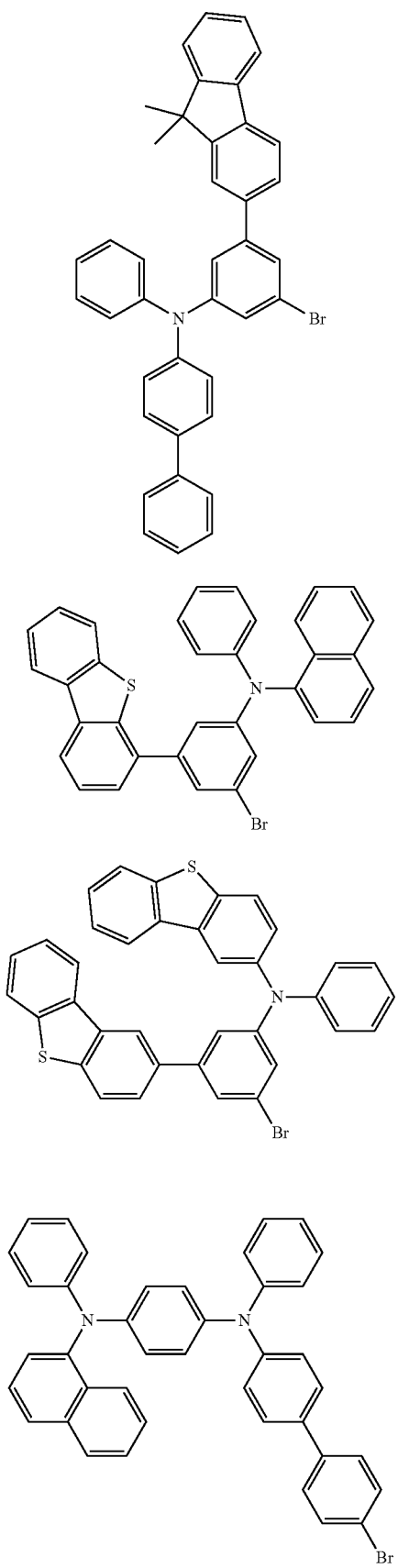
Sub 2-59
Sub 2-60
Sub 2-61
Sub 2-62
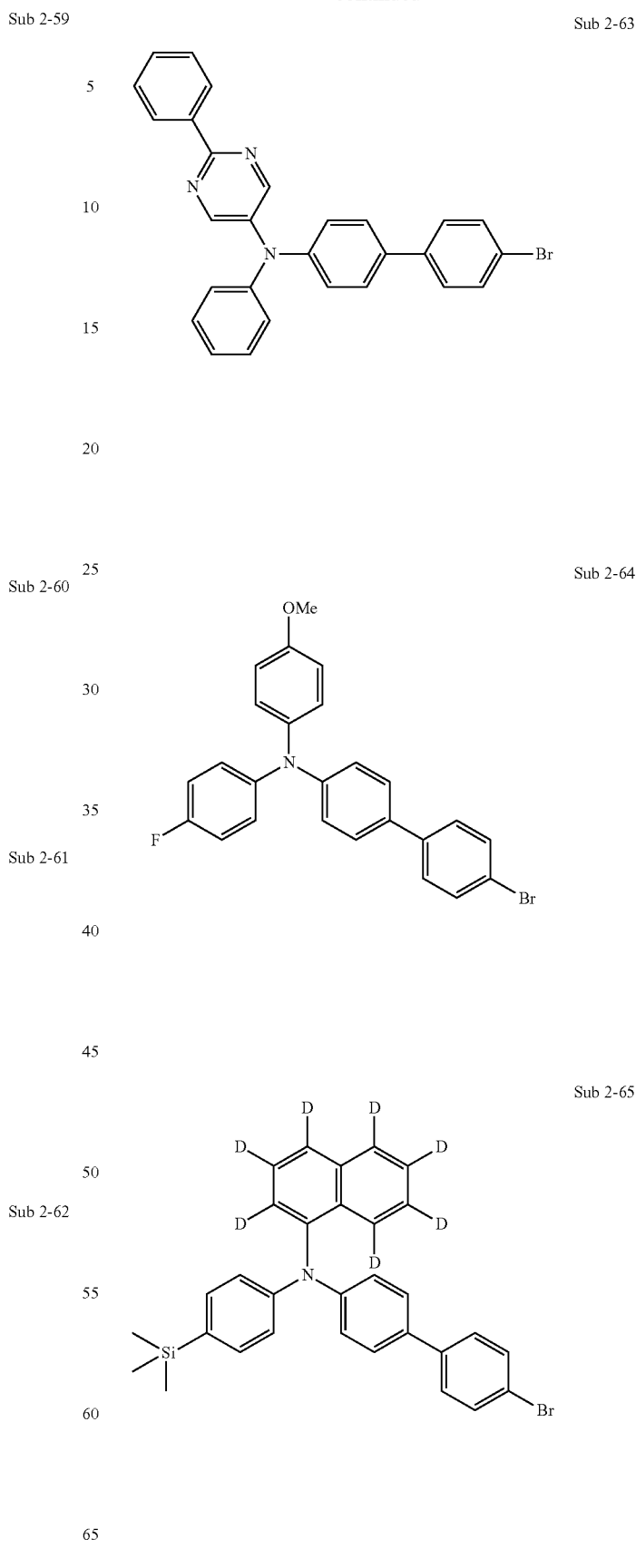
Sub 2-63
Sub 2-64
Sub 2-65

TABLE 2

| compound | FD-MS | compound | FD-MS |
|---|---|---|---|
| Sub 2A-1 | m/z = 397.05 ($C_{24}H_{16}BrN$ = 398.29) | Sub 2A-2 | m/z = 474.07 ($C_{29}H_{19}BrN_2$ = 475.38) |
| Sub 2A-3 | m/z = 397.05 ($C_{24}H_{16}BrN$ = 398.29) | Sub 2A-4 | m/z = 397.05 ($C_{24}H_{16}BrN$ = 398.29) |
| Sub 2A-5 | m/z = 397.05 ($C_{24}H_{16}BrN$ = 398.29) | Sub 2A-6 | m/z = 397.05 ($C_{24}H_{16}BrN$ = 398.29) |
| Sub 2A-7 | m/z = 397.05 ($C_{24}H_{16}BrN$ = 398.29) | Sub 2A-8 | m/z = 474.96 ($C_{24}H_{15}Br_2N$ = 477.20) |
| Sub 2A-9 | m/z = 473.08 ($C_{30}H_{20}BrN$ = 474.39) | Sub 2A-10 | m/z = 478.11 ($C_{30}H_{15}D_5BrN$ = 479.43) |
| Sub 2A-11 | m/z = 550.10 ($C_{35}H_{23}BrN_2$ = 551.49) | Sub 2A-12 | m/z = 579.07 ($C_{36}H_{22}BrNS$ = 580.54) |
| Sub 2A-13 | m/z = 638.14 ($C_{42}H_{27}BrN_2$ = 639.58) | Sub 2A-14 | m/z = 321.02 ($C_{13}H_{12}BrN$ = 322.20) |
| Sub 2A-15 | m/z = 447.06 ($C_{28}H_{18}BrN$ = 448.35) | Sub 2A-16 | m/z = 473.08 ($C_{30}H_{20}BrN$ = 474.40) |
| Sub 2A-17 | m/z = 493.14 ($C_{31}H_{28}BrN$ = 494.48) | Sub 2A-18 | m/z = 527.03 ($C_{32}H_{18}BrNS$ = 528.46) |
| Sub 2A-19 | m/z = 411.03 ($C_{24}H_{14}BrNO$ = 412.28) | Sub 2A-20 | m/z = 427.00 ($C_{24}H_{14}BrNS$ = 428.34) |
| Sub 2A-21 | m/z = 411.03 ($C_{24}H_{14}BrNO$ = 412.28) | Sub 2A-22 | m/z = 437.08 ($C_{27}H_{20}BrN$ = 438.36) |
| Sub 2A-23 | m/z = 561.11 ($C_{37}H_{24}BrN$ = 562.50) | Sub 2A-24 | m/z = 487.09 ($C_{31}H_{22}BrN$ = 488.42) |
| Sub 2A-25 | m/z = 561.11 ($C_{37}H_{24}BrN$ = 562.50) | Sub 2A-26 | m/z = 611.12 ($C_{41}H_{26}BrN$ = 612.56) |
| Sub 2A-27 | m/z = 559.09 ($C_{37}H_{22}BrN$ = 560.48) | Sub 2A-28 | m/z = 447.06 ($C_{28}H_{18}BrN$ = 448.35) |
| Sub 2A-29 | m/z = 447.06 ($C_{28}H_{18}BrN$ = 448.35) | Sub 2A-30 | m/z = 447.06 ($C_{28}H_{18}BrN$ = 448.35) |
| Sub 2A-31 | m/z = 497.08 ($C_{32}H_{20}BrN$ = 498.41) | Sub 2A-32 | m/z = 497.08 ($C_{32}H_{20}BrN$ = 498.41) |
| Sub 2A-33 | m/z = 497.08 ($C_{32}H_{20}BrN$ = 498.41) | Sub 2A-34 | m/z = 548.09 ($C_{35}H_{21}BrN_2$ = 549.46) |
| Sub 2A-35 | m/z = 597.11 ($C_{40}H_{24}BrN$ = 598.53) | Sub 2A-36 | m/z = 497.08 ($C_{32}H_{20}BrN$ = 498.41) |
| Sub 2-1 | m/z = 449.08 ($C_{28}H_{20}BrN$ = 450.37) | Sub 2-2 | m/z = 525.11 ($C_{34}H_{24}BrN$ = 526.48) |
| Sub 2-3 | m/z = 551.12 ($C_{36}H_{26}BrN$ = 552.50) | Sub 2-4 | m/z = 499.09 ($C_{32}H_{22}BrN$ = 500.43) |
| Sub 2-5 | m/z = 530.14 ($C_{34}H_{19}D_5BrN$ = 531.51) | Sub 2-6 | m/z = 506.14 ($C_{32}H_{15}D_7BrN$ = 507.48) |
| Sub 2-7 | m/z = 480.12 ($C_{30}H_{17}D_5BrN$ = 481.45) | Sub 2-8 | m/z = 565.14 ($C_{37}H_{28}BrN$ = 566.54) |
| Sub 2-9 | m/z = 631.19 ($C_{42}H_{34}BrN$ = 632.65) | Sub 2-10 | m/z = 576.12 ($C_{37}H_{25}BrN_2$ = 577.53) |
| Sub 2-11 | m/z = 555.07 ($C_{34}H_{22}BrNS$ = 556.51) | Sub 2-12 | m/z = 581.08 ($C_{36}H_{24}BrNS$ = 582.55) |
| Sub 2-13 | m/z = 611.04 ($C_{36}H_{22}BrNS_2$ = 612.60) | Sub 2-14 | m/z = 581.08 ($C_{36}H_{24}BrNS$ = 582.55) |
| Sub 2-15 | m/z = 704.28 ($C_{52}H_{36}N_2O$ = 704.87) | Sub 2-16 | m/z = 520.06 ($C_{30}H_{21}BrN_2S$ = 521.48) |
| Sub 2-17 | m/z = 539.09 ($C_{34}H_{22}BrNO$ = 540.45) | Sub 2-18 | m/z = 564.12 ($C_{36}H_{25}BrN_2$ = 565.50) |
| Sub 2-19 | m/z = 690.17 ($C_{46}H_{31}BrN_2$ = 691.67) | Sub 2-20 | m/z = 657.11 ($C_{42}H_{28}BrNS$ = 658.65) |
| Sub 2-21 | m/z = 564.12 ($C_{36}H_{25}BrN_2$ = 565.50) | Sub 2-22 | m/z = 664.15 ($C_{44}H_{29}BrN_2$ = 665.63) |
| Sub 2-23 | m/z = 525.11 ($C_{34}H_{24}BrN$ = 526.47) | Sub 2-24 | m/z = 601.14 ($C_{40}H_{28}BrN$ = 602.58) |
| Sub 2-25 | m/z = 551.12 ($C_{36}H_{26}BrN$ = 552.52) | Sub 2-26 | m/z = 525.11 ($C_{34}H_{24}BrN$ = 526.47) |
| Sub 2-27 | m/z = 525.11 ($C_{34}H_{24}BrN$ = 526.47) | Sub 2-28 | m/z = 525.11 ($C_{34}H_{24}BrN$ = 526.47) |
| Sub 2-29 | m/z = 581.08 ($C_{36}H_{24}BrNS$ = 582.55) | Sub 2-30 | m/z = 615.12 ($C_{40}H_{26}BrNO$ = 616.54) |
| Sub 2-31 | m/z = 641.14 ($C_{42}H_{28}BrNO$ = 642.58) | Sub 2-32 | m/z = 716.18 ($C_{48}H_{33}BrN_2$ = 717.71) |
| Sub 2-33 | m/z = 475.09 ($C_{30}H_{22}BrN$ = 476.41) | Sub 2-34 | m/z = 625.14 ($C_{42}H_{28}BrN$ = 626.58) |
| Sub 2-35 | m/z = 503.12 ($C_{32}H_{26}BrN$ = 504.46) | Sub 2-36 | m/z = 538.10 ($C_{34}H_{23}BrN_2$ = 539.46) |
| Sub 2-37 | m/z = 449.08 ($C_{28}H_{20}BrN$ = 450.38) | Sub 2-38 | m/z = 499.09 ($C_{32}H_{22}BrN$ = 500.43) |
| Sub 2-39 | m/z = 499.09 ($C_{32}H_{22}BrN$ = 500.43) | Sub 2-40 | m/z = 549.11 ($C_{36}H_{24}BrN$ = 550.50) |
| Sub 2-41 | m/z = 651.16 ($C_{44}H_{30}BrN$ = 652.64) | Sub 2-42 | m/z = 538.10 ($C_{34}H_{23}BrN_2$ = 539.46) |
| Sub 2-43 | m/z = 538.10 ($C_{34}H_{23}BrN_2$ = 539.46) | Sub 2-44 | m/z = 569.04 ($C_{34}H_{20}BrNOS$ = 570.50) |
| Sub 2-45 | m/z = 479.03 ($C_{28}H_{18}BrNS$ = 480.42) | Sub 2-46 | m/z = 544.06 ($C_{32}H_{21}BrN_2S$ = 545.49) |
| Sub 2-47 | m/z = 605.08 ($C_{38}H_{24}BrNS$ = 606.57) | Sub 2-48 | m/z = 579.12 ($C_{37}H_{26}BrNO$ = 580.53) |
| Sub 2-49 | m/z = 515.12 ($C_{33}H_{26}BrN$ = 516.48) | Sub 2-50 | m/z = 505.05 ($C_{30}H_{20}BrNS$ = 506.46) |
| Sub 2-51 | m/z = 559.06 ($C_{36}H_{22}BrNOS$ = 596.54) | Sub 2-52 | m/z = 519.03 ($C_{30}H_{18}BrNOS$ = 520.44) |
| Sub 2-53 | m/z = 595.10 ($C_{37}H_{26}BrNS$ = 596.59) | Sub 2-54 | m/z = 612.12 ($C_{39}H_{25}BrN_2O$ = 617.55) |
| Sub 2-55 | m/z = 640.15 ($C_{42}H_{29}BrN_2$ = 641.61) | Sub 2-56 | m/z = 681.20 ($C_{46}H_{36}BrN$ = 682.71) |
| Sub 2-57 | m/z = 489.07 ($C_{30}H_{20}BrNO$ = 490.40) | Sub 2-58 | m/z = 627.16 ($C_{42}H_{30}BrN$ = 628.61) |
| Sub 2-59 | m/z = 591.16 ($C_{39}H_{30}BrN$ = 592.58) | Sub 2-60 | m/z = 555.07 ($C_{34}H_{22}BrNS$ = 556.52) |
| Sub 2-61 | m/z = 611.04 ($C_{36}H_{22}BrNS_2$ = 612.60) | Sub 2-62 | m/z = 616.15 ($C_{40}H_{29}BrN_2$ = 617.59) |
| Sub 2-63 | m/z = 477.08 ($C_{28}H_{20}BrN_3$ = 478.39) | Sub 2-64 | m/z = 447.06 ($C_{25}H_{19}BrFNO$ = 448.34) |
| Sub 2-65 | m/z = 528.16 ($C_{31}H_{21}D_5BrNSi$ = 529.60) | | |

Synthesis Example of Final Products 1

Sub 2 or Sub 2A (1 eq.) was dissolved in toluene in a round bottom flask, and Sub 1 (1.1 eq.), Pd$_2$(dba)$_3$ (0.03 eq.), P(t-Bu)$_3$ (0.1 eq.), NaOt-Bu (3 eq.) were added and stirred at 100° C. When the reaction was complete, the reaction mixture was extracted with CH$_2$Cl$_2$ and water. The organic layer was dried over MgSO$_4$ and concentrated. The resulting compound was separated by silicagel column chromatography and recrystallization to obtain the Final products.

Synthesis of 1-3

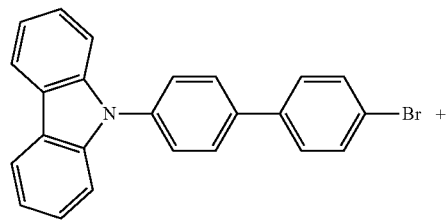

Sub 2A-1

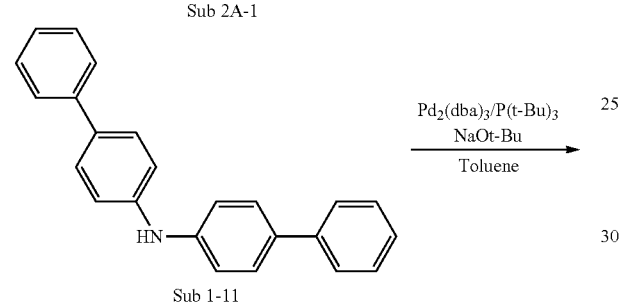

Sub 1-11

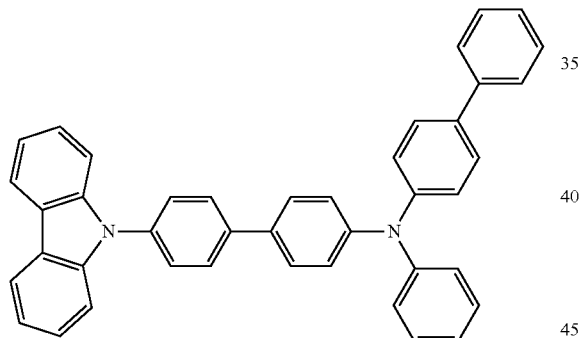

1-3

Sub 2A-1 (10 g, 25.11 mmol) was dissolved in toluene (264 ml) in a round bottom flask, and Sub 1-11 (8.88 g, 27.62 mmol), Pd$_2$(dba)$_3$ (0.69 g, 0.75 mmol), P(t-Bu)$_3$ (0.51 g, 2.51 mmol), NaOt-Bu (7.24 g, 75.32 mmol) were added and stirred at 100° C. When the reaction was complete, the reaction mixture was extracted with CH$_2$Cl$_2$ and water. The organic layer was dried over MgSO$_4$ and concentrated. The resulting compound was separated by silicagel column chromatography and recrystallization to obtain 13.31 g of product. (Yield: 83%)

Synthesis of 1-23

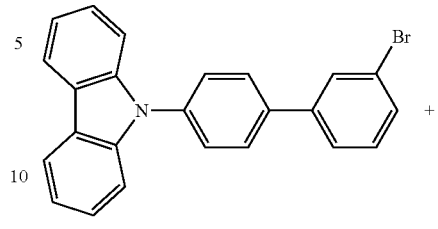

Sub 2A-3

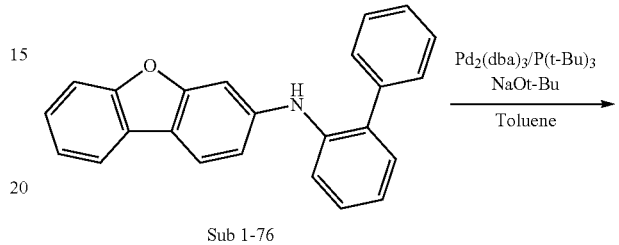

Sub 1-76

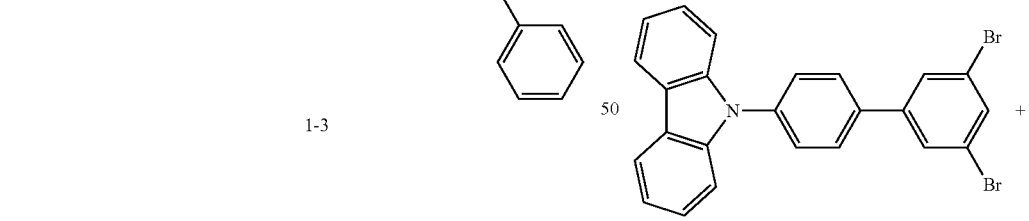

1-23

Sub 2A-3 (10 g, 25.11 mmol), toluene (264 ml), Sub 1-76 (9.26 g, 27.62 mmol), Pd$_2$(dba)$_3$ (0.69 g, 0.75 mmol), P(t-Bu)$_3$ (0.51 g, 2.51 mmol), NaOt-Bu (7.24 g, 75.32 mmol) were carried out in the same manner as 1-3 to obtain 12.78 g of the product. (Yield: 78%)

Synthesis of 1-31

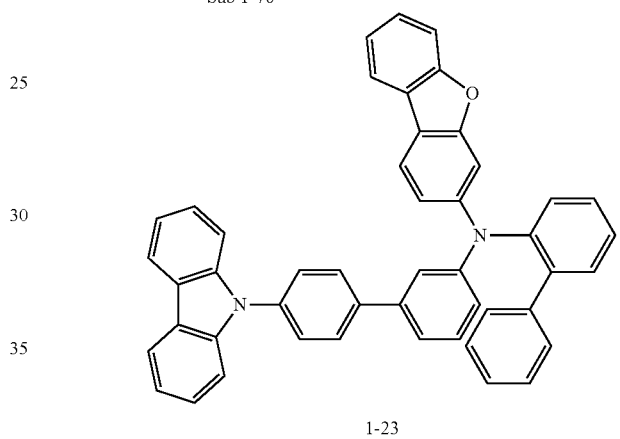

Sub 2A-8

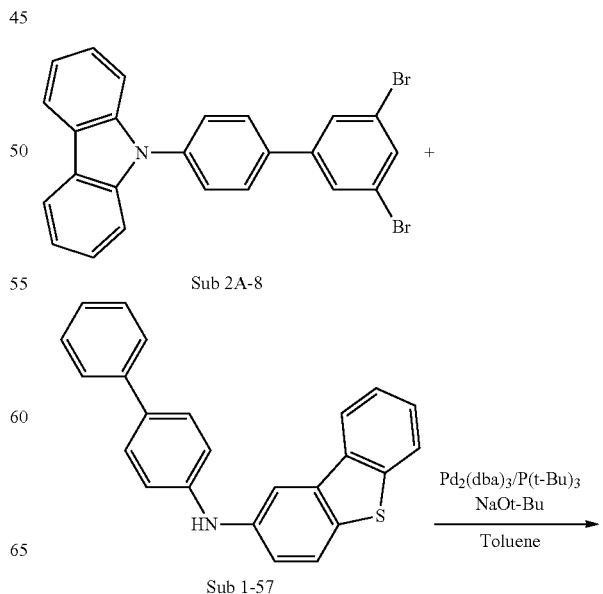

Sub 1-57

217

-continued

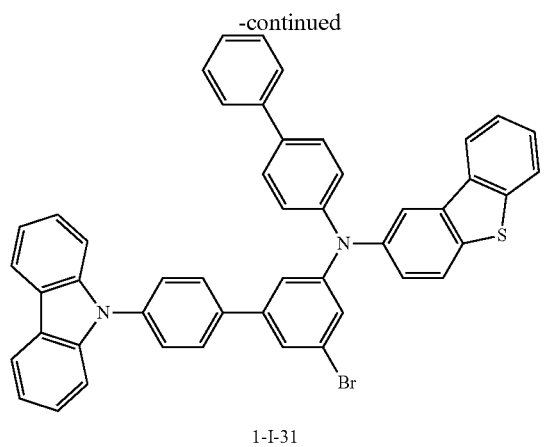
1-I-31

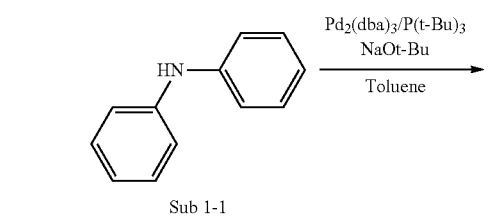
Sub 1-1

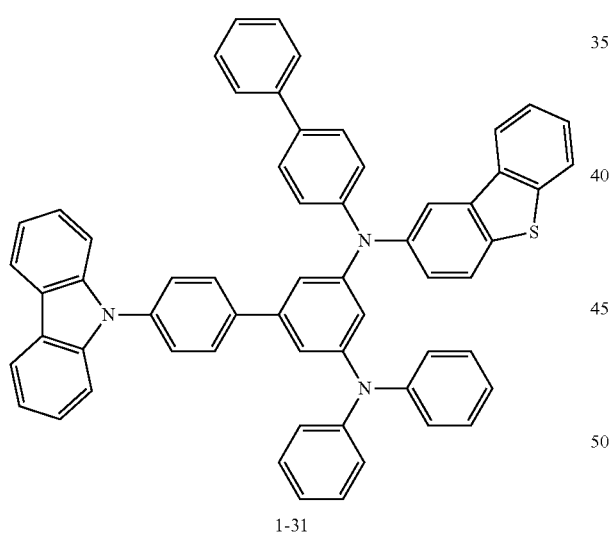
1-31

1) Synthesis of Intermediate 1-I-31

Sub 2A-8 (20 g, 41.91 mmol), toluene (440 ml), Sub 1-57 (16.20 g, 46.10 mmol), Pd$_2$(dba)$_3$ (0.58 g, 0.63 mmol), P(t-Bu)$_3$ (0.42 g, 2.10 mmol), NaOt-Bu (6.04 g, 62.87 mmol) were carried out in the same manner as 1-3 to obtain 22.25 g of the product. (Yield: 71%)

2) Synthesis of 1-31

1-I-31 (22.25 g, 29.76 mmol), toluene (312 ml), Sub 1-1 (5.54 g, 32.73 mmol), Pd$_2$(dba)$_3$ (0.82 g, 0.89 mmol), P(t-Bu)$_3$ (0.60 g, 2.98 mmol), NaOt-Bu (8.58 g, 89.27 mmol) were carried out in the same manner as 1-3 to obtain 20.65 g of the product. (Yield: 83%) Synthesis of 1-34

218

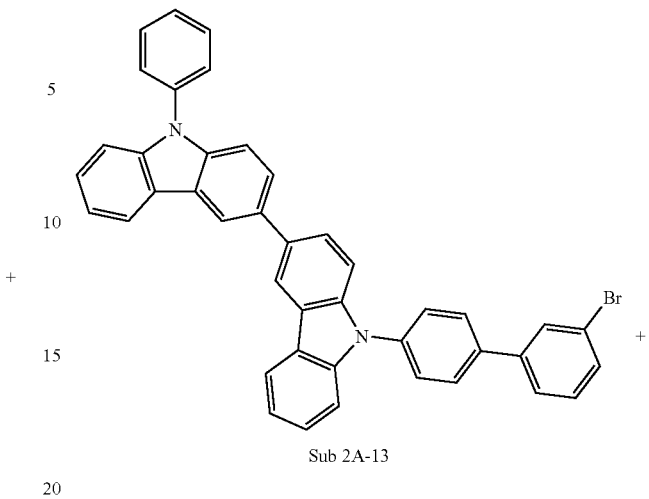
Sub 2A-13

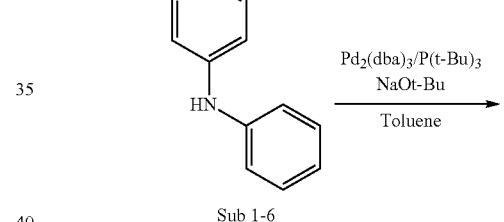
Sub 1-6

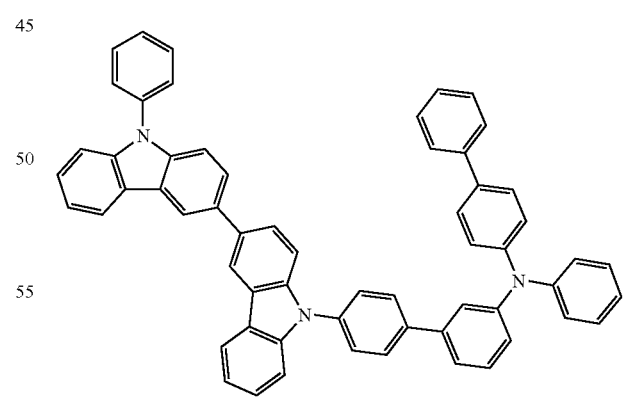
1-34

Sub 2A-13 (11 g, 17.20 mmol), toluene (181 ml), Sub 1-6 (4.64 g, 18.92 mmol), Pd$_2$(dba)$_3$ (0.47 g, 0.52 mmol), P(t-Bu)$_3$ (0.35 g, 1.72 mmol), NaOt-Bu (4.96 g, 51.59 mmol) were carried out in the same manner as 1-3 to obtain 10.65 g of the product. (Yield: 77%)

Synthesis of 1-43

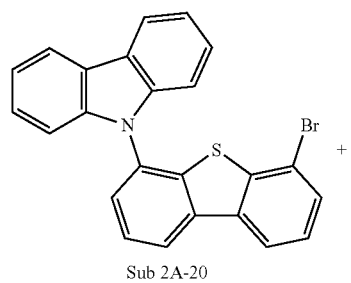
Sub 2A-20

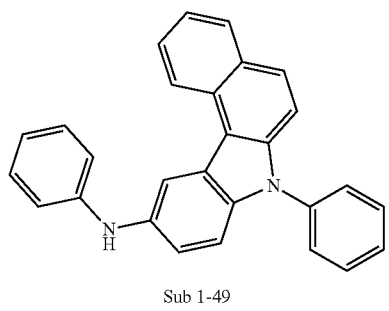
Sub 1-49

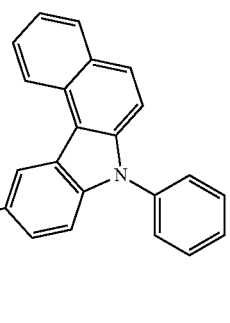
1-43

Sub 2A-20 (11 g, 25.68 mmol), toluene (270 ml), Sub 1-49 (10.86 g, 28.25 mmol), Pd$_2$(dba)$_3$ (0.71 g, 0.77 mmol), P(t-Bu)$_3$ (0.52 g, 2.57 mmol), NaOt-Bu (7.40 g, 77.04 mmol) were carried out in the same manner as 1-3 to obtain 13.16 g of the product. (Yield: 70%)

Synthesis of 1-45

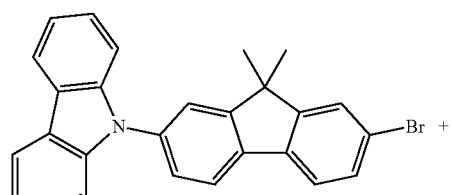
Sub 2A-22

-continued

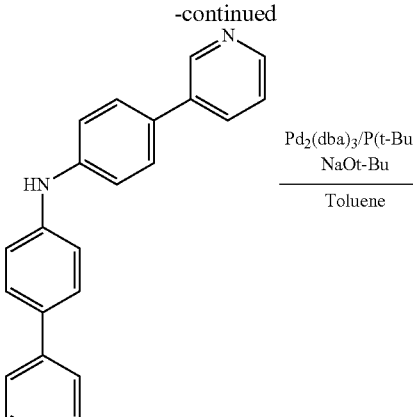
Sub 1-89

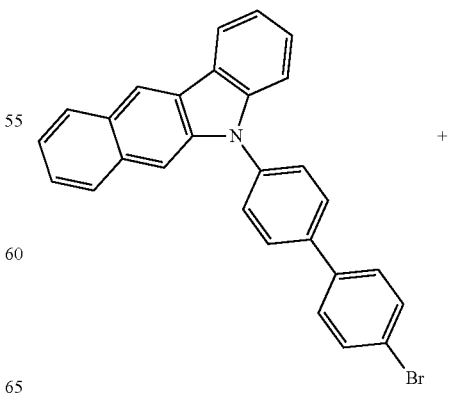
1-45

Sub 2A-22 (11 g, 25.09 mmol), toluene (263 ml), Sub 1-89 (8.90 g, 27.60 mmol), Pd$_2$(dba)$_3$ (0.69 g, 0.75 mmol), P(t-Bu)$_3$ (0.51 g, 2.51 mmol), NaOt-Bu (7.23 g, 75.28 mmol) were carried out in the same manner as 1-3 to obtain 11.43 g of the product. (Yield: 67%)

Synthesis of 1-54

Sub 2A-30

-continued
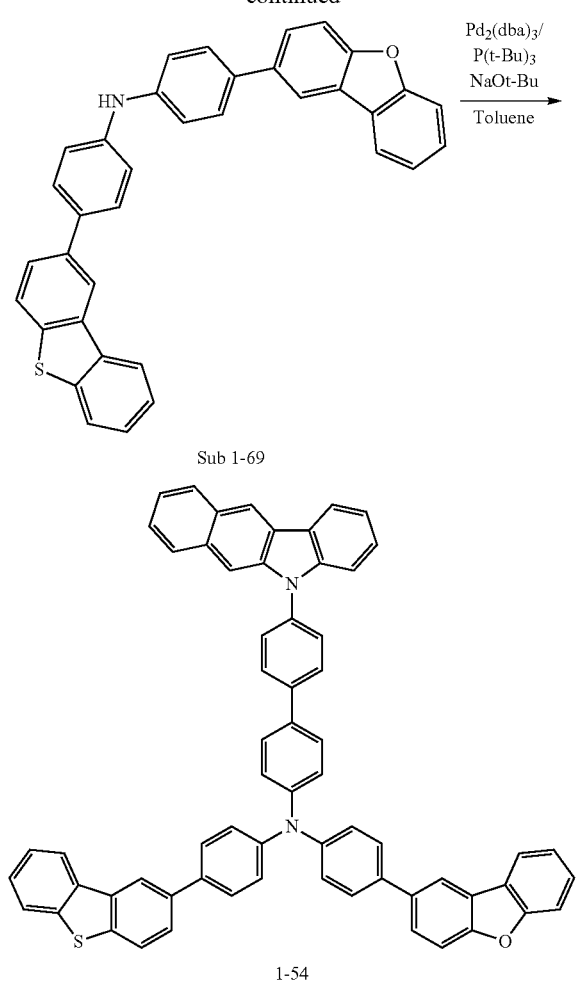
Sub 1-69
1-54
Sub 2A-30 (7 g, 15.61 mmol), toluene (164 ml), Sub 1-69 (8.89 g, 17.17 mmol), Pd$_2$(dba)$_3$ (0.43 g, 0.47 mmol), P(t-Bu)$_3$ (0.32 g, 1.56 mmol), NaOt-Bu (4.50 g, 46.84 mmol) were carried out in the same manner as 1-3 to obtain 10.23 g of the product. (Yield: 74%)
Synthesis of 1-56
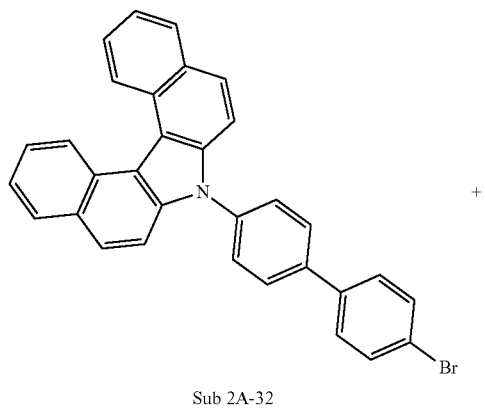
Sub 2A-32
-continued
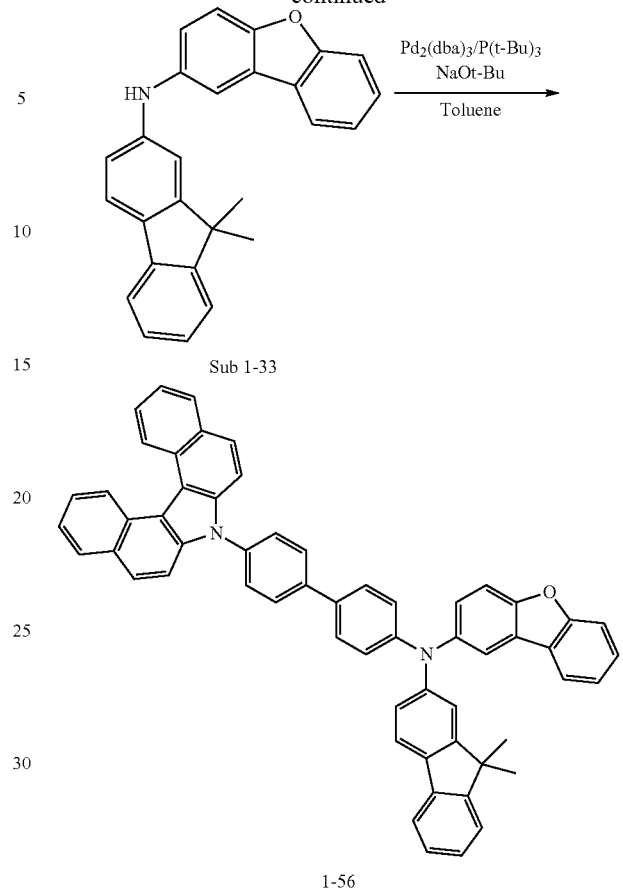
Sub 1-33
1-56
Sub 2A-32 (9 g, 18.06 mmol), toluene (190 ml), Sub 1-33 (7.46 g, 19.86 mmol), Pd$_2$(dba)$_3$ (0.50 g, 0.54 mmol), P(t-Bu)$_3$ (0.37 g, 1.81 mmol), NaOt-Bu (5.21 g, 54.17 mmol) were carried out in the same manner as 1-3 to obtain 10.17 g of the product. (Yield: 71%)
Synthesis of 2-1
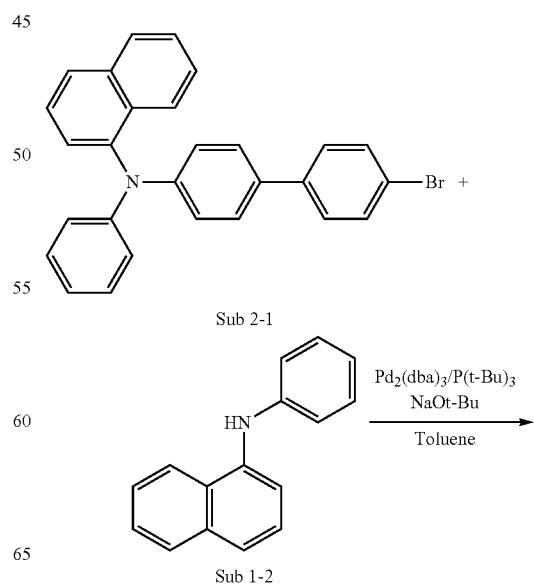
Sub 2-1
Sub 1-2

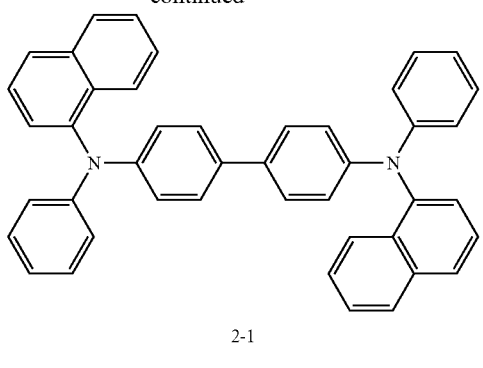

2-1

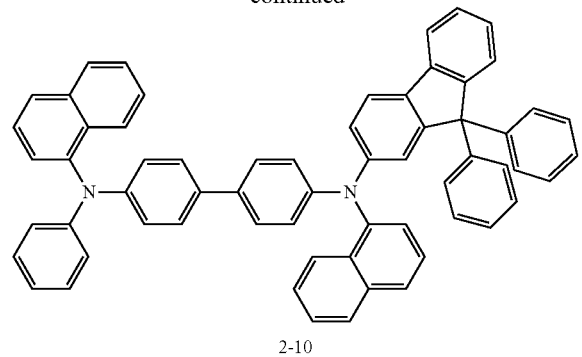

2-10

Sub 2-1 (8 g, 17.76 mmol), toluene (187 ml), Sub 1-35 (8.98 g, 19.54 mmol), Pd$_2$(dba)$_3$ (0.49 g, 0.53 mmol), P(t-Bu)$_3$ (0.36 g, 1.78 mmol), NaOt-Bu (5.12 g, 53.29 mmol) were carried out in the same manner as 2-1 to obtain 10.6 g of the product. (Yield: 72%)

Synthesis of 2-23

Sub 2-1 (10 g, 22.20 mmol) was dissolved in toluene(233 ml) in a round bottom flask, and Sub 1-12 (5.36 g, 24.42 mmol), Pd$_2$(dba)$_3$ (0.61 g, 0.67 mmol), P(t-Bu)$_3$ (0.45 g, 2.22 mmol), NaOt-Bu (6.40 g, 66.61 mmol) were added and stirred at 100° C. When the reaction was complete, the reaction mixture was extracted with CH$_2$Cl$_2$ and water. The organic layer was dried over MgSO$_4$ and concentrated. The resulting compound was separated by silicagel column chromatography and recrystallization to obtain 10.46 g of product. (Yield: 80%)

Synthesis of 2-10

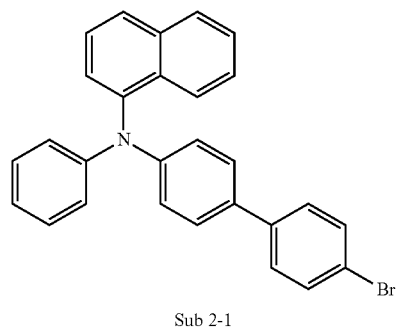

Sub 2-1

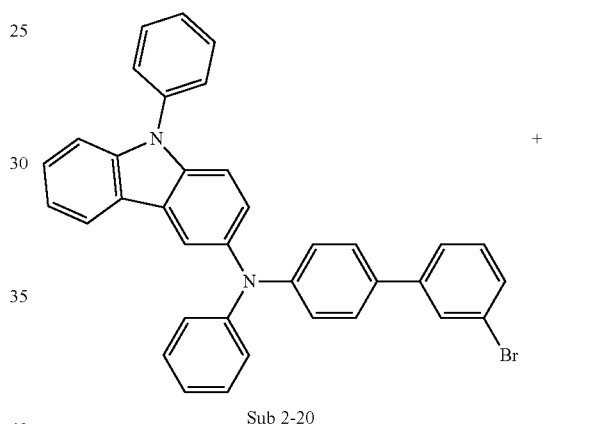

Sub 2-20

Sub 1-47

Pd$_2$(dba)$_3$/P(t-Bu)$_3$
NaOt-Bu
Toluene

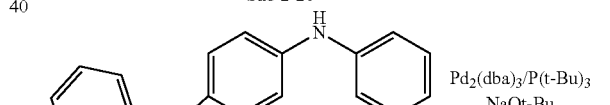

Sub 1-35

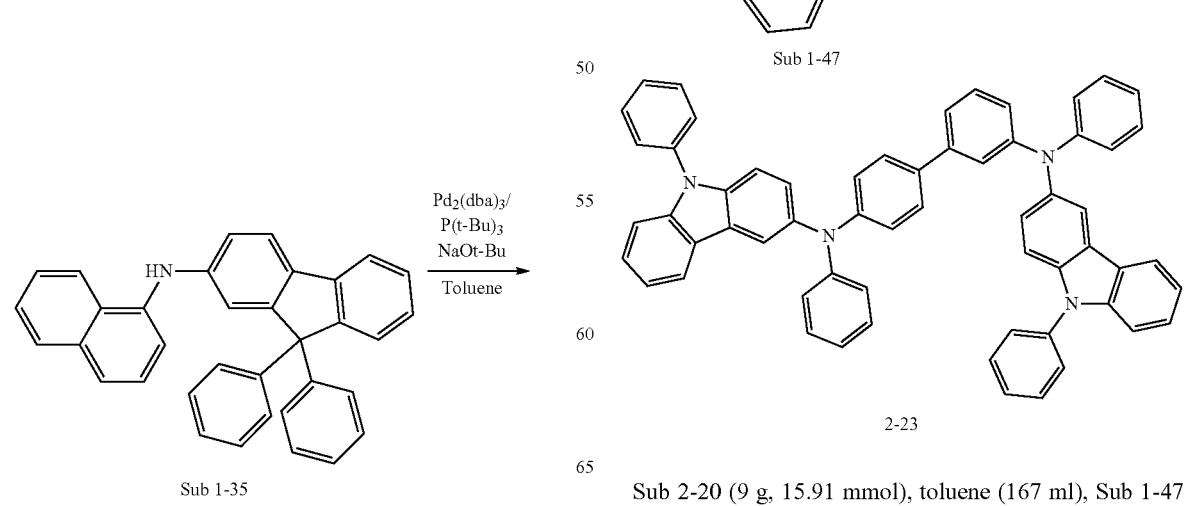

2-23

Sub 2-20 (9 g, 15.91 mmol), toluene (167 ml), Sub 1-47 (5.85 g, 17.51 mmol), Pd$_2$(dba)$_3$ (0.44 g, 0.48 mmol), P(t-Bu)₃ (0.32 g, 1.59 mmol), NaOt-Bu (4.59 g, 47.74 mmol) were carried out in the same manner as 2-1 to obtain 10.04 g of the product. (Yield: 77%)

Synthesis of 2-25

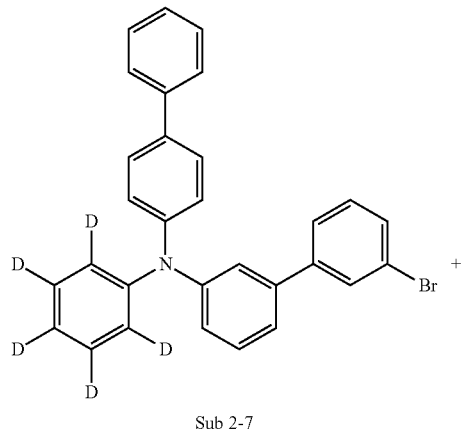
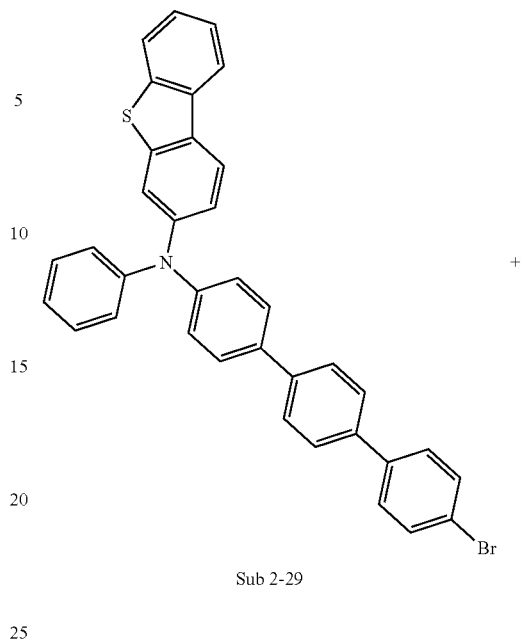
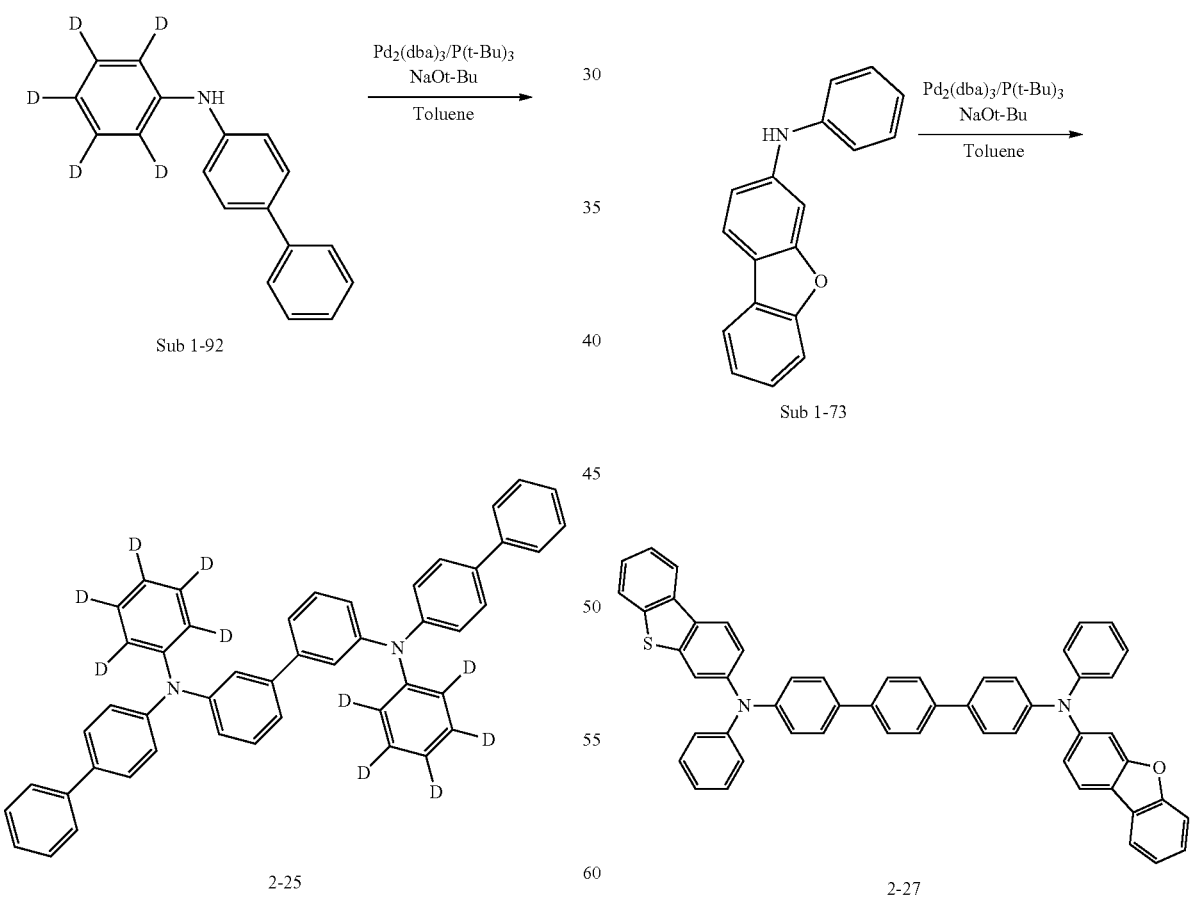

Sub 2-7 (10 g, 20.77 mmol), toluene (218 ml), Sub 1-92 (5.72 g, 22.85 mmol), Pd₂(dba)₃ (0.57 g, 0.62 mmol), P(t-Bu)₃ (0.42 g, 2.08 mmol), NaOt-Bu (5.99 g, 62.31 mmol) were carried out in the same manner as 2-1 to obtain 10.68 g of the product. (Yield: 79%) Synthesis of 2-27

Sub 2-29 (11 g, 18.88 mmol), toluene (198 ml), Sub 1-73 (5.39 g, 20.77 mmol), Pd₂(dba)₃ (0.52 g, 0.57 mmol), P(t-Bu)₃ (0.38 g, 1.89 mmol), NaOt-Bu (5.44 g, 56.65 mmol) were carried out in the same manner as 2-1 to obtain 10.49 g of the product. (Yield: 73%)

Synthesis of 2-41

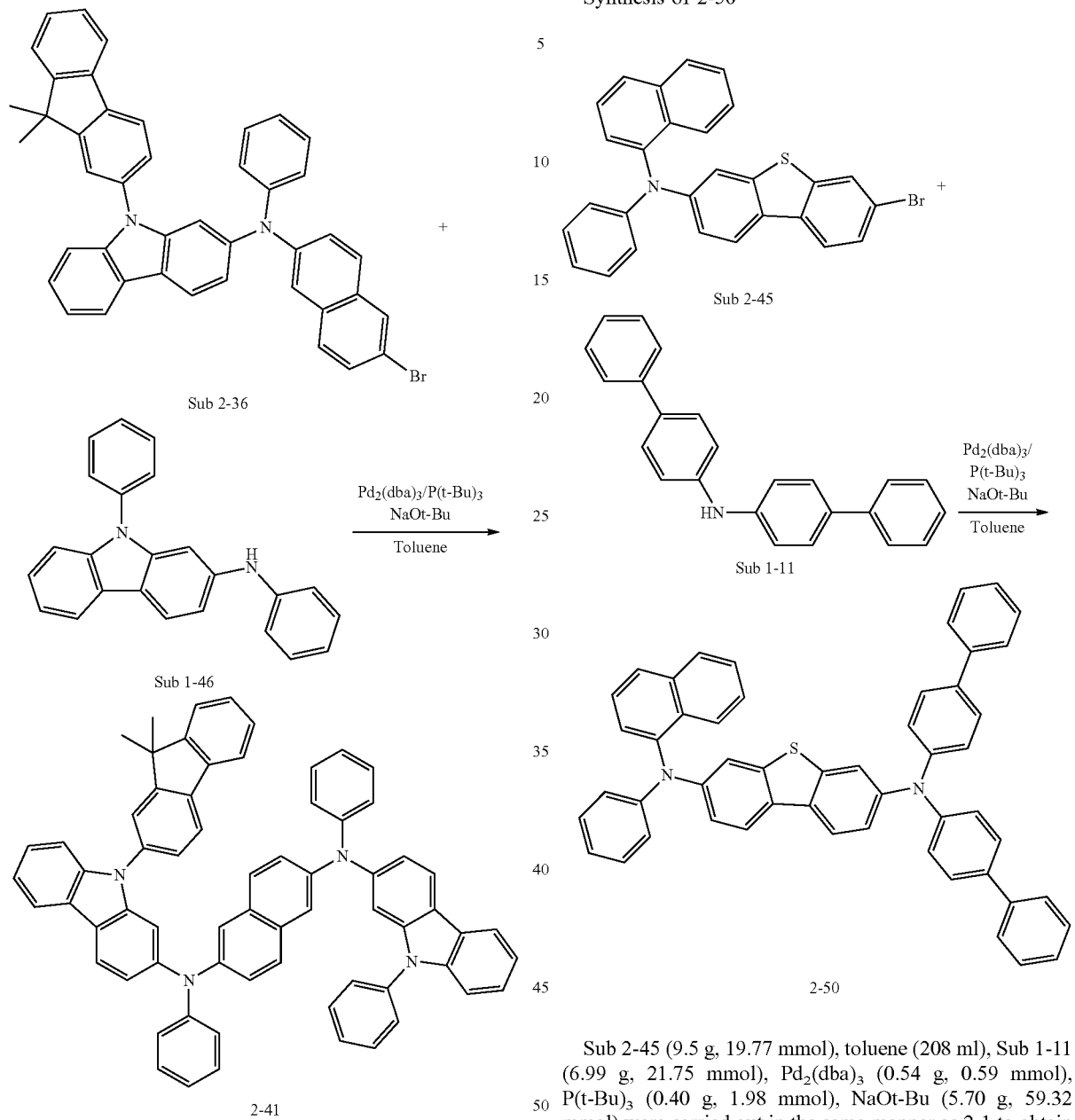

Sub 2-36 (11 g, 16.78 mmol), toluene (176 ml), Sub 1-46 (6.17 g, 18.46 mmol), Pd$_2$(dba)$_3$ (0.46 g, 0.50 mmol), P(t-Bu)$_3$ (0.34 g, 1.68 mmol), NaOt-Bu (4.84 g, 50.33 mmol) were carried out in the same manner as 2-1 to obtain 10.22 g of the product. (Yield: 67%)

Synthesis of 2-50

Sub 2-45 (9.5 g, 19.77 mmol), toluene (208 ml), Sub 1-11 (6.99 g, 21.75 mmol), Pd$_2$(dba)$_3$ (0.54 g, 0.59 mmol), P(t-Bu)$_3$ (0.40 g, 1.98 mmol), NaOt-Bu (5.70 g, 59.32 mmol) were carried out in the same manner as 2-1 to obtain 10.41 g of the product. (Yield: 73%)

Meanwhile, FD-MS values of the compounds 1-1 to 1-60 and 2-1 to 2-70 of the present invention prepared according to the above synthesis examples are shown in Table 3 below.

TABLE 3

| compound | FD-MS | compound | FD-MS |
|---|---|---|---|
| 1-1 | m/z = 473.21 (C$_{36}$H$_{27}$N = 473.61) | 1-2 | m/z = 523.23 (C$_{40}$H$_{29}$N = 523.66) |
| 1-3 | m/z = 573.25 (C$_{44}$H$_{31}$N = 573.72) | 1-4 | m/z = 623.26 (C$_{48}$H$_{33}$N = 623.78) |
| 1-5 | m/z = 738.30 (C$_{59}$H$_{38}$N$_2$ = 738.91) | 1-6 | m/z = 688.29 (C$_{52}$H$_{36}$N$_2$ = 688.87) |
| 1-7 | m/z = 653.28 (C$_{48}$H$_{35}$N$_3$ = 653.81) | 1-8 | m/z = 820.36 (C$_{60}$H$_{44}$N$_4$ = 821.02) |
| 1-9 | m/z = 727.30 (C$_{54}$H$_{37}$N$_3$ = 727.89) | 1-10 | m/z = 668.23 (C$_{48}$H$_{32}$N$_2$S = 668.85) |
| 1-11 | m/z = 802.30 (C$_{60}$H$_{38}$N$_2$O = 802.98) | 1-12 | m/z = 698.19 (C$_{48}$H$_{30}$N$_2$S = 698.90) |
| 1-13 | m/z = 911.33 (C$_{66}$H$_{45}$N$_3$S = 912.17) | 1-14 | m/z = 759.23 (C$_{53}$H$_{33}$N$_3$OS = 759.93) |
| 1-15 | m/z = 652.29 (C$_{49}$H$_{36}$N$_2$ = 652.84) | 1-16 | m/z = 692.28 (C$_{51}$H$_{36}$N$_2$O = 692.84) |
| 1-17 | m/z = 794.37 (C$_{60}$H$_{46}$N$_2$ = 795.02) | 1-18 | m/z = 903.36 (C$_{68}$H$_{45}$N$_3$ = 904.10) |

TABLE 3-continued

| compound | FD-MS | compound | FD-MS |
|---|---|---|---|
| 1-19 | m/z = 638.27 ($C_{48}H_{34}N_2$ = 638.80) | 1-20 | m/z = 880.29 ($C_{65}H_{40}N_2S$ = 881.11) |
| 1-21 | m/z = 777.31 ($C_{58}H_{39}N_3$ = 777.97) | 1-22 | m/z = 718.24 ($C_{52}H_{34}N_2S$ = 718.92) |
| 1-23 | m/z = 652.25 ($C_{48}H_{32}N_2O$ = 652.78) | 1-24 | m/z = 688.29 ($C_{52}H_{36}N_2$ = 688.87) |
| 1-25 | m/z = 668.23 ($C_{48}H_{32}N_2S$ = 668.85) | 1-26 | m/z = 698.19 ($C_{48}H_{30}N_2S_2$ = 698.90) |
| 1-27 | m/z = 612.26 ($C_{46}H_{32}N_2$ = 612.76) | 1-28 | m/z = 769.26 ($C_{55}H_{35}N_3S$ = 769.95) |
| 1-29 | m/z = 782.24 ($C_{56}H_{34}N_2OS$ = 782.95) | 1-30 | m/z = 943.39 ($C_{71}H_{49}N_3$ = 944.19) |
| 1-31 | m/z = 835.30 ($C_{60}H_{41}N_3S$ = 836.07) | 1-32 | m/z = 714.30 ($C_{54}H_{38}N_2$ = 714.89) |
| 1-33 | m/z = 805.31 ($C_{59}H_{39}N_3O$ = 805.96) | 1-34 | m/z = 803.33 ($C_{60}H_{41}N_3$ = 803.99) |
| 1-35 | m/z = 768.26 ($C_{56}H_{36}N_2S$ = 768.96) | 1-36 | m/z = 767.33 ($C_{58}H_{33}D_5N_2$ = 767.99) |
| 1-37 | m/z = 778.37 ($C_{56}H_{50}N_2Si$ = 779.12) | 1-38 | m/z = 610.24 ($C_{43}H_{31}FN_2O$ = 610.73) |
| 1-39 | m/z = 749.24 ($C_{50}H_{31}N_5O_3$ = 749.83) | 1-40 | m/z = 769.26 ($C_{55}H_{35}N_3S$ = 769.97) |
| 1-41 | m/z = 742.24 ($C_{54}H_{34}N_2S$ = 742.93) | 1-42 | m/z = 732.22 ($C_{52}H_{32}N_2OS$ = 732.89) |
| 1-43 | m/z = 731.24 ($C_{52}H_{33}N_3S$ = 731.92) | 1-44 | m/z = 652.25 ($C_{48}H_{32}N_2O$ = 652.78) |
| 1-45 | m/z = 679.30 ($C_{50}H_{37}N_3$ = 679.87) | 1-46 | m/z = 642.30 ($C_{48}H_{38}N_2$ = 642.83) |
| 1-47 | m/z = 830.29 ($C_{61}H_{38}N_2O_2$ = 830.99) | 1-48 | m/z = 907.36 ($C_{67}H_{45}N_3O$ = 908.09) |
| 1-49 | m/z = 776.32 ($C_{59}H_{40}N_2$ = 776.96) | 1-50 | m/z = 865.35 ($C_{65}H_{43}N_3$ = 866.06) |
| 1-51 | m/z = 936.35 ($C_{72}H_{44}N_2$ = 937.13) | 1-52 | m/z = 688.29 ($C_{52}H_{36}N_2$ = 688.86) |
| 1-53 | m/z = 794.28 ($C_{58}H_{38}N_2S$ = 795.00) | 1-54 | m/z = 884.29 ($C_{64}H_{40}N_2OS$ = 885.08) |
| 1-55 | m/z = 738.30 ($C_{56}H_{38}N_2$ = 738.91) | 1-56 | m/z = 792.31 ($C_{59}H_{40}N_2O$ = 792.98) |
| 1-57 | m/z = 907.30 ($C_{66}H_{41}N_3S$ = 908.14) | 1-58 | m/z = 879.32 ($C_{65}H_{41}N_{30}$ = 880.04) |
| 1-59 | m/z = 795.37 ($C_{60}H_{37}D_5N_2$ = 796.02) | 1-60 | m/z = 864.35 ($C_{66}H_{44}N_2$ = 865.07) |
| 2-1 | m/z = 588.26 ($C_{44}H_{32}N_2$ = 588.74) | 2-2 | m/z = 816.35 ($C_{62}H_{44}N_2$ = 817.05) |
| 2-3 | m/z = 792.35 ($C_{60}H_{44}N_2$ = 793.03) | 2-4 | m/z = 763.30 ($C_{57}H_{37}N_3$ = 763.94) |
| 2-5 | m/z = 700.37 ($C_{52}H_{28}D_{10}N_2$ = 700.95) | 2-6 | m/z = 730.33 ($C_{55}H_{42}N_2$ = 730.96) |
| 2-7 | m/z = 877.44 ($C_{66}H_{43}D_7N_2$ = 878.18) | 2-8 | m/z = 876.35 ($C_{64}H_{48}N_2S$ = 877.16) |
| 2-9 | m/z = 952.48 ($C_{72}H_{60}N_2$ = 953.29) | 2-10 | m/z = 828.35 ($C_{63}H_{44}N_2$ = 829.06) |
| 2-11 | m/z = 863.33 ($C_{62}H_{45}N_3S$ = 864.12) | 2-12 | m/z = 981.41 ($C_{74}H_{51}N_3$ = 982.24) |
| 2-13 | m/z = 816.31 ($C_{61}H_{40}N_2O$ = 817.00) | 2-14 | m/z = 770.28 ($C_{56}H_{38}N_2S$ = 770.99) |
| 2-15 | m/z = 794.29 ($C_{58}H_{38}N_2O_2$ = 794.95) | 2-16 | m/z = 852.26 ($C_{60}H_{40}N_2S_2$ = 853.10) |
| 2-17 | m/z = 912.18 ($C_{60}H_{36}N_2S_4$ = 913.20) | 2-18 | m/z = 852.26 ($C_{60}H_{40}N_2S_2$ = 853.10) |
| 2-19 | m/z = 905.38 ($C_{68}H_{47}N_3$ = 906.15) | 2-20 | m/z = 935.33 ($C_{68}H_{45}N_3S$ = 936.19) |
| 2-21 | m/z = 709.26 ($C_{50}H_{35}N_3S$ = 709.91) | 2-22 | m/z = 800.23 ($C_{56}H_{36}N_2S_2$ = 801.04) |
| 2-23 | m/z = 818.34 ($C_{60}H_{42}N_4$ = 819.02) | 2-24 | m/z = 818.34 ($C_{60}H_{42}N_4$ = 819.02) |
| 2-25 | m/z = 650.35 ($C_{48}H_{26}D_{10}N_2$ = 650.89) | 2-26 | m/z = 664.29 ($C_{50}H_{36}N_2$ = 664.85) |
| 2-27 | m/z = 760.25 ($C_{54}H_{36}N_2OS$ = 760.96) | 2-28 | m/z = 664.29 ($C_{50}H_{36}N_2$ = 664.85) |
| 2-29 | m/z = 740.32 ($C_{56}H_{40}N_2$ = 740.95) | 2-30 | m/z = 878.37 ($C_{67}H_{46}N_2$ = 879.12) |
| 2-31 | m/z = 911.33 ($C_{66}H_{45}N_3S$ = 912.17) | 2-32 | m/z = 664.29 ($C_{50}H_{36}N_2$ = 664.85) |
| 2-33 | m/z = 844.31 ($C_{62}H_{40}N_2O_2$ = 844.99) | 2-34 | m/z = 664.29 ($C_{50}H_{36}N_2$ = 664.85) |
| 2-35 | m/z = 664.29 ($C_{50}H_{36}N_2$ = 664.85) | 2-36 | m/z = 820.31 ($C_{60}H_{40}N_2O_2$ = 820.99) |
| 2-37 | m/z = 640.29 ($C_{48}H_{36}N_2$ = 640.83) | 2-38 | m/z = 881.38 ($C_{66}H_{47}N_3$ = 882.10) |
| 2-39 | m/z = 764.32 ($C_{58}H_{40}N_2$ = 764.97) | 2-40 | m/z = 648.35 ($C_{48}H_{44}N_2$ = 648.89) |
| 2-41 | m/z = 908.39 ($C_{67}H_{48}N_4$ = 909.15) | 2-42 | m/z = 538.24 ($C_{40}H_{30}N_2$ = 538.69) |
| 2-43 | m/z = 588.26 ($C_{44}H_{32}N_2$ = 588.75) | 2-44 | m/z = 588.26 ($C_{44}H_{32}N_2$ = 588.75) |
| 2-45 | m/z = 764.32 ($C_{58}H_{40}N_2$ = 764.97) | 2-46 | m/z = 846.31 ($C_{62}H_{42}N_2S$ = 847.09) |
| 2-47 | m/z = 677.28 ($C_{50}H_{35}N_3$ = 677.85) | 2-48 | m/z = 627.27 ($C_{46}H_{33}N_3$ = 627.79) |
| 2-49 | m/z = 814.21 ($C_{56}H_{34}N_2OS_2$ = 815.02) | 2-50 | m/z = 720.26 ($C_{52}H_{36}N_2S$ = 720.93) |
| 2-51 | m/z = 748.27 ($C_{52}H_{36}N_4S$ = 748.95) | 2-52 | m/z = 744.26 ($C_{54}H_{36}N_2S$ = 744.96) |
| 2-53 | m/z = 774.27 ($C_{55}H_{38}N_2OS$ = 774.98) | 2-54 | m/z = 731.33 ($C_{54}H_{41}N_3$ = 731.94) |
| 2-55 | m/z = 670.24 ($C_{48}H_{34}N_2S$ = 670.87) | 2-56 | m/z = 866.24 ($C_{60}H_{38}N_2OS_2$ = 867.10) |
| 2-57 | m/z = 698.20 ($C_{48}H_{30}N_2O_2S$ = 698.84) | 2-58 | m/z = 850.34 ($C_{62}H_{46}N_2S$ = 851.12) |
| 2-59 | m/z = 782.30 ($C_{56}H_{38}N_4$ = 782.95) | 2-60 | m/z = 729.31 ($C_{54}H_{39}N_3$ = 729.93) |
| 2-61 | m/z = 936.44 ($C_{71}H_{56}N_2$ = 937.24) | 2-62 | m/z = 744.28 ($C_{54}H_{36}N_2O_2$ = 744.89) |
| 2-63 | m/z = 792.35 ($C_{60}H_{44}N_2$ = 793.03) | 2-64 | m/z = 756.35 ($C_{57}H_{44}N_4$ = 756.99) |
| 2-65 | m/z = 694.24 ($C_{50}H_{34}N_2S$ = 694.90) | 2-66 | m/z = 852.26 ($C_{60}H_{40}N_2S_2$ = 853.11) |
| 2-67 | m/z = 922.40 ($C_{68}H_{50}N_4$ = 923.18) | 2-68 | m/z = 631.27 ($C_{44}H_{33}N_5$ = 631.78) |
| 2-69 | m/z = 626.24 ($C_{43}H_{31}FN_2O_2$ = 626.73) | 2-70 | m/z = 723.40 ($C_{51}H_{41}D_7N_2Si$ = 724.09) |

Synthesis Examples 2

I. Synthesis of Formula (2)

The final product 2 represented by Formula (2) of the present invention is prepared by reacting Sub 3 and Sub 4 as shown in the following Reaction Scheme 6.

<Reaction Scheme 6>

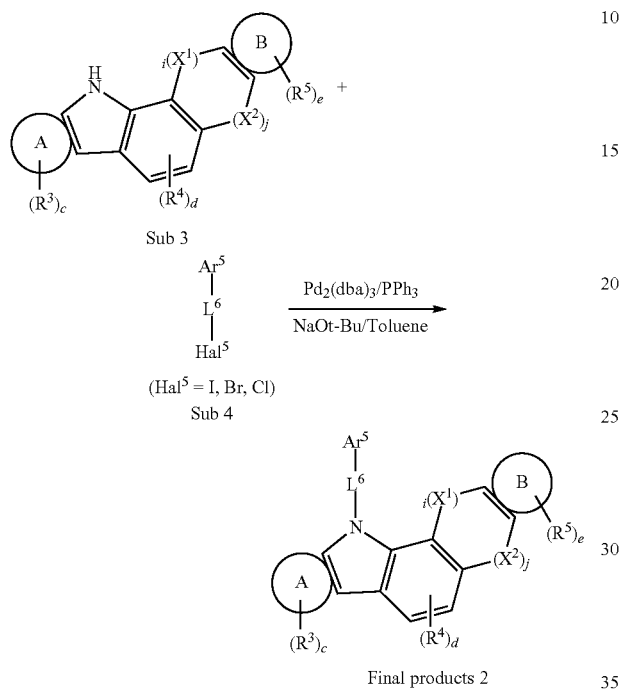

Sub 3

Sub 4

(Hal⁵ = I, Br, Cl)

Final products 2

Synthesis Example of Sub 3

Sub 3 of Reaction Scheme 6 can be synthesized by the reaction path of the following Reaction Scheme 7, but is not limited thereto.

<Reaction Scheme 7>

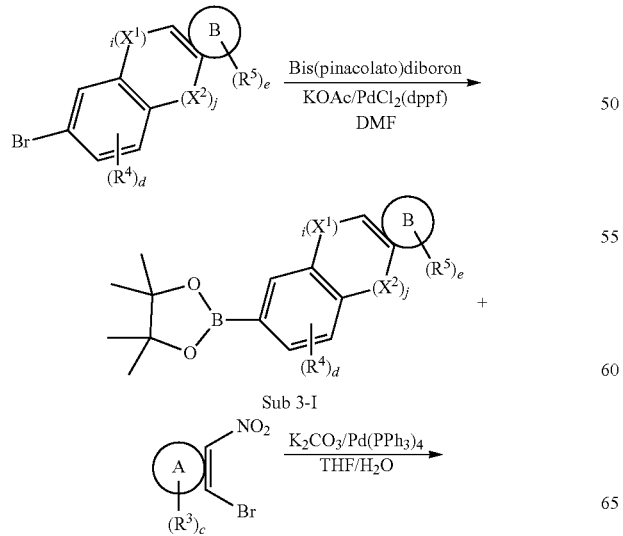

Sub 3-I

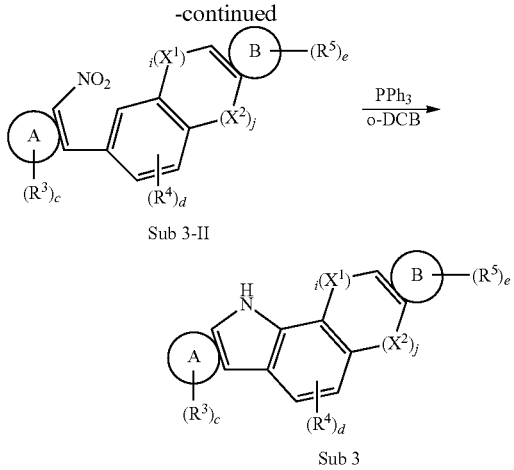

Sub 3-II

Sub 3

Synthesis Example of Sub 3-1

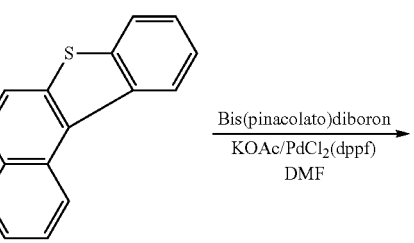

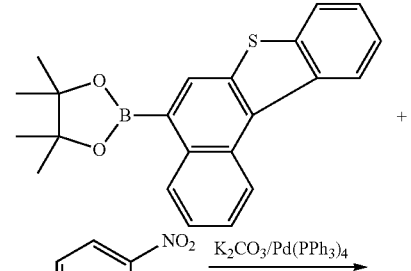

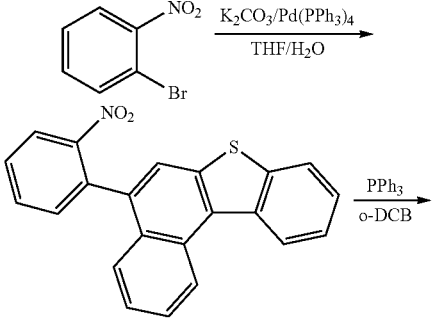

Sub 3-II-1

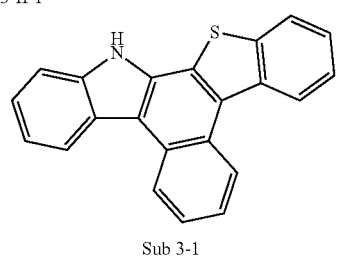

Sub 3-1

(1) Synthesis of Sub 3-I-1

After 5-bromobenzo[b]naphtha[1,2-d]thiophene (50 g, 159.64 mmol), bis(pinacolato)diboron (44.59 g, 175.60 mmol), KOAc (47 g, 478.91 mmol), PdCl₂(dppf) (3.50 g, 4.79 mmol) were dissolved in DMF (1006 mL), and refluxed at 120° C. for 12 hours. When the reaction was completed, the temperature of the reaction was cooled to room temperature, extracted with CH₂Cl₂ and wiped with water. The organic layer was dried over MgSO₄ and concentrated. The resulting compound was recrystallized by CH₂Cl₂ and methanol solvent to obtain the product. (46.01 g, 80%)

(2) Synthesis of Sub 3-II-1

Sub 3-I-1 (45.94 g, 156.17 mmol), 1-bromo-2-nitrobenzene (38.90 g, 156.17 mmol), K₂CO₃ (64.75 g, 468.51 mmol), Pd(PPh₃)₄ (5.41 g, 4.69 mmol) were added in a round bottom flask and THF (687 mL) and water (344 mL) were added to dissolve and refluxed at 80° C. for 12 hours. When the reaction was completed, the temperature of the reaction was cooled to room temperature, extracted with CH₂Cl₂ and wiped with water. The organic layer was dried over MgSO₄ and concentrated. The resulting compound was separated by silicagel column chromatography to obtain the product. (38.85 g, 70%)

(3) Synthesis of Sub 3-1

Sub 3-II-1 (38.85 g, 109.31 mmol) and triphenylphosphine (71.68 g, 273.28 mmol) were dissolved in o-dichlorobenzene (547 mL) and refluxed for 24 hours. When the reaction was completed, the solvent was removed using reduced pressure distillation. The resulting compound was separated by silicagel column chromatography and recrystallized to obtain the product. (25.81 g, 73%)

Synthesis of Sub 3-2

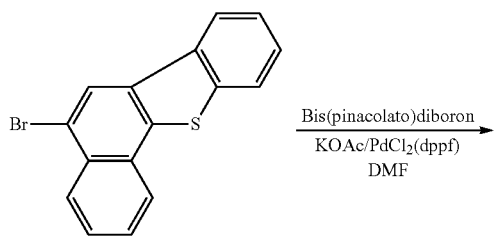

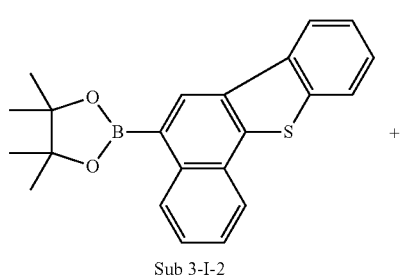

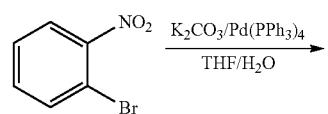

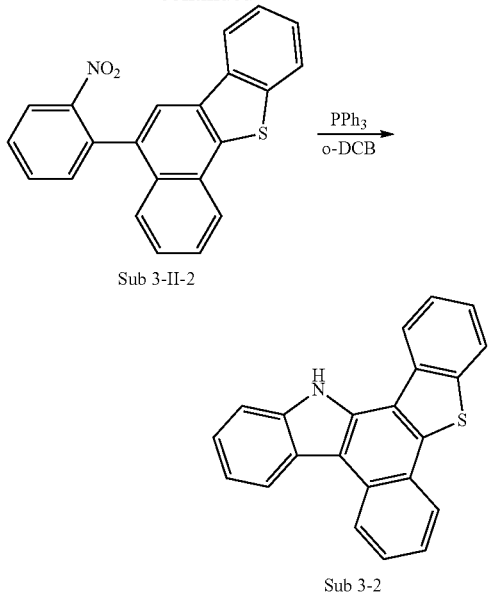

Sub 3-II-2

Sub 3-2

(1) Synthesis of Sub 3-I-2

5-bromobenzo[b]naphtho[2,1-d]thiophene (55 g, 175.60 mmol), bis(pinacolato)diboron (49.05 g, 193.16 mmol), KOAc (51.7 g, 526.80 mmol), PdCl₂(dppf) (3.86 g, 5.27 mmol) and DMF (1.11 L) were carried out in the same manner as in Sub 3-I-1 to give the product. (49.35 g, 78%).

(2) Synthesis of Sub 3-II-2

Sub 3-I-2 (49.22 g, 136.63 mmol), 1-bromo-2-nitrobenzene (27.60 g, 136.63 mmol), K₂CO₃ (56.65 g, 409.88 mmol), Pd(PPh₃)₄ (4.74 g, 4.1 mmol), THF (601 ml) and water (301 ml) were carried out in the same manner as in Sub 3-II-1 to give the product. (26.16 g, 67%).

(3) Synthesis of Sub 3-2

Sub 3-II-2 (26.16 g, 73.61 mmol), triphenylphosphine (48.26 g, 184.01 mmol), o-dichlorobenzene (368 ml) were carried out in the same manner as in Sub 3-1 to give the product. (15.95 g, 67%).

Synthesis of Sub 3-7

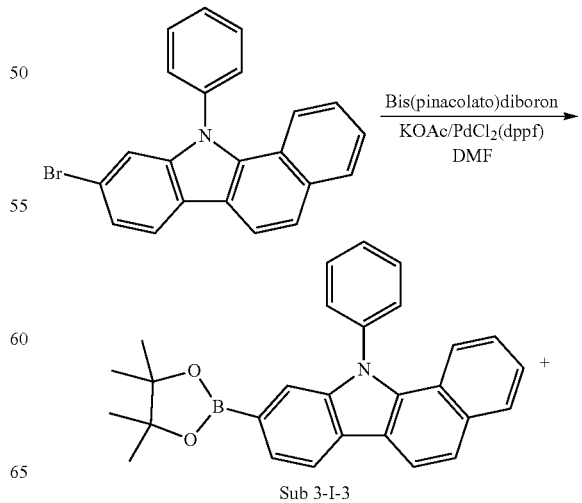

Sub 3-I-3

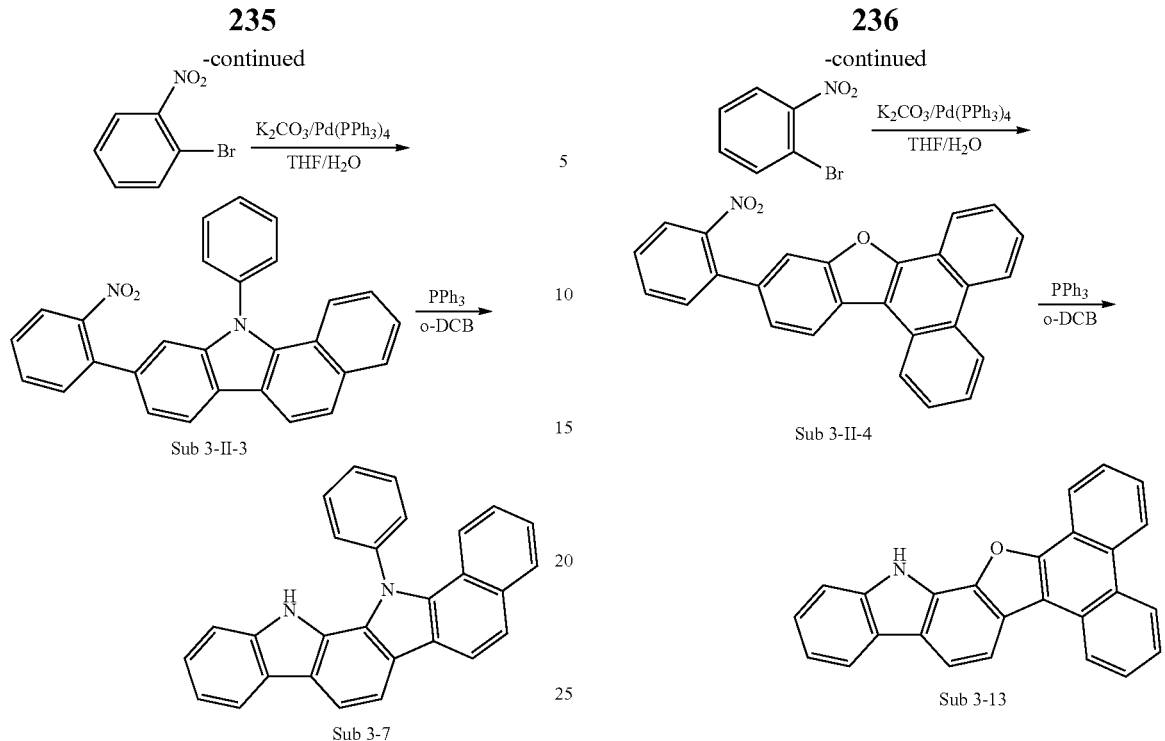

(1) Synthesis of Sub 3-I-3
9-bromo-11-phenyl-11H-benzo[a]carbazole (55 g, 147.74 mmol), bis(pinacolato)diboron (41.27 g, 162.52 mmol), KOAc (43.5 g, 443.23 mmol), PdCl₂(dppf) (3.24 g, 4.43 mmol) were carried out in the same manner as in Sub 3-I-1 to give the product. (51.42 g, 83%).

(2) Synthesis of Sub 3-II-3
Sub 3-I-3 (51.42 g, 122.62 mmol), 1-bromo-2-nitrobenzene (24.77 g, 122.62 mmol), K₂CO₃ (50.84 g, 367.87 mmol), Pd(PPh₃)₄ (4.25 g, 3.68 mmol)), THF (540 ml) and water (270 ml) were carried out in the same manner as in Sub 3-II-1 to give the product. (38.63 g, 76%).

(3) Synthesis of Sub 3-7
Sub 3-II-3 (38.63 g, 93.21 mmol), triphenylphosphine (61.12 g, 233.01 mmol) and o-dichlorobenzene (466 mL) were carried out in the same manner as in Sub 3-1 to give the product. (14.97 g, 42%).

Synthesis of Sub 3-13

(1) Synthesis of Sub 3-I-4
11-bromophenanthro[9,10-b]benzofuran (60 g, 172.81 mmol), bis(pinacolato)diboron (48.27 g, 190.09 mmol), KOAc (50.88 g, 518.42 mmol), PdCl₂(dppf) (3.79 g, 5.18 mmol) were carried out in the same manner as in Sub 3-I-1 to give the product. (52.46 g, 77%).

(2) Synthesis of Sub 3-II-4
Sub 3-I-4 (52.46 g, 133.05 mmol), 1-bromo-2-nitrobenzene (26.88 g, 133.05 mmol), K₂CO₃ (55.17 g, 399.16 mmol), Pd(PPh₃)₄ (4.61 g, 3.99 mmol), THF (574 ml) and water (287 ml) were carried out in the same manner as in Sub 3-II-1 to give the product. (40.93 g, 79%).

(3) Synthesis of Sub 3-13
Sub 3-II-4 (40.93 g, 105.11 mmol), triphenylphosphine (68.92 g, 262.77 mmol), o-dichlorobenzene (526 ml) were carried out in the same manner as in Sub 3-1 to give Sub 3-13. (15.03 g, 40%).

Synthesis of Sub 3-26

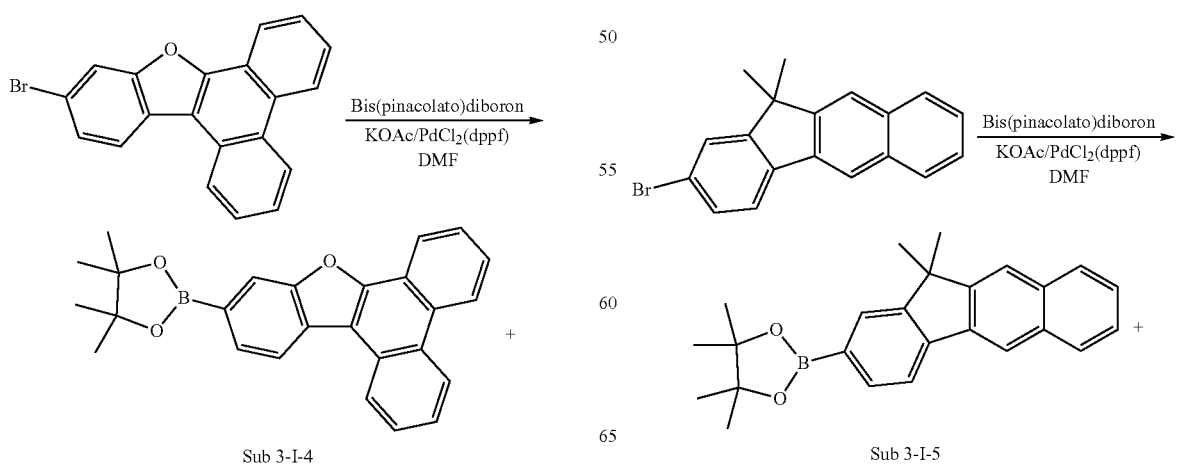

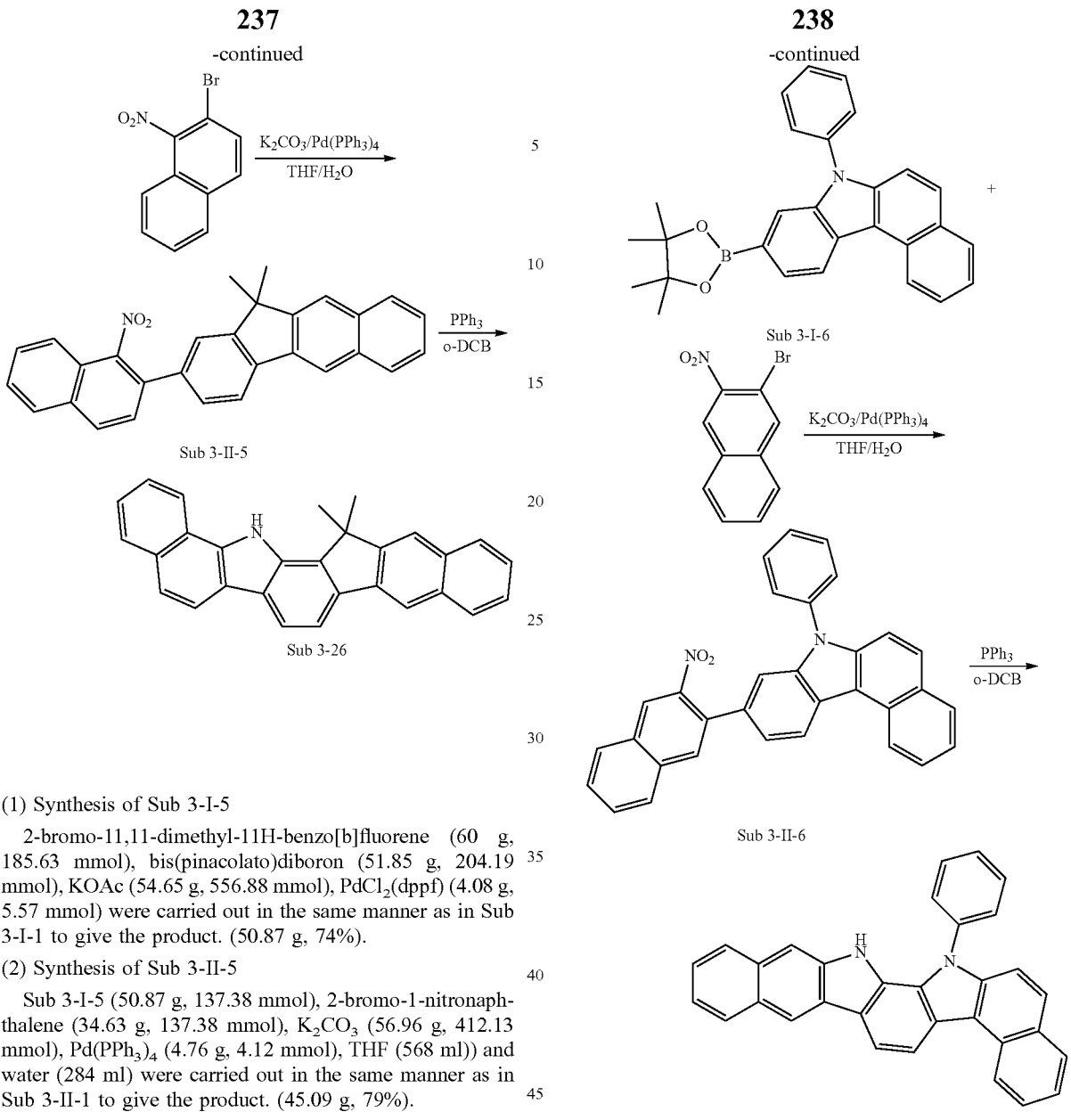

(1) Synthesis of Sub 3-I-5

2-bromo-11,11-dimethyl-11H-benzo[b]fluorene (60 g, 185.63 mmol), bis(pinacolato)diboron (51.85 g, 204.19 mmol), KOAc (54.65 g, 556.88 mmol), PdCl₂(dppf) (4.08 g, 5.57 mmol) were carried out in the same manner as in Sub 3-I-1 to give the product. (50.87 g, 74%).

(2) Synthesis of Sub 3-II-5

Sub 3-I-5 (50.87 g, 137.38 mmol), 2-bromo-1-nitronaphthalene (34.63 g, 137.38 mmol), K₂CO₃ (56.96 g, 412.13 mmol), Pd(PPh₃)₄ (4.76 g, 4.12 mmol), THF (568 ml)) and water (284 ml) were carried out in the same manner as in Sub 3-II-1 to give the product. (45.09 g, 79%).

(3) Synthesis of Sub 3-26

Sub 3-II-5 (45.09 g, 108.52 mmol), triphenylphosphine (71.16 g, 271.31 mmol), o-dichlorobenzene (543 ml) were carried out in the same manner as in Sub 3-1 to give the product. (15.81 g, 38%).

Synthesis of Sub 3-39

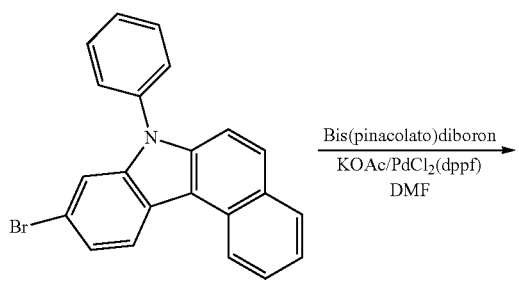

(1) Synthesis of Sub 3-I-6

9-bromo-7-phenyl-7H-benzo[c]carbazole (60 g, 161.17 mmol), bis(pinacolato)diboron (45.02 g, 177.29 mmol), KOAc (47.45 g, 483.52 mmol), PdCl₂(dppf) (3.54 g, 4.84 mmol) were carried out in the same manner as in Sub 3-I-1 to give the product. (52.04 g, 77%).

(2) Synthesis of Sub 3-II-6

Sub 3-I-6 (52.04 g, 124.10 mmol), 2-bromo-3-nitronaphthalene (31.28 g, 124.10 mmol), K₂CO₃ (51.46 g, 372.31 mmol), Pd(PPh₃)₄ (4.30 g, 3.72 mmol), THF (546 ml) and water (273 ml) were carried out in the same manner as in Sub 3-II-1 to give the product. (45.54 g, 79%).

(3) Synthesis of Sub 3-39

Sub 3-II-6 (45.54 g, 98.04 mmol), triphenylphosphine (64.29 g, 245.09 mmol), o-dichlorobenzene (490 ml) were carried out in the same manner as in Sub 3-1 to give the product. (16.96 g, 40%).

Synthesis of Sub 3-45

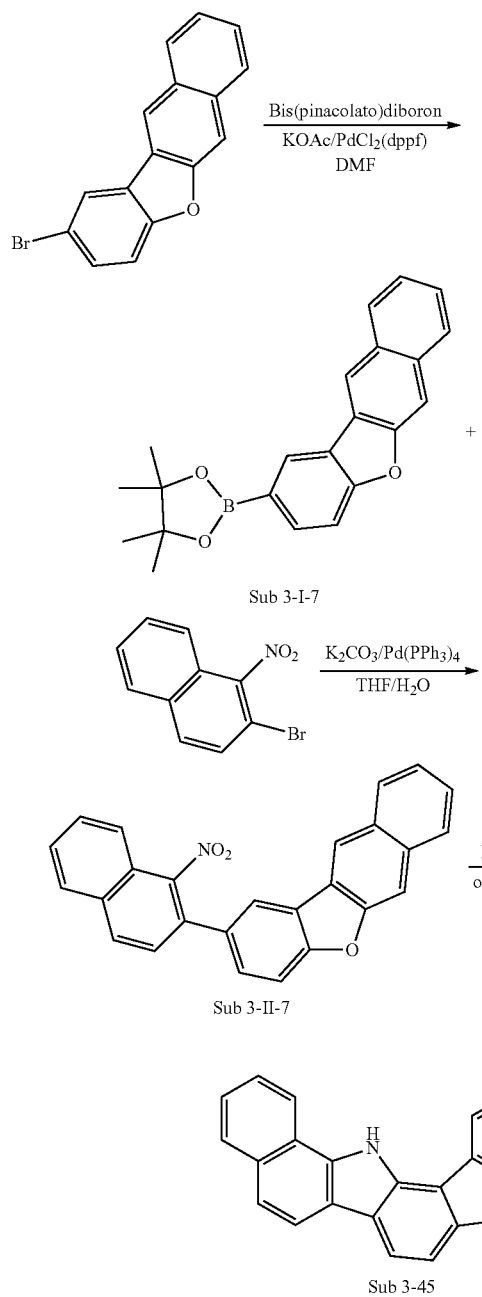

Sub 3-45

(3) Synthesis of Sub 3-45
Sub 3-II-7 (45.55 g, 116.97 mmol), triphenylphosphine (76.7 g, 292.43 mmol), o-dichlorobenzene (585 ml) were carried out in the same manner as in Sub 3-1 to give the product. (15.89 g, 38%).

Synthesis of Sub 3-61

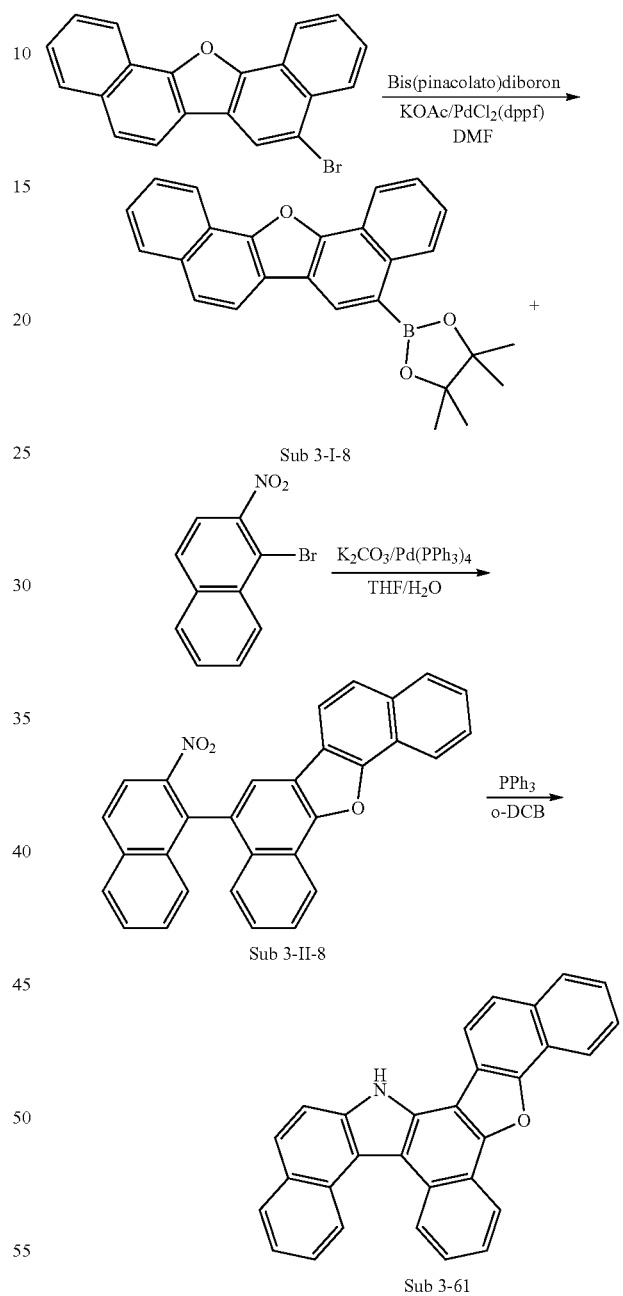

Sub 3-61

(1) Synthesis of Sub 3-I-7
2-bromonaphtho[2,3-b]benzofuran (60 g, 201.92 mmol), bis(pinacolato)diboron (56.40 g, 222.11 mmol), KOAc (59.45 g, 605.75 mmol), PdCl₂(dppf) (4.43 g, 6.06 mmol) were carried out in the same manner as in Sub 3-I-1 to give the product. (55.60 g, 80%).

(2) Synthesis of Sub 3-II-7
Sub 3-I-7 (55.60 g, 161.52 mmol), 1-bromo-2-nitronaphthalene (40.72 g, 161.52 mmol), K₂CO₃ (66.97 g, 484.57 mmol), Pd(PPh₃)₄ (5.60 g, 4.85 mmol), THF (711 ml) and water (355 ml) were carried out in the same manner as in Sub 3-II-1 to give the product. (45.55 g, 74%).

(1) Synthesis of Sub 3-I-8
5-bromodinaphtho[1,2-b:2',1'-d]furan (60 g, 172.81 mmol), bis(pinacolato)diboron (48.27 g, 190.09 mmol), KOAc (50.88 g, 518.42 mmol), PdCl₂(dppf) (3.79 g, 5.18 mmol) were carried out in the same manner as in Sub 3-I-1 to give the product. (52.46 g, 77%).

(2) Synthesis of Sub 3-II-8
Sub 3-I-8 (52.46 g, 133.05 mmol), 1-bromo-2-nitronaphthalene (33.54 g, 133.05 mmol), K₂CO₃ (55.17 g, 399.16 mmol), Pd(PPh₃)₄ (4.61 g, 3.99 mmol), THF (585 ml) and water (293 ml) were carried out in the same manner as in Sub 3-II-1 to give the product. (40.93 g, 70%).

(3) Synthesis of Sub 3-61

Sub 3-II-8 (40.93 g, 93.13 mmol), triphenylphosphine (61.07 g, 232.84 mmol), o-dichlorobenzene (466 ml) were carried out in the same manner as in Sub 3-1 to give the product. (23.15 g, 61%).

Synthesis of Sub 3-66

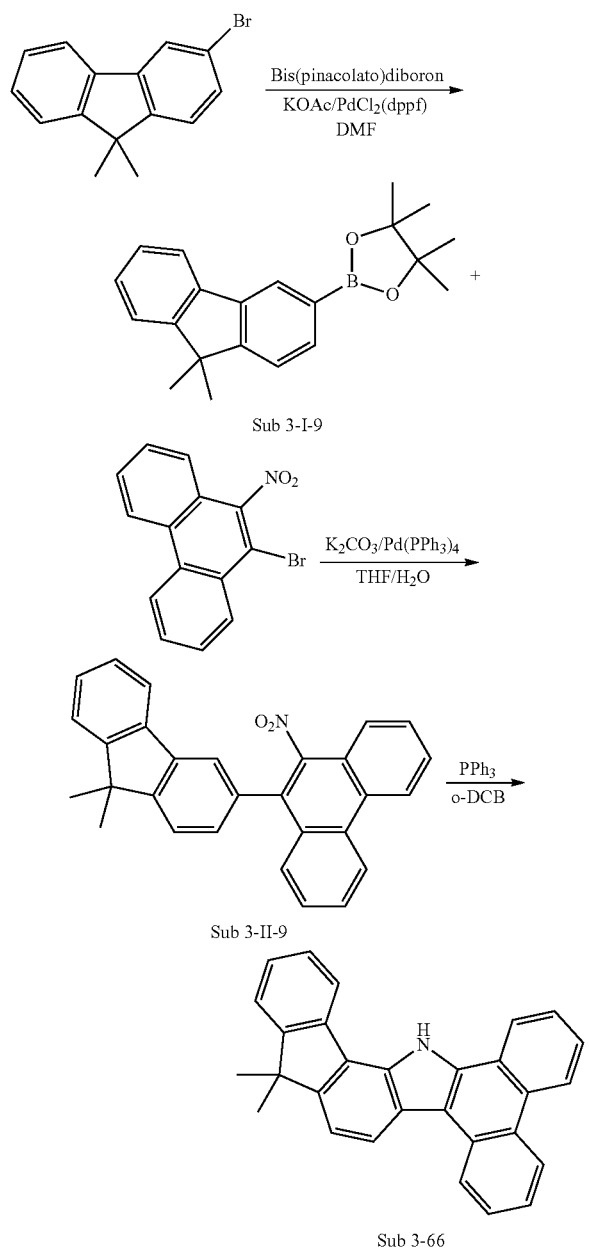

Sub 3-66

(1) Synthesis of Sub 3-I-9

Sub 3-I-9 (60 g, 219.64 mmol), bis(pinacolato)diboron (61.35 g, 241.61 mmol), KOAc (64.67 g, 658.93 mmol), PdCl₂(dppf) (4.82 g, 6.59 mmol) were carried out in the same manner as in Sub 3-I-1 to give the product. (52.05 g, 74%).

(2) Synthesis of Sub 3-II-9

Sub 3-I-8 (52.05 g, 162.53 mmol), 9-bromo-10-nitrophenanthrene (49.11 g, 162.53 mmol), K₂CO₃ (67.39 g, 487.60 mmol), Pd(PPh₃)₄ (5.63 g, 4.88 mmol), THF (715 ml) and water (358 ml) were carried out in the same manner as in Sub 3-II-1 to give the product. (47.95 g, 71%).

(3) Synthesis of Sub 3-66

Sub 3-II-9 (47.95 g, 115.41 mmol), triphenylphosphine (75.67 g, 288.51 mmol), o-dichlorobenzene (577 ml) were carried out in the same manner as in Sub 3-1 to give the product. (18.59 g, 42%).

Synthesis of Sub 3-67

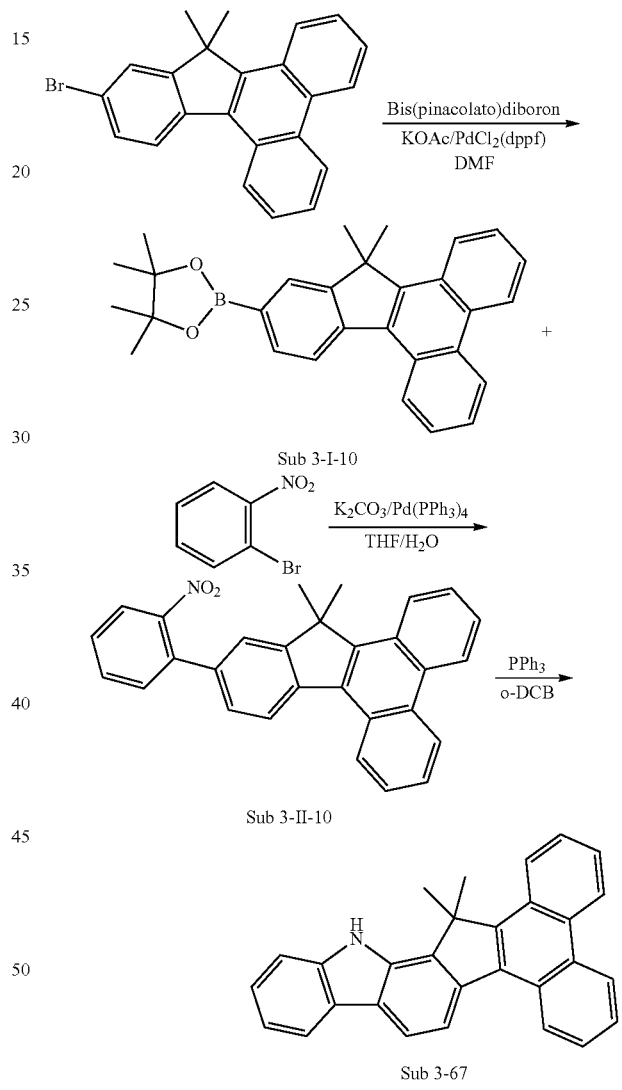

Sub 3-67

(1) Synthesis of Sub 3-I-10

Sub 3-I-10 (60 g, 219.64 mmol), bis(pinacolato)diboron (61.35 g, 241.61 mmol), KOAc (64.67 g, 658.93 mmol), PdCl₂(dppf) (4.82 g, 6.59 mmol) were carried out in the same manner as in Sub 3-I-1 to give the product. (52.05 g, 74%).

(2) Synthesis of Sub 3-II-10

Sub 3-I-10 (52.05 g, 162.53 mmol), 1-bromo-2-nitrobenzene (49.11 g, 162.53 mmol), K₂CO₃ (67.39 g, 487.60 mmol), Pd(PPh₃)₄ (5.63 g, 4.88 mmol), THF (715 ml) and water (358 ml) were carried out in the same manner as in Sub 3-II-1 to give the product. (47.95 g, 71%).

(3) Synthesis of Sub 3-67

Sub 3-II-10 (47.95 g, 115.41 mmol), triphenylphosphine (75.67 g, 288.51 mmol), o-dichlorobenzene (577 ml) were carried out in the same manner as in Sub 3-1 to give the product. (18.59 g, 42%).

Synthesis of Sub 3-79

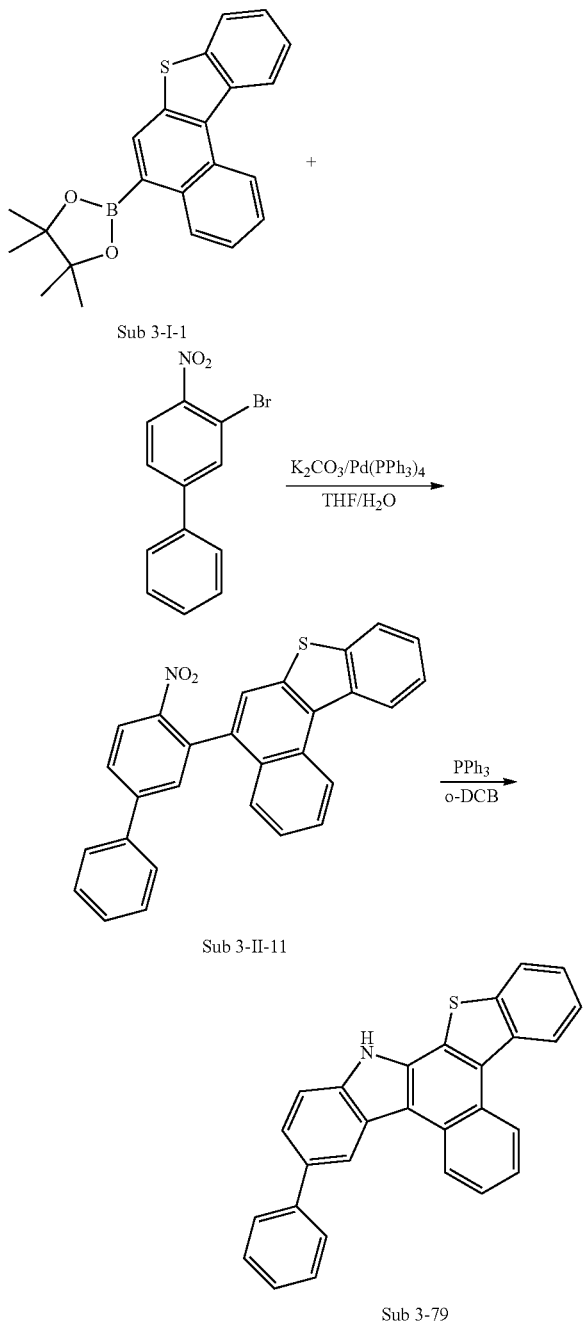

Sub 3-79

(1) Synthesis of Sub 3-II-11

Sub 3-I-1 (40 g, 111.02 mmol), 3-bromo-4-nitro-1,1'-biphenyl (30.88 g, 111.02 mmol), K₂CO₃ (46.03 g, 333.07 mmol), Pd(PPh₃)₄ (3.85 g, 3.33 mmol), THF (489 ml) and water (244 ml) were carried out in the same manner as in Sub 3-II-1 to give the product. (34.97 g, 73%).

(2) Synthesis of Sub 3-79

Sub 3-II-11 (34.97 g, 81.04 mmol), triphenylphosphine (53.14 g, 202.60 mmol), o-dichlorobenzene (405 ml) were carried out in the same manner as in Sub 3-1 to give the product. (21.69 g, 67%).

Synthesis of Sub 3-82

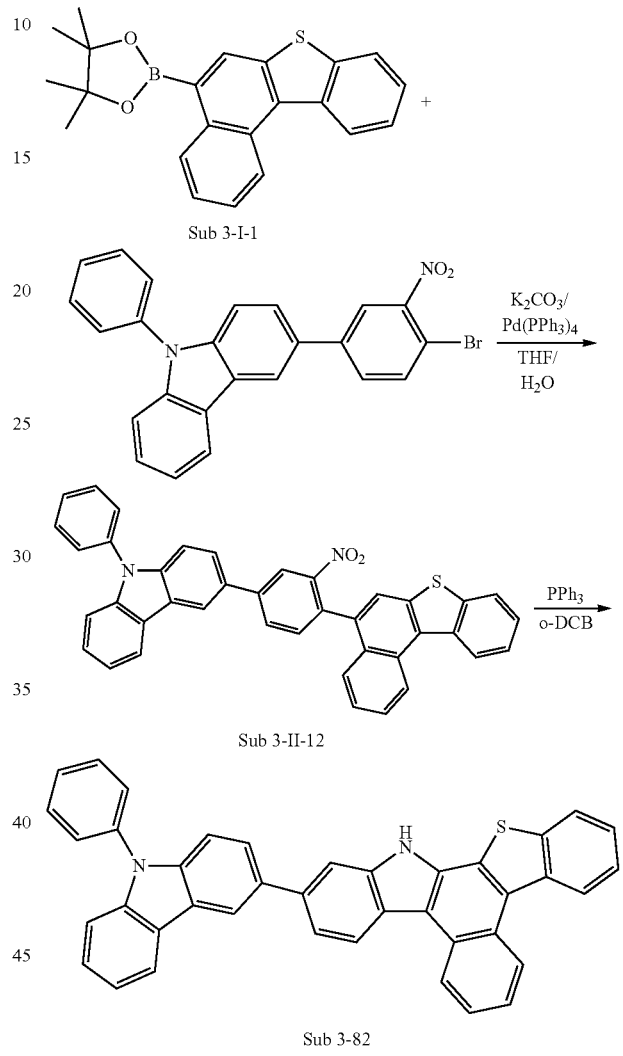

(1) Synthesis of Sub 3-II-12

Sub 3-I-1 (40 g, 111.02 mmol), 3-(4-bromo-3-nitrophenyl)-9-phenyl-9H-carbazole (49.22 g, 111.02 mmol), K₂CO₃ (46.03 g, 333.07 mmol), Pd(PPh₃)₄ (3.85 g, 3.33 mmol), THF (489 ml) and water (244 ml) were carried out in the same manner as in Sub 3-II-1 to give the product. (42.40 g, 64%).

(2) Synthesis of Sub 3-82

Sub 3-II-12 (42.40 g, 71.06 mmol), triphenylphosphine (46.59 g, 177.64 mmol), o-dichlorobenzene (355 ml) were carried out in the same manner as in Sub 3-1 to give the product. (24.48 g, 61%).

Synthesis of Sub 3-88

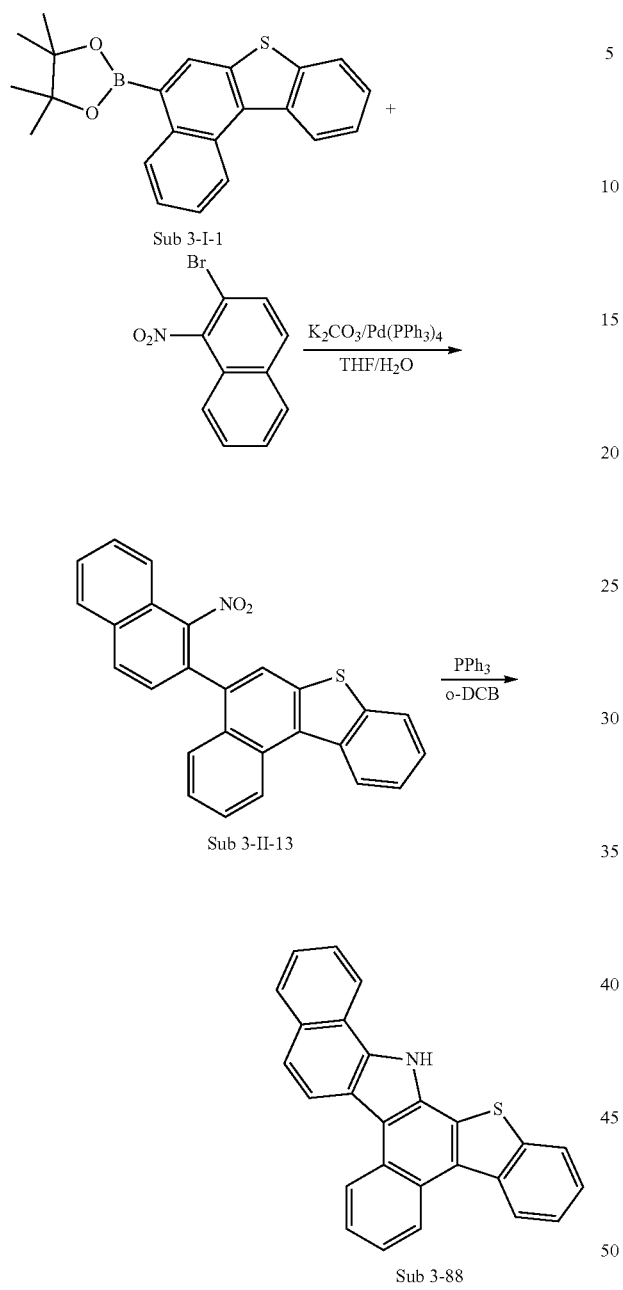

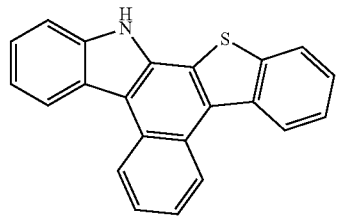
Sub 3-1

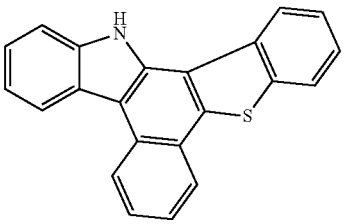
Sub 3-2

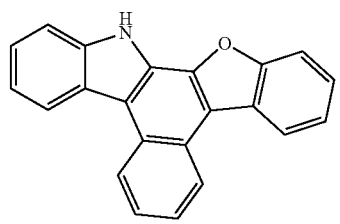
Sub 3-3

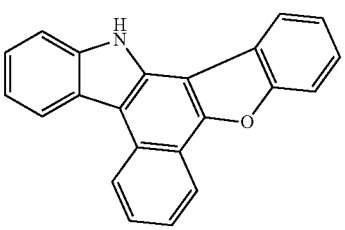
Sub 3-4

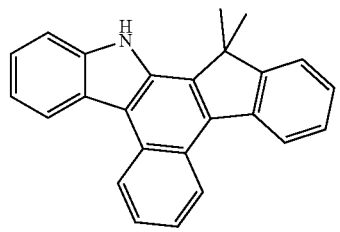
Sub 3-5

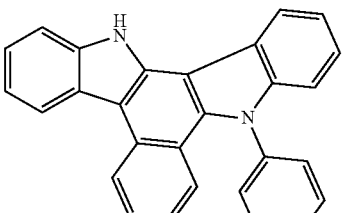
Sub 3-6

(1) Synthesis of Sub 3-II-13

Sub 3-I-1 (57.17 g, 158.69 mmol), 2-bromo-1-nitronaphthalene (40 g, 158.69 mmol), K₂CO₃ (65.80 g, 476.06 mmol), Pd(PPh₃)₄ (5.50 g, 4.76 mmol), THF (698 ml) and water (349 ml) were carried out in the same manner as in Sub 3-II-1 to give the product. (47.61 g, 74%).

(2) Synthesis of Sub 3-88

Sub 3-II-13 (47.61 g, 117.42 mmol), triphenylphosphine (76.99 g, 293.55 mmol), o-dichlorobenzene (587 ml) were carried out in the same manner as in Sub 3-1 to give the product. (28.07 g, 64%).

Examples of Sub 3 include, but are not limited to, the followings.

Sub 3-7
Sub 3-8
Sub 3-9
Sub 3-10
Sub 3-11
Sub 3-12
Sub 3-13
Sub 3-14
Sub 3-15
Sub 3-16
Sub 3-17
Sub 3-18
Sub 3-19
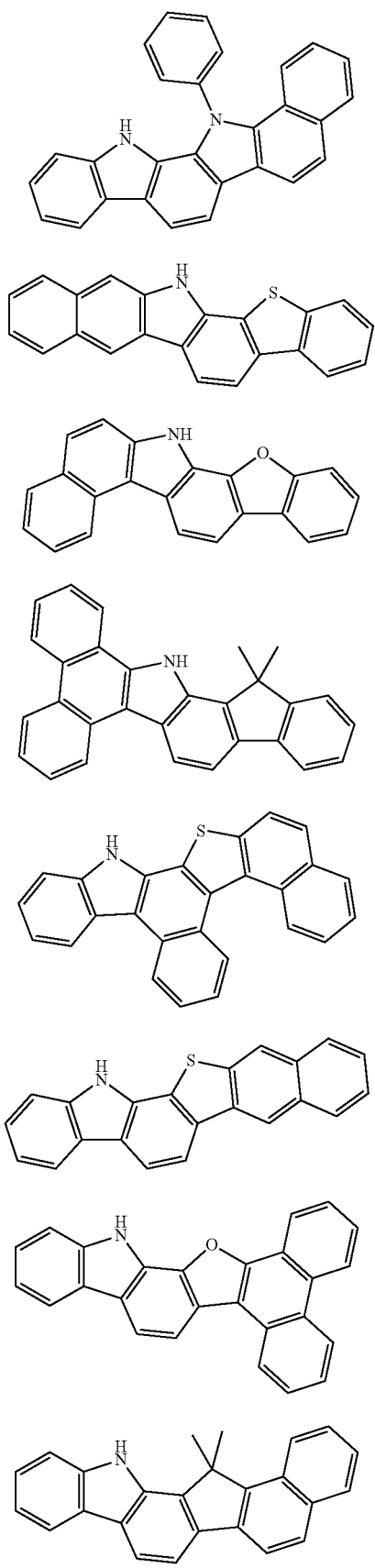
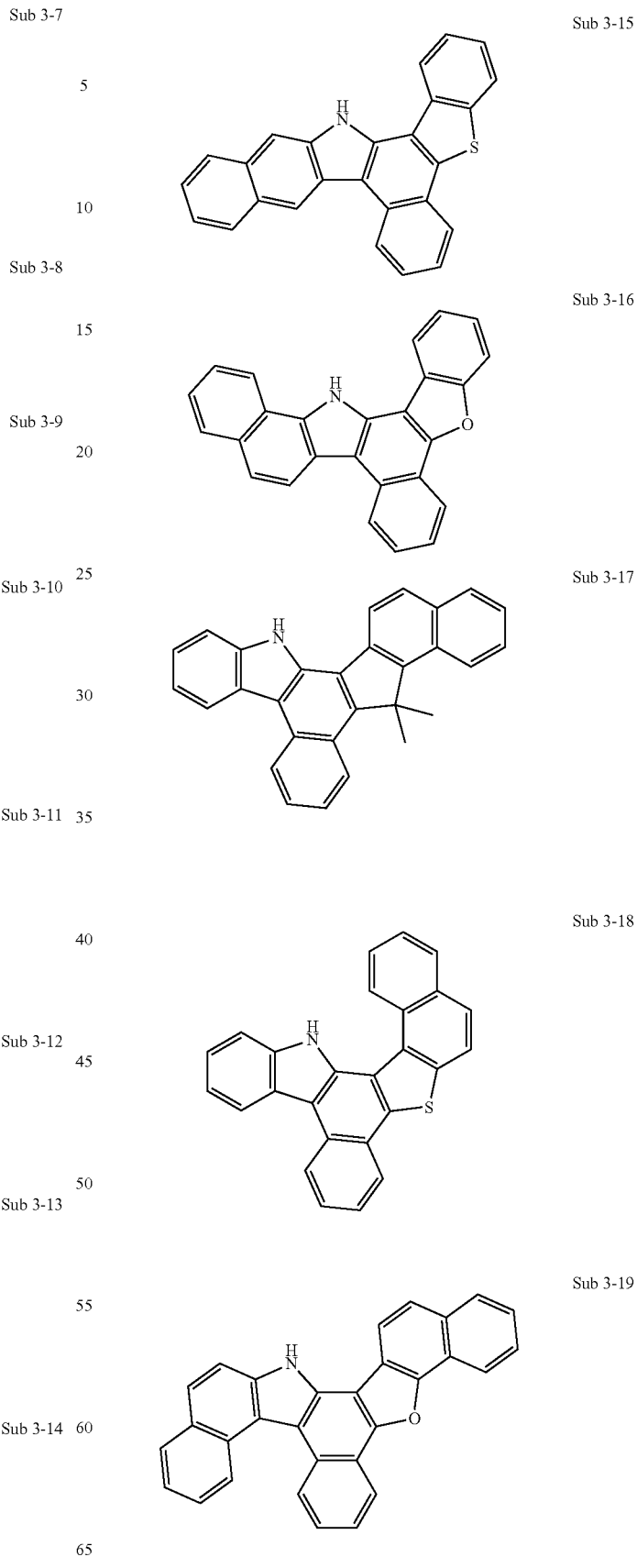

-continued
Sub 3-20
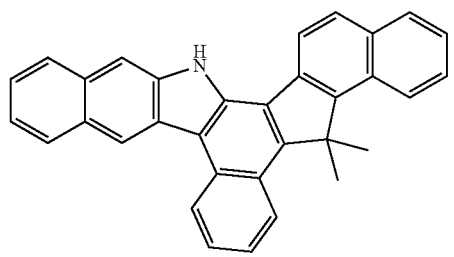
Sub 3-21
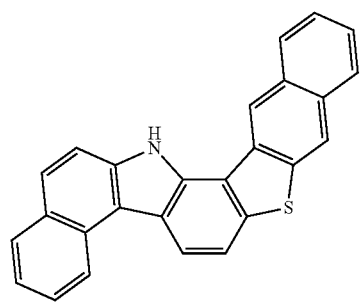
Sub 3-22
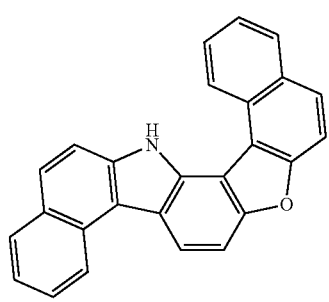
Sub 3-23
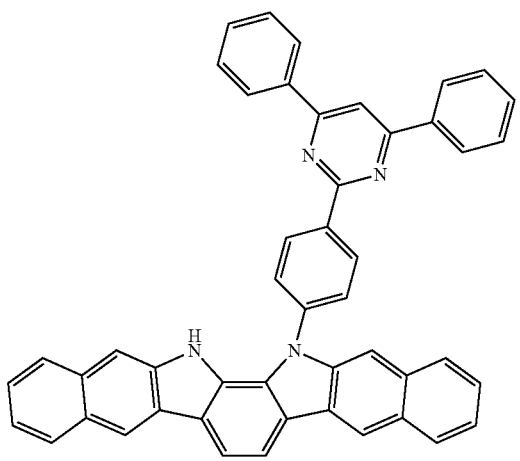
Sub 3-24
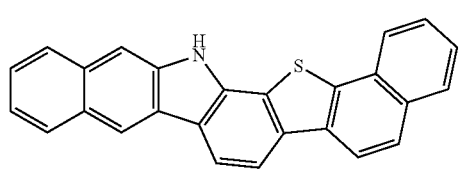
-continued
Sub 3-25
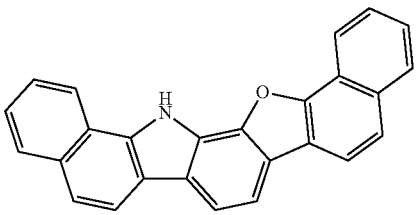
Sub 3-26
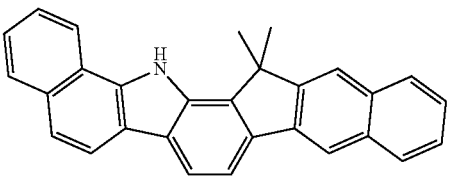
Sub 3-27
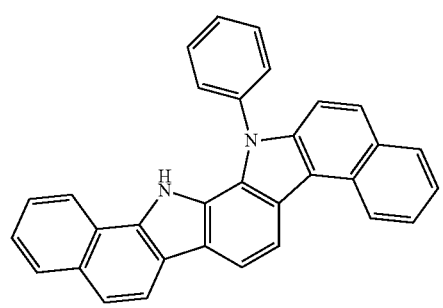
Sub 3-28
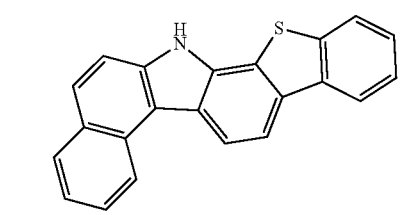
Sub 3-29
Sub 3-30
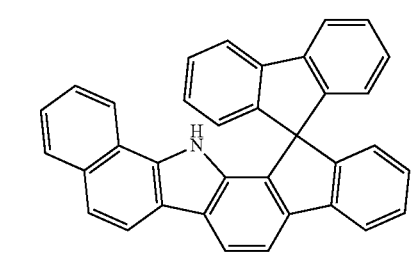
Sub 3-31
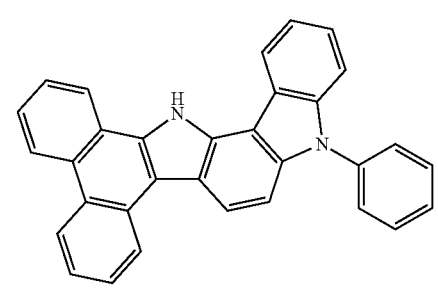

Sub 3-32
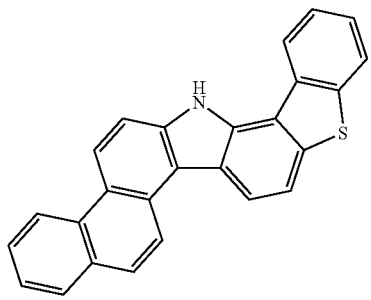
Sub 3-33
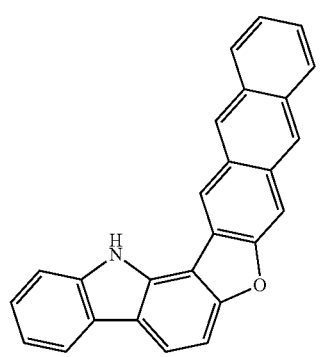
Sub 3-34
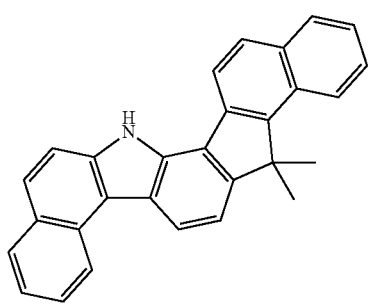
Sub 3-35
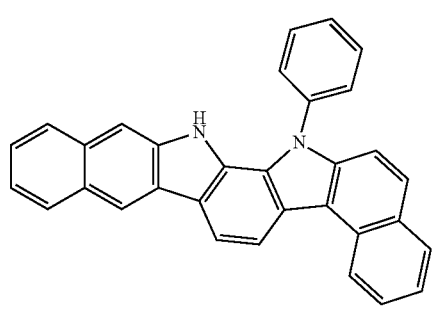
Sub 3-36
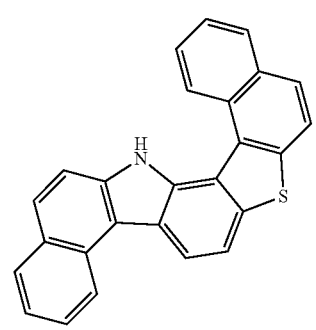
Sub 3-37
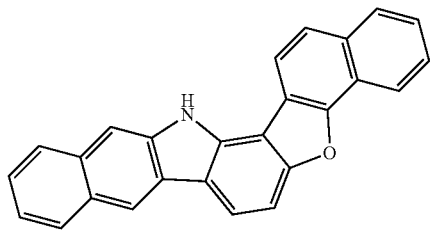
Sub 3-38
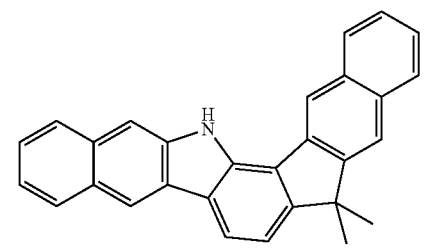
Sub 3-39
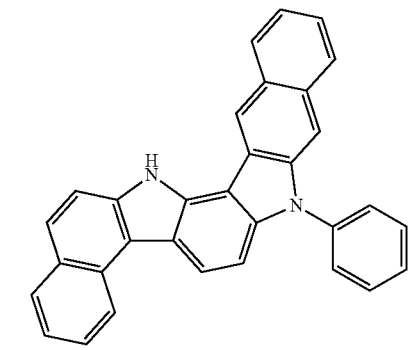
Sub 3-40
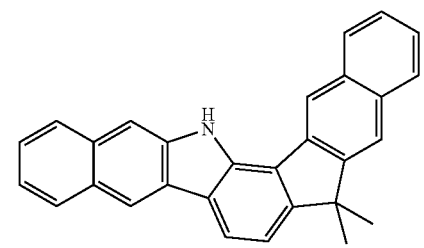
Sub 3-41
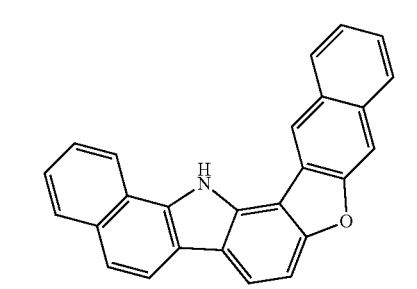

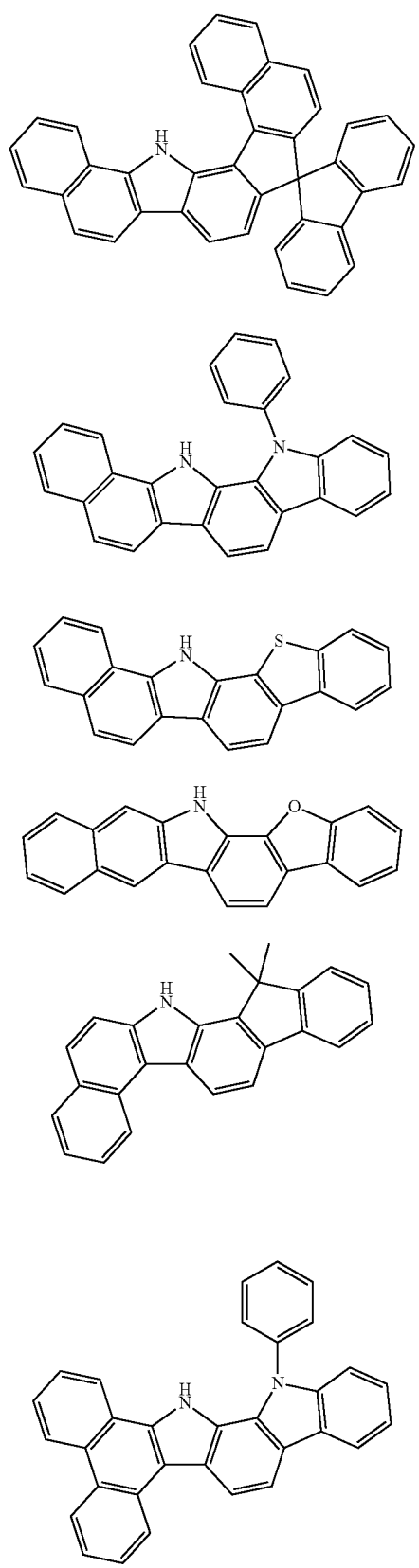
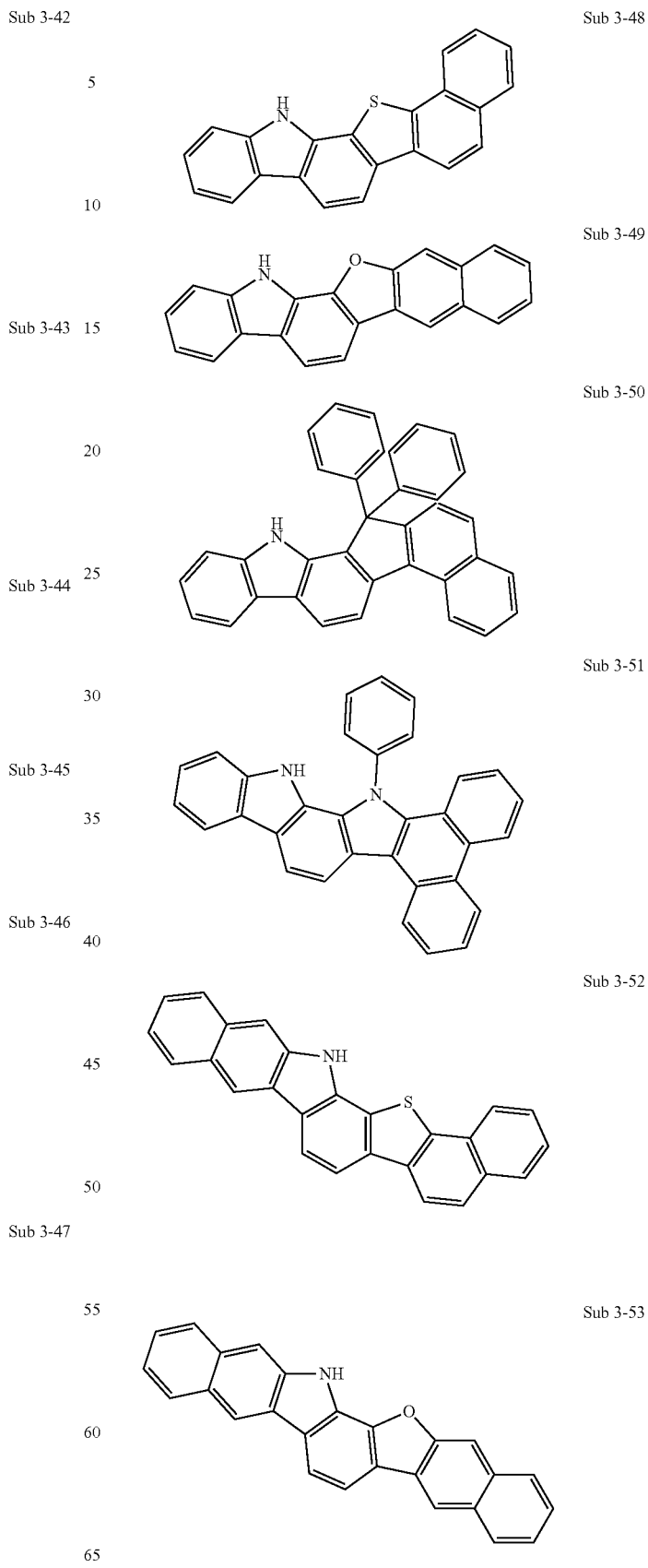

Sub 3-54
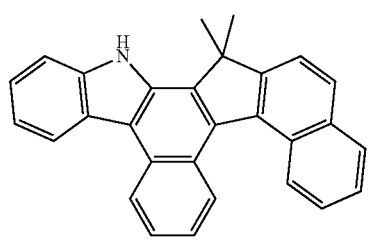
Sub 3-55
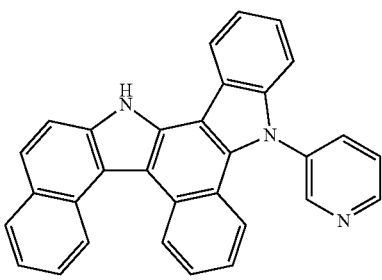
Sub 3-56
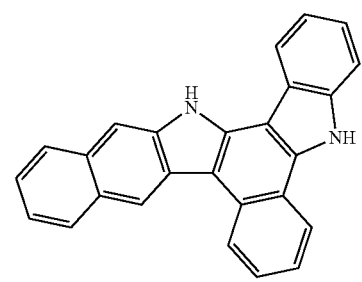
Sub 3-57
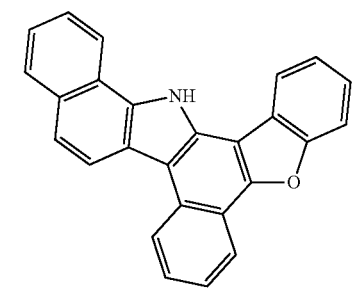
Sub 3-58
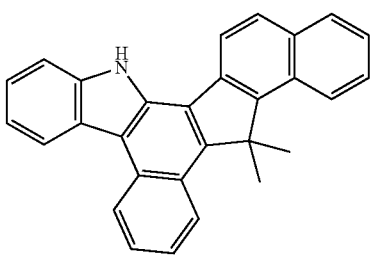
Sub 3-59
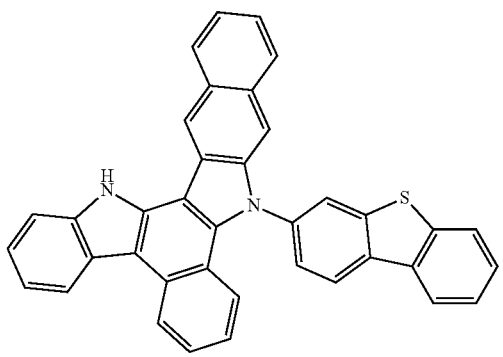
Sub 3-60
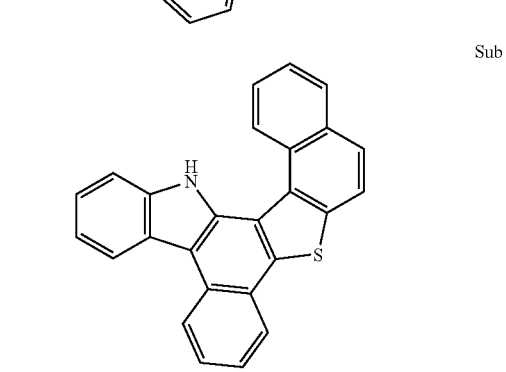
Sub 3-61
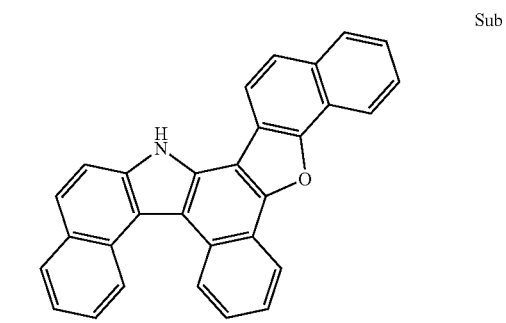
Sub 3-62
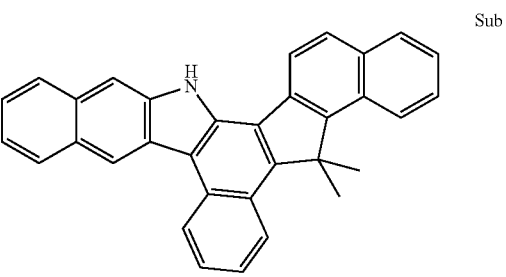
Sub 3-63
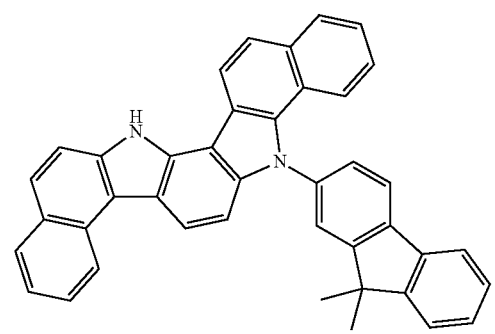

Sub 3-64
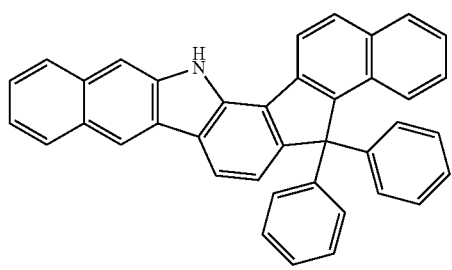
Sub 3-65
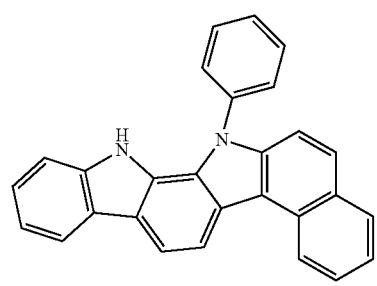
Sub 3-66
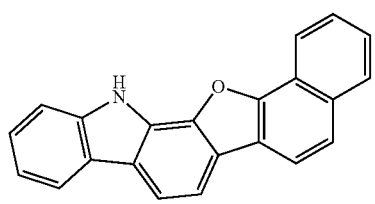
Sub 3-67
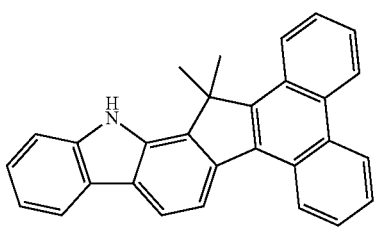
Sub 3-68
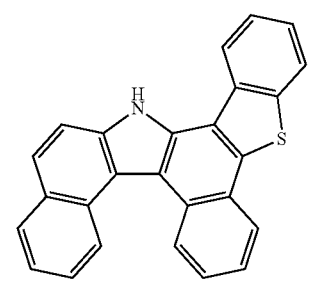
Sub 3-69
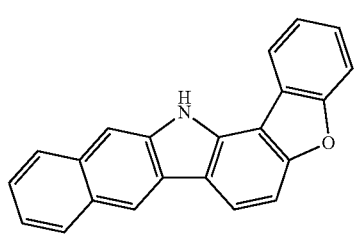
Sub 3-70
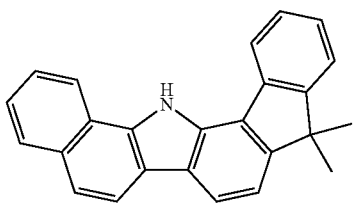
Sub 3-71
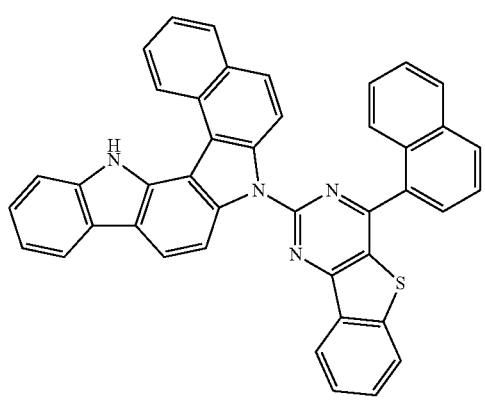
Sub 3-72
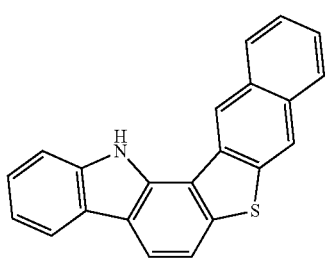
Sub 3-73
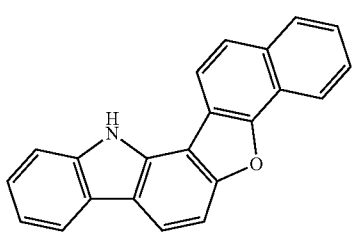
Sub 3-74
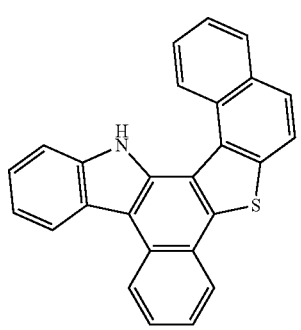

Sub 3-75
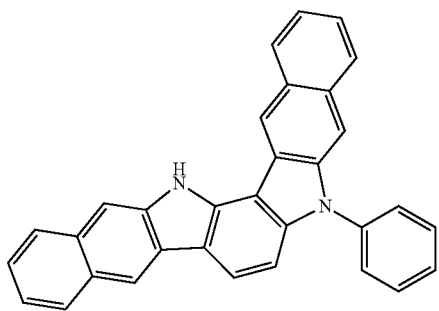
Sub 3-76
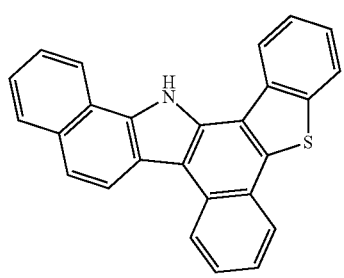
Sub 3-77
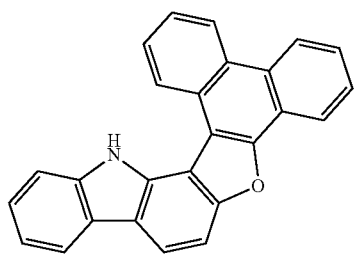
Sub 3-78
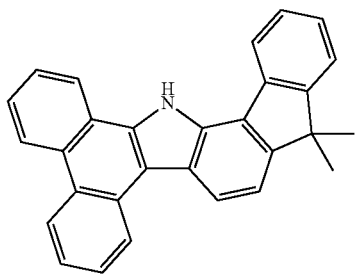
Sub 3-79
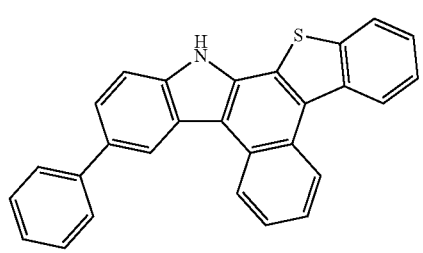
Sub 3-80
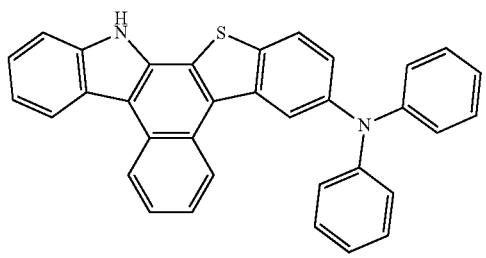
Sub 3-81
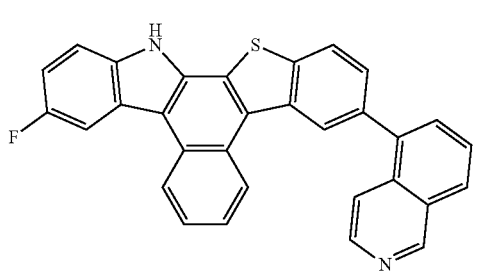
Sub 3-82
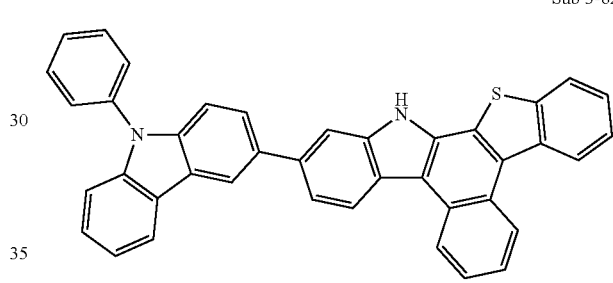
Sub 3-83
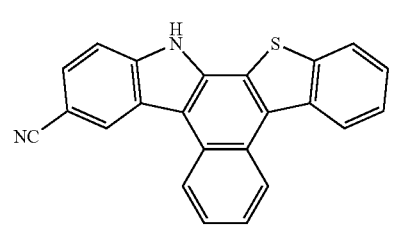
Sub 3-84
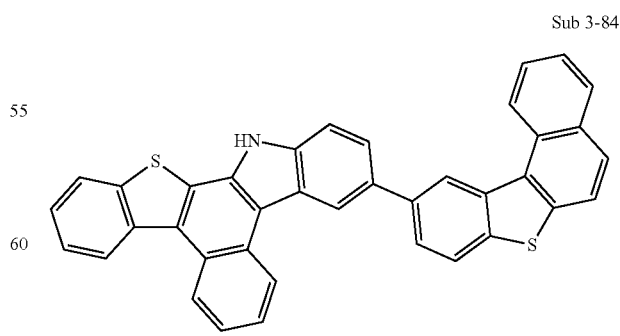

Sub 3-85

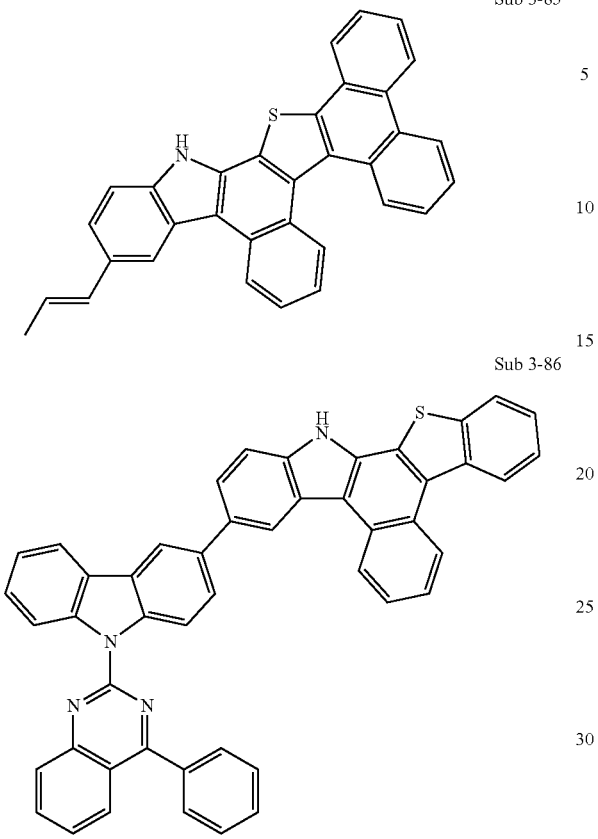

Sub 3-86

Sub 3-87

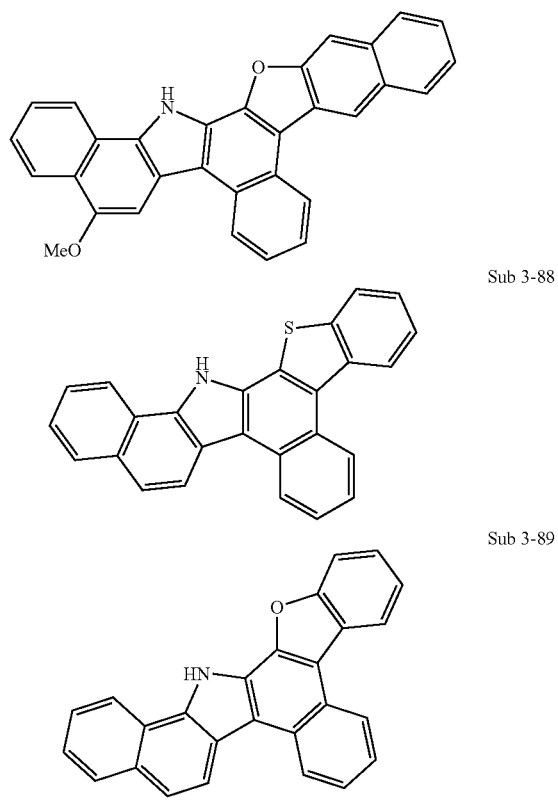

Sub 3-88

Sub 3-89

TABLE 4

| compound | FD-MS | compound | FD-MS |
| --- | --- | --- | --- |
| Sub 3-1 | m/z = 323.08 ($C_{22}H_{13}NS$ = 323.41) | Sub 3-2 | m/z = 323.08 ($C_{22}H_{13}NS$ = 323.41) |
| Sub 3-3 | m/z = 307.10 ($C_{22}H_{13}NO$ = 307.34) | Sub 3-4 | m/z = 307.10 ($C_{22}H_{13}NO$ = 307.34) |
| Sub 3-5 | m/z = 333.15 ($C_{25}H_{19}N$ = 333.43) | Sub 3-6 | m/z = 382.15 ($C_{28}H_{18}N_2$ = 382.46) |
| Sub 3-7 | m/z = 382.15 ($C_{28}H_{18}N_2$ = 382.46) | Sub 3-8 | m/z = 323.08 ($C_{22}H_{13}NS$ = 323.41) |
| Sub 3-9 | m/z = 307.10 ($C_{22}H_{13}NO$ = 307.34) | Sub 3-10 | m/z = 383.17 ($C_{29}H_{21}N$ = 383.49) |
| Sub 3-11 | m/z = 373.09 ($C_{26}H_{15}NS$ = 373.47) | Sub 3-12 | m/z = 323.08 ($C_{22}H_{13}NS$ = 323.41) |
| Sub 3-13 | m/z = 357.12 ($C_{26}H_{15}NO$ = 357.41) | Sub 3-14 | m/z = 333.15 ($C_{25}H_{19}N$ = 333.43) |
| Sub 3-15 | m/z = 373.09 ($C_{26}H_{15}NS$ = 373.47) | Sub 3-16 | m/z = 357.12 ($C_{26}H_{15}NO$ = 357.41) |
| Sub 3-17 | m/z = 383.17 ($C_{29}H_{21}N$ = 383.49) | Sub 3-18 | m/z = 373.09 ($C_{26}H_{15}NS$ = 373.47) |
| Sub 3-19 | m/z = 407.13 ($C_{30}H_{12}NO$ = 407.47) | Sub 3-20 | m/z = 433.18 ($C_{33}H_{23}N$ = 433.55) |
| Sub 3-21 | m/z = 373.09 ($C_{26}H_{15}NS$ = 373.47) | Sub 3-22 | m/z = 357.12 ($C_{26}H_{15}NO$ = 357.41) |
| Sub 3-23 | m/z = 662.25 ($C_{48}H_{30}N_4$ = 662.80) | Sub 3-24 | m/z = 373.09 ($C_{26}H_{15}NS$ = 373.47) |
| Sub 3-25 | m/z = 357.12 ($C_{26}H_{15}NO$ = 357.41) | Sub 3-26 | m/z = 383.17 ($C_{29}H_{21}N$ = 383.49) |
| Sub 3-27 | m/z = 432.16 ($C_{32}H_{20}N_2$ = 432.53) | Sub 3-28 | m/z = 323.08 ($C_{22}H_{13}NS$ = 323.41) |
| Sub 3-29 | m/z = 307.10 ($C_{22}H_{13}NO$ = 307.35) | Sub 3-30 | m/z = 455.17 ($C_{35}H_{21}N$ = 455.56) |
| Sub 3-31 | m/z = 432.16 ($C_{32}H_{20}N_2$ = 432.53) | Sub 3-32 | m/z = 373.09 ($C_{26}H_{15}NS$ = 373.47) |
| Sub 3-33 | m/z = 357.12 ($C_{26}H_{15}NO$ = 357.41) | Sub 3-34 | m/z = 383.17 ($C_{29}H_{21}N$ = 383.49) |
| Sub 3-35 | m/z = 432.16 ($C_{32}H_{20}N_2$ = 432.53) | Sub 3-36 | m/z = 373.09 ($C_{26}H_{15}NS$ = 373.47) |
| Sub 3-37 | m/z = 357.12 ($C_{26}H_{15}NO$ = 357.41) | Sub 3-38 | m/z = 383.17 ($C_{29}H_{21}N$ = 383.49) |
| Sub 3-39 | m/z = 432.16 ($C_{32}H_{20}N_2$ = 432.53) | Sub 3-40 | m/z = 373.09 ($C_{26}H_{15}NS$ = 373.47) |
| Sub 3-41 | m/z = 357.12 ($C_{26}H_{15}NO$ = 357.41) | Sub 3-42 | m/z = 505.18 ($C_{39}H_{23}N$ = 505.62) |
| Sub 3-43 | m/z = 382.15 ($C_{28}H_{18}N_2$ = 382.47) | Sub 3-44 | m/z = 323.08 ($C_{22}H_{13}NS$ = 323.41) |
| Sub 3-45 | m/z = 307.10 ($C_{22}H_{13}NO$ = 307.35) | Sub 3-46 | m/z = 333.15 ($C_{25}H_{19}N$ = 333.43) |
| Sub 3-47 | m/z = 432.16 ($C_{32}H_{20}N_2$ = 439.53) | Sub 3-48 | m/z = 323.08 ($C_{22}H_{13}NS$ = 323.41) |
| Sub 3-49 | m/z = 307.10 ($C_{22}H_{13}NO$ = 307.35) | Sub 3-50 | m/z = 457.18 ($C_{35}H_{23}N$ = 457.58) |
| Sub 3-51 | m/z = 432.16 ($C_{32}H_{20}N_2$ = 432.53) | Sub 3-52 | m/z = 373.09 ($C_{26}H_{15}NS$ = 373.47) |
| Sub 3-53 | m/z = 357.12 ($C_{26}H_{15}NO$ = 357.41) | Sub 3-54 | m/z = 383.17 ($C_{29}H_{21}N$ = 383.49) |
| Sub 3-55 | m/z = 433.16 ($C_{31}H_{19}N_3$ = 433.51) | Sub 3-56 | m/z = 356.13 ($C_{26}H_{16}N_2$ = 356.43) |
| Sub 3-57 | m/z = 357.12 ($C_{26}H_{15}NO$ = 357.41) | Sub 3-58 | m/z = 383.17 ($C_{29}H_{21}N$ = 383.49) |
| Sub 3-59 | m/z = 538.15 ($C_{38}H_{22}N_2S$ = 538.67) | Sub 3-60 | m/z = 373.09 ($C_{26}H_{15}NS$ = 373.47) |
| Sub 3-61 | m/z = 407.13 ($C_{30}H_{12}NO$ = 407.47) | Sub 3-62 | m/z = 433.18 ($C_{33}H_{23}N$ = 433.55) |
| Sub 3-63 | m/z = 548.23 ($C_{41}H_{28}N_2$ = 548.69) | Sub 3-64 | m/z = 507.20 ($C_{39}H_{25}N$ = 507.64) |
| Sub 3-65 | m/z = 382.15 ($C_{28}H_{18}N_2$ = 382.47) | Sub 3-66 | m/z = 307.10 ($C_{22}H_{13}NO$ = 307.35) |
| Sub 3-67 | m/z = 383.17 ($C_{29}H_{21}N$ = 383.49) | Sub 3-68 | m/z = 373.09 ($C_{26}H_{15}NS$ = 373.47) |

TABLE 4-continued

| compound | FD-MS | compound | FD-MS |
|---|---|---|---|
| Sub 3-69 | m/z = 307.10 ($C_{22}H_{13}NO$ = 307.35) | Sub 3-70 | m/z = 333.15 ($C_{25}H_{19}N$ = 333.43) |
| Sub 3-71 | m/z = 616.17 ($C_{42}H_{24}N_4S$ = 616.74) | Sub 3-72 | m/z = 323.08 ($C_{22}H_{13}NS$ = 323.41) |
| Sub 3-73 | m/z = 307.10 ($C_{22}H_{13}NO$ = 307.35) | Sub 3-74 | m/z = 373.09 ($C_{26}H_{15}NS$ = 373.47) |
| Sub 3-75 | m/z = 432.16 ($C_{32}H_{20}N_2$ = 432.53) | Sub 3-76 | m/z = 373.09 ($C_{26}H_{15}NS$ = 373.47) |
| Sub 3-77 | m/z = 357.12 ($C_{26}H_{15}NO$ = 357.41) | Sub 3-78 | m/z = 383.17 ($C_{29}H_{21}N$ = 383.49) |
| Sub 3-79 | m/z = 399.11 ($C_{28}H_{17}NS$ = 399.51) | Sub 3-80 | m/z = 490.15 ($C_{34}H_{22}N_2S$ = 490.62) |
| Sub 3-81 | m/z = 468.11 ($C_{31}H_{17}FN_2S$ = 468.55) | Sub 3-82 | m/z = 564.17 ($C_{40}H_{24}N_2S$ = 564.71) |
| Sub 3-83 | m/z = 348.07 ($C_{23}H_{12}N_2S$ = 348.42) | Sub 3-84 | m/z = 555.11 ($C_{38}H_{21}NS_2$ = 555.71) |
| Sub 3-85 | m/z = 463.14 ($C_{33}H_{21}NS$ = 463.60) | Sub 3-86 | m/z = 692.20 ($C_{48}H_{28}N_4S$ = 692.84) |
| Sub 3-87 | m/z = 437.14 ($C_{31}H_{19}NO_2$ = 437.50) | Sub 3-88 | m/z = 373.09 ($C_{26}H_{15}NS$ = 373.47) |
| Sub 3-89 | m/z = 357.12 ($C_{26}H_{15}NO$ = 357.41) | | |

Synthesis Example of Sub 4

Sub 4 of Scheme 6 can be synthesized by the reaction path of Scheme 7 below, but is not limited thereto.

At this time, $Hal^5$=I, Br, Cl; $Hal^6$=Br, Cl

<Reaction Scheme 7>

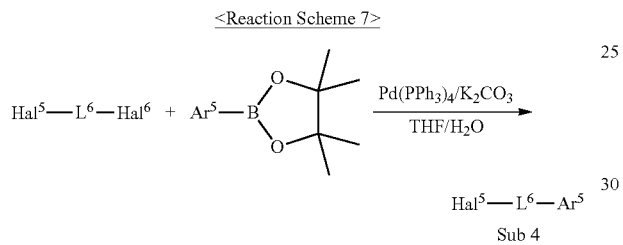

Synthesis of Sub 4-35

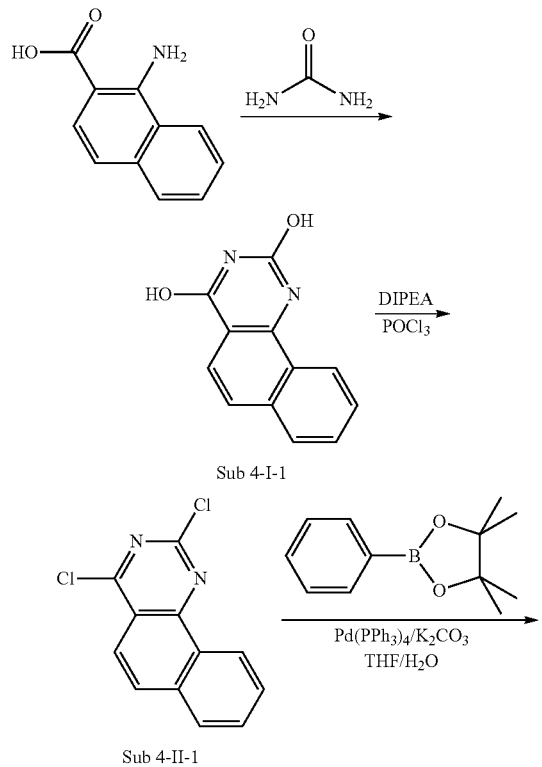

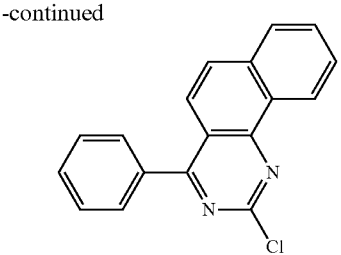

Sub 4-35

(1) Synthesis of Sub 4-I-1

The starting material, 1-amino-2-naphthoic acid (CAS Registry Number: 4919-43-1) (75.11 g, 401.25 mmol), was placed in a round bottom flask with urea (CAS Registry Number: 4919-43-1) (168.69 g, 2808.75 mmol) and stirred at 160° C. After confirming the reaction by TLC, the reaction mixture was cooled to 100° C., water (200 ml) was added, and the mixture was stirred for 1 hour. When the reaction was completed, the resulting solid was filtered under reduced pressure, washed with water, and then dried to obtain 63.86 g (yield: 75%) of the product.

(2) Synthesis of Sub 4-II-1

Sub 4-I-1 (63.86 g, 300.94 mmol) was dissolved in $POCl_3$ (200 ml) at room temperature in a round bottom flask, and N, N-Diisopropylethylamine (97.23 g, 752.36 mmol) was slowly added dropwise thereto, followed by stirring at 90° C. After the reaction was completed, the reaction mixture was concentrated, and then ice water (500 ml) was added thereto, followed by stirring at room temperature for 1 hour. The resulting solid was filtered under reduced pressure and dried to obtain 67.47 g (yield: 90%) of the product.

(3) Synthesis of Sub 4-35

After Sub 4-II-1 (67.47 g, 270.86 mmol) was dissolved in THF (950 ml) in a round bottom flask, 4,4,5,5-tetramethyl-2-phenyl-1,3,2-dioxaborolane (CAS Registry Number: 24388-23-6) (60.80 g, 297.94 mmol), $Pd(PPh_3)_4$ (12.52 g, 10.83 mmol), $K_2CO_3$ (112.30 g, 812.57 mmol) and water (475 mL) were added to dissolve and stirred at 90° C. After the reaction was completed, the reaction mixture was extracted with $CH_2Cl_2$ and water. The organic layer was dried over $MgSO_4$ and concentrated. The resulting compound was purified by silicagel column and recrystallized to obtain 44.89 g (yield: 57%) of the product.

Synthesis of Sub 4-40

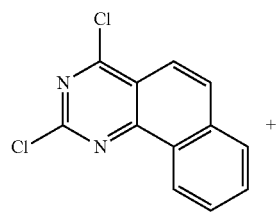

Sub 4-II-1

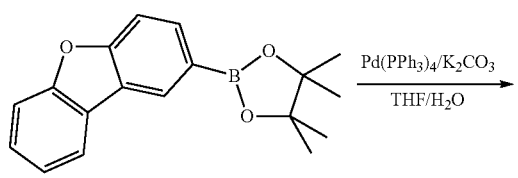

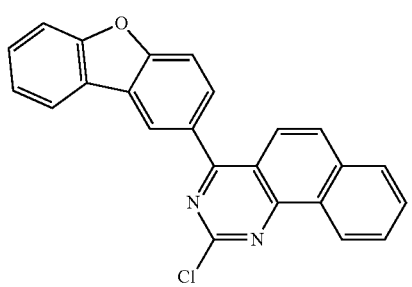

Sub 4-40

Sub 4-II-1 (19 g, 76.28 mmol), 2-(dibenzo[b,d]furan-2-yl)-4,4,5,5-tetramethyl-1,3,2-dioxaborolane (CAS Registry Number: 947770-80-1) (22.44 g, 76.28 mmol), Pd(PPh₃)₄ (1.32 g, 1.14 mmol), K₂CO₃ (15.81 g, 114.42 mmol), THF (336 ml) and water (168 ml) were added and carried out in the same manner as in Sub 4-35 to give the product. (15.69 g, 54%).

Synthesis of Sub 4-43

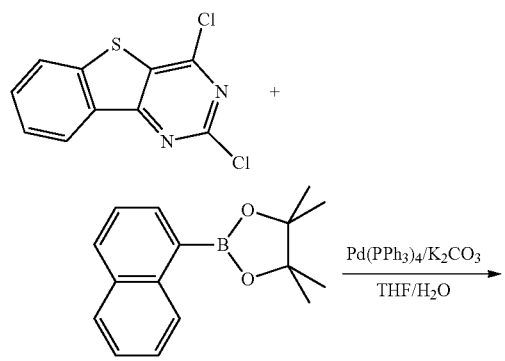

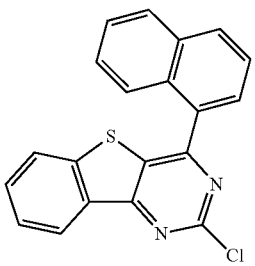

Sub 4-43

2,4-dichlorobenzo[4,5]thieno[3,2-d]pyrimidine (CAS Registry Number: 160199-05-3) (32.01 g, 125.47 mmol), 4,4,5,5-tetramethyl-2-(naphthalen-1-yl)-1,3,2-dioxaborolane (CAS Registry Number: 68716-52-9) (35.07 g, 138.02 mmol), Pd(PPh₃)₄ (5.80 g, 5.02 mmol), K₂CO₃ (52.02 g, 376.41 mmol), THF (440 ml) and water (220 ml) were added and carried out in the same manner as in Sub 4-35 to give the product. (19.58 g, 45%).

The compounds belonging to Sub 4 may be, but not limited to, the following compounds, and Table 5 shows FD-MS (Field Desorption-Mass Spectrometry) values of Sub 4 compounds.

Examples of Sub 4 include, but are not limited to, the followings.

Sub 4-1

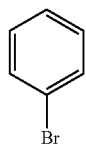

Sub 4-2

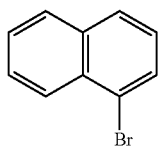

Sub 4-3

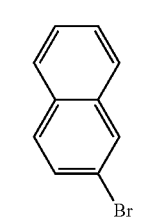

Sub 4-4

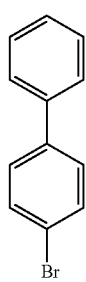

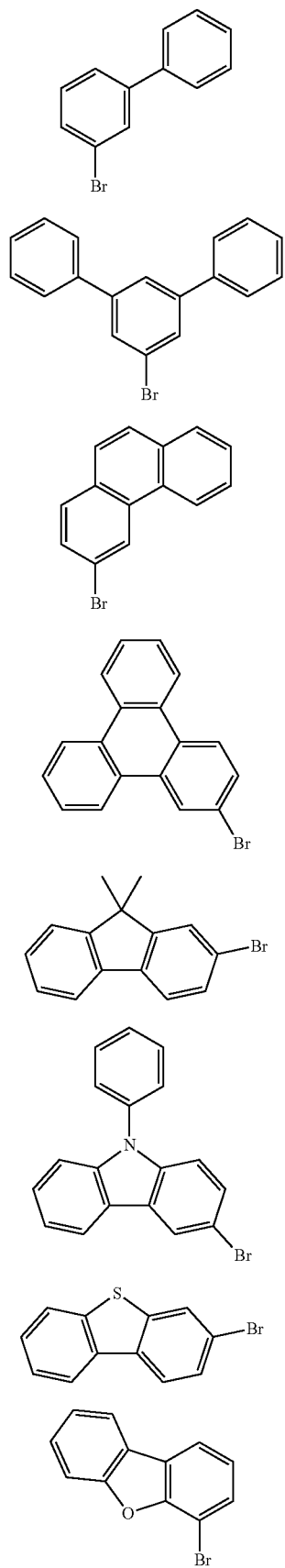
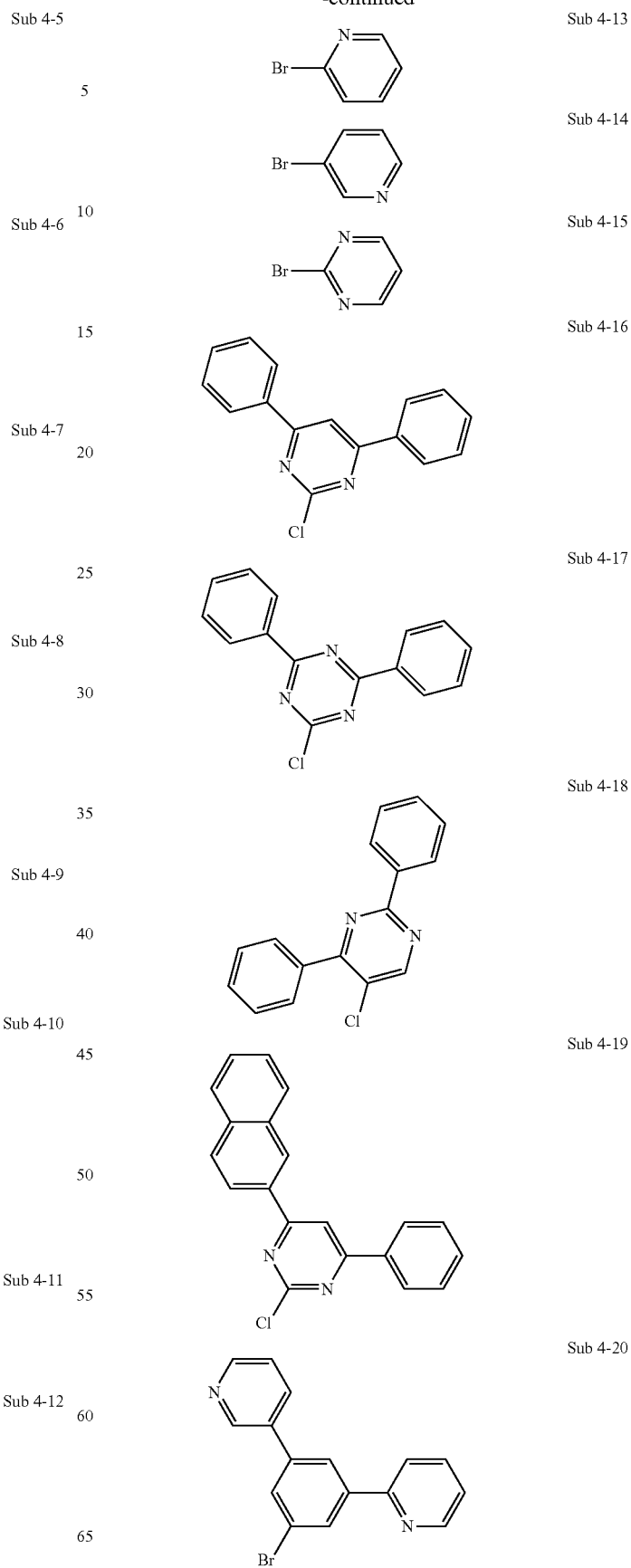

Sub 4-21
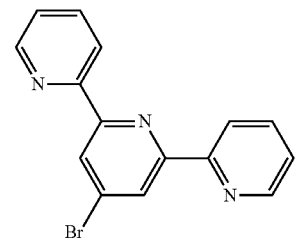
Sub 4-22
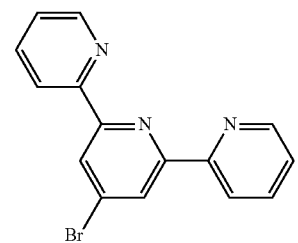
Sub 4-23
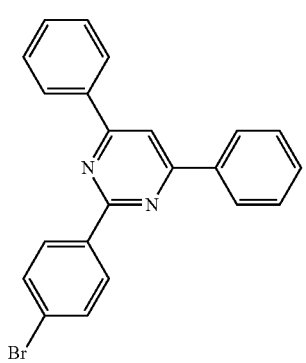
Sub 4-24
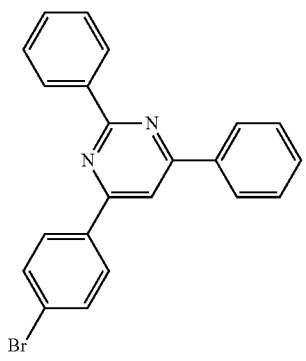
Sub 4-25
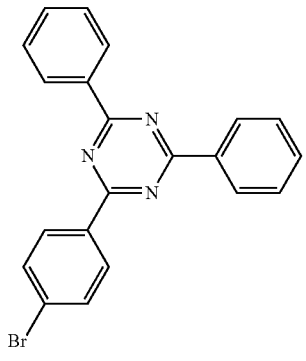
Sub 4-26
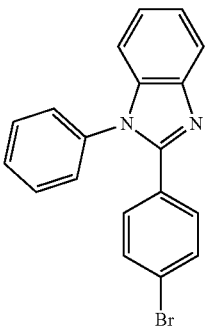
Sub 4-27
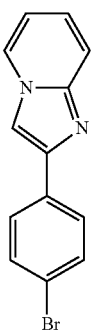
Sub 4-28
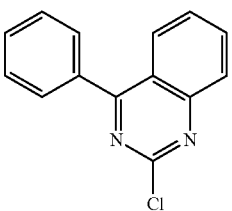
Sub 4-29
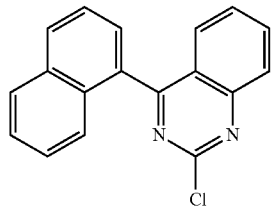
Sub 4-30
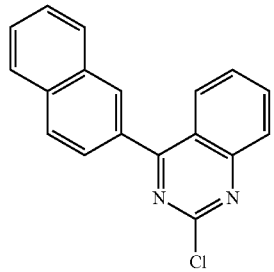

Sub 4-31
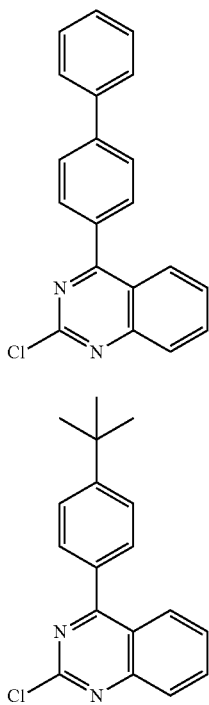
Sub 4-32
Sub 4-33
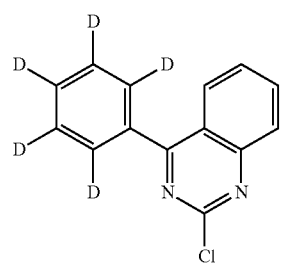
Sub 4-34
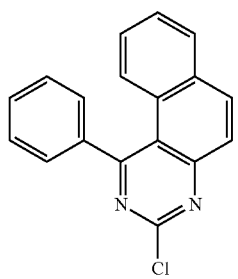
Sub 4-35
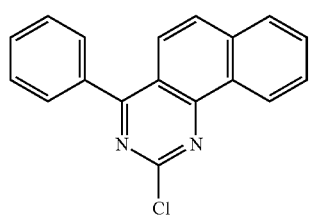
Sub 4-36
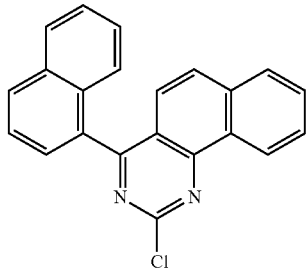
Sub 4-37
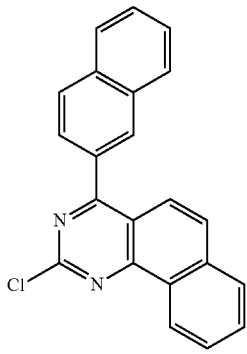
Sub 4-38
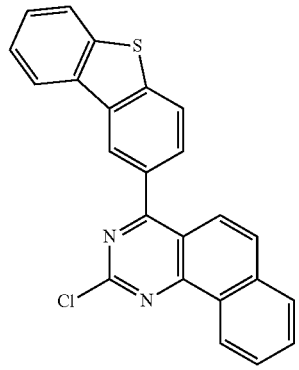
Sub 4-39
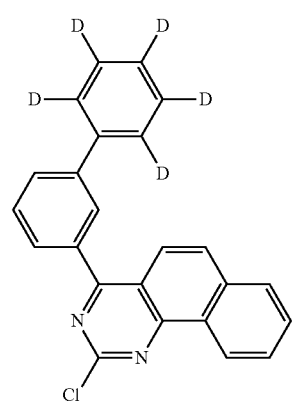

Sub 4-40
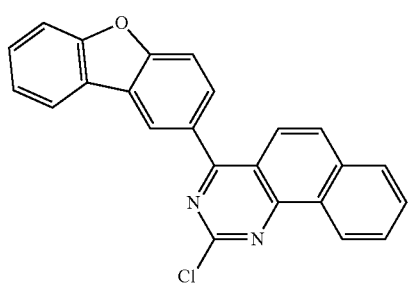
Sub 4-41
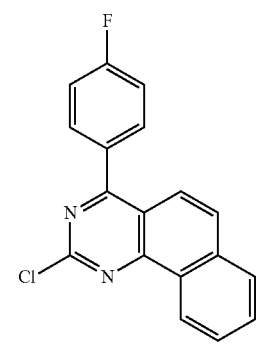
Sub 4-42
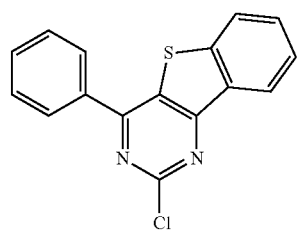
Sub 4-43
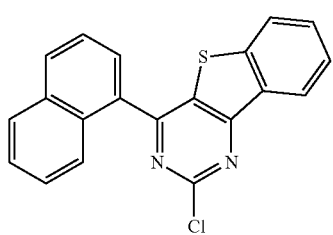
Sub 4-44
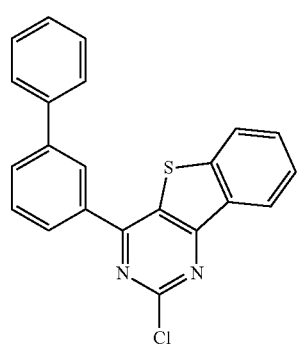
Sub 4-45
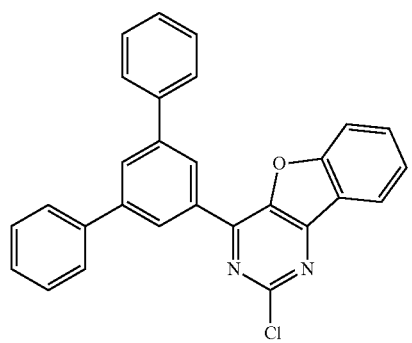
Sub 4-46
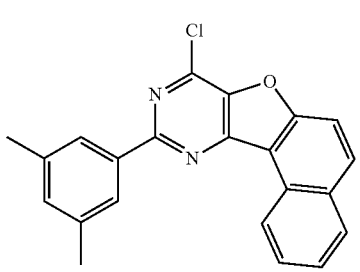
Sub 4-47
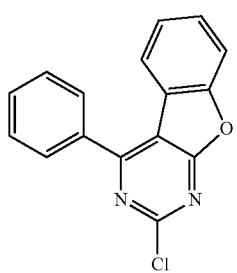
Sub 4-48
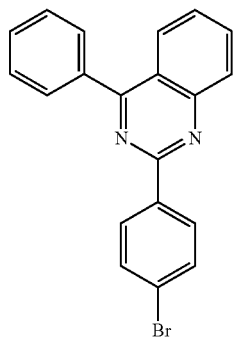
Sub 4-49
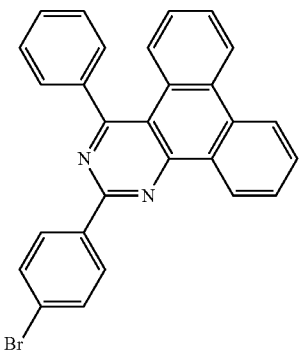

-continued

Sub 4-50

Sub 4-51

Sub 4-52

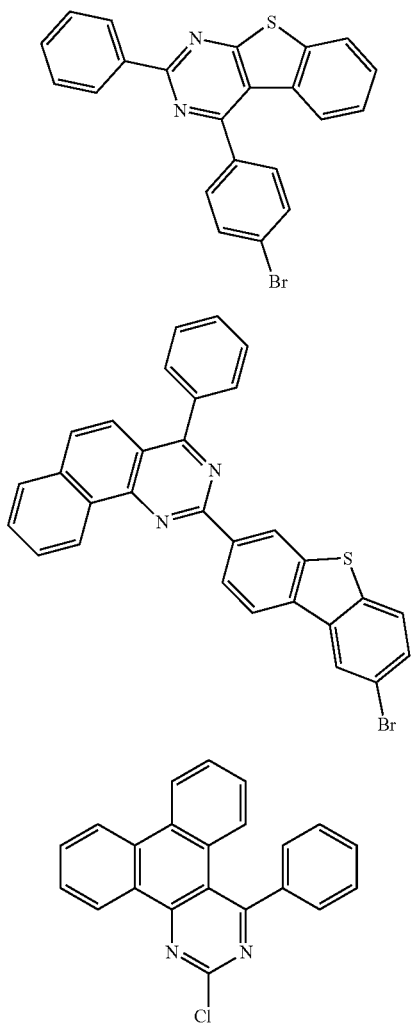

-continued

Sub 4-53

Sub 4-54

Sub 4-55

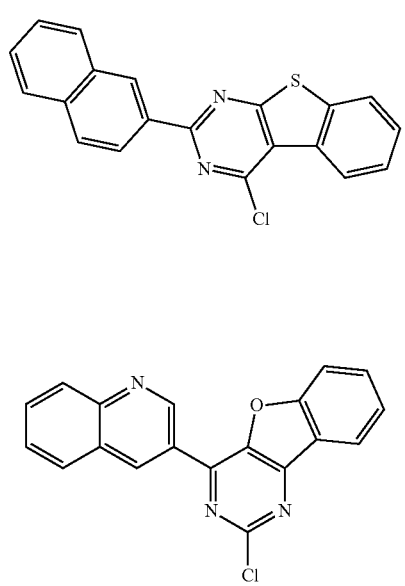

TABLE 5

| compound | FD-MS | compound | FD-MS |
| --- | --- | --- | --- |
| Sub 4-1 | m/z = 155.96 ($C_6H_5Br$ = 157.01) | Sub 4-2 | m/z = 205.97 ($C_{10}H_7Br$ = 207.07) |
| Sub 4-3 | m/z = 205.97 ($C_{10}H_7Br$ = 207.07) | Sub 4-4 | m/z = 231.99 ($C_{12}H_9Br$ = 233.11) |
| Sub 4-5 | m/z = 231.99 ($C_{12}H_9Br$ = 233.11) | Sub 4-6 | m/z = 308.02 ($C_{18}H_{13}Br$ = 309.21) |
| Sub 4-7 | m/z = 255.99 ($C_{14}H_9Br$ = 257.13) | Sub 4-8 | m/z = 306.00 ($C_{18}H_{11}Br$ = 307.19) |
| Sub 4-9 | m/z = 272.02 ($C_{15}H_{13}Br$ = 273.17) | Sub 4-10 | m/z = 321.02 ($C_{18}H_{12}BrN$ = 322.21) |
| Sub 4-11 | m/z = 261.95 ($C_{12}H_7BrS$ = 263.15) | Sub 4-12 | m/z = 245.97 ($C_{12}H_7BrO$ = 247.09) |
| Sub 4-13 | m/z = 156.95 ($C_5H_4BrN$ = 158.00) | Sub 4-14 | m/z = 156.95 ($C_5H_4BrN$ = 158.00) |
| Sub 4-15 | m/z = 157.95 ($C_4H_3BrN_2$ = 158.99) | Sub 4-16 | m/z = 266.06 ($C_{16}H_{11}ClN_2$ = 266.72) |
| Sub 4-17 | m/z = 267.06 ($C_{15}H_{10}ClN_3$ = 267.72) | Sub 4-18 | m/z = 266.06 ($C_{16}H_{11}ClN_2$ = 266.72) |
| Sub 4-19 | m/z = 316.08 ($C_{20}H_{13}ClN_2$ = 316.79) | Sub 4-20 | m/z = 310.01 ($C_{16}H_{11}BrN_2$ = 311.18) |
| Sub 4-21 | m/z = 311.01 ($C_{15}H_{10}BrN_3$ = 312.17) | Sub 4-22 | m/z = 311.01 ($C_{15}H_{10}BrN_3$ = 312.17) |
| Sub 4-23 | m/z = 386.04 ($C_{22}H_{15}BrN_2$ = 387.28) | Sub 4-24 | m/z = 386.04 ($C_{22}H_{15}BrN_2$ = 387.28) |
| Sub 4-25 | m/z = 387.04 ($C_{21}H_{14}BrN_3$ = 388.27) | Sub 4-26 | m/z = 348.03 ($C_{19}H_{13}BrN_2$ = 349.23) |
| Sub 4-27 | m/z = 273.13 ($C_{13}H_9BrN_2$ = 273.13) | Sub 4-28 | m/z = 240.05 ($C_{14}H_9ClN_2$ = 240.69) |
| Sub 4-29 | m/z = 290.06 ($C_{18}H_{11}ClN_2$ = 290.75) | Sub 4-30 | m/z = 290.06 ($C_{18}H_{11}ClN_2$ = 290.75) |
| Sub 4-31 | m/z = 316.08 ($C_{20}H_{13}ClN_2$ = 316.79) | Sub 4-32 | m/z = 296.11 ($C_{18}H_{17}ClN_2$ = 296.80) |
| Sub 4-33 | m/z = 245.08 ($C_{14}H_4D_5ClN_2$ = 245.72) | Sub 4-34 | m/z = 290.06 ($C_{18}H_{11}ClN_2$ = 290.75) |
| Sub 4-35 | m/z = 290.06 ($C_{18}H_{11}ClN_2$ = 290.75) | Sub 4-36 | m/z = 340.08 ($C_{22}H_{13}ClN_2$ = 340.81) |
| Sub 4-37 | m/z = 340.08 ($C_{22}H_{13}ClN_2$ = 340.81) | Sub 4-38 | m/z = 396.05 ($C_{24}H_{13}ClN_2S$ = 396.89) |
| Sub 4-39 | m/z = 371.12 ($C_{24}H_{10}D_5ClN_2$ = 371.88) | Sub 4-40 | m/z = 380.07 ($C_{24}H_{13}ClN_2O$ = 380.83) |
| Sub 4-41 | m/z = 308.05 ($C_{18}H_{10}ClFN_2$ = 308.74) | Sub 4-42 | m/z = 296.02 ($C_{16}H_9ClN_2S$ = 296.77) |
| Sub 4-43 | m/z = 346.03 ($C_{20}H_{11}ClN_2S$ = 346.83) | Sub 4-44 | m/z = 372.05 ($C_{22}H_{13}ClN_2S$ = 372.87) |
| Sub 4-45 | m/z = 432.10 ($C_{28}H_{17}ClN_2O$ = 432.91) | Sub 4-46 | m/z = 358.09 ($C_{22}H_{15}ClN_2O$ = 358.83) |
| Sub 4-47 | m/z = 280.04 ($C_{16}H_9ClN_2O$ = 280.71) | Sub 4-48 | m/z = 360.03 ($C_{20}H_{13}BrN_2$ = 361.24) |
| Sub 4-49 | m/z = 460.06 ($C_{28}H_{17}BrN_2$ = 461.36) | Sub 4-50 | m/z = 416.00 ($C_{22}H_{13}BrN_2S$ = 417.32) |

TABLE 5-continued

| compound | FD-MS | compound | FD-MS |
|---|---|---|---|
| Sub 4-51 | m/z = 516.03 ($C_{30}H_{17}BrN_2S$ = 517.44) | Sub 4-52 | m/z = 340.08 ($C_{22}H_{13}ClN_2$ = 340.81) |
| Sub 4-53 | m/z = 346.03 ($C_{20}H_{11}ClN_2S$ = 346.83) | Sub 4-54 | m/z = 331.05 ($C_{19}H_{10}ClN_3O$ = 331.76) |
| Sub 4-55 | m/z = 360.03 ($C_{20}H_{13}BrN_2$ = 361.24) | | |

Synthesis of Final Products 2

After Sub 3 (1 eq.) was dissolved in toluene in a round bottom flask, Sub 4 (1.1 eq.), Pd$_2$(dba)$_3$ (0.03 eq.), P(t-Bu)$_3$ (0.1 eq.), NaOt-Bu (3 eq.) were added and stirred at 100° C. When the reaction was complete, the reaction mixture was extracted with CH$_2$Cl$_2$ and water. The organic layer was dried over MgSO$_4$ and concentrated. The resulting compound was separated by silicagel column chromatography and recrystallization to obtain the Final products.

Synthesis Example of 3-1

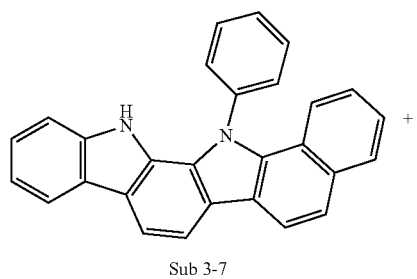

Sub 3-7

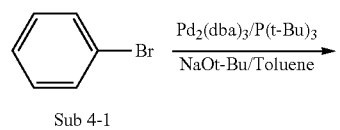

Sub 4-1

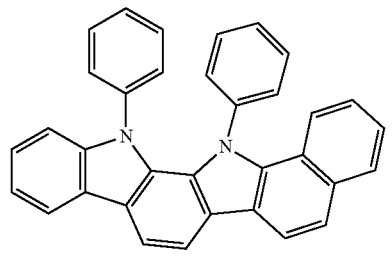

3-1

Sub 3-7 (11 g, 28.76 mmol) was dissolved in toluene (302 mL) in a round bottom flask, and Sub 4-1 (4.52 g, 28.76 mmol), Pd$_2$(dba)$_3$ (0.79 g, 0.86 mmol), P(t-Bu)$_3$ (0.35 g, 1.73 mmol), NaOt-Bu (8.29 g, 86.28 mmol) were added and stirred at 100° C. After the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 9.50 g of the product. (Yield: 72%)

Synthesis Example of 3-6

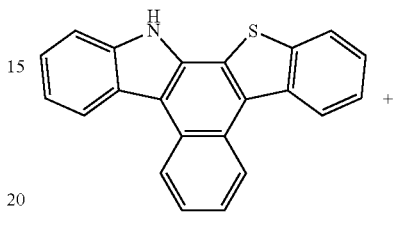

Sub 3-1

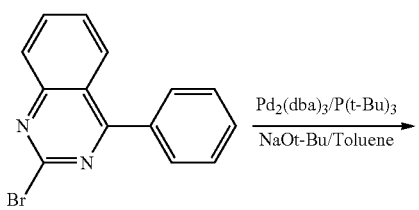

Sub 4-28

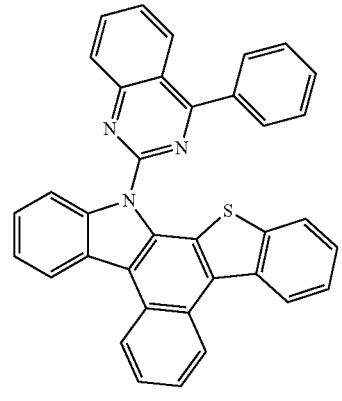

3-6

Sub 3-1 (15.3 g, 47.3 mmol), toluene (500 mL), Sub 4-28 (14.8 g, 52.0 mmol), Pd$_2$(dba)$_3$ (1.3 g, 1.42 mmol), P(t-Bu)$_3$ (0.57 g, 2.84 mmol), NaOt-Bu (13.64 g, 141.93 mmol) were carried out in the same manner as in 3-1 to give the product. (18.97 g, 72%).

Synthesis Example of 3-7
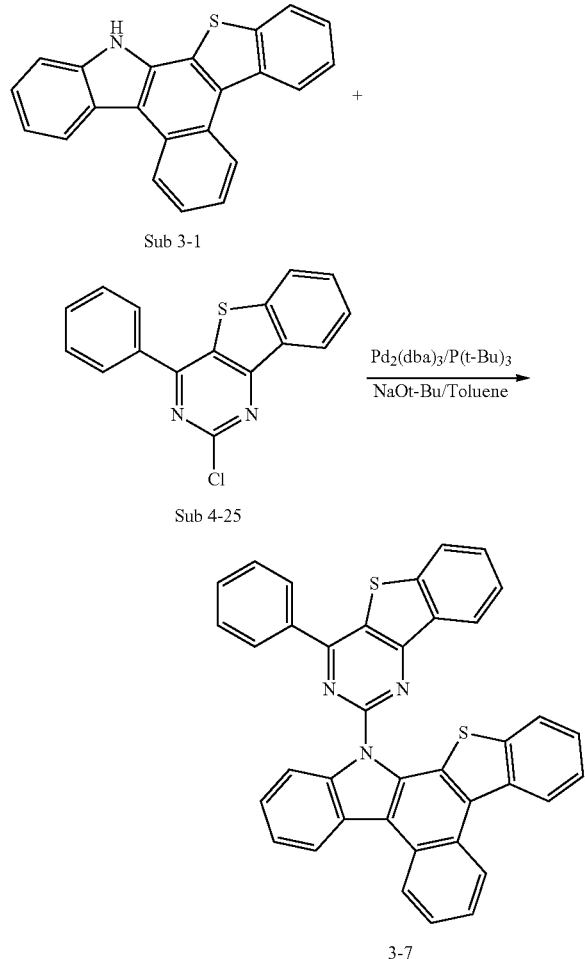
Sub 3-1 (10 g, 30.92 mmol), toluene (325 ml), Sub 4-25 (10.0 g, 34.01 mmol), Pd$_2$(dba)$_3$ (0.85 g, 0.93 mmol), P(t-Bu)$_3$ (0.38 g, 1.86 mmol), NaOt-Bu (8.91 g, 92.76 mmol) were carried out in the same manner as in 3-1 to give the product. (12.81 g, 71%).
Synthesis Example of 3-8
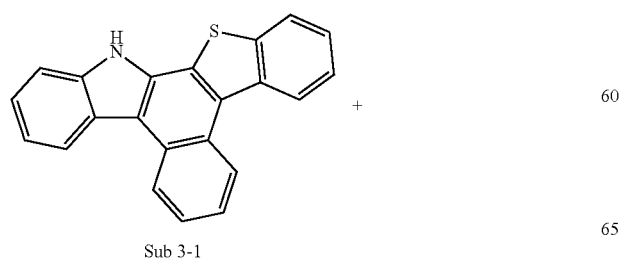
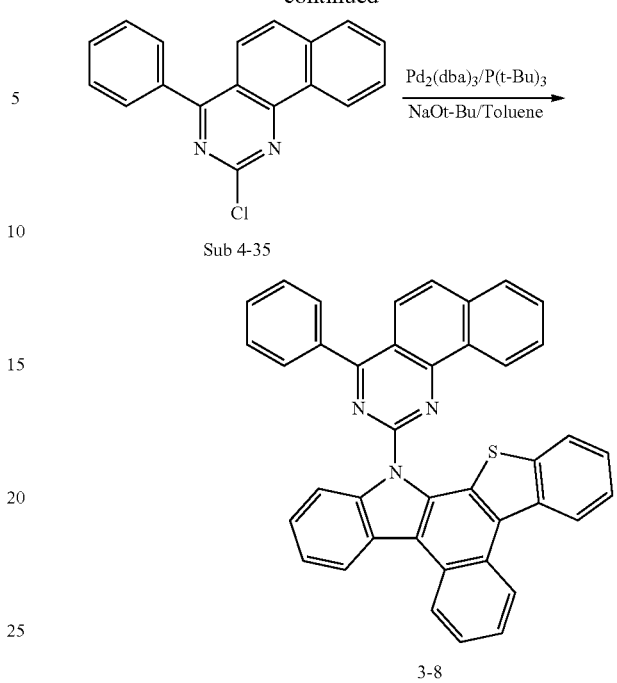
Sub 3-1 (10 g, 30.92 mmol), toluene (325 mL), Sub 4-35 (9.89 g, 34.01 mmol), Pd$_2$(dba)$_3$ (0.85 g, 0.93 mmol), P(t-Bu)$_3$ (0.38 g, 1.86 mmol), NaOt-Bu (8.91 g, 92.76 mmol) were carried out in the same manner as in 3-1 to give the product. (13.04 g, 73%).
Synthesis Example of 3-11
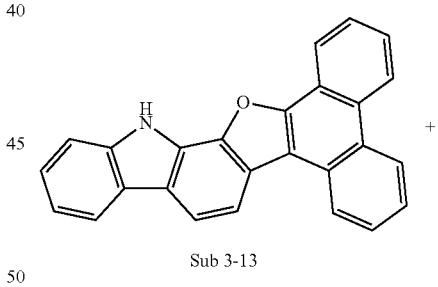
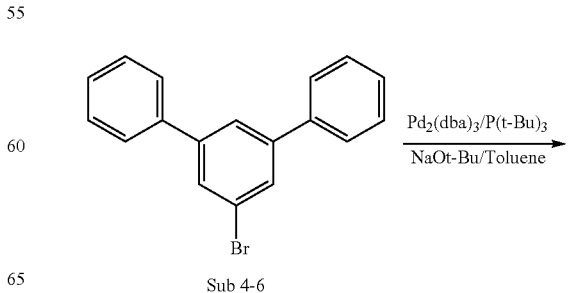

-continued
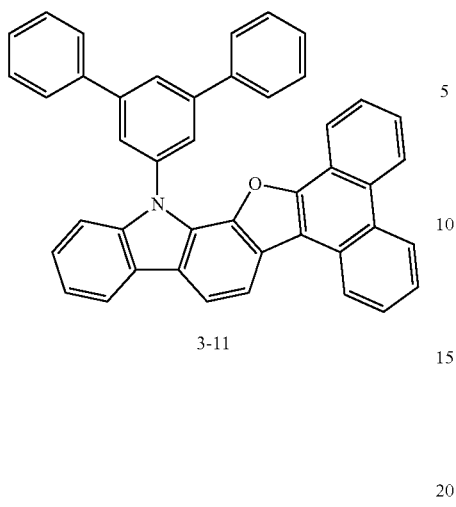
3-11
Sub 3-13 (10 g, 27.98 mmol), toluene (294 ml), Sub 4-6 (9.52 g, 30.78 mmol), Pd$_2$(dba)$_3$ (0.77 g, 0.84 mmol), P(t-Bu)$_3$ (0.34 g, 1.68 mmol), NaOt-Bu (8.07 g, 83.94 mmol) were carried out in the same manner as in 3-1 to give the product. (12.45 g, 76%).
Synthesis Example of 3-16
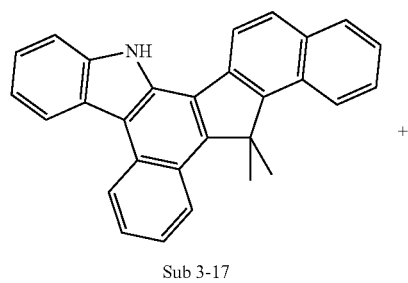
Sub 3-17
+
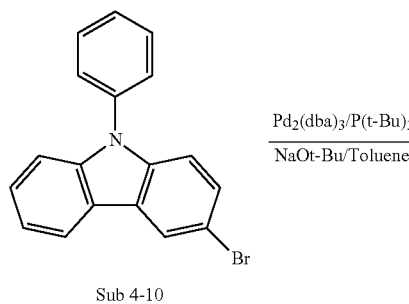
Sub 4-10
-continued
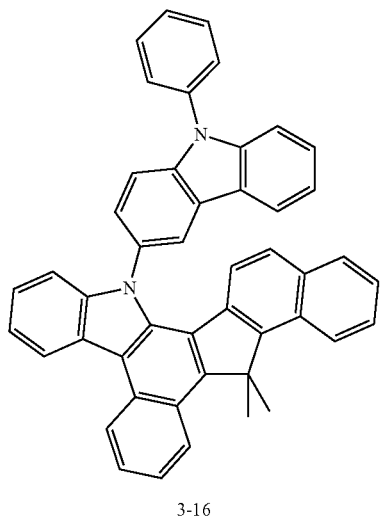
3-16
Sub 3-17 (10 g, 26.08 mmol), toluene (274 ml), Sub 4-10 (9.24 g, 28.68 mmol), Pd$_2$(dba)$_3$ (0.72 g, 0.78 mmol), P(t-Bu)$_3$ (0.32 g, 1.56 mmol), NaOt-Bu (7.52 g, 78.23 mmol) were carried out in the same manner as in 3-1 to give the product. (11.08 g, 68%).
Synthesis Example of 3-17
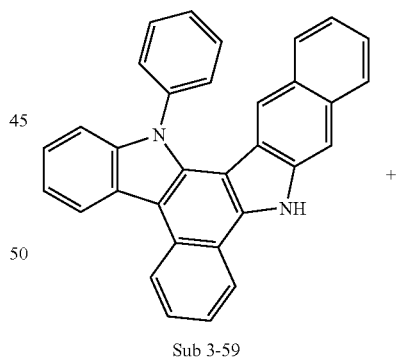
Sub 3-59
+
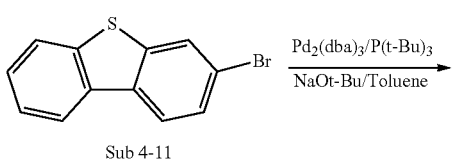
Sub 4-11

283
-continued
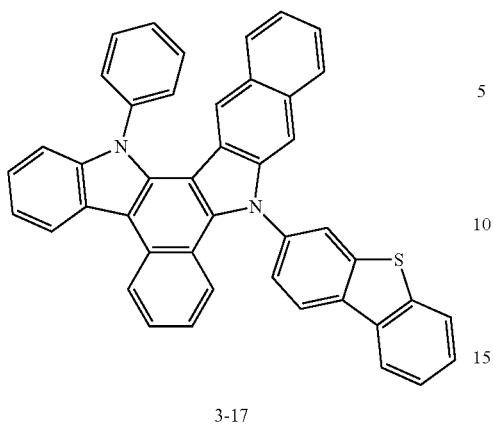
3-17
Sub 3-59 (10 g, 23.12 mmol), toluene (243 ml), Sub 4-11 (6.69 g, 25.43 mmol), Pd$_2$(dba)$_3$ (0.64 g, 0.69 mmol), P(t-Bu)$_3$ (0.28 g, 1.39 mmol), NaOt-Bu (6.67 g, 69.36 mmol) were carried out in the same manner as in 3-1 to give the product. (11.8 g, 83%).
Synthesis Example of 3-47
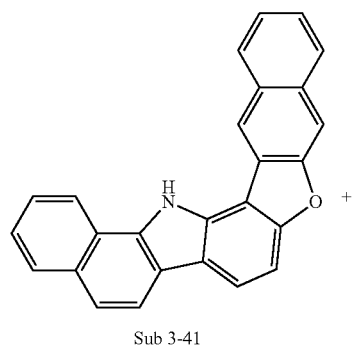
Sub 3-41
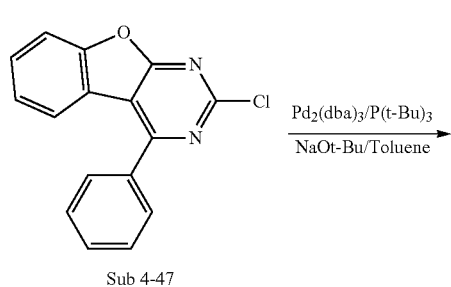
Sub 4-47
284
-continued
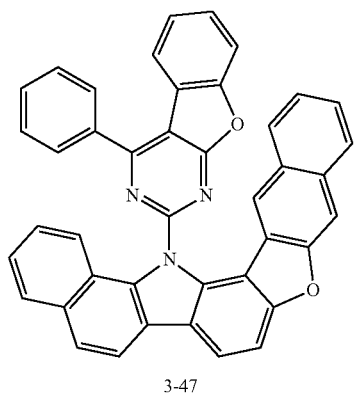
3-47
Sub 3-41 (10 g, 27.98 mmol), toluene (294 ml), Sub 4-47 (8.64 g, 30.78 mmol), Pd$_2$(dba)$_3$ (0.77 g, 0.84 mmol), P(t-Bu)$_3$ (0.34 g, 1.68 mmol), NaOt-Bu (8.07 g, 83.94 mmol) were carried out in the same manner as in 3-1 to give the product. (11.45 g, 68%).
Synthesis Example of 3-52
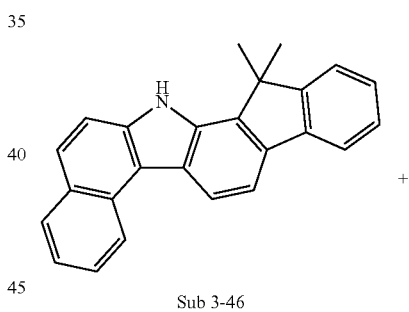
Sub 3-46
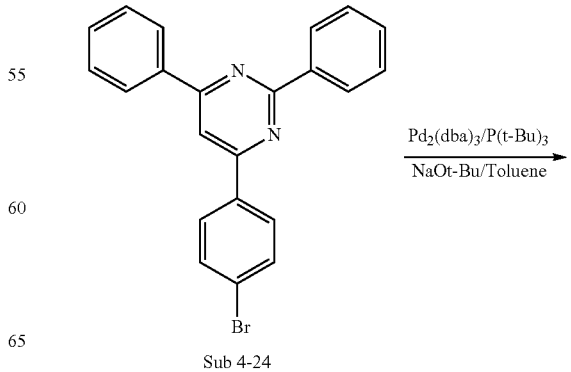
Sub 4-24

-continued
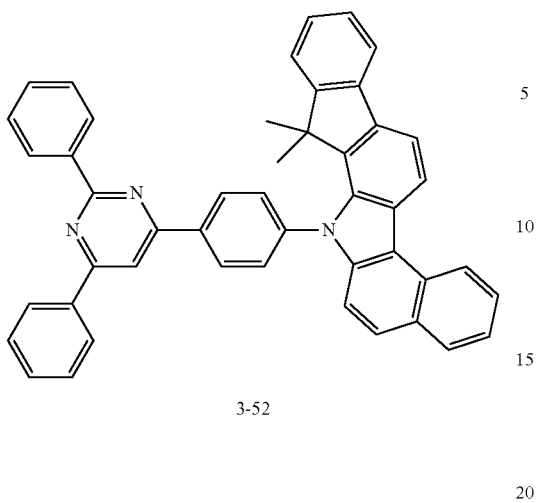
3-52
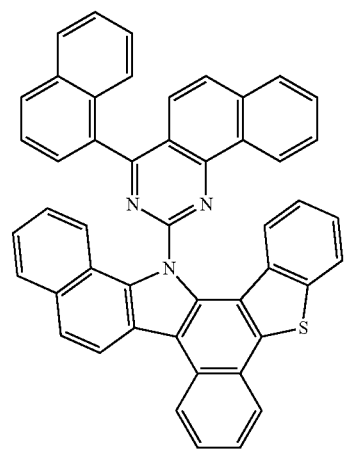
3-70
Sub 3-46 (10 g, 29.99 mmol), toluene (500 mL), Sub 4-24 (12.78 g, 32.99 mmol), Pd₂(dba)₃ (0.82 g, 0.90 mmol), P(t-Bu)₃ (0.36 g, 1.80 mmol), NaOt-Bu (8.65 g, 89.97 mmol) were carried out in the same manner as in 3-1 to give the product. (13.82 g, 72%).
Synthesis Example of 3-70
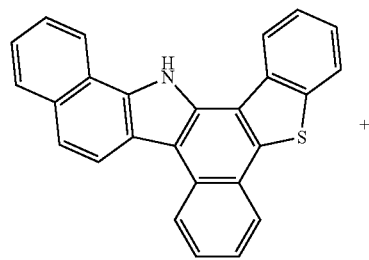
Sub 3-76
Sub 3-76 (10 g, 26.78 mmol), toluene (281 ml), Sub 4-36 (10.04 g, 29.45 mmol), Pd₂(dba)₃ (0.74 g, 0.80 mmol), P(t-Bu)₃ (0.33 g, 1.61 mmol), NaOt-Bu (7.72 g, 80.33 mmol) were carried out in the same manner as in 3-1 to give the product. (12.16 g, 67%).
Synthesis Example of 3-92
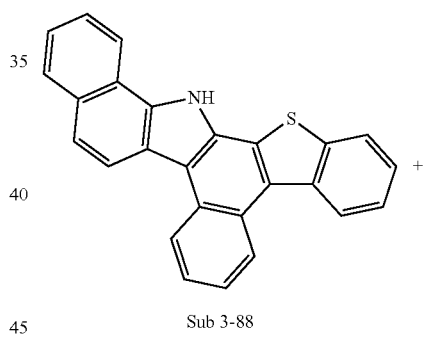
Sub 3-88
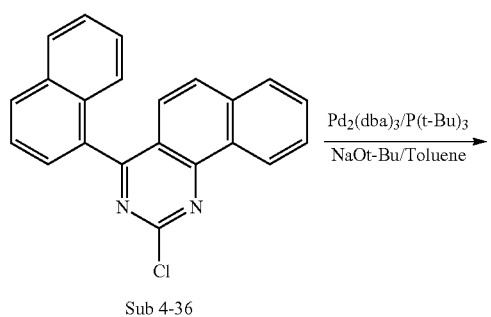
Sub 4-36
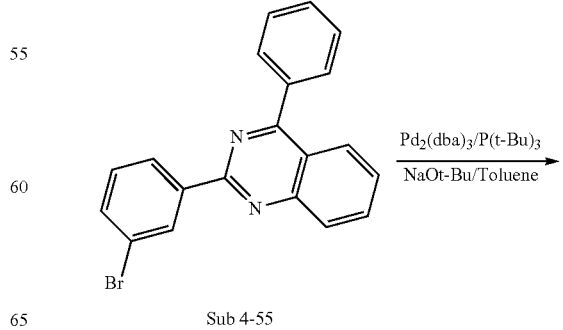
Sub 4-55

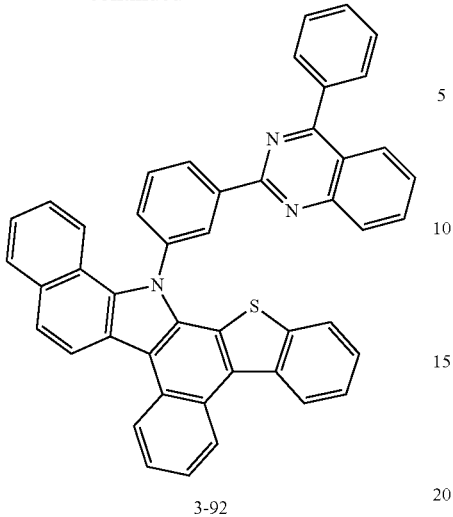

3-92

Sub 3-88 (10 g, 26.78 mmol), toluene (281 ml), Sub 4-55 (9.67 g, 26.78 mmol), Pd$_2$(dba)$_3$ (0.37 g, 0.40 mmol), P(t-Bu)$_3$ (0.16 g, 0.80 mmol), NaOt-Bu (3.86 g, 40.16 mmol) were carried out in the same manner as in 3-1 to give the product. (12.25 g, 70%).

TABLE 6

| compound | FD-MS | compound | FD-MS |
|---|---|---|---|
| 3-1 | m/z = 458.18 (C$_{34}$H$_{22}$N$_2$ = 458.56) | 3-2 | m/z = 449.12 (C$_{32}$H$_{19}$NS = 449.57) |
| 3-3 | m/z = 433.15 (C$_{32}$H$_{19}$NO = 433.51) | 3-4 | m/z = 535.23 (C$_{41}$H$_{29}$N = 535.69) |
| 3-5 | m/z = 399.11 (C$_{28}$H$_{17}$NS = 399.51) | 3-6 | m/z = 527.15 (C$_{36}$H$_{21}$N$_3$S = 527.65) |
| 3-7 | m/z = 583.12 (C$_{38}$H$_{21}$N$_3$S$_2$ = 583.73) | 3-8 | m/z = 577.16 (C$_{40}$H$_{23}$N$_3$S = 577.71) |
| 3-9 | m/z = 627.18 (C$_{44}$H$_{25}$N$_3$S = 627.77) | 3-10 | m/z = 475.14 (C$_{34}$H$_{21}$NS = 475.61) |
| 3-11 | m/z = 585.21 (C$_{44}$H$_{27}$NO = 585.71) | 3-12 | m/z = 509.21 (C$_{39}$H$_{27}$N = 509.65) |
| 3-13 | m/z = 509.19 (C$_{37}$H$_{23}$N$_3$ = 509.61) | 3-14 | m/z = 451.11 (C$_{30}$H$_{17}$N$_2$S = 451.55) |
| 3-15 | m/z = 588.20 (C$_{41}$H$_{24}$N$_4$O = 588.67) | 3-16 | m/z = 624.26 (C$_{47}$H$_{32}$N$_2$ = 624.79) |
| 3-17 | m/z = 614.18 (C$_{44}$H$_{26}$N$_2$S = 614.77) | 3-18 | m/z = 449.12 (C$_{32}$H$_{19}$NS = 449.57) |
| 3-19 | m/z = 573.17 (C$_{42}$H$_{23}$NO$_2$ = 573.65) | 3-20 | m/z = 664.26 (C$_{48}$H$_{32}$N$_4$ = 664.81) |
| 3-21 | m/z = 624.26 (C$_{47}$H$_{32}$N$_2$ = 624.79) | 3-22 | m/z = 603.18 (C$_{42}$H$_{25}$N$_3$S = 603.74) |
| 3-23 | m/z = 664.23 (C$_{47}$H$_{28}$N$_4$O = 664.77) | 3-24 | m/z = 737.28 (C$_{55}$H$_{35}$N$_3$ = 737.91) |
| 3-25 | m/z = 738.28 (C$_{54}$H$_{34}$N$_4$ = 738.89) | 3-26 | m/z = 679.21 (C$_{48}$H$_{29}$N$_3$S = 679.84) |
| 3-27 | m/z = 625.22 (C$_{45}$H$_{27}$N$_3$O = 625.73) | 3-28 | m/z = 575.24 (C$_{42}$H$_{29}$N$_3$ = 575.72) |
| 3-29 | m/z = 508.19 (C$_{38}$H$_{24}$N$_2$ = 508.62) | 3-30 | m/z = 449.12 (C$_{32}$H$_{19}$NS = 449.57) |
| 3-31 | m/z = 433.15 (C$_{32}$H$_{19}$NO = 433.51) | 3-32 | m/z = 531.20 (C$_{41}$H$_{25}$N = 531.66) |
| 3-33 | m/z = 608.23 (C$_{46}$H$_{28}$N$_2$ = 608.74) | 3-34 | m/z = 475.14 (C$_{34}$H$_{21}$NS = 475.61) |
| 3-35 | m/z = 384.13 (C$_{27}$H$_{16}$N$_2$O = 384.44) | 3-36 | m/z = 614.25 (C$_{44}$H$_{30}$N$_4$ = 614.75) |
| 3-37 | m/z = 508.19 (C$_{38}$H$_{24}$N$_2$ = 508.62) | 3-38 | m/z = 449.12 (C$_{32}$H$_{19}$NS = 449.57) |
| 3-39 | m/z = 433.15 (C$_{32}$H$_{19}$NO = 433.51) | 3-40 | m/z = 459.20 (C$_{35}$H$_{25}$N = 459.59) |
| 3-41 | m/z = 663.24 (C$_{47}$H$_{29}$N$_5$ = 663.78) | 3-42 | m/z = 603.18 (C$_{42}$H$_{25}$N$_3$S = 603.74) |
| 3-43 | m/z = 587.20 (C$_{42}$H$_{25}$N$_3$O = 587.68) | 3-44 | m/z = 613.25 (C$_{45}$H$_{31}$N$_3$ = 613.76) |
| 3-45 | m/z = 662.25 (C$_{48}$H$_{30}$N$_4$ = 662.80) | 3-46 | m/z = 577.16 (C$_{40}$H$_{23}$N$_3$S = 577.71) |
| 3-47 | m/z = 601.18 (C$_{42}$H$_{23}$N$_3$O$_2$ = 601.67) | 3-48 | m/z = 759.27 (C$_{57}$H$_{33}$N$_3$ = 759.91) |
| 3-49 | m/z = 589.22 (C$_{42}$H$_{26}$N$_4$ = 586.70) | 3-50 | m/z = 630.19 (C$_{43}$H$_{26}$N$_4$S = 630.77) |
| 3-51 | m/z = 613.22 (C$_{44}$H$_{27}$N$_3$O = 613.72) | 3-52 | m/z = 639.27 (C$_{47}$H$_{33}$N$_3$ = 639.80) |
| 3-53 | m/z = 508.19 (C$_{38}$H$_{24}$N$_2$ = 508.62) | 3-54 | m/z = 449.12 (C$_{32}$H$_{19}$NS = 449.57) |
| 3-55 | m/z = 433.15 (C$_{32}$H$_{19}$NO = 433.51) | 3-56 | m/z = 609.25 (C$_{47}$H$_{31}$N = 609.77) |
| 3-57 | m/z = 663.24 (C$_{47}$H$_{29}$N$_5$ = 663.78) | 3-58 | m/z = 604.17 (C$_{41}$H$_{24}$N$_4$S = 604.73) |
| 3-59 | m/z = 587.20 (C$_{42}$H$_{25}$N$_3$O = 587.68) | 3-60 | m/z = 613.25 (C$_{45}$H$_{31}$N$_3$ = 613.76) |
| 3-61 | m/z = 527.15 (C$_{36}$H$_{21}$N$_3$S = 527.65) | 3-62 | m/z = 603.18 (C$_{42}$H$_{25}$N$_3$S = 603.74) |
| 3-63 | m/z = 516.20 (C$_{36}$H$_{16}$D$_5$N$_3$O = 516.61) | 3-64 | m/z = 605.23 (C$_{43}$H$_{28}$FN$_3$ = 587.73) |
| 3-65 | m/z = 692.20 (C$_{48}$H$_{28}$N$_4$S = 692.84) | 3-66 | m/z = 577.16 (C$_{40}$H$_{23}$N$_3$S = 577.71) |
| 3-67 | m/z = 561.18 (C$_{40}$H$_{23}$N$_3$O = 561.64) | 3-68 | m/z = 653.19 (C$_{46}$H$_{27}$N$_3$O = 653.80) |
| 3-69 | m/z = 736.26 (C$_{54}$H$_{32}$N$_4$ = 736.88) | 3-70 | m/z = 677.19 (C$_{48}$H$_{27}$N$_3$S = 677.83) |
| 3-71 | m/z = 692.26 (C$_{50}$H$_{24}$D$_5$N$_3$O = 692.83) | 3-72 | m/z = 743.24 (C$_{53}$H$_{33}$N$_3$S = 743.93) |
| 3-73 | m/z = 703.21 (C$_{50}$H$_{29}$N$_3$S = 703.86) | 3-74 | m/z = 603.18 (C$_{42}$H$_{25}$N$_3$S = 603.74) |
| 3-75 | m/z = 659.15 (C$_{44}$H$_{25}$N$_3$S$_2$ = 659.83) | 3-76 | m/z = 759.18 (C$_{52}$H$_{29}$N$_3$S$_2$ = 759.95) |
| 3-77 | m/z = 475.14 (C$_{34}$H$_{21}$NS = 475.61) | 3-78 | m/z = 616.20 (C$_{44}$H$_{28}$N$_2$S = 616.78) |
| 3-79 | m/z = 728.15 (C$_{47}$H$_{25}$FN$_4$S$_2$ = 728.86) | 3-80 | m/z = 818.25 (C$_{58}$H$_{34}$N$_4$S = 819.00) |

TABLE 6-continued

| compound | FD-MS | compound | FD-MS |
|---|---|---|---|
| 3-81 | m/z = 628.17 ($C_{43}H_{24}N_4S$ = 628.75) | 3-82 | m/z = 809.20 ($C_{56}H_{31}N_3S_2$ = 810.01) |
| 3-83 | m/z = 659.15 ($C_{44}H_{25}N_3S_2$ = 659.83) | 3-84 | m/z = 723.27 ($C_{51}H_{37}N_3S$ = 629.72) |
| 3-85 | m/z = 844.27 ($C_{60}H_{36}N_4S$ = 845.04) | 3-86 | m/z = 667.17 ($C_{46}H_{25}N_3OS$ = 667.79) |
| 3-87 | m/z = 703.23 ($C_{50}H_{29}N_3O$ = 703.80) | 3-88 | m/z = 759.25 ($C_{53}H_{33}N_3O_3$ = 759.87) |
| 3-89 | m/z = 677.19 ($C_{48}H_{27}N_3S$ = 677.83) | 3-90 | m/z = 683.15 ($C_{46}H_{25}N_3S_2$ = 683.85) |
| 3-91 | m/z = 668.17 ($C_{45}H_{24}N_4OS$ = 668.77) | 3-92 | m/z = 653.80 ($C_{46}H_{27}N_3S$ = 653.80) |
| 3-93 | m/z = 604.17 ($C_{41}H_{24}N_4S$ = 604.73) | 3-94 | m/z = 650.27 ($C_{49}H_{34}N_2$ = 650.83) |
| 3-95 | m/z = 878.30 ($C_{64}H_{38}N_4O$ = 879.04) | 3-96 | m/z = 775.26 ($C_{57}H_{33}N_3O$ = 775.91) |
| 3-97 | m/z = 588.20 ($C_{41}H_{24}N_4O$ = 588.67) | 3-98 | m/z = 561.18 ($C_{40}H_{23}N_3O$ = 561.64) |
| 3-99 | m/z = 601.18 ($C_{42}H_{23}N_3O_2$ = 601.67) | 3-100 | m/z = 664.23 ($C_{47}H_{28}N_4O$ = 664.77) |

Otherwise, the synthesis examples of the present invention represented by Formulas (1) and (2) have been described, but these are all based on the Buchwald-Hartwig cross coupling reaction, Suzuki cross-coupling reaction, Intramolecular acid-induced cyclization reaction (J. mater. Chem. 1999, 9, 2095.), Pd(II)-catalyzed oxidative cyclization reaction (Org. Lett.2011, 13, 5504), Grignard reaction, Cyclic Dehydration reaction and PPh3-mediated reductive cyclization reaction (J. Org. Chem. 2005, 70, 5014.), and those skilled in the art will readily understand that the above reaction proceeds even when, besides the substituent specified in the specific synthesis example, other substituents (Substituents such as $Ar^1$ to $Ar^6$, $L^1$ to $L^6$, $R^1$ to $R^5$, $X^1$, $X^2$, A and B) defined in Formula (1) and Formula (2) are bonded.

Evaluation of Manufacture of Organic Electric element

Example 1) Manufacture and Evaluation of Red Organic Light Emitting Diode (Emitting Layer Mixed Phosphorescent Host)

First, on an ITO layer (anode) formed on a glass substrate, $N^1$-(naphthalen-2-yl)-$N^4$,$N^4$-bis(4-(naphthalen-2-yl(phenyl)amino)phenyl)-Ni-phenyl benzene-1,4-diamine (hereinafter will be abbreviated as 2-TNATA) was vacuum-deposited to form a hole injection layer with a thickness of 60 nm, and N,N'-bis(1-naphthalenyl)-N,N'-bis-phenyl-(1,1'-biphenyl)-4,4'-diamine (hereinafter will be abbreviated as NPB) was vacuum-deposited to form a hole transport layer with a thickness of 60 nm. On the hole transport layer, a mixture of the compounds represented by Formulas (1) and (2) as a host in a ratio of 3:7 was used as a host, and as a dopant, an emitting layer with a thickness of 30 nm was deposited on the hole transport layer by doping (piq)2Ir(acac) [bis-(1-phenylisoquinolyl)iridium(III)acetylacetonate]with a weight of 5%. (1,1'-bisphenyl)-4-olato)bis(2-methyl-8-quinolinolato)aluminum (hereinafter abbreviated as BAlq) was vacuum deposited as a hole blocking layer to a thickness of 10 nm, and tris(8-quinolinol)aluminum (hereinafter abbreviated as Alq3) was deposited to a thickness of 40 nm as an electron transport layer. After that, an alkali metal halide, LiF was vacuum deposited as an electron injection layer to a thickness of 0.2 nm, and Al was deposited to a thickness of 150 nm to form a cathode to manufacture an OLED.

[Example 2] to [Example 61] Red Organic Light Emitting Diode (Emitting Layer Mixed Phosphorescent Host)

The inventive compound represented by Formula (1) and Formula (2) of the present invention as the host material of the emitting layer was prepared in the same manner as in Example 1 to prepare an organic electroluminescent device, except for using the compounds of the present invention described in Table 7 below, Comparative Examples 1 to 3

An organic electroluminescent device was manufactured in the same manner as in Example 1, except that the compound represented by Formula (2) was used as a host alone.

Comparative Example 4

An organic electroluminescent device was manufactured in the same manner as in Example 1, except that the comparative compound 1 was used as a host alone.

Comparative Example 5

An organic electroluminescent device was manufactured in the same manner as in Example 1, except that the comparative compound 2 was used as a host alone.

Comparative Example 6

An organic electroluminescent device was manufactured in the same manner as in Example 1, except that the comparative compound 3 was used as a host alone.

Comparative Example 7

An organic electroluminescent device was manufactured in the same manner as in Example 1, except that the comparative compound 4 was used as a host alone.

Comparative Example 8

An organic electroluminescent device was manufactured in the same manner as in Example 1, except that comparative compound 1 and 2 were mixed and used as a host.

Comparative Example 9

An organic electroluminescent device was manufactured in the same manner as in Example 1, except that comparative compound 3 and 4 were mixed and used as a host.

To the OLEDs which were manufactured by example 1 to 61 and comparative examples 1 to 9, a forward bias direct current voltage was applied, and electroluminescent(EL) properties were measured using PR-650 of Photoresearch Co., and T95 life was measured using a life measuring apparatus manufactured by McScience Inc. with a reference luminance of 2500 cd/m². The measurement results are shown in Tables 7 and 8 below.

comparative compound 1

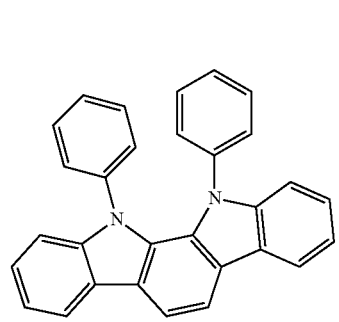

comparative compound 2

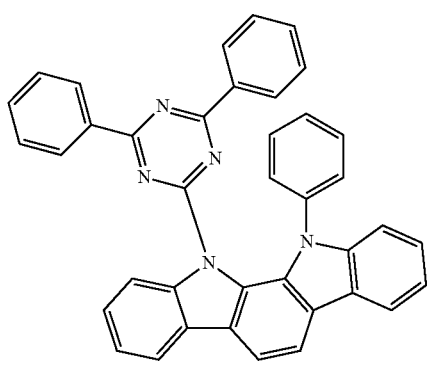

comparative compound 3

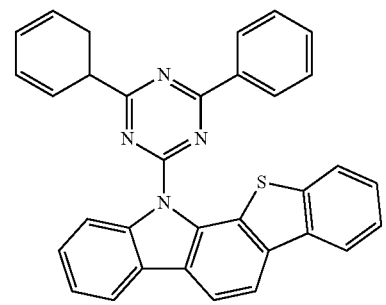

comparative compound 4

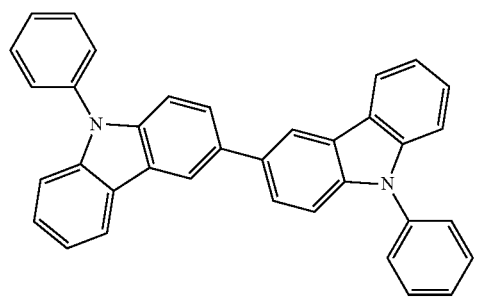

When the second host is fixed and various first hosts are mixed.

TABLE 7

| | First host | Second host | Voltage | Current Density | Brightness (cd/m²) | Efficiency | Lifetime T(95) |
|---|---|---|---|---|---|---|---|
| comparative example(1) | — | compound (3-6) | 6.1 | 15.7 | 2500 | 15.9 | 108.9 |
| comparative example(2) | — | compound (3-61) | 6.3 | 16.2 | 2500 | 15.5 | 104.2 |
| comparative example(3) | — | compound (3-74) | 6.4 | 16.2 | 2500 | 15.4 | 103.2 |
| comparative example(4) | — | comparative compound 1 | 6.9 | 18.6 | 2500 | 13.4 | 84.3 |
| comparative example(5) | — | comparative compound 2 | 6.8 | 18.3 | 2500 | 13.7 | 83.3 |
| comparative example(6) | — | comparative compound 3 | 6.7 | 17.5 | 2500 | 14.3 | 87.4 |
| comparative example(7) | — | comparative compound 4 | 6.9 | 18.4 | 2500 | 13.6 | 82.9 |
| comparative example(8) | comparative compound 1 | comparative compound 2 | 5.9 | 13 | 2500 | 19.3 | 103.8 |
| comparative example(9) | comparative compound 3 | comparative compound 4 | 5.6 | 10.5 | 2500 | 23.9 | 108.9 |
| example(1) | compound 1-3 | compound 3-6 | 4.3 | 6.2 | 2500 | 40.5 | 142.4 |
| example(2) | compound 1-5 | compound 3-6 | 4.6 | 8.0 | 2500 | 31.1 | 128.2 |
| example(3) | compound 1-10 | compound 3-6 | 4.5 | 7.1 | 2500 | 35.2 | 137.8 |
| example(4) | compound 1-15 | compound 3-6 | 4.4 | 8.2 | 2500 | 30.5 | 131.4 |
| example(5) | compound 1-16 | compound 3-6 | 4.5 | 7.4 | 2500 | 33.6 | 135.5 |
| example(6) | compound 1-19 | compound 3-6 | 4.5 | 7.6 | 2500 | 32.8 | 133.9 |
| example(7) | compound 2-1 | compound 3-6 | 4.4 | 5.9 | 2500 | 42.3 | 137.8 |
| example(8) | compound 2-5 | compound 3-6 | 4.4 | 6.2 | 2500 | 40.6 | 134.5 |

TABLE 7-continued

| | First host | Second host | Voltage | Current Density | Brightness (cd/m$^2$) | Efficiency | Lifetime T(95) |
|---|---|---|---|---|---|---|---|
| example(9) | compound 2-6 | compound 3-6 | 4.6 | 8.1 | 2500 | 30.7 | 129.1 |
| example(10) | compound 2-10 | compound 3-6 | 4.6 | 8.4 | 2500 | 29.8 | 127.4 |
| example(11) | compound 2-14 | compound 3-6 | 4.5 | 7.1 | 2500 | 35.2 | 133.9 |
| example(12) | compound 2-15 | compound 3-6 | 4.5 | 7.2 | 2500 | 34.8 | 130.5 |
| example(13) | compound 2-18 | compound 3-6 | 4.6 | 7.5 | 2500 | 33.5 | 129.2 |
| example(14) | compound 2-26 | compound 3-6 | 4.5 | 6.7 | 2500 | 37.2 | 132.4 |
| example(15) | compound 2-36 | compound 3-6 | 4.5 | 6.9 | 2500 | 36.3 | 132.7 |
| example(16) | compound 2-63 | compound 3-6 | 4.6 | 7.9 | 2500 | 31.6 | 128.8 |
| example(17) | compound 2-65 | compound 3-6 | 4.6 | 8.3 | 2500 | 30.3 | 127.5 |
| example(17‿) | compound 2-76 | compound 3-6 | 4.4 | 6.2 | 2500 | 40.1 | 144.5 |

When the first host material and various second host materials are mixed.

TABLE 8

| | First host | Second host | Voltage | Current Density | Brightness (cd/m$^2$) | Efficiency | Lifetime T(95) |
|---|---|---|---|---|---|---|---|
| example(18) | compound 1-3 | compound 3-7 | 4.4 | 7.2 | 2500 | 34.6 | 134.4 |
| example(19) | | compound 3-8 | 4.4 | 7.2 | 2500 | 34.7 | 132.7 |
| example(20) | | compound 3-9 | 4.4 | 7.1 | 2500 | 35.1 | 132.1 |
| example(21) | | compound 3-15 | 4.4 | 7.8 | 2500 | 32.0 | 130.3 |
| example(22) | | compound 3-37 | 4.5 | 8.6 | 2500 | 29.1 | 128.5 |
| example(23) | | compound 3-46 | 4.4 | 7.1 | 2500 | 35.1 | 132.1 |
| example(24) | | compound 3-50 | 4.5 | 7.7 | 2500 | 32.4 | 129.5 |
| example(25) | | compound 3-61 | 4.3 | 6.6 | 2500 | 37.9 | 139.2 |
| example(26) | | compound 3-74 | 4.4 | 7.1 | 2500 | 35.4 | 130.8 |
| example(27) | | compound 3-89 | 4.3 | 7.1 | 2500 | 35.3 | 132.8 |
| example(28) | | compound 3-90 | 4.3 | 7.1 | 2500 | 35.3 | 132.5 |
| example(29) | compound 1-10 | compound 3-7 | 4.6 | 8.0 | 2500 | 31.4 | 132.2 |
| example(30) | | compound 3-8 | 4.6 | 7.9 | 2500 | 31.6 | 131.7 |
| example(31) | | compound 3-9 | 4.6 | 8.6 | 2500 | 29.1 | 130.2 |
| example(32) | | compound 3-15 | 4.6 | 9.1 | 2500 | 27.4 | 127.1 |
| example(33) | | compound 3-37 | 4.7 | 9.6 | 2500 | 26.2 | 126.4 |
| example(34) | | compound 3-46 | 4.6 | 8.6 | 2500 | 29.0 | 130.1 |
| example(35) | | compound 3-50 | 4.6 | 9.3 | 2500 | 26.8 | 126.5 |
| example(36) | | compound 3-61 | 4.5 | 7.5 | 2500 | 33.3 | 134.5 |
| example(37) | | compound 3-74 | 4.6 | 8.0 | 2500 | 31.1 | 131.8 |

TABLE 8-continued

| | First host | Second host | Voltage | Current Density | Brightness (cd/m²) | Efficiency | Lifetime T(95) |
|---|---|---|---|---|---|---|---|
| example(38) | | compound 3-89 | 4.4 | 8.4 | 2500 | 29.9 | 129.2 |
| example(39) | | compound 3-90 | 4.4 | 8.5 | 2500 | 29.4 | 130.2 |
| example(40) | compound 2-1 | compound 3-7 | 4.5 | 7.3 | 2500 | 34.0 | 128.0 |
| example(41) | | compound 3-8 | 4.5 | 7.5 | 2500 | 33.3 | 128.3 |
| example(42) | | compound 3-9 | 4.5 | 7.4 | 2500 | 33.8 | 128.9 |
| example(43) | | compound 3-15 | 4.5 | 8.3 | 2500 | 30.1 | 126.0 |
| example(44) | | compound 3-37 | 4.6 | 9.9 | 2500 | 25.1 | 123.9 |
| example(45) | | compound 3-46 | 4.5 | 8.0 | 2500 | 31.2 | 128.1 |
| example(46) | | compound 3-50 | 4.6 | 8.2 | 2500 | 30.4 | 126.9 |
| example(47) | | compound 3-61 | 4.5 | 6.2 | 2500 | 40.5 | 133.8 |
| example(48) | | compound 3-74 | 4.5 | 7.1 | 2500 | 35.4 | 130.6 |
| example(49) | | compound 3-89 | 4.4 | 8.1 | 2500 | 30.9 | 126.2 |
| example(50) | | compound 3-90 | 4.4 | 8.1 | 2500 | 30.7 | 125.2 |
| example(51) | compound 2-14 | compound 3-7 | 4.5 | 7.9 | 2500 | 31.6 | 127.9 |
| example(52) | | compound 3-8 | 4.5 | 7.9 | 2500 | 31.5 | 127.9 |
| example(53) | | compound 3-9 | 4.5 | 8.5 | 2500 | 29.6 | 128.3 |
| example(54) | | compound 3-15 | 4.6 | 9.2 | 2500 | 27.2 | 128.1 |
| example(55) | | compound 3-37 | 4.7 | 9.3 | 2500 | 26.9 | 125.8 |
| example(56) | | compound 3-46 | 4.5 | 8.4 | 2500 | 29.9 | 128.8 |
| example(57) | | compound 3-50 | 4.6 | 9.0 | 2500 | 27.7 | 128.4 |
| example(58) | | compound 3-61 | 4.5 | 7.1 | 2500 | 35.2 | 133.9 |
| example(59) | | compound 3-74 | 4.5 | 8.2 | 2500 | 30.6 | 126.4 |
| example(60) | | compound 3-89 | 4.4 | 8.1 | 2500 | 30.8 | 129.0 |
| example(61) | | compound 3-90 | 4.4 | 8.5 | 2500 | 29.4 | 128.2 |
| example(61') | compound 2-76 | compound 3-101 | 4.3 | 5.9 | 2500 | 42.5 | 143.8 |

As can be seen from the results of Table 7 and 8, when the organic electric element material of the present invention represented by Formulas (1) and (2) is mixed and used as a phosphorescent host (Examples 1 to 61), it was confirmed that the driving voltage, efficiency, and life span were significantly improved as compared with the element using a single material (comparative examples 1 to 7).

More specifically, in Comparative Examples 1 to 7, wherein the compounds of the present invention represented by Formula (2) and comparative compounds 1 to 4 are used alone as a phosphorescent host, Comparative Examples 1 to 3 using the compounds (3-6, 3-61, and 3-74) of the present invention had higher efficiency and longer life span than Comparative Examples 4 to 7 using the comparative compound.

Also, Comparative Example 8 and 9 wherein Comparative Compound 1 and 2 or Comparative Compound 3 and 4 were mixed and used as a phosphorescent host were found to exhibit higher efficiency than Comparative Examples 1 to 7 using the single substance.

Comparing Comparative Example 8 with 9, Comparative Example 9 using a mixture containing a polycyclic compound having a different heteroatom (N, S) among the 5-membered compounds had higher efficiency than Comparative Example 8 mixed a 5-membered heterocyclic compound having the same nitrogen atom.

And it was confirmed that Example 1 to 61 using the mixture of the compound of Formula (1) and (2) as a host exhibited remarkably high efficiency and long life span than the Comparative Example 1 to 9.

On the basis of the above experimental results, the inventors of the present invention have found that, in the case of a mixture of the substance of Formulas (1) and (2), they have novel characteristics other than those for the respective materials, and have measured the PL lifetime using the substance of Formula (1), the substance of Formula (2), and the mixture of the present invention. As a result, it was confirmed that a new PL wavelength was formed when the compounds of Formulas (1) and (2) were mixed, and the decreasing and disappearing time of the newly formed PL wavelength increased from about 60 times to about 360 times compared to the reduction and disappearance times of substances Formula (1) and (2), respectively. It is considered when mixed with the compound of the present invention, not only electrons and holes are moved through the energy level of each substance, but also the efficiency and life span are increased by electron, hole transport or energy transfer by a new region(exciplex) having a new energy level formed due to mixing. As a result, when the mixture of the present invention is used, the mixed thin film is an important example showing exciplex energy transfer and light emitting process.

The reason why the combination of the present invention is superior to Comparative Examples 8 to 9 in which a comparative compound is used as a phosphorescent host is that the high Ti and high LUMO energy values improve the electron blocking ability and allow more holes to be moved to the emitting layer more quickly and easily when a compound represented by Formula (1) having a strong hole property is mixed with a polycyclic compound represented by Formula (2), which is characterized not only by electron but also by hole stability and high Ti. As a result, the charge balance in the emitting layer of holes and electrons is increased, so that light emission is well performed inside the emitting layer rather than at the interface of the hole transport layer, and therefore the deterioration in the HTL interface is also reduced, thereby maximizing the driving voltage, efficiency and life span of the device.

Among the compounds represented by Formula (1), 1) when $Ar^1$ and $Ar^2$ are of the type in which the ring is curled, it has been confirmed that compounds having at least one of $Ar^3$ and $Ar^4$ substituted with biphenyl exhibits the best results in terms of the driving voltage, the efficiency and the lifetime, and compounds having at least one of $Ar^3$ and $Ar^4$ substituted with Dibenzothiophen or Dibenzofuran were found to be excellent in efficiency and lifetime, and in the case of compounds in which at least one of $Ar^3$ and $Ar^4$ is substituted with fluorene, the driving voltage is excellent. 2) When $Ar^1$ and $Ar^2$ do not form a ring, compounds in which both $Ar^3$ and $Ar^4$ were substituted with naphthyl showed the best results in terms of driving voltage, efficiency, and lifetime, and compounds having at least one of $Ar^3$ and $Ar^4$ substituted with Dibenzothiophen or Dibenzofuran were confirmed to have excellent efficiency and lifetime. That is, it is concluded that the combination of Formula (1) and Formula (2) is electrochemically synergistic to improve the performance of the device as a whole.

Also, Table 8 shows the results obtained using Table 7, in which a first host with high performance was fixed and a variety of second hosts were mixed. As a result, as the first host, when compounds 1-3, 1-10, 2-1 and 2-14 having the best driving voltage, efficiency, and lifetime and, as the second host, the compounds 3-7, 3-8, 3-9, 3-15, 3-37, 3-46, 3-50, 3-61, 3-74, 3-89 and 3-90 were mixed, it can be seen that the driving voltage, efficiency and lifetime can be remarkably improved by using two mixed host materials as compared with the case of using a single host material.

[Example 62] to [Example 69] Manufacture and Evaluation of Red Organic Light Emitting Diode by Mixing Ratio An organic electroluminescent device was manufactured in the same manner as in Example 1, except that the materials are used in different mixing ratios as listed in Table 9.

TABLE 9

| | First host | Second host | Mixing ratio (fist host: second host) | Voltage | Current Density | Brightness (cd/m$^2$) | Efficiency | Lifetime T(95) |
|---|---|---|---|---|---|---|---|---|
| example(62) | compound | compound | 2:8 | 4.3 | 6.1 | 2500 | 41.2 | 140.5 |
| example(63) | 1-3 | 3-6 | 3:7 | 4.3 | 6.2 | 2500 | 40.5 | 142.4 |
| example(64) | | | 4:6 | 4.6 | 6.7 | 2500 | 37.1 | 136.2 |
| example(65) | | | 5:5 | 4.7 | 7.8 | 2500 | 31.9 | 127.5 |
| example(66) | compound | compound | 2:8 | 4.4 | 6.4 | 2500 | 39.1 | 136.4 |
| example(67) | 2-1 | 3-61 | 3:7 | 4.5 | 6.2 | 2500 | 40.5 | 133.8 |
| example(68) | | | 4:6 | 4.6 | 7.0 | 2500 | 35.6 | 130.5 |
| example(69) | | | 5:5 | 4.8 | 8.0 | 2500 | 31.3 | 124.6 |

As shown in Table 9, the mixture of the compound of the present invention was measured by fabricating the device in (2:8, 3:7, 4:6, 5:5). To explain the results in detail, in the result of the mixture of the compound 1-3 and 3-6, the results of the driving voltage, the efficiency and the life span were similarly excellent at 2:8 and 3:7, but as the ratio of the first host increases, such as 4:6 and 5:5, the results of the driving voltage, the efficiency and the life span are gradually decreased, this was also the same in the result of the mixture of the compound 2-1 and 3-61. This can be explained by the fact that the charge balance in the emitting layer is maximized when an appropriate amount of the compound represented by Formula (1) having strong hole properties such as 2:8 and 3:7 is mixed.

Example 70

Red Organic Light Emitting Diode
(Emitting Auxiliary Layer, Phosphorescent Host)

First, on an ITO layer (anode) formed on a glass substrate, $N^1$-(naphthalen-2-yl)-$N^4$,$N^4$-bis(4-(naphthalen-2-yl(phenyl)amino)phenyl)-$N^1$-phenyl benzene-1,4-diamine (hereinafter will be abbreviated as 2-TNATA) was vacuum-deposited to form a hole injection layer with a thickness of 60 nm, and N,N'-bis(1-naphthalenyl)-N,N'-bis-phenyl-(1,1'-biphenyl)-4,4'-diamine (hereinafter will be abbreviated as NPB) was vacuum-deposited to form a hole transport layer with a thickness of 60 nm. Subsequently, 4,4-bis [N-(1-naphthyl)-N-phenylamino] biphenyl (hereinafter abbreviated as -NPD) was vapor-deposited as a hole transport compound on the film to a thickness of 60 nm to form a hole transport layer. Subsequently, Compound 2-76 of the present invention was vacuum-deposited as an emitting auxiliary layer material to a thickness of 20 nm to form an emitting auxiliary layer. Subsequently, on the hole transport layer, the compound 3-6 of the present invention was doped as a host material and bis-(1-phenylisoquinolyl)iridium (III)acetylacetonate (hereinafter abbreviated as "(piq)2Ir(acac)") was doped as a dopant in a weight ratio of 95:5, followed by vacuum evaporation to a thickness of 30 nm to form an emitting layer. Subsequently, ((1,1'-biphenyl)-4-oleato)bis(2-methyl-8-quinolinolato)aluminum (hereinafter will be abbreviated as BAlq) was vacuum deposited on the emitting layer to a thickness of 5 nm to form a hole blocking layer, and Bis(10-hydroxybenzo[h]quinolinato)beryllium(hereinafter will be abbreviated as BeBq$_2$) was vacuum deposited on the hole blocking layer to a thickness of 40 nm to form an electron transport layer. After that, on the electron transport layer, an alkali metal halide, LiF was vacuum deposited as an electron injection layer to a thickness of 0.2 nm, and Al was deposited to a thickness of 150 nm to form a cathode to manufacture an OLED.

[Example 71] to [Example 85] Red Organic Light Emitting Diode (Emitting Auxiliary Layer, Phosphorescent Host)

An organic electroluminescent device was manufactured in the same manner as in Example 70, except that the compound represented by Formula (1) shown in Table 10 was used as the emitting auxiliary layer material, and the compound represented by Formula (2) shown in Table 10 of the present invention was used as the host material of the emitting layer.

To the OLEDs which were manufactured by examples and comparative examples, a forward bias direct current voltage was applied, and electroluminescent (EL) properties were measured using PR-650 of Photoresearch Co., and T95 life was measured using a life measuring apparatus manufactured by McScience Inc. with a reference luminance of 2500 cd/m$^2$. In the following table, the manufacture of a device and the results of evaluation are shown.

Comparative 10

An organic electroluminescent device was manufactured in the same manner as in Example 70, except that the emitting auxiliary layer was not used and Comparative Compound 5 was used as a host.

Comparative Compound 5

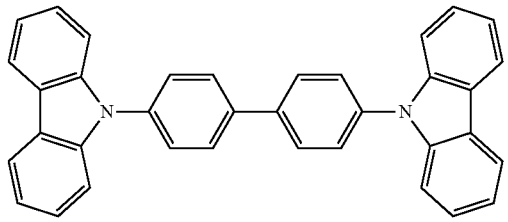

Comparative 11-14

An organic electroluminescent device was manufactured in the same manner as in Example 70, except that the emitting auxiliary layer was not used.

TABLE 10

| | Emitting auxiliary layer | host | Voltage | Current Density | Brightness (cd/m$^2$) | Efficiency | Lifetime T(95) |
|---|---|---|---|---|---|---|---|
| comparative example(10) | | comparative compound 5 | 6.7 | 34.2 | 2500 | 7.3 | 63.5 |
| example(11) | | compound 3-6 | 6.2 | 24.5 | 2500 | 10.2 | 117.9 |
| comparative example(12) | | compound 3-7 | 6.0 | 21.6 | 2500 | 11.6 | 115.5 |
| comparative example(13) | | compound 3-8 | 6.1 | 18.0 | 2500 | 13.9 | 117.0 |
| comparative example(14) | | compound 3-101 | 5.9 | 14.1 | 2500 | 17.7 | 122.5 |
| example(70) | compound 2-1 | compound 3-6 | 6.1 | 16.3 | 2500 | 23.8 | 127.2 |
| example(71) | | compound 3-7 | 6.1 | 13.7 | 2500 | 25.7 | 125.2 |
| example(72) | | compound 3-8 | 6.0 | 12.3 | 2500 | 26.5 | 126.9 |
| example(73) | | compound 3-101 | 5.8 | 10.3 | 2500 | 27.2 | 129.6 |
| example(74) | compound 2-76 | compound 3-6 | 5.6 | 9.3 | 2500 | 28.5 | 137.8 |
| example(75) | | compound 3-7 | 5.7 | 8.6 | 2500 | 30.4 | 137.3 |
| example(76) | | compound 3-8 | 5.7 | 6.8 | 2500 | 32.2 | 138.7 |
| example(77) | | compound 3-101 | 5.4 | 6.0 | 2500 | 34.4 | 141.5 |
| example(78) | compound 2-88 | compound 3-6 | 5.7 | 10.5 | 2500 | 30.5 | 137.3 |
| example(79) | | compound 3-7 | 5.7 | 9.5 | 2500 | 31.7 | 135.6 |
| example(80) | | compound 3-8 | 5.7 | 7.3 | 2500 | 34.5 | 136.6 |
| example(81) | | compound 3-101 | 5.5 | 6.3 | 2500 | 36.1 | 139.3 |

TABLE 10-continued

| | Emitting auxiliary layer | host | Voltage | Current Density | Brightness (cd/m$^2$) | Efficiency | Lifetime T(95) |
|---|---|---|---|---|---|---|---|
| example(82) | compound 2-106 | compound 3-6 | 5.9 | 8.4 | 2500 | 27.3 | 136.4 |
| example(83) | | compound 3-7 | 5.8 | 7.8 | 2500 | 29.4 | 135.8 |
| example(84) | | compound 3-8 | 5.9 | 6.2 | 2500 | 31.1 | 138.2 |
| example(85) | | compound 3-101 | 5.7 | 5.6 | 2500 | 33.7 | 140.4 |

As can be seen from the results of Table 10, when the compound of the present invention represented by Formula (1) is used as a material for the emitting auxiliary layer and the compound of the present invention represented by Formula (2) is used as a phosphorescent host material (Examples 70 to 85), the driving voltage, the efficiency, and the lifetime were significantly improved as compared with the device using a single material (Comparative Examples 10 to 14).

In detail, in Comparative Examples 10 to 14 using the compound of the present invention represented by the formula (2) or Comparative Compound 5 alone as a phosphorescent host, Comparative Examples 11 to 14 using the compounds of the present invention (3-6, 3-7, 3-8, and 3-101) exhibited higher efficiency and longer lifetime than Comparative Example 1 using Comparative Compound 5.

It was also confirmed that Examples 70 to 85 using the compounds of Formula (1) and Formula (2) of the present invention, as the emitting auxiliary layer and the phosphorescent host, respectively, show significantly higher efficiency, lifetime and low driving voltage than the Comparative Examples 10 to 14.

In general, there is an injection barrier between HTL and EML, so that the hole can not be transferred easily, and the charge balance is not matched so that the driving voltage is increased. Therefore, it is considered that the charge balance in the emitting layer of the hole and electron is adjusted by the introduction of the emitting auxiliary layer having a proper HOMO level between HTL and EML when the emitting auxiliary layer of the present invention is applied.

Specially, a compound in which at least one of Ar$^1$, Ar$^2$, Ar$^3$, Ar$^4$, L$^1$, L$^2$, L$^3$, L$^4$, and L$^5$ is substituted with a dibenzothiophene or dibenzofuran exhibited remarkably higher refractive index and higher Tg as compared with the case where the substituent of the general aryl group was substituted, so that the efficiency and the thermal stability were improved, and it was judged that the compound showed improved device results.

The compound of the present invention represented by Formula (1) suitably align the barriers of HTL and EML so that the device has a feature of high hole mobility, and compounds of the present invention represented by Formula (2) have characteristics of not only fast electron mobility but also hole stability and high Ti as compared with Comparative compound 6. Therefore, the combination of the two makes it possible to move more holes to the emissive layer quickly and easily. As a result, the charge balance in the emitting layer of holes and electrons is increased, so that light emission is well performed inside the emitting layer rather than at the interface of the hole transport layer, and therefore the deterioration in the ITO and HTL interface is also reduced, thereby maximizing the driving voltage, efficiency and life span of the device. That is, it is judged that the combination of the compound of the present invention represented by Formula (1) and the compound of the present invention represented by Formula (2) is electrochemically synergistic to improve the performance of the device as a whole.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. An organic electric element comprising a first electrode, a second electrode, and an organic material layer formed between the first electrode and the second electrode,
wherein the organic material layer comprises an emitting layer,
wherein the emitting layer comprises a first host compound represented by Formula (3-20) and a second host compound represented by Formula (2) as a phosphorescent light emitting layer:

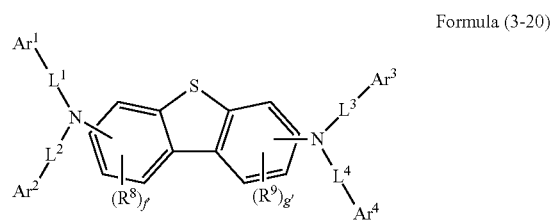
Formula (3-20)

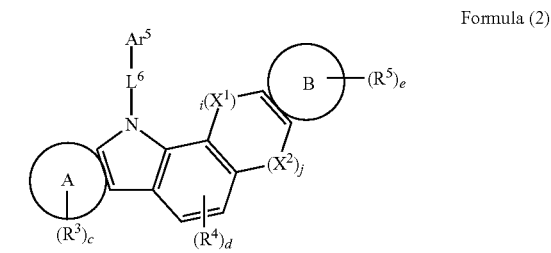
Formula (2)

wherein:
1) Ar$^1$, Ar$^2$, Ar$^3$, Ar$^4$ and Ar$^5$ are each independently selected from the group consisting of a C$_6$-C$_{60}$ aryl group, a dibenzothiophenyl, and dibenzofuranyl group, with the proviso that: i) neither Ar¹ and Ar², nor Ar³ and Ar⁴ are bonded to each other to form a ring, and ii) at least one of L³-Ar³ and L⁴-Ar⁴ is a dibenzothiophenyl or dibenzofuranyl group, and none of the remaining Ar¹, Ar², Ar³ and Ar⁴ is a fluorenyl group, 2) c and e are an integer of 0 to 10, d is an integer of 0 to 2, and f' and g' are integer of 0 to 3, 3) $R^3$, $R^4$, $R^5$, $R^8$ and $R^9$ are the same or different from each other, and are each independently selected from the group consisting of hydrogen; deuterium; halogen; a $C_6$-$C_{60}$ aryl group; a $C_2$-$C_{60}$ heterocyclic group including at least one heteroatom of O, N, S, Si or P; a $C_1$-$C_{50}$ alkyl group; a $C_2$-$C_{20}$ alkenyl group; a $C_2$-$C_{20}$ alkynyl group; or in case a, b, c, d, e, f' and g' are 2 or more, $R_3$, $R^4$, $R^5$, $R^8$ and $R^9$ are each in plural being the same or different, and a plurality of $R^3$ or a plurality of $R^4$ or a plurality of $R^5$ or a plurality of $R^8$ or a plurality of $R^9$, or two adjacent $R^8$ and $R^9$ may be bonded to each other to form an aromatic or heteroaromatic ring, 4) $L^1$, $L^2$, $L^3$, $L^4$, and $L^6$ are each independently selected from the group consisting of a single bond; a $C_6$-$C_{60}$ arylene group; and a $C_2$-$C_{60}$ heterocyclic group, 5) A and B are each independently a $C_6$-$C_{60}$ aryl group or a $C_2$-$C_{20}$ heterocyclic group, provided that when both A and B are a substituted or unsubstituted $C_6$ aryl group (phenyl group), d is 2, and $R^4$s are bonded to each other to form an aromatic or heterocyclic group, 6) i and j are 0 or 1, with the proviso that i+j is 1 or more, and when i or j is 0, it means a direct bond, 7) $X^1$ and $X^2$ are each independently N-$L^7$-$Ar^6$, O, S, or $CR^6R^7$, wherein $L^7$ is the same as $L^1$ to $L^4$ or $L^6$, wherein $Ar^6$ is the same as $Ar^1$ to $Ar^5$, and $R^6$ and $R^7$ are each independently hydrogen; a $C_6$-$C_{60}$ aryl group; a $C_2$-$C_{60}$ heterocyclic group; or a $C_1$-$C_{50}$ alkyl group and $R^6$ and $R^7$ may combine to each other to form a spiro ring, wherein, the aryl group, arylene group, heterocyclic group, alkyl group, alkenyl group, may be substituted with one or more substituents selected from the group consisting of deuterium; halogen; cyano group; nitro group; $C_1$-$C_{20}$ alkoxyl group; $C_1$-$C_{20}$ alkyl group; $C_2$-$C_{20}$ alkenyl group; $C_6$-$C_{20}$ aryl group; $C_6$-$C_{20}$ aryl group substituted with deuterium; $C_2$-$C_{20}$ heterocyclic group; wherein the substituents may combine each other and form a saturated or unsaturated ring, wherein the term 'ring' means $C_3$-$C_{60}$ aliphatic ring or $C_6$-$C_{60}$ aromatic ring or a $C_2$-$C_{60}$ heterocyclic group or a fused ring formed by the combination of thereof and includes a saturated or unsaturated ring, and wherein Formula (3-20) has one of the following structures regarding the bonding position of the two amino substituents-N($L^1$-$Ar^1$)($L^2$-$Ar^2$) and N($L^3$-$Ar^3$)($L^4$-$Ar^4$):

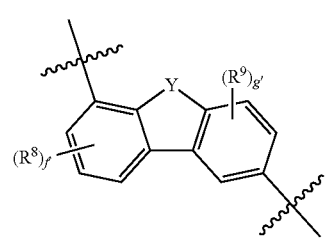

C-3

-continued

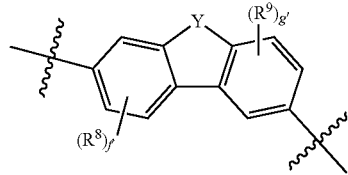

C-6

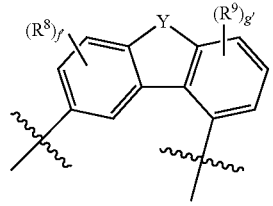

C-9 wherein Y is S, and $R^8$, $R^9$, f, g' are the same as defined above for Formula (3-20).

2. The organic electric element according to claim 1, wherein $L^1$, $L^2$, $L^3$, and $L^4$ in Formula (3-20) are each independently any one of the following Formulas (A-1) to (A-13) and $L^3$ and $L^4$ can be each independently a single bond:

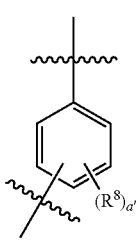

(A-1)

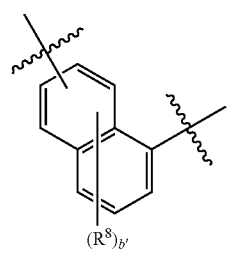

(A-2)

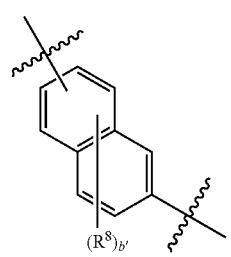

(A-3)

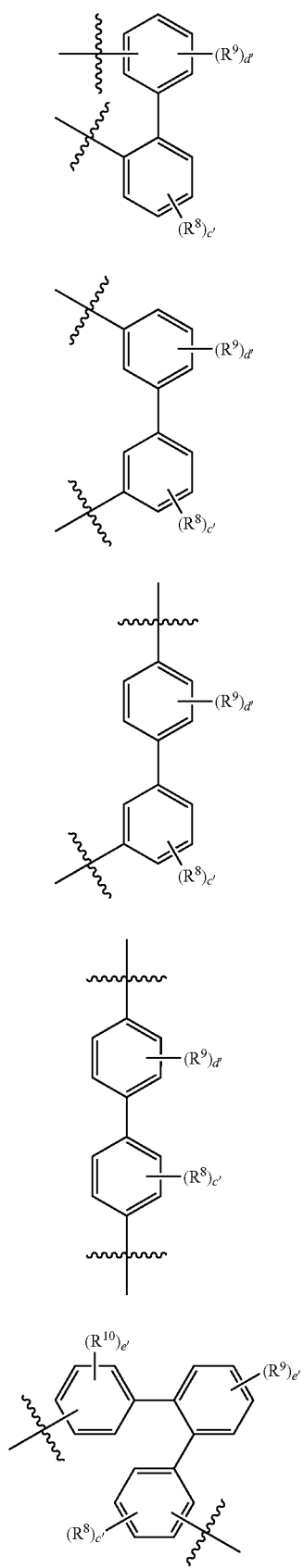
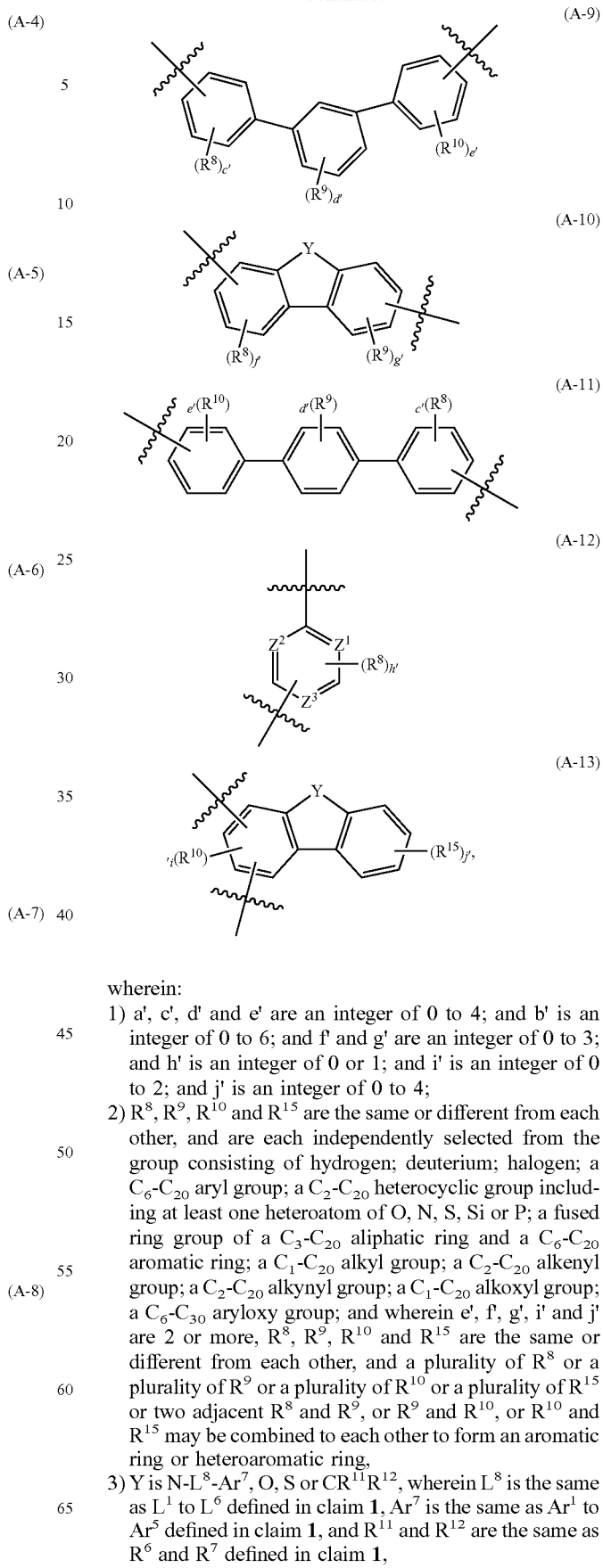

wherein:
1) a', c', d' and e' are an integer of 0 to 4; and b' is an integer of 0 to 6; and f' and g' are an integer of 0 to 3; and h' is an integer of 0 or 1; and i' is an integer of 0 to 2; and j' is an integer of 0 to 4;
2) $R^8$, $R^9$, $R^{10}$ and $R^{15}$ are the same or different from each other, and are each independently selected from the group consisting of hydrogen; deuterium; halogen; a $C_6$-$C_{20}$ aryl group; a $C_2$-$C_{20}$ heterocyclic group including at least one heteroatom of O, N, S, Si or P; a fused ring group of a $C_3$-$C_{20}$ aliphatic ring and a $C_6$-$C_{20}$ aromatic ring; a $C_1$-$C_{20}$ alkyl group; a $C_2$-$C_{20}$ alkenyl group; a $C_2$-$C_{20}$ alkynyl group; a $C_1$-$C_{20}$ alkoxyl group; a $C_6$-$C_{30}$ aryloxy group; and wherein e', f', g', i' and j' are 2 or more, $R^8$, $R^9$, $R^{10}$ and $R^{15}$ are the same or different from each other, and a plurality of $R^8$ or a plurality of $R^9$ or a plurality of $R^{10}$ or a plurality of $R^{15}$ or two adjacent $R^8$ and $R^9$, or $R^9$ and $R^{10}$, or $R^{10}$ and $R^{15}$ may be combined to each other to form an aromatic ring or heteroaromatic ring,
3) Y is N-$L^8$-$Ar^7$, O, S or $CR^{11}R^{12}$, wherein $L^8$ is the same as $L^1$ to $L^6$ defined in claim 1, $Ar^7$ is the same as $Ar^1$ to $Ar^5$ defined in claim 1, and $R^{11}$ and $R^{12}$ are the same as $R^6$ and $R^7$ defined in claim 1, 4) $Z^1$, $Z^2$ and $Z^3$ are $CR^{13}$ or N and at least one is N, and $R^{13}$ is the same as $R^8$ and $R^{10}$ defined in claim 1.

3. The organic electric element according to claim 1, wherein at least one of $L^1$, $L^2$, $L^3$, and $L^4$ in Formula (3-20) is substituted on an m(meta)-position.

4. The organic electric element according to claim 1, wherein the second host compound represented by Formula (2) is represented by the following Formula (4) or (5):

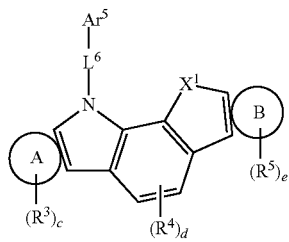

Formula (4)

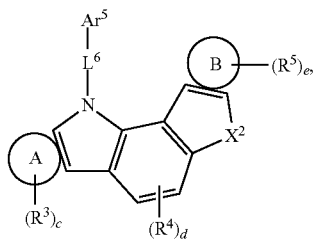

Formula (5)

wherein $R^3$, $R^4$, $R^5$, $L^6$, $Ar^5$, $X^1$, $X^2$, A, B, c, d, and e are the same as defined in claim 1.

5. The organic electric element according to claim 1, wherein A and B in Formula (2) are selected from the group consisting of the following Formulas (B-1) to (B-7):

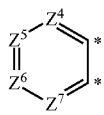

(B-1)

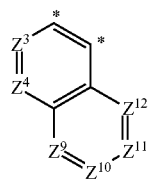

(B-2)

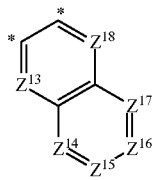

(B-3)

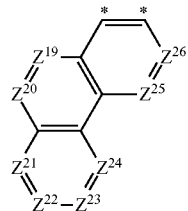

(B-4)

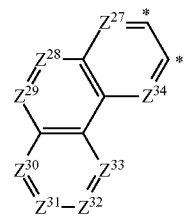

(B-5)

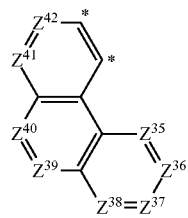

(B-6)

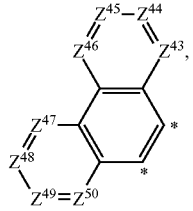

(B-7)

wherein:

1) $Z^4$ to $Z^{50}$ are $CR^{14}$ or N,

2) $R^{14}$ is the same as $R^3$ to $R^5$ defined in claim 1,

3) * indicates the position to be condensed.

6. The organic electric element according to claim 1, wherein the second host compound represented by Formula (2) comprises a compound represented by any of the following Formulas (4-1) to (4-36):

Formula (4-1)

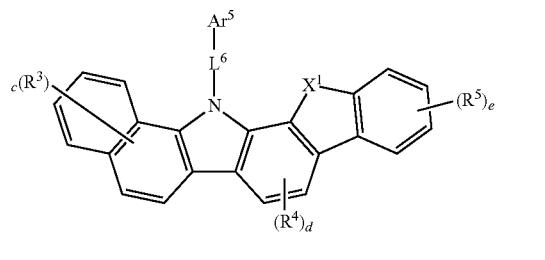

Formula (4-2)
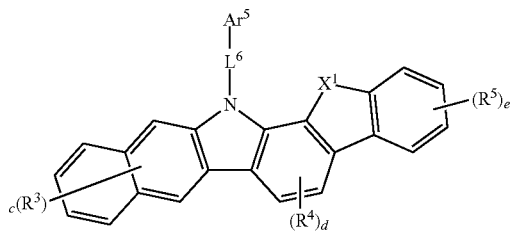
Formula (4-3)
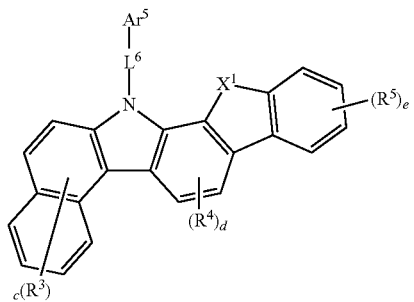
Formula (4-4)
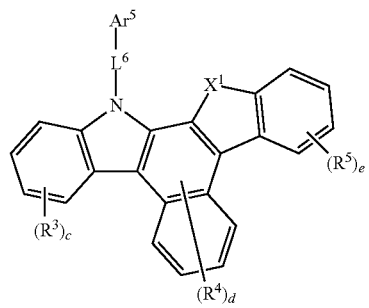
Formula (4-5)
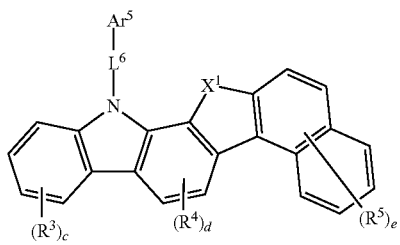
Formula (4-6)
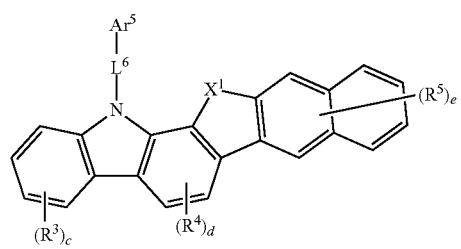
Formula (4-7)
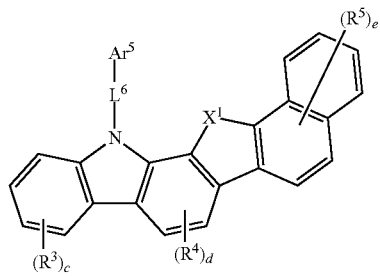
Formula (4-8)
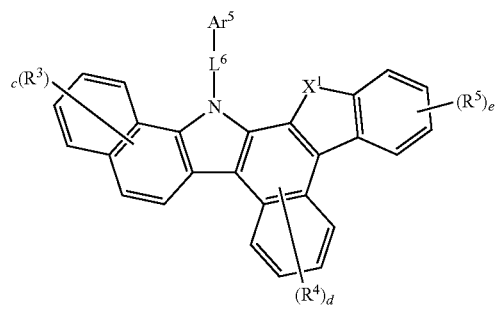
Formula (4-9)
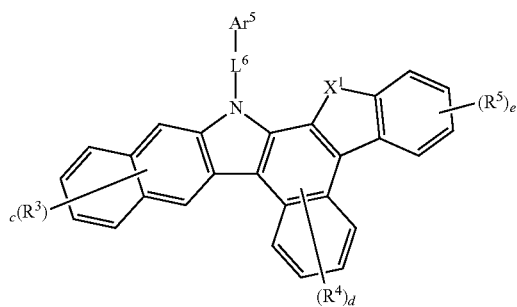
Formula (4-10)
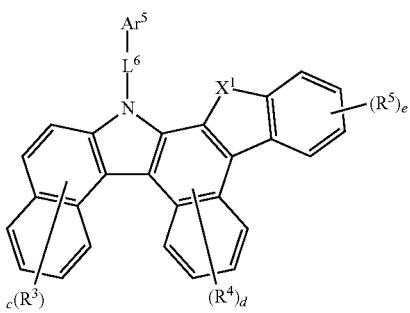
Formula (4-11)
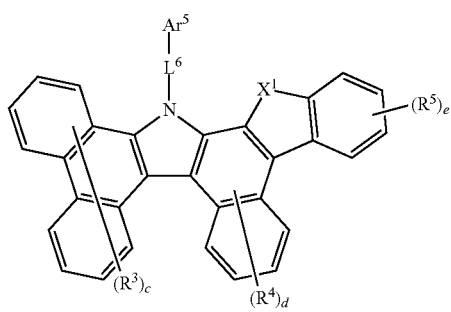

Formula (4-12)
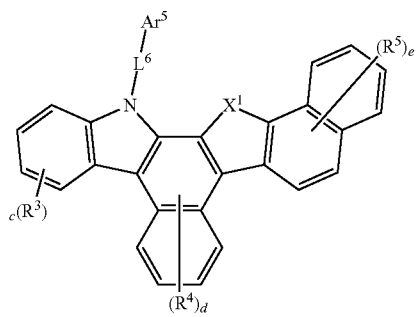
Formula (4-13)
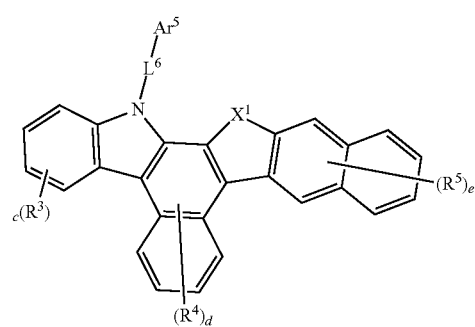
Formula (4-14)
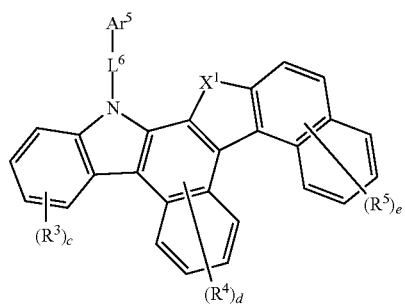
Formula (4-15)
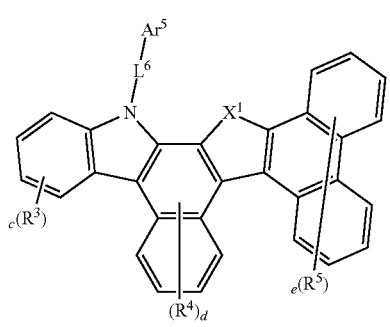
Formula (4-16)
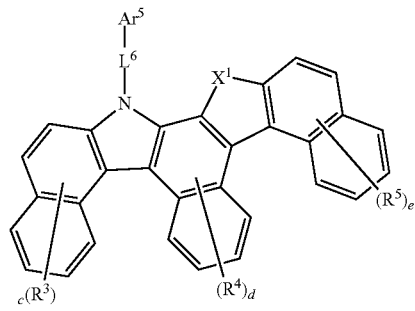
Formula (4-17)
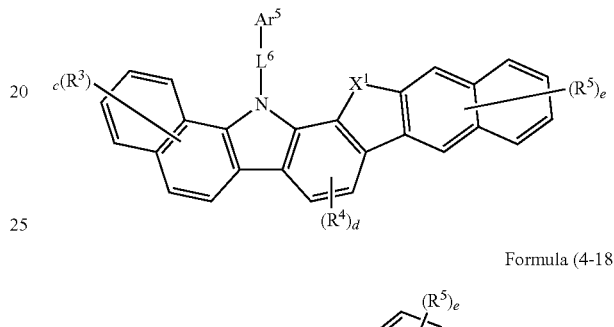
Formula (4-18)
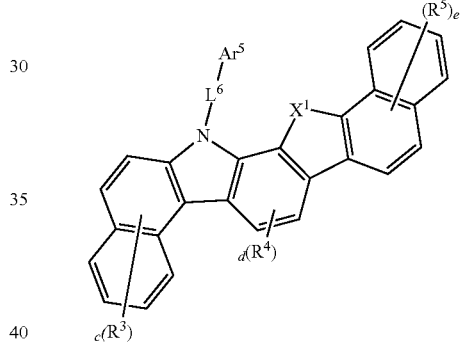
Formula (4-19)
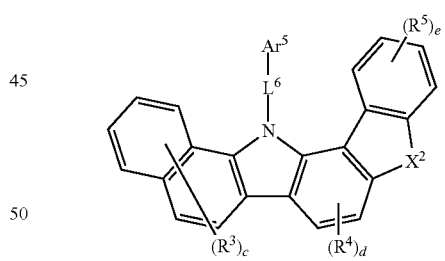
Formula (4-20)
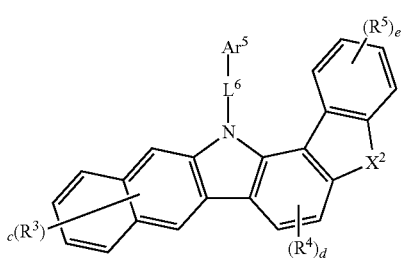

Formula (4-21)
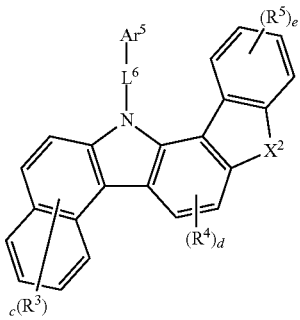
Formula (4-22)
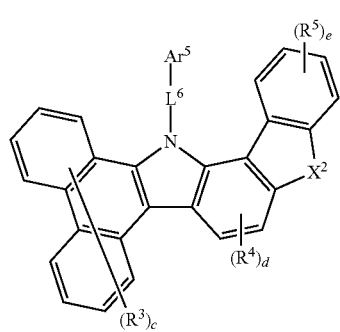
Formula (4-23)
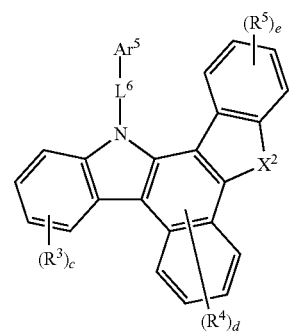
Formula (4-24)
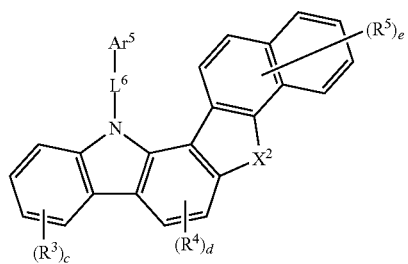
Formula (4-25)
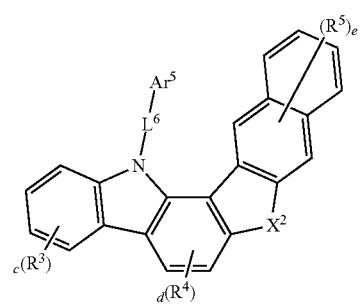
Formula (4-26)
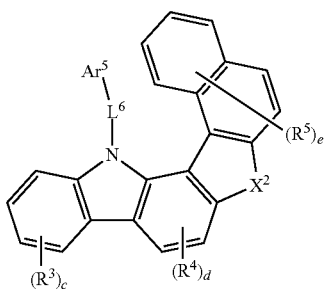
Formula (4-27)
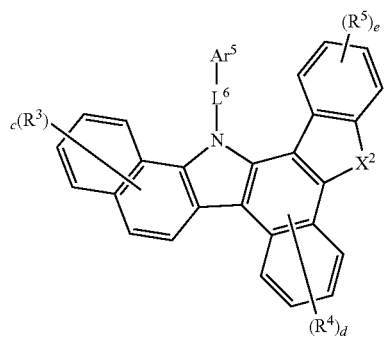
Formula (4-28)
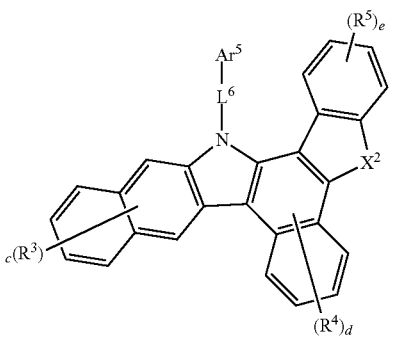
Formula (4-29)
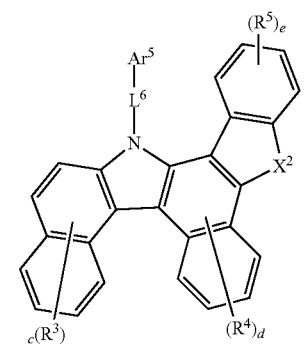
Formula (4-30)
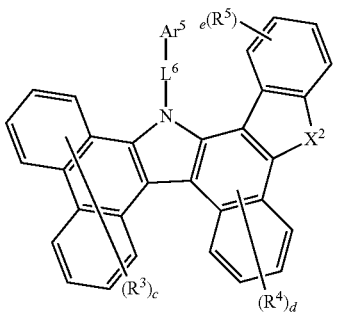

Formula (4-31)
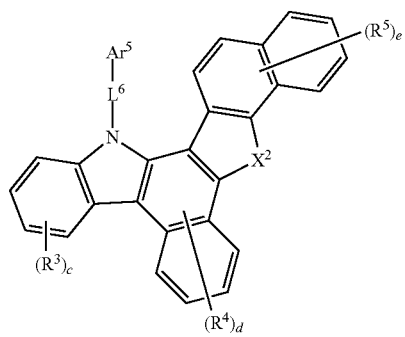
Formula (4-32)
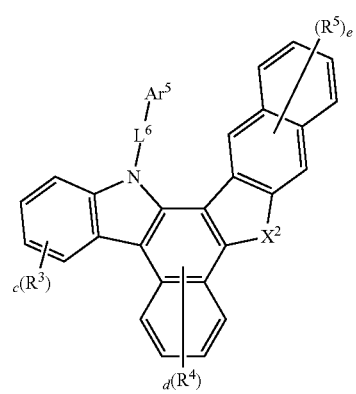
Formula (4-33)
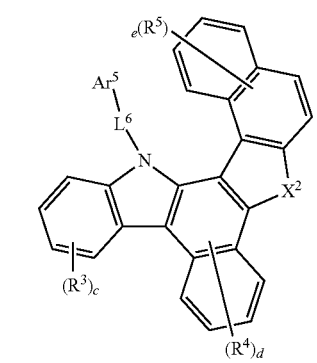
Formula (4-34)
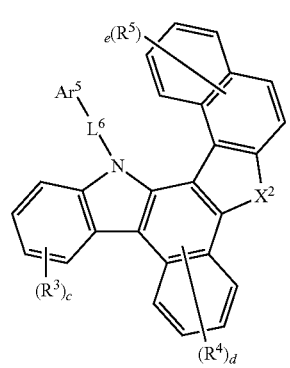
Formula (4-35)
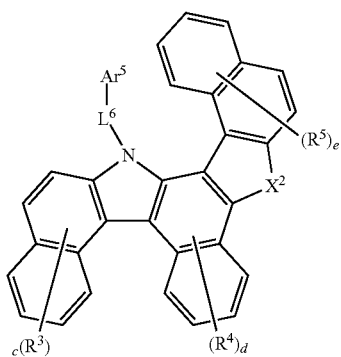
Formula (4-36)
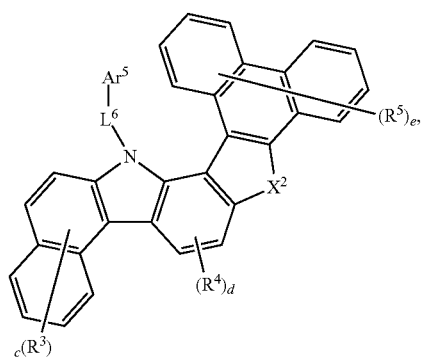
wherein $Ar^5$, $L^6$, $R^3$, $R^4$, $R^5$, $X^1$, $X^2$, c and e are the same as defined in claim 1, and d is any one of integer of 0 to 4.
7. The organic electric element according to claim 1, wherein the second host compound represented by Formula (2) comprises compounds represented by the following Formulas (6-1) to (6-8):
Formula (6-1)
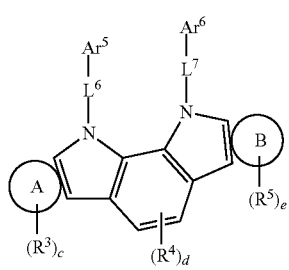
Formula (6-2)
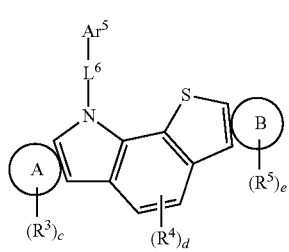

-continued
Formula (6-3)
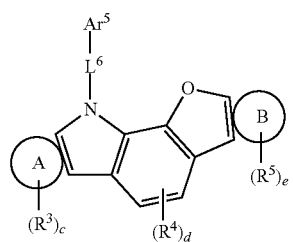
Formula (6-4)
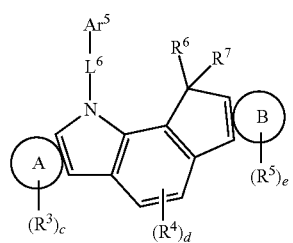
Formula (6-5)
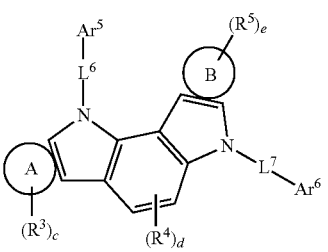
Formula (6-6)
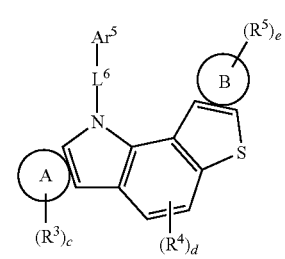
Formula (6-7)
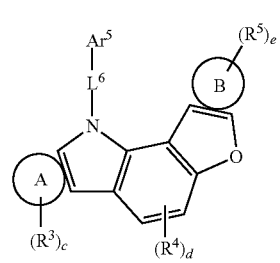
Formula (6-8)
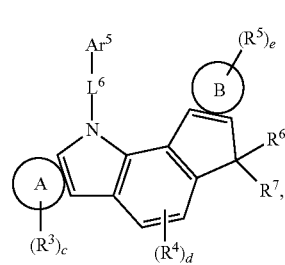
wherein $R^3$, $R^4$, $R^5$, $R^6$, $R^7$, $L^6$, $L^7$, $Ar^5$, $Ar^6$, c, d, e, A and B are the same as defined in claim 1.
8. The organic electric element according to claim 1, wherein the first host compound represented by Formula (3-20) comprises the following Compounds 2-71 to 2-71, 2-100, and 2-106:
2-71
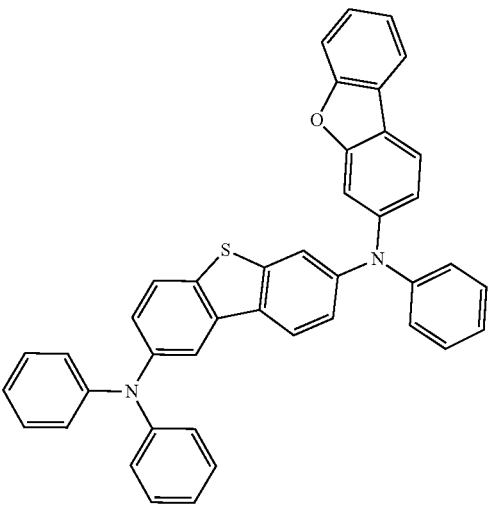
2-72
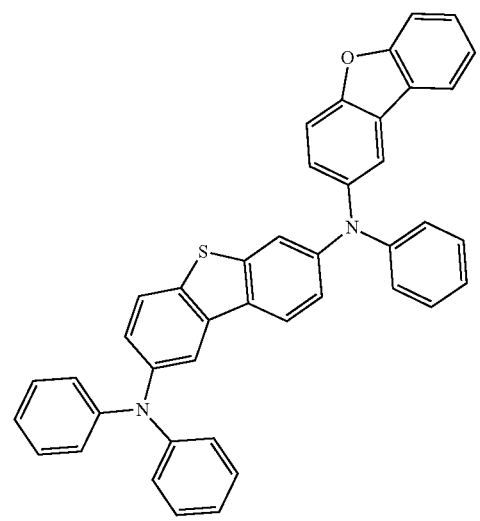

2-73
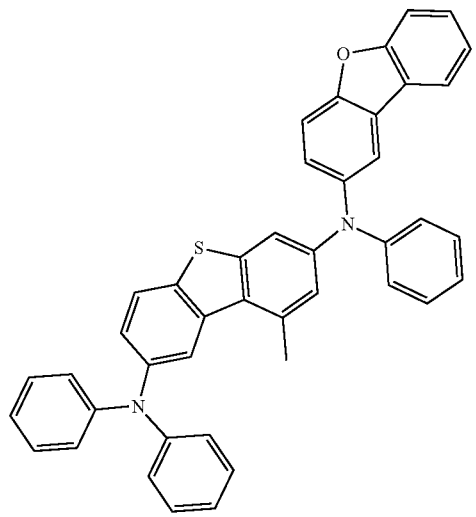
2-74
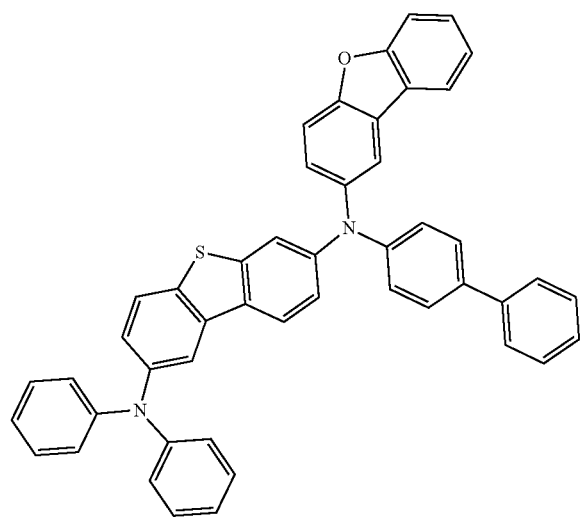
2-75
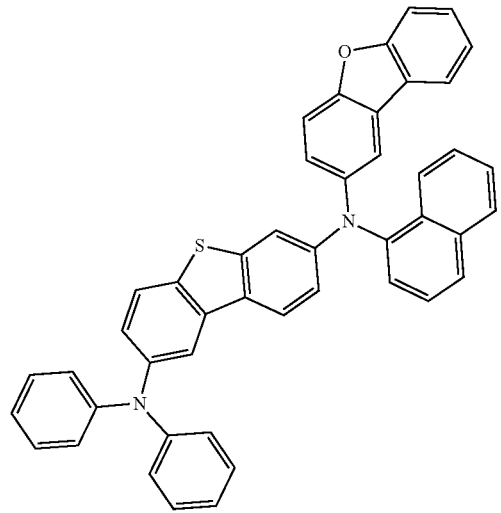
2-76
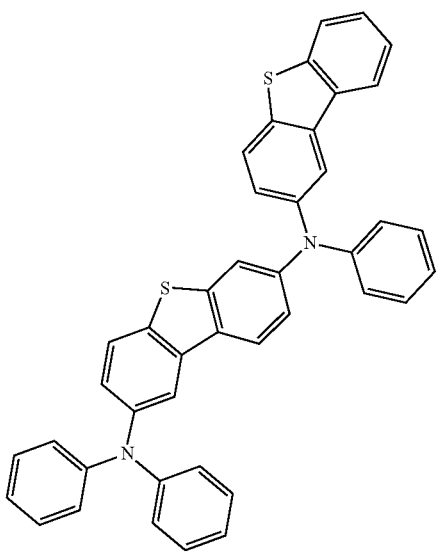
2-77
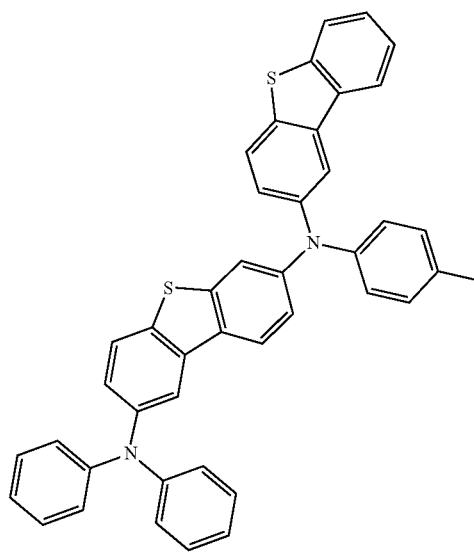

2-78
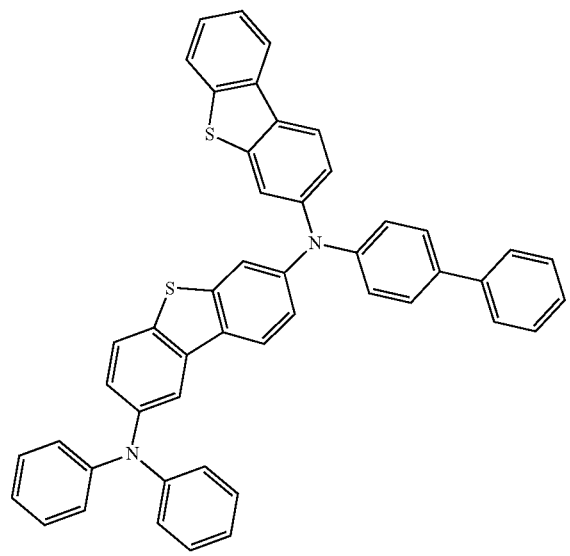
2-80
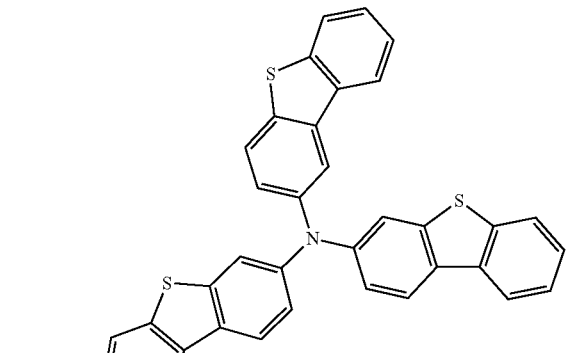
2-81
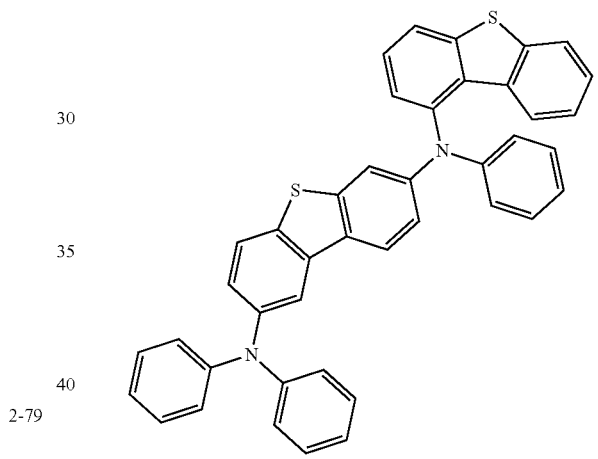
2-79
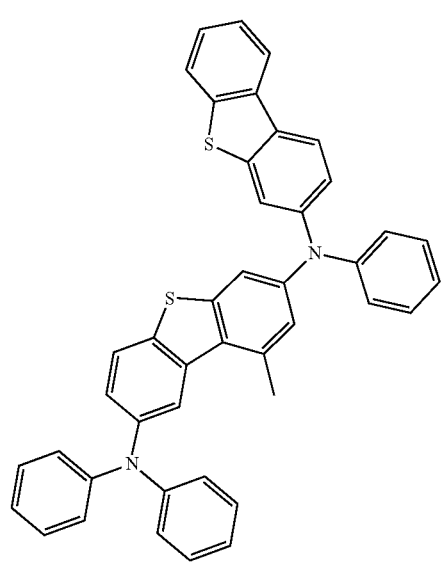
2-82
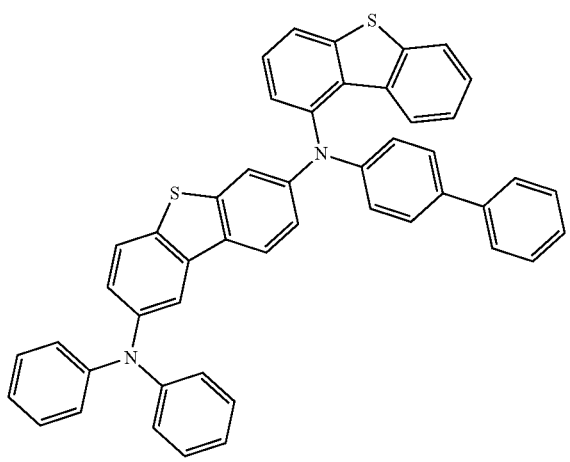

2-83
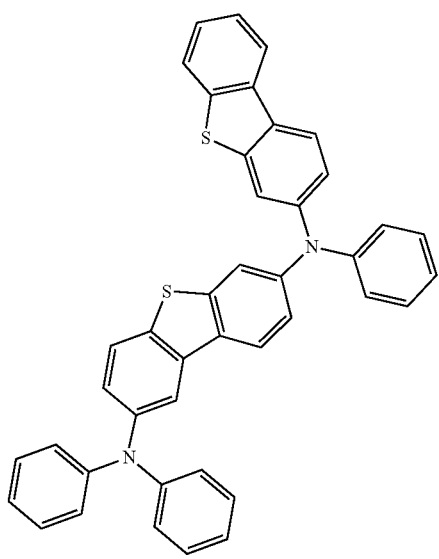
2-84
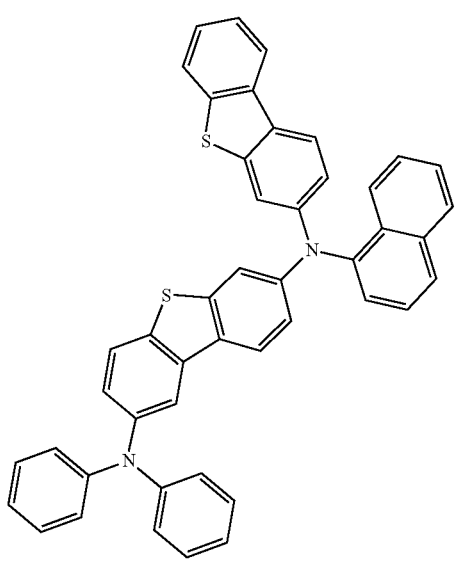
2-85
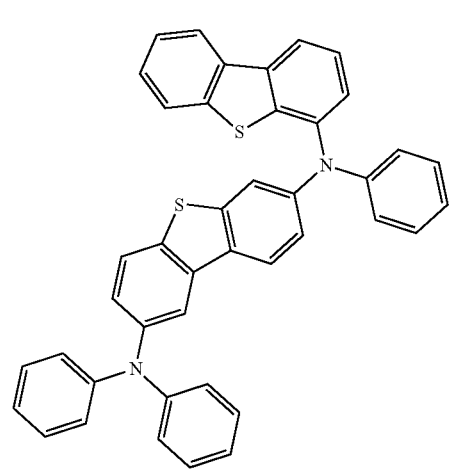
2-86
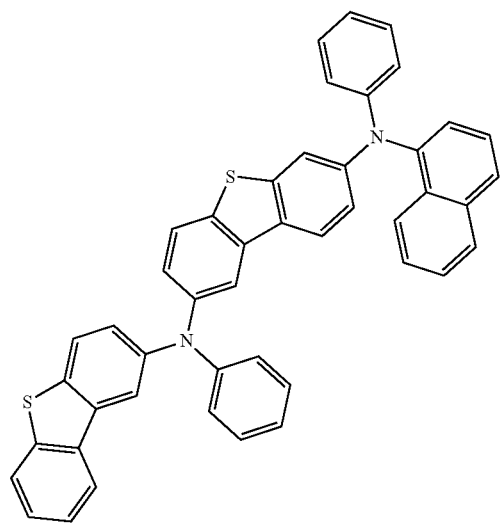
2-87
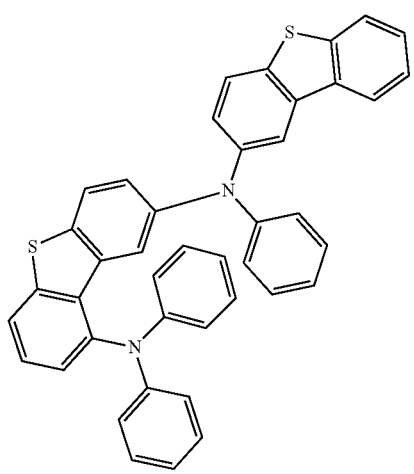
2-88
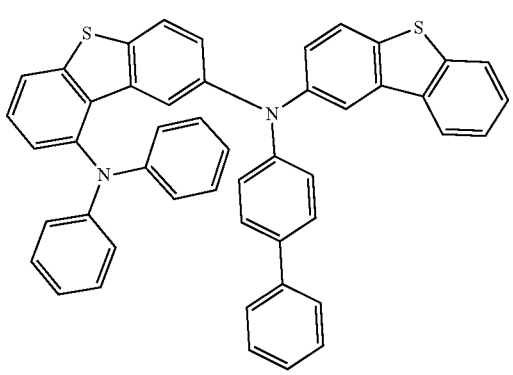

2-89
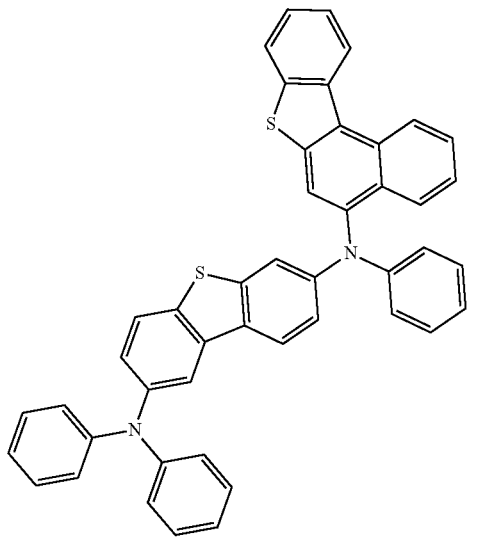
2-90
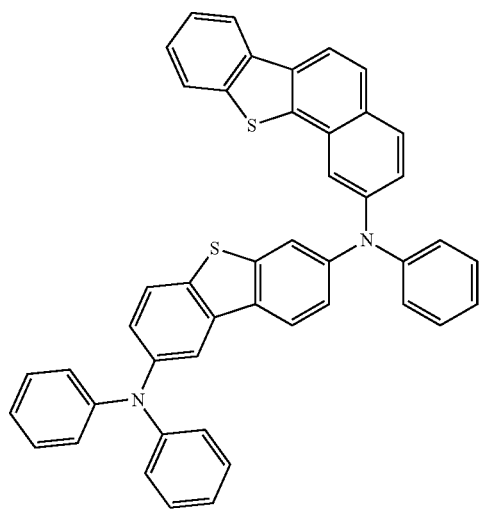
2-92
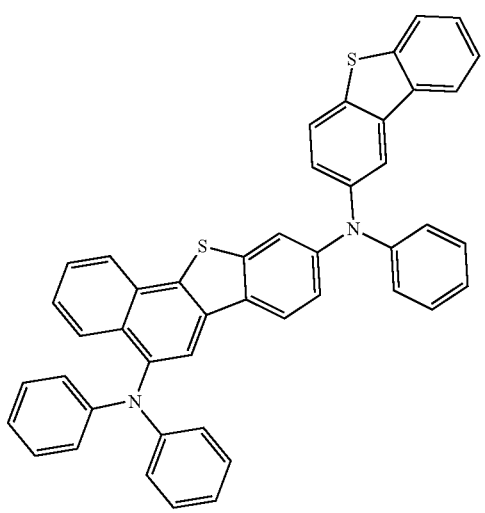
2-94
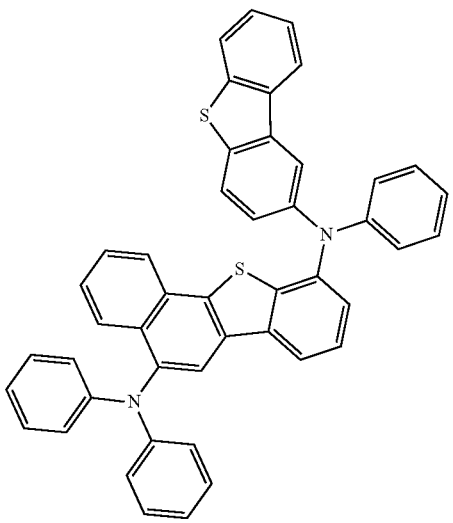
2-95
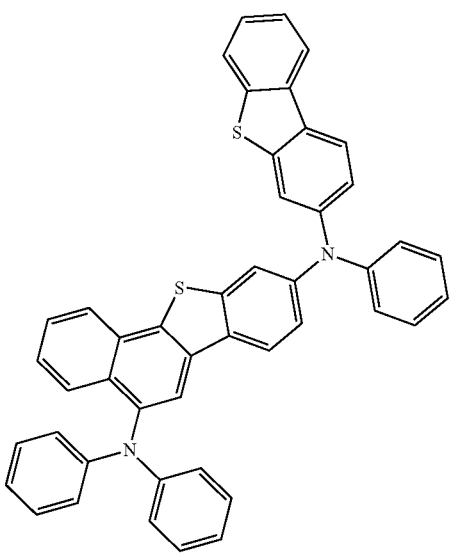
2-96
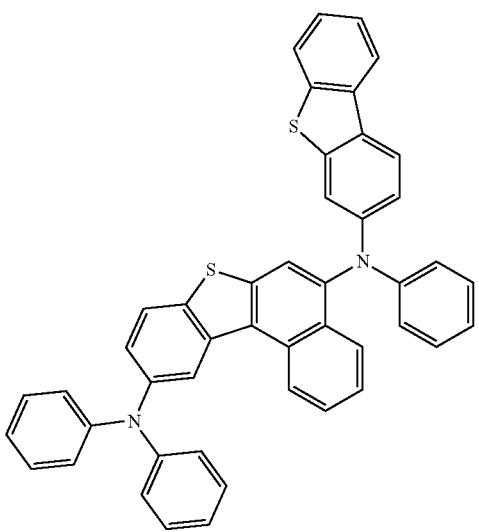

-continued
2-97
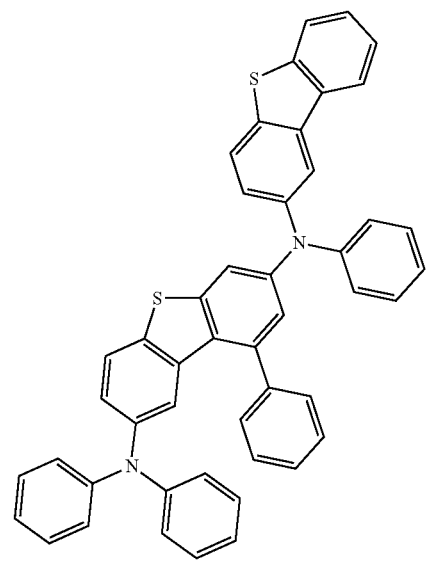
2-106
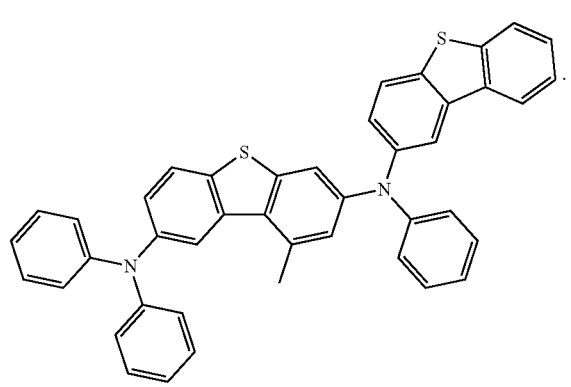
9. The organic electric element according to claim 1, wherein the second host compound represented by Formula (2) comprises any one of the following Compounds 3-1 to 3-124:
3-1
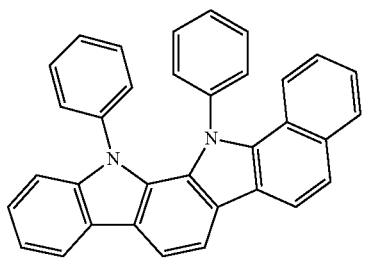
-continued
3-2
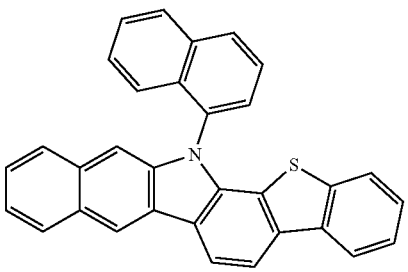
3-3
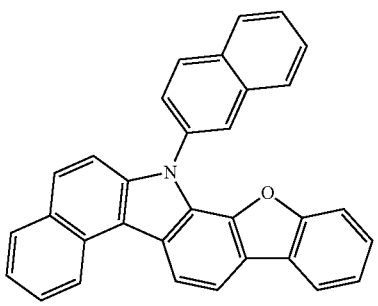
3-4
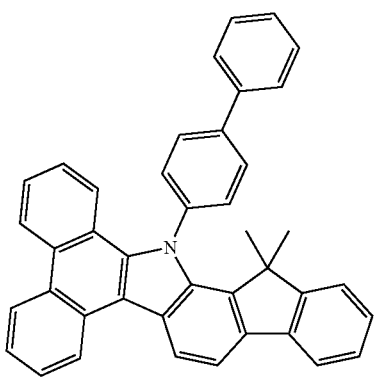
3-5
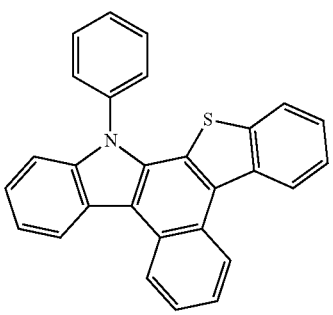
3-6
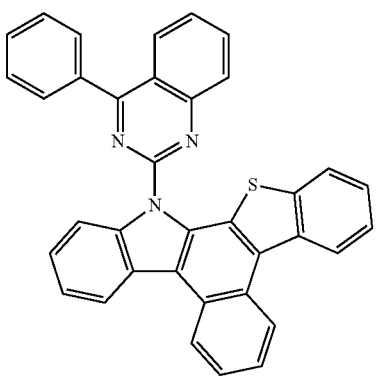

3-7
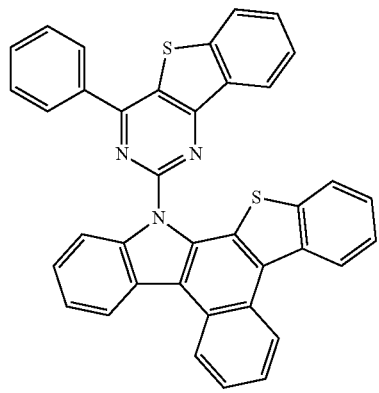
3-8
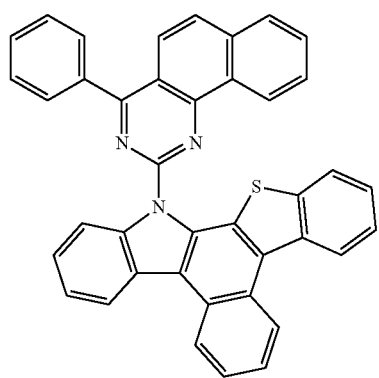
3-9
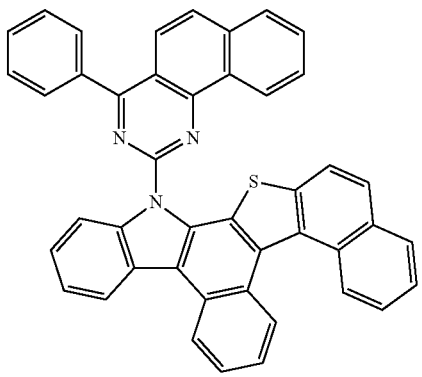
3-10
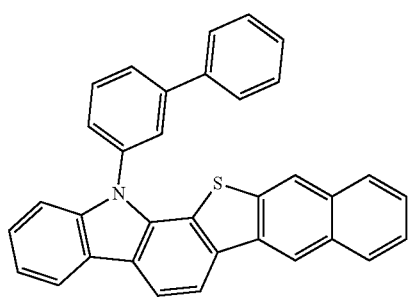
3-11
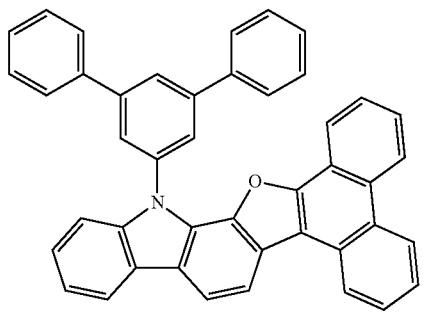
3-12
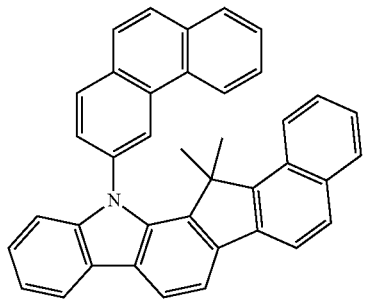
3-13
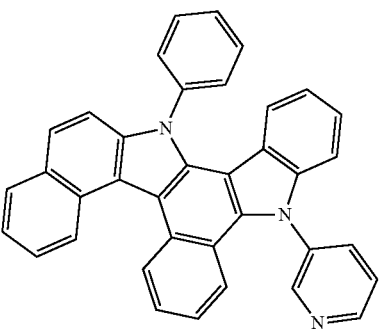
3-14
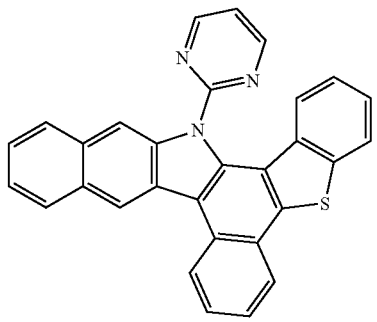

331
-continued
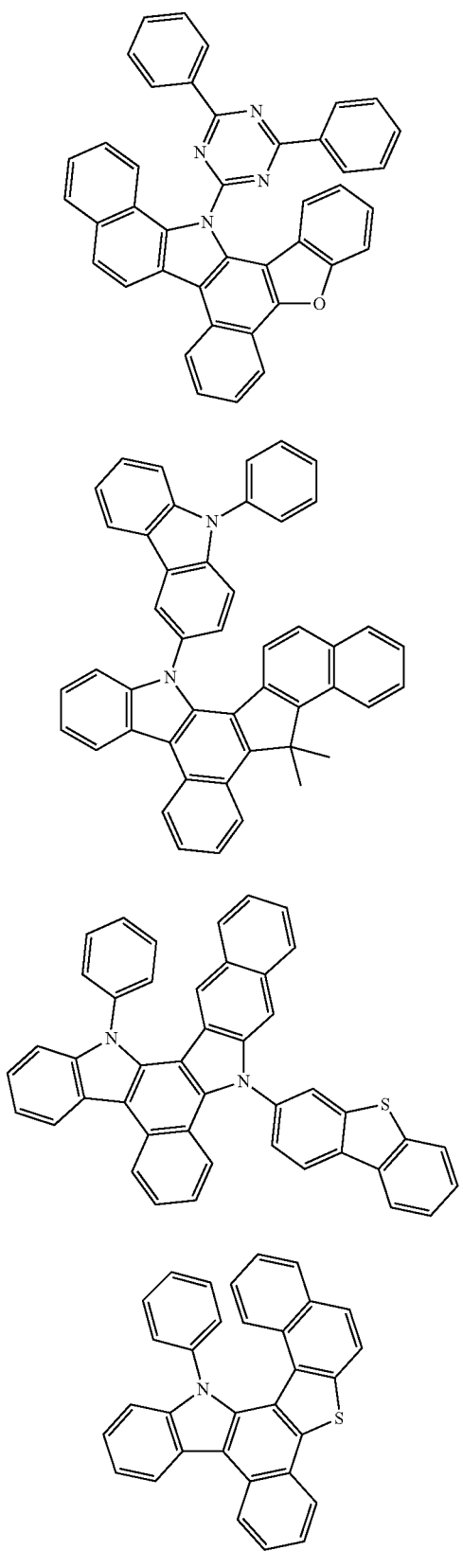
3-15
3-16
3-17
3-18
332
-continued
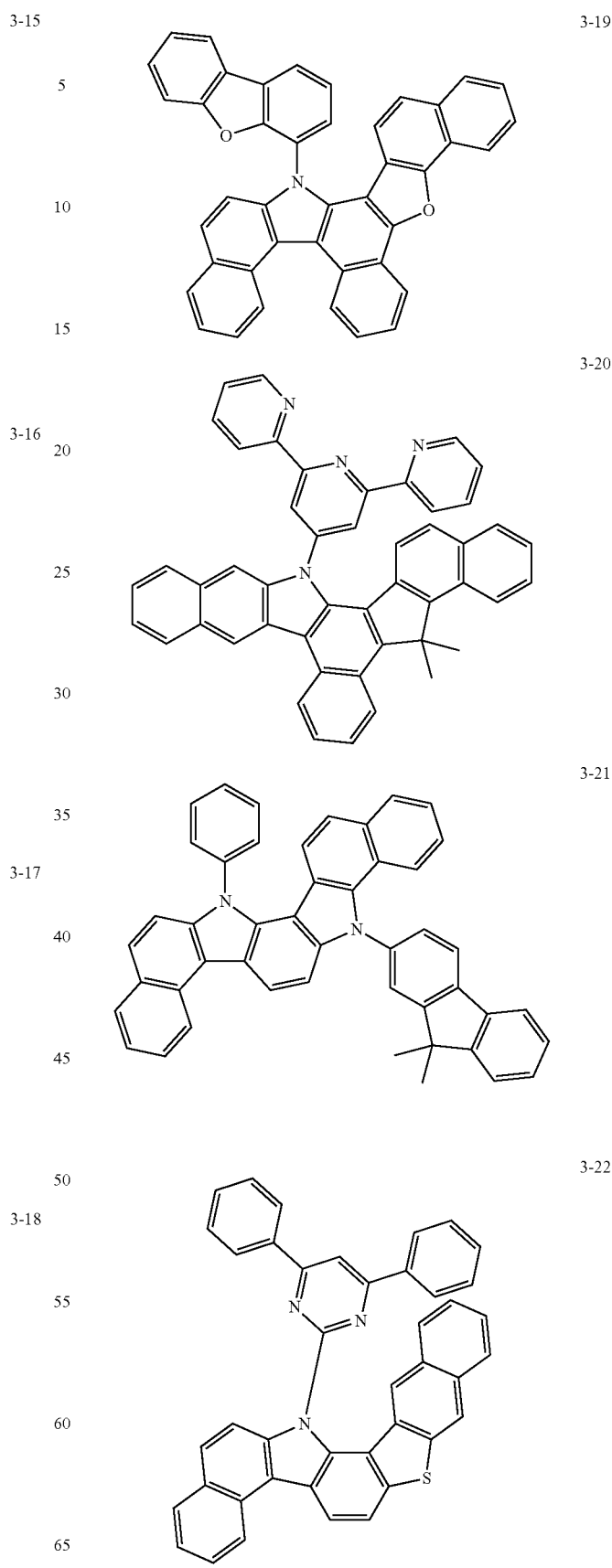
3-19
3-20
3-21
3-22

-continued
3-23
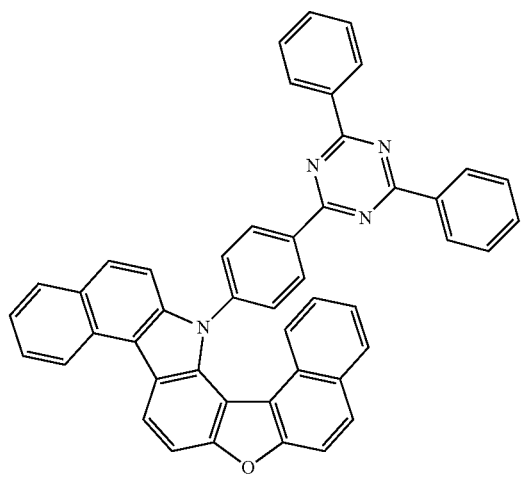
3-24
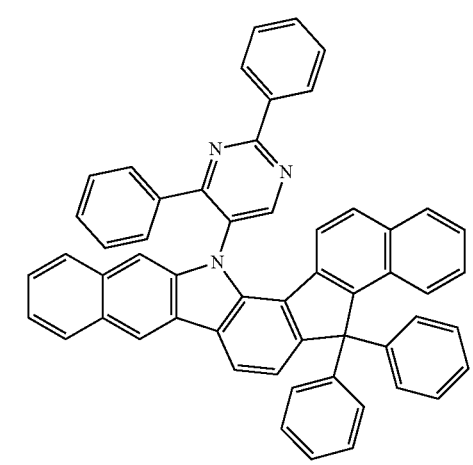
3-25
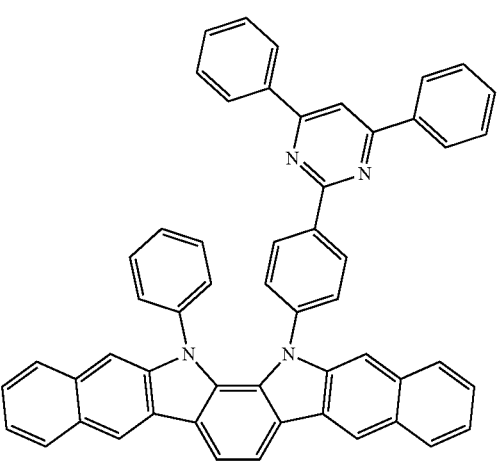
-continued
3-26
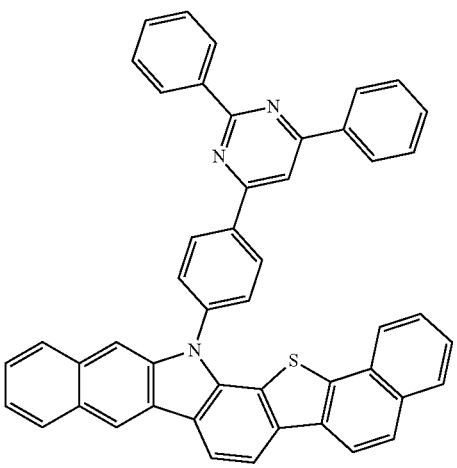
3-27
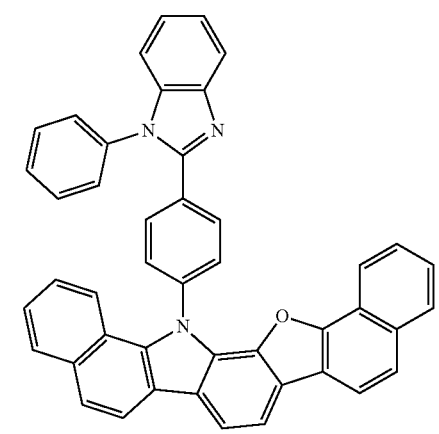
3-28
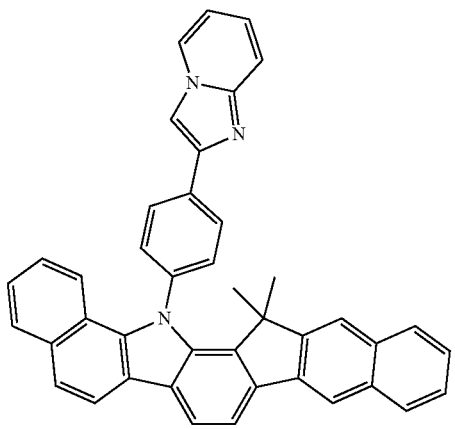
3-29
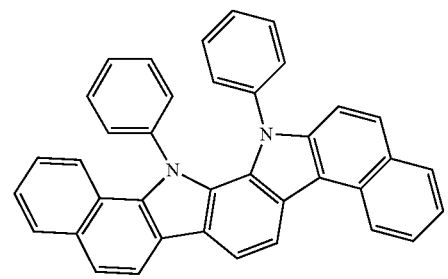

3-30
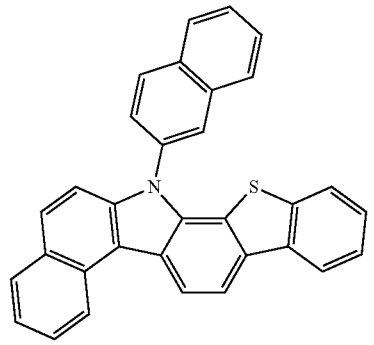
3-31
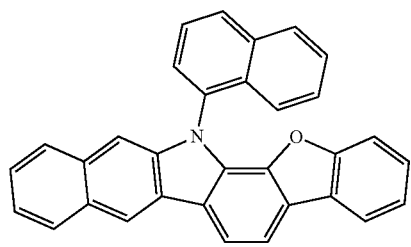
3-32
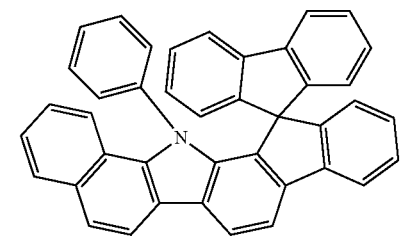
3-33
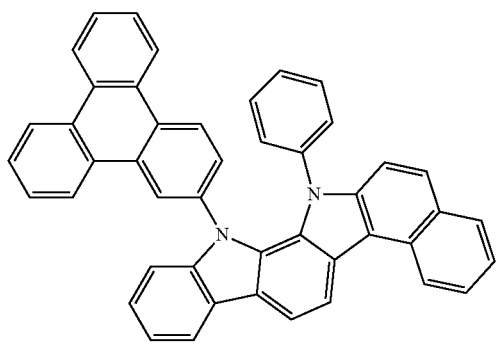
3-34
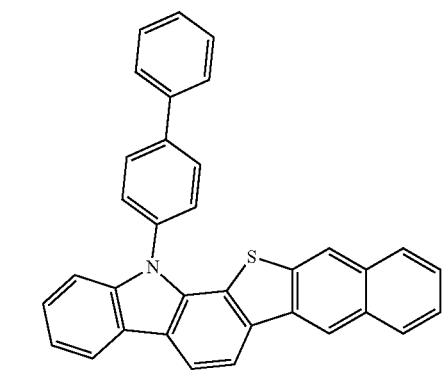
3-35
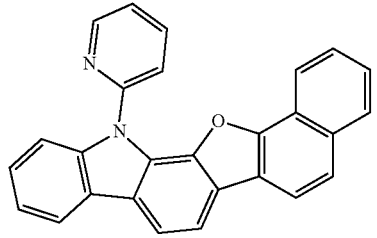
3-36
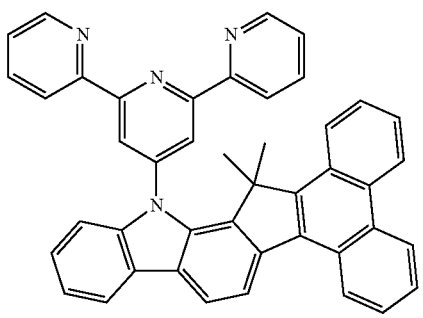
3-37
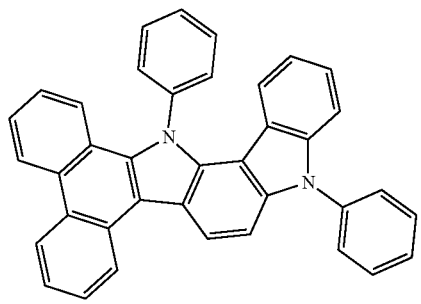
3-38
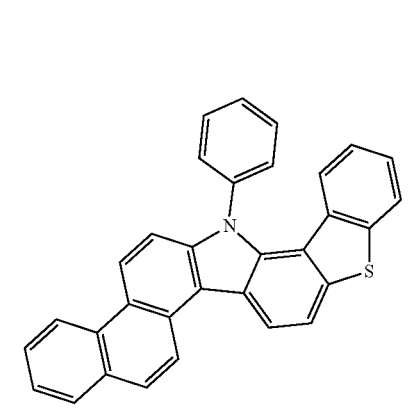
3-39
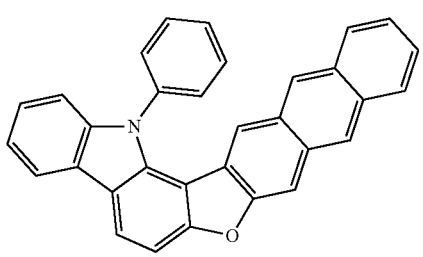

337
-continued
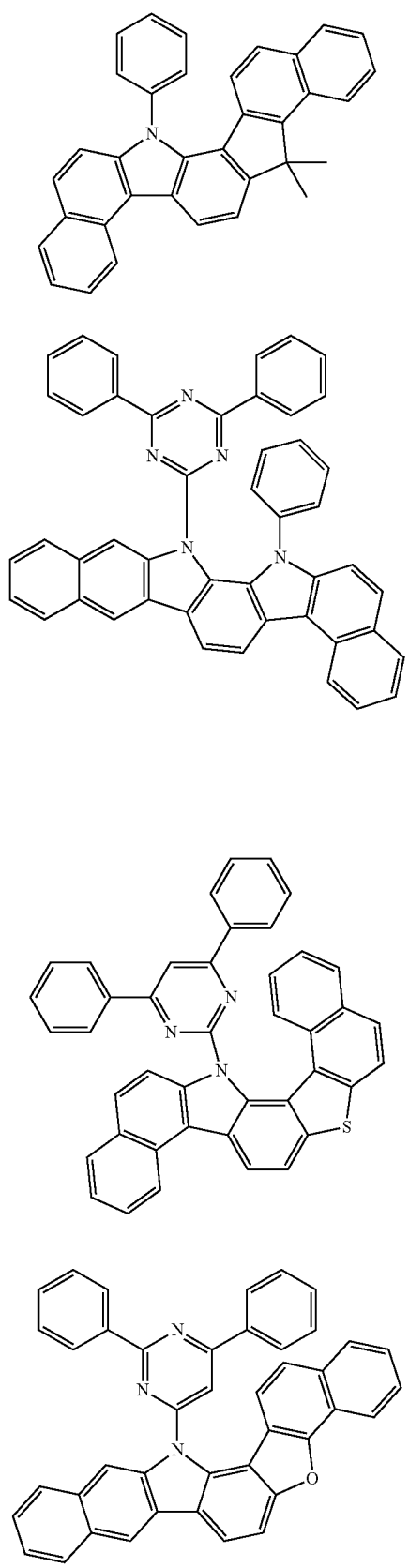
3-40
3-41
3-42
3-43
338
-continued
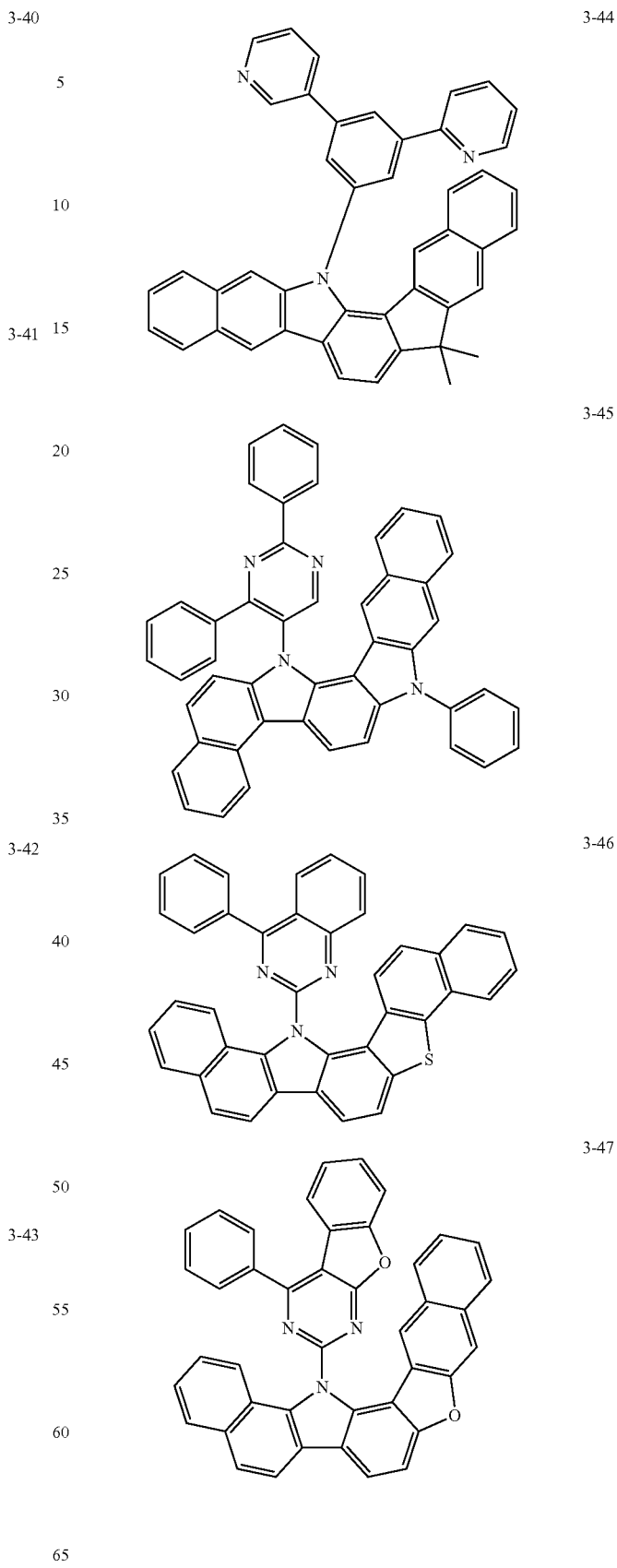
3-44
3-45
3-46
3-47

3-48
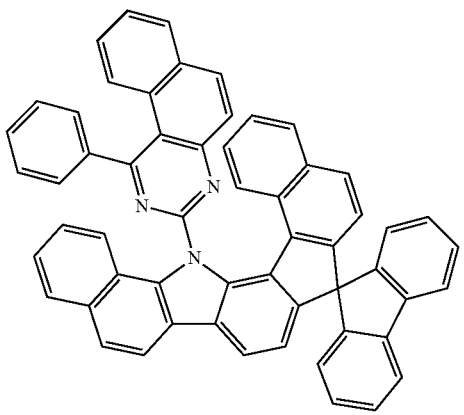
3-49
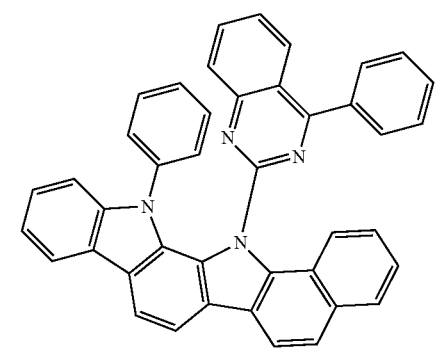
3-50
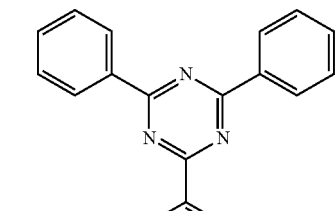
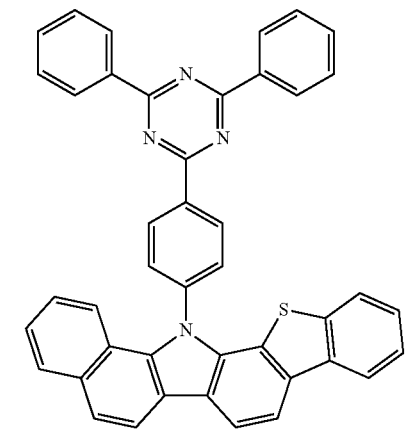
3-51
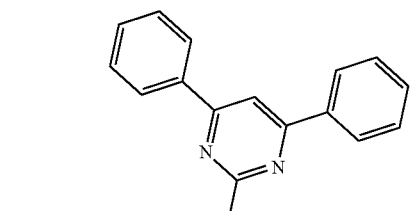
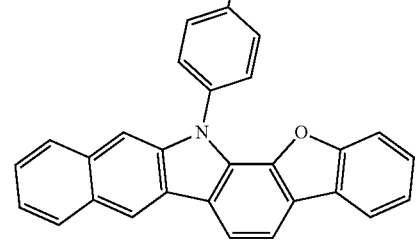
3-52
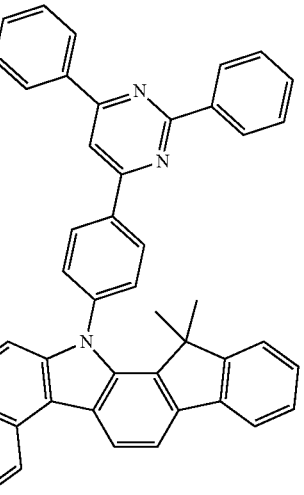
3-53
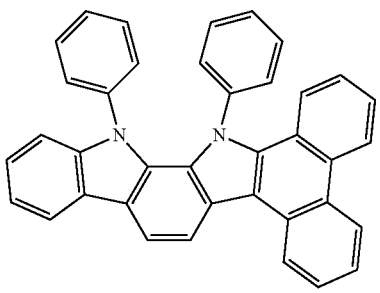
3-54
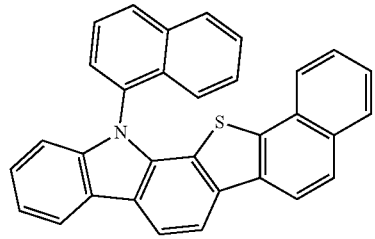
3-55
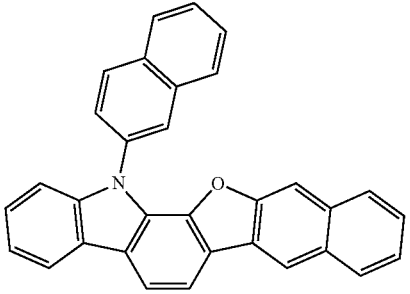
3-56
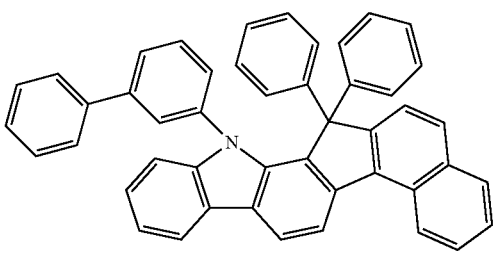

| 3-57 | 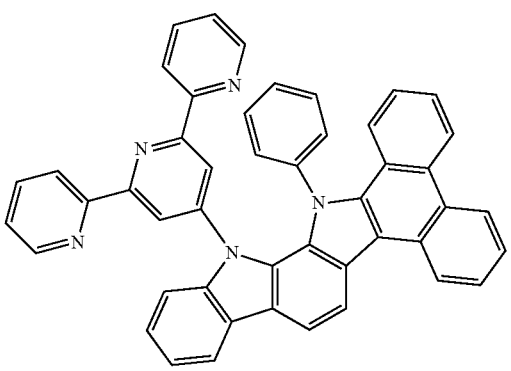 | 3-61 | 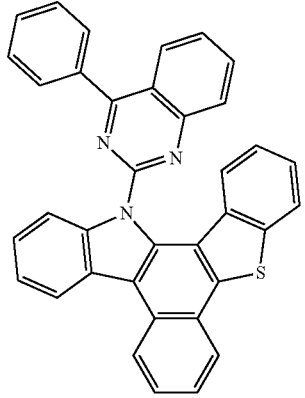 |
| 3-58 | 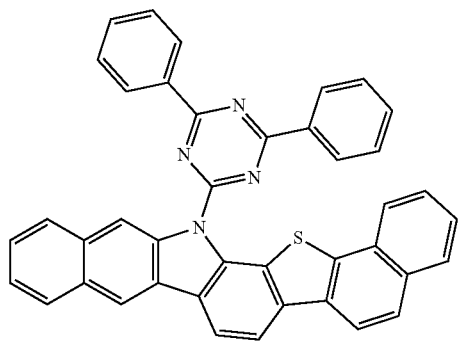 | 3-62 | 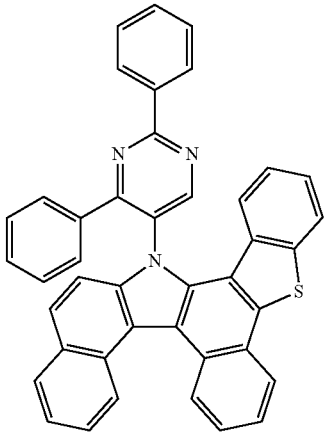 |
| 3-59 | 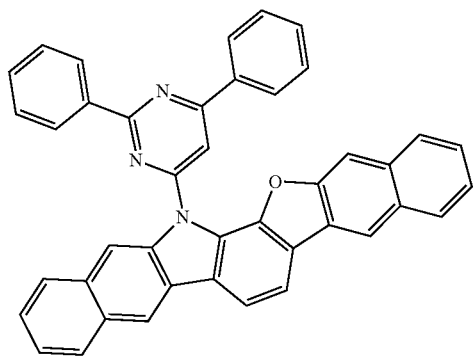 | 3-63 | 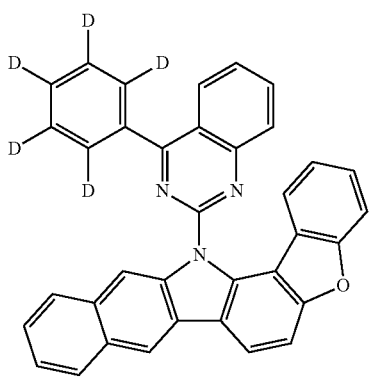 |
| 3-60 | 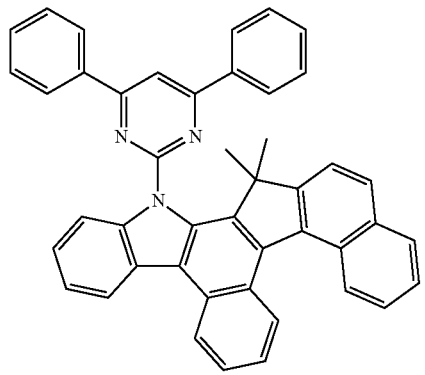 | 3-64 | 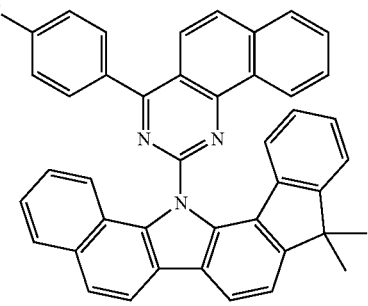 |

343
-continued
3-65
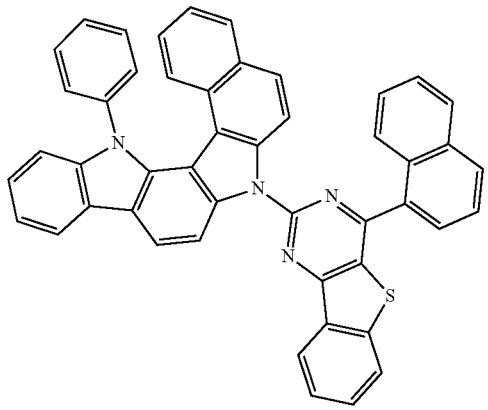
3-66
3-67
3-68
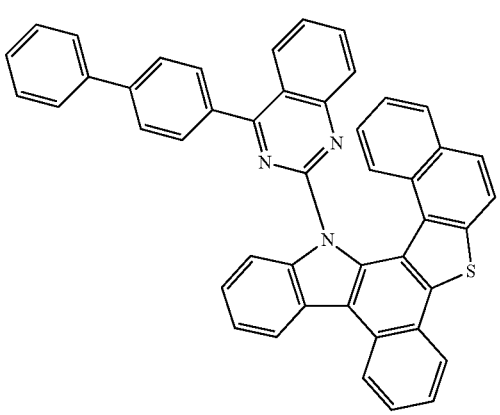
344
-continued
3-69
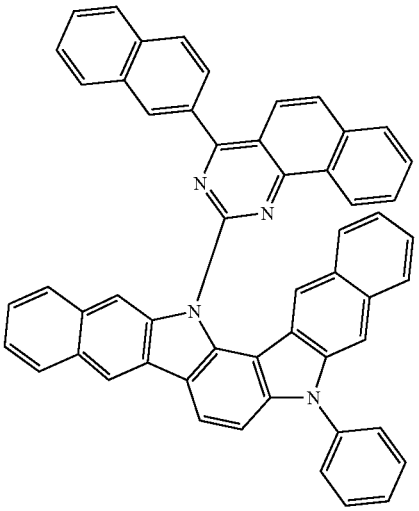
3-70
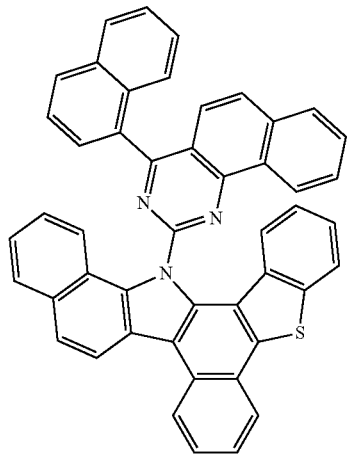
3-71
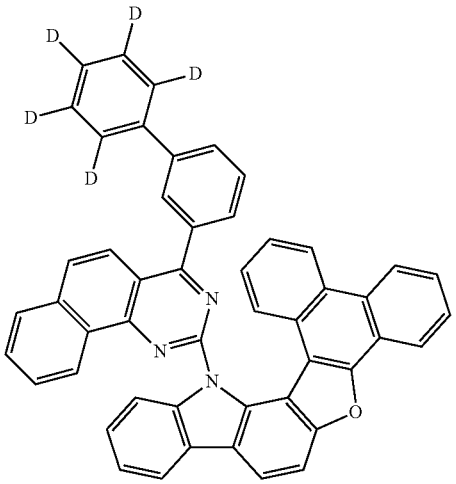

3-72
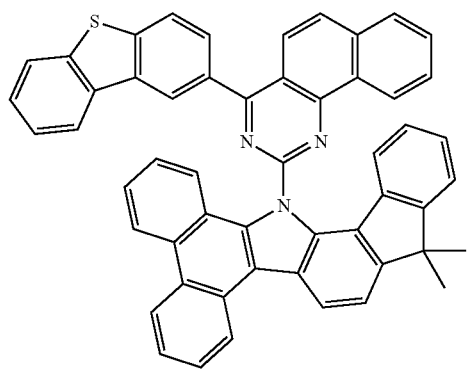
3-73
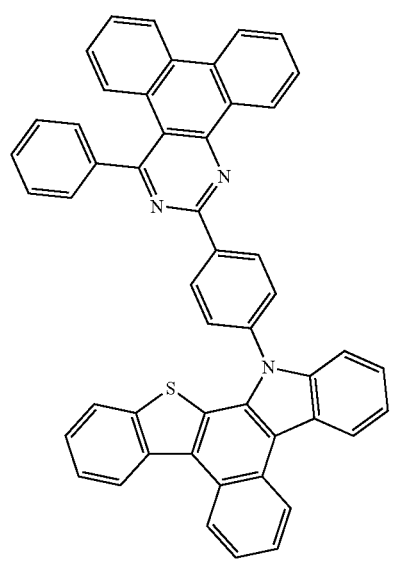
3-74
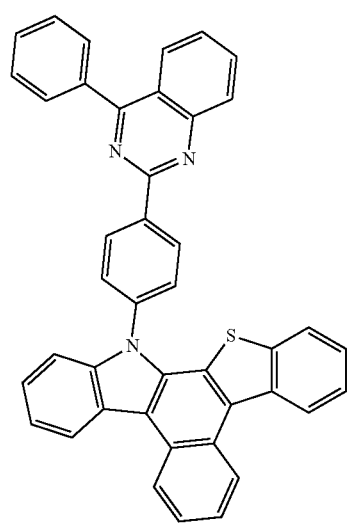
3-75
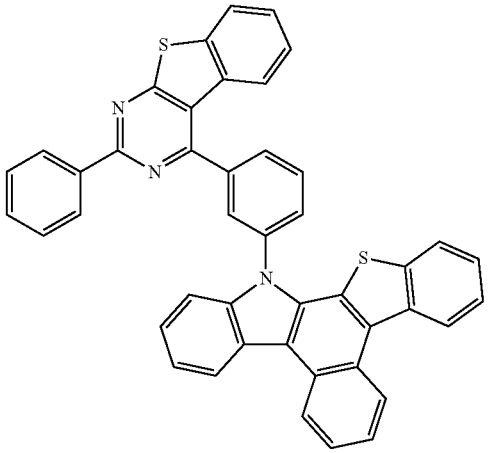
3-76
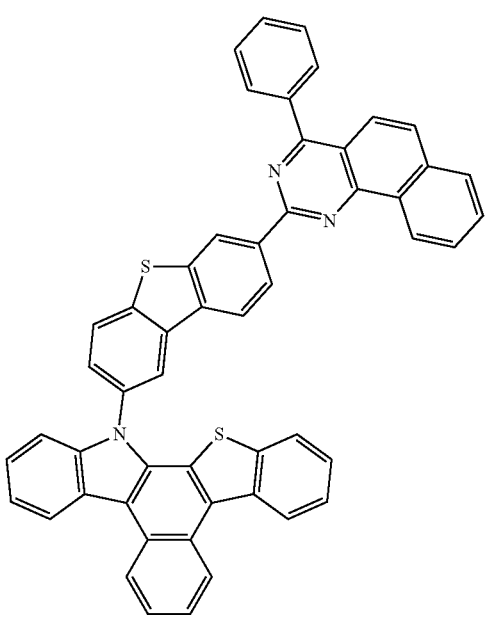
3-77
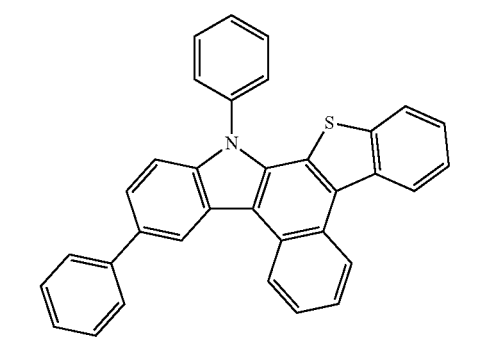

3-78
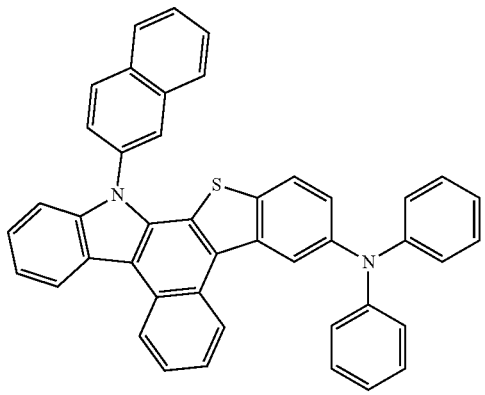
3-79
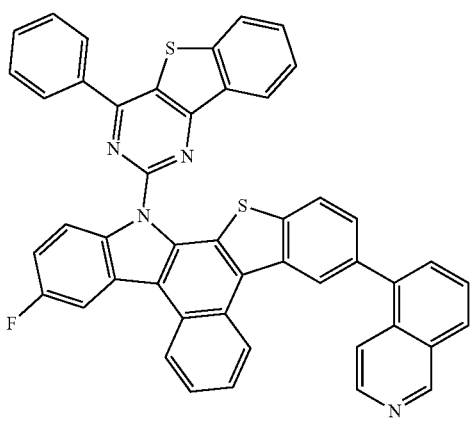
3-80
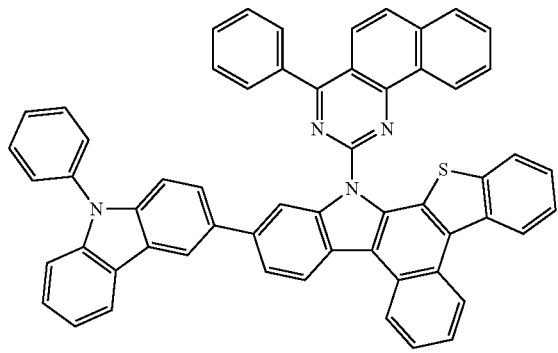
3-81
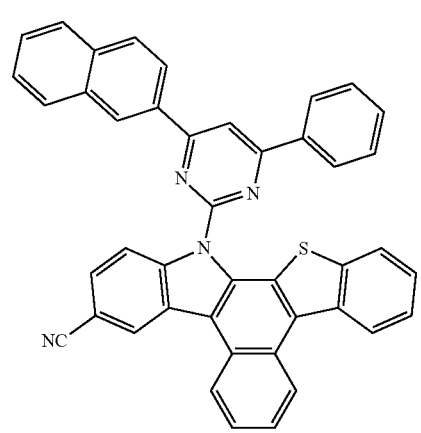
3-82
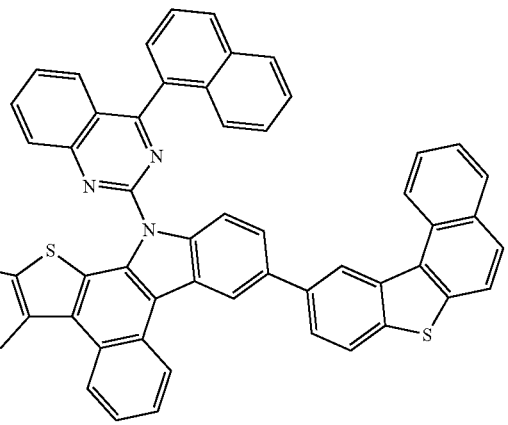
3-83
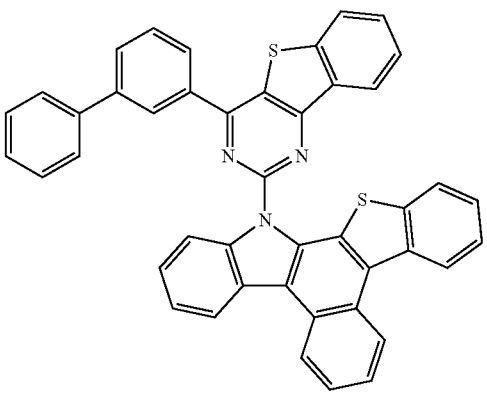
3-84
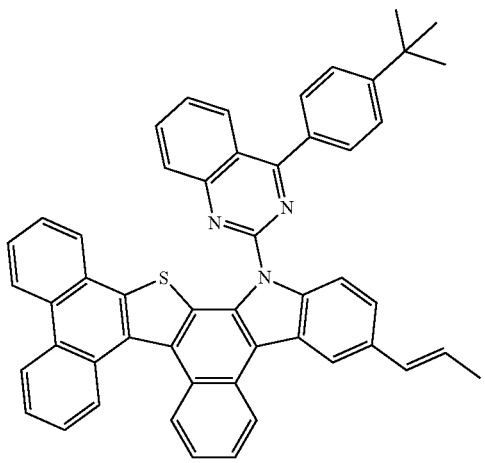

3-85
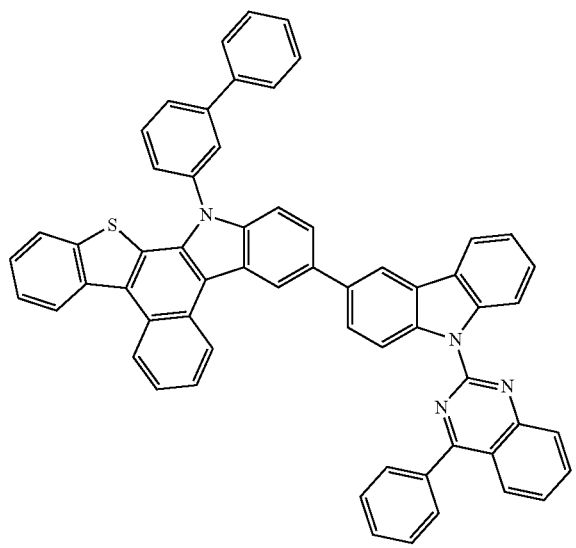
3-86
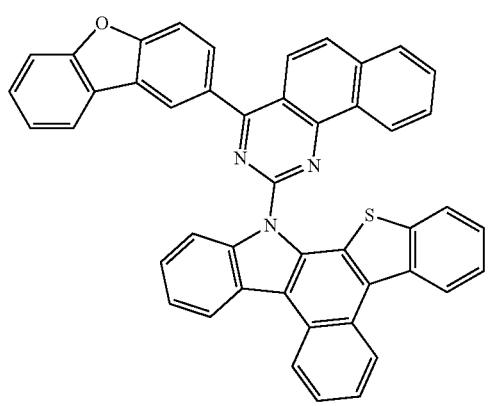
3-87
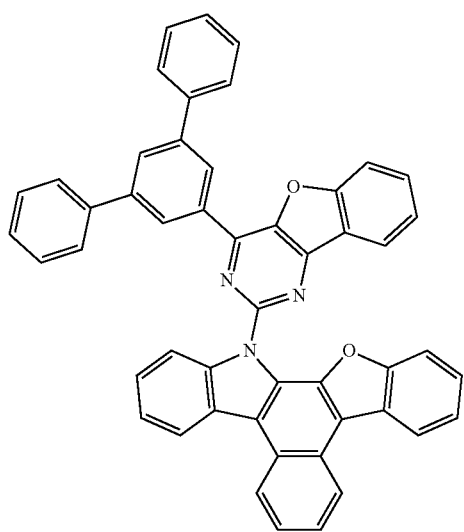
3-88
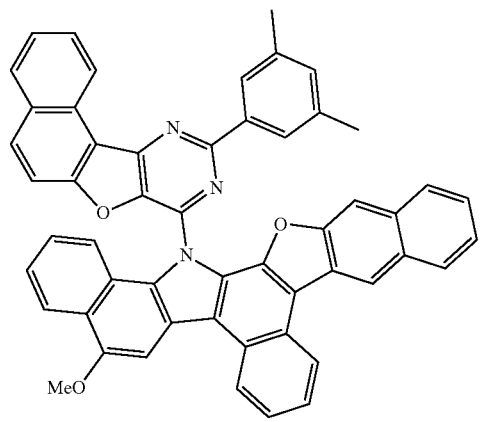
3-89
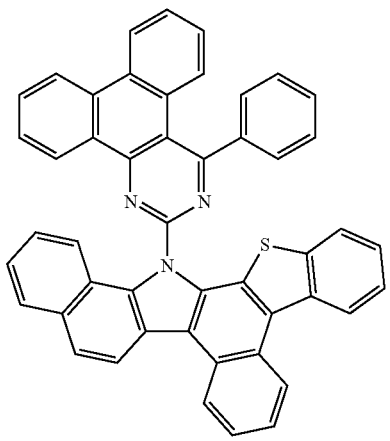
3-90
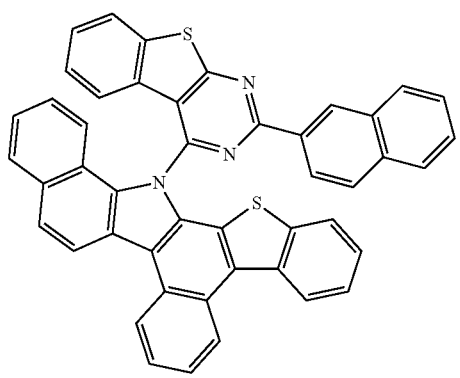

351
-continued
3-91
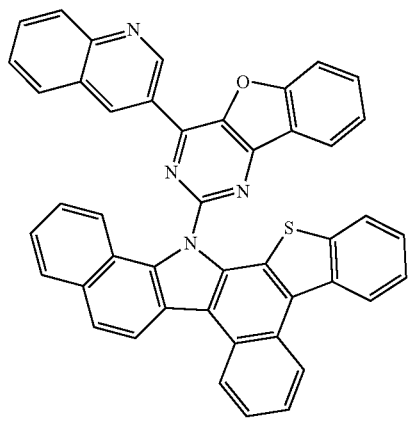
3-92
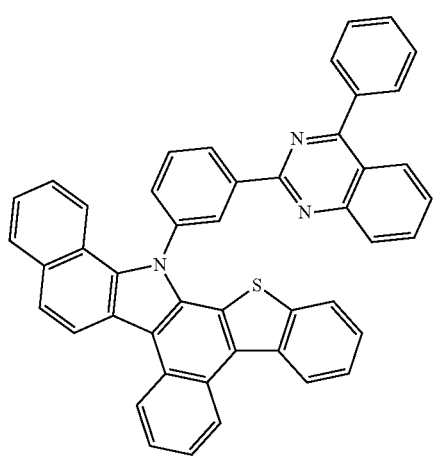
3-93
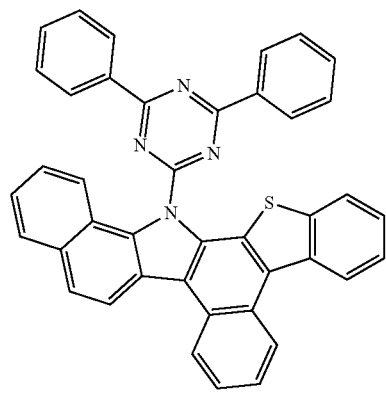
352
-continued
3-94
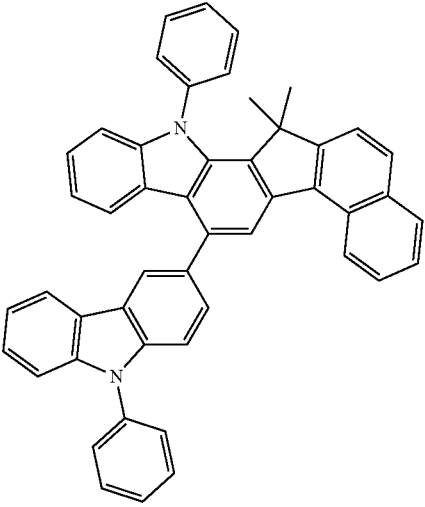
3-95
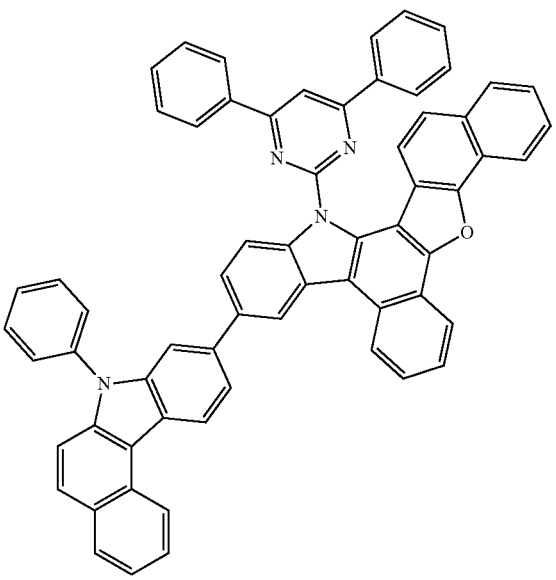
3-96
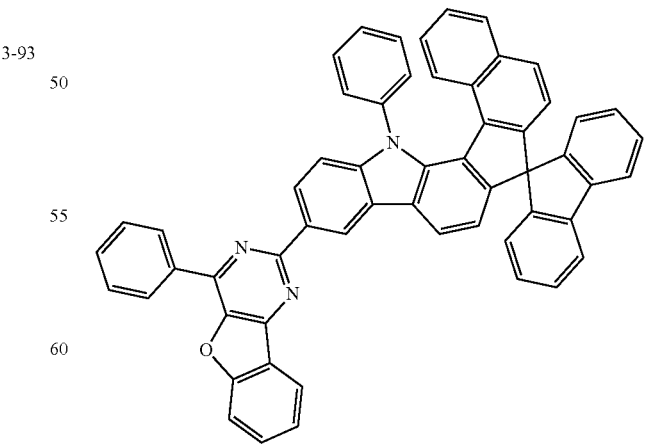

-continued
3-97
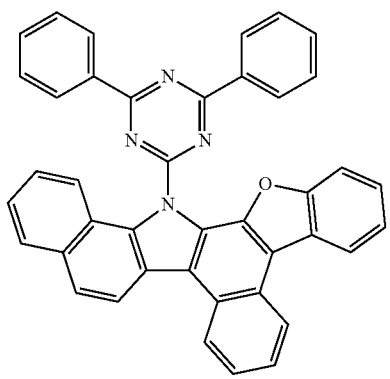
3-98
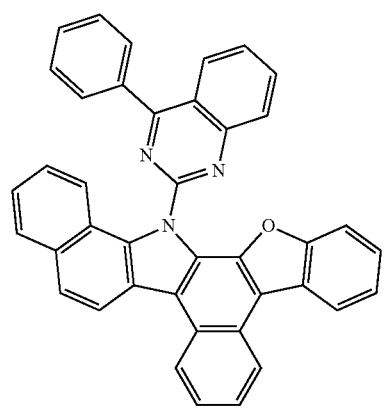
3-99
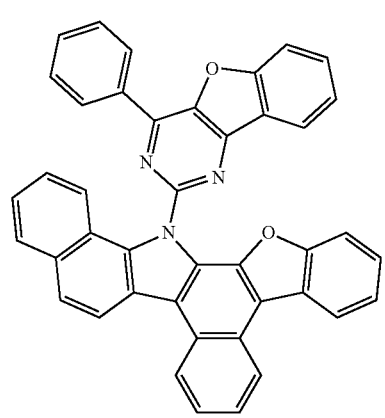
-continued
3-100
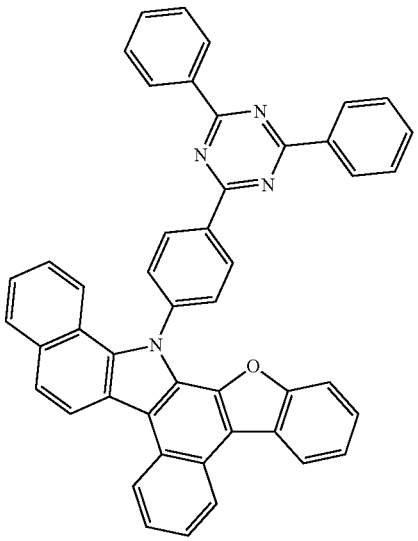
3-101
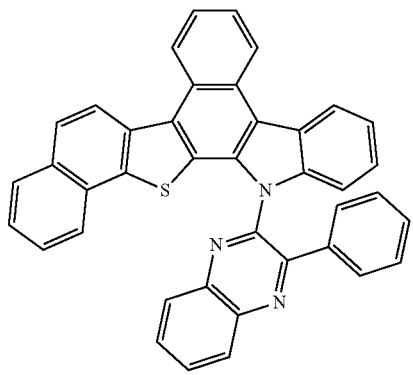
3-102
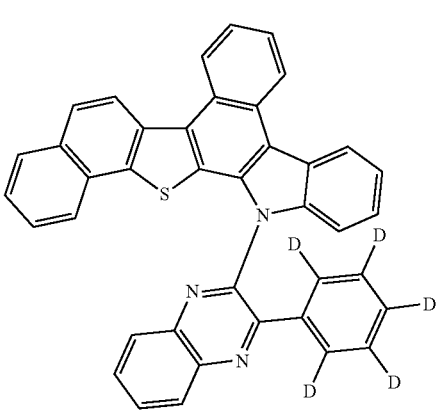

3-103
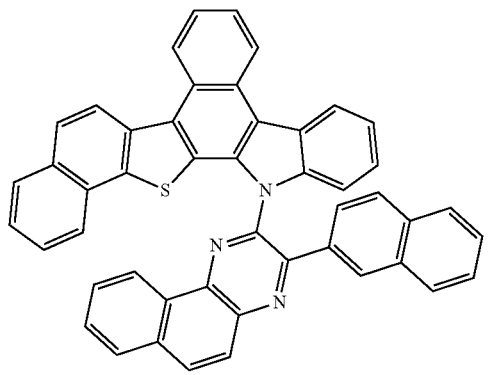
3-104
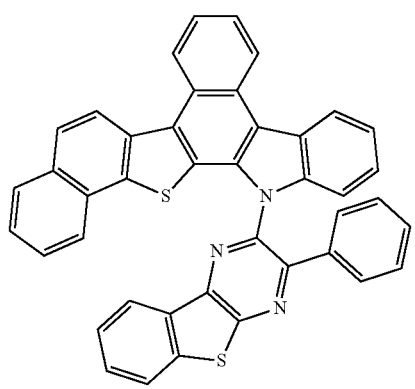
3-105
3-106
3-107
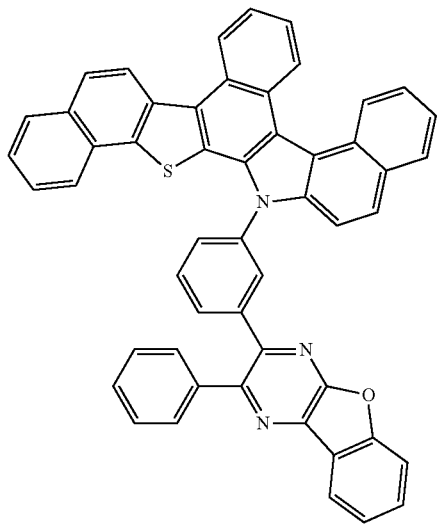
3-108
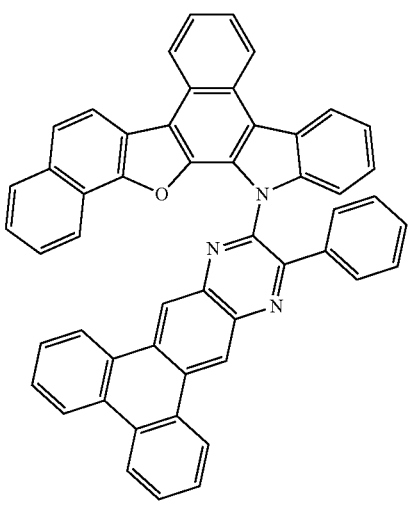
3-109
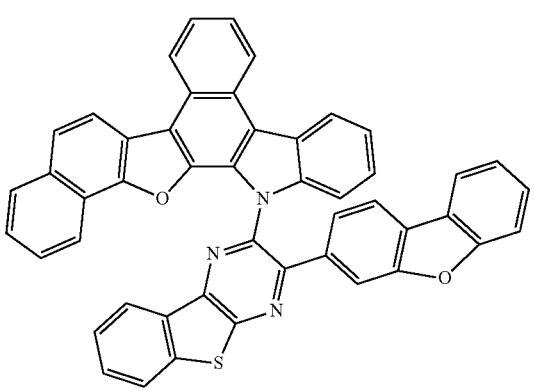

-continued
3-110
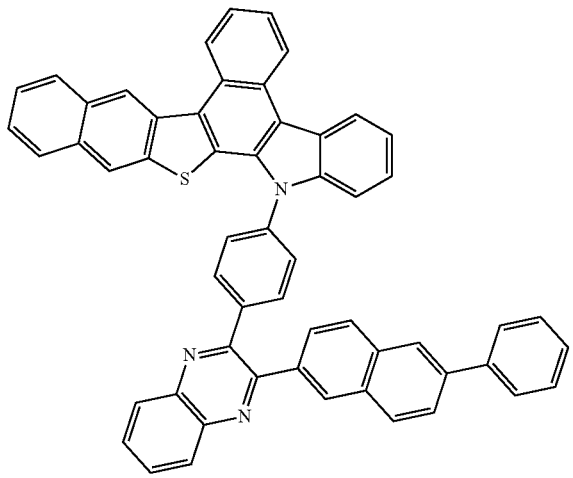
3-111
3-112
-continued
3-113
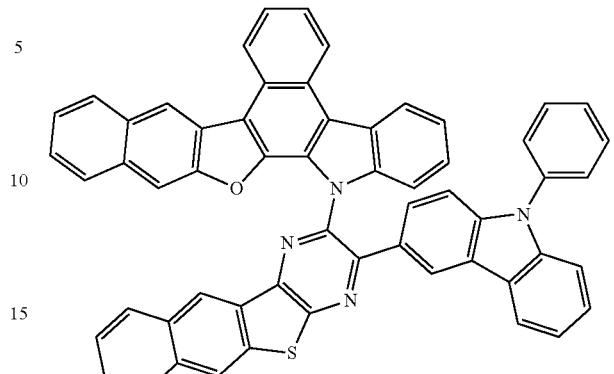
3-114
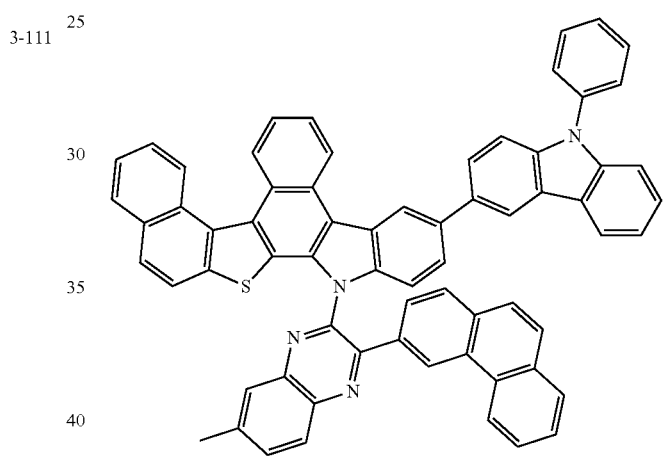
3-115
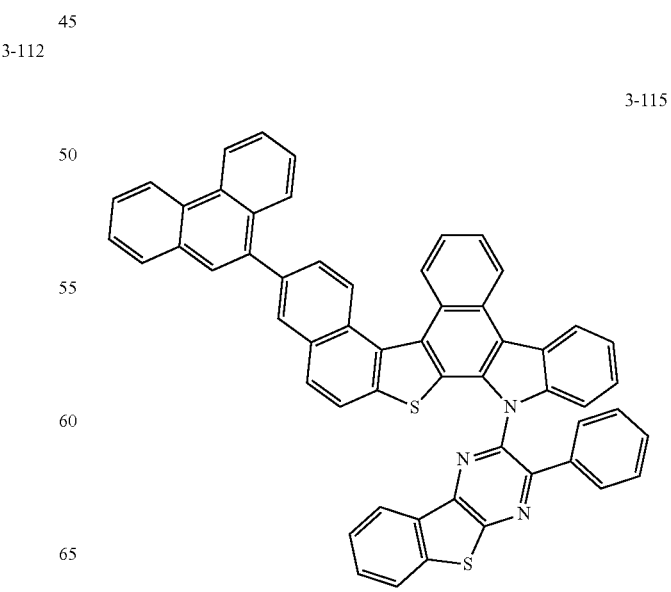

3-116
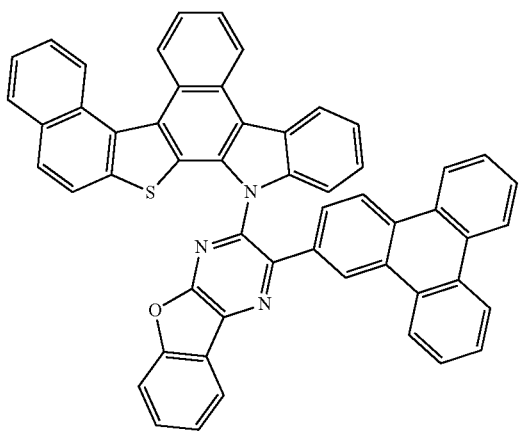
3-117
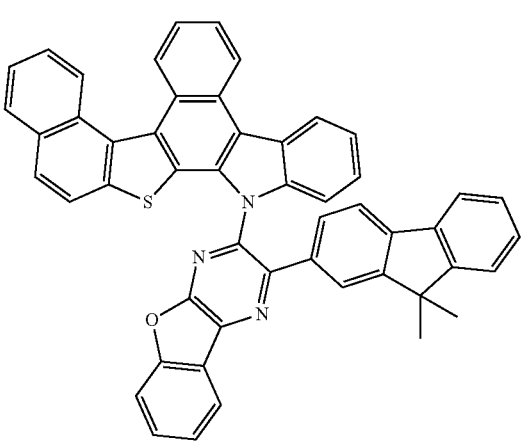
3-118
3-119
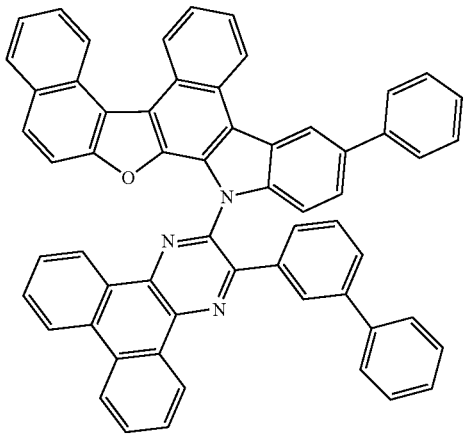
3-120
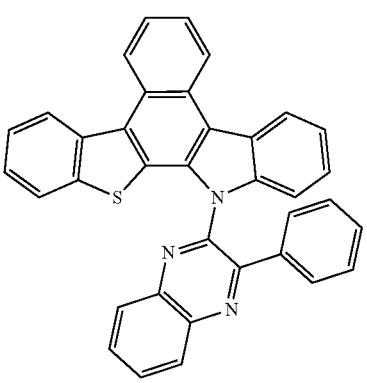
3-121
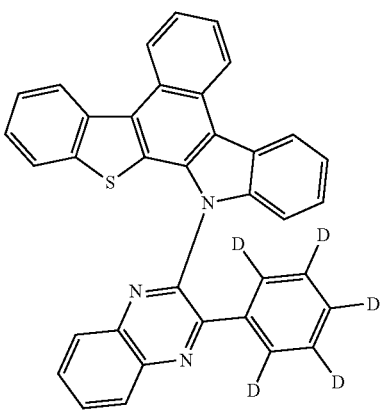
3-122
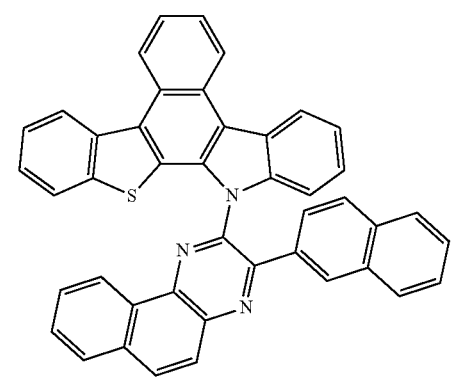

3-123

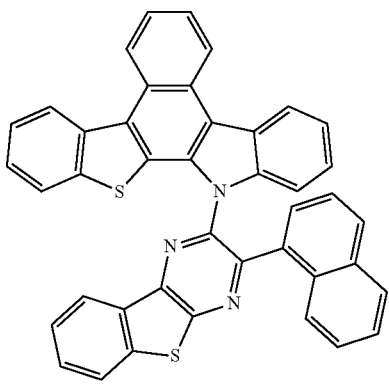

3-124

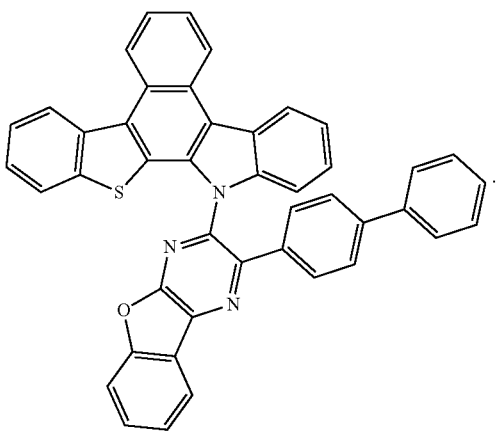

10. The organic electric element of claim 1, further comprising at least one hole transporting band layer between the first electrode and the emitting layer, wherein the hole transporting band layer comprises a hole transport layer, an emitting auxiliary layer, or both, and the hole transporting band layer comprises a compound represented by Formula (3-20).

11. The organic electric element according to claim 1, wherein the compounds represented by Formulas (3-20) and (2) are mixed in a ratio of 1: 9 to 9: 1 to be included in the emitting layer.

12. An organic electric element comprising:
a first electrode; a second electrode; and an organic material layer disposed between the first electrode and the second electrode and comprising at least an emitting auxiliary layer and an emitting layer, wherein the emitting auxiliary layer comprises a compound represented by Formula (3-20) and the emitting layer comprises a compound represented by Formula (2):

Formula (3-20)

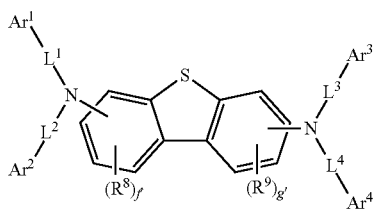

Formula (2)

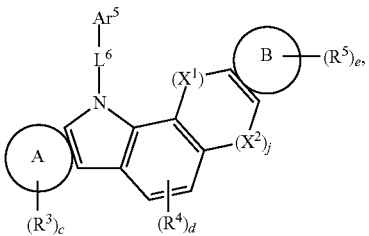

wherein
1) $Ar^1$, $Ar^2$, $Ar^3$, $Ar^4$ and $Ar^5$ are each independently selected from the group consisting of a $C_6$-$C_{60}$ aryl group, a dibenzothiophenyl, and dibenzofuranyl group, with the proviso that: i) neither $Ar^1$ and $Ar^2$, nor $Ar^3$ and $Ar^4$ are bonded to each other to form a ring, and ii) at least one of $L^3$-$Ar^3$ and $L^4$-$Ar^4$ is a dibenzothiophenyl or dibenzofuranyl group, and none of the remaining $Ar^1$, $Ar^2$, $Ar^3$ and $Ar^4$ is a fluorenyl group,
2) c and e are an integer of 0 to 10, d is an integer of 0 to 2, and f' and g' are integer of 0 to 3,
3) $R^3$, $R^4$, $R^5$, $R^8$ and $R^9$ are the same or different from each other, and are each independently selected from the group consisting of hydrogen; deuterium; halogen; a $C_6$-$C_{60}$ aryl group; a $C_2$-$C_{60}$ heterocyclic group including at least one heteroatom of O, N, S, Si or P; a $C_1$-$C_{50}$ alkyl group; a $C_2$-$C_{20}$ alkenyl group; a $C_2$-$C_{20}$ alkynyl group; or in case a, b, c, d, e, f' and g' are 2 or more, $R^3$, $R^4$, $R^5$, $R^8$ and $R^9$ are each in plural being the same or different, and a plurality of $R^3$ or a plurality of $R^4$ or a plurality of $R^5$ or a plurality of $R^8$ or a plurality of $R^9$, or two adjacent $R^8$ and $R^9$ may be bonded to each other to form an aromatic or heteroaromatic ring,
4) $L^1$, $L^2$, $L^3$, $L^4$, and $L^6$ are each independently selected from the group consisting of a single bond; a $C_6$-$C_{60}$ arylene group; and a $C_2$-$C_{60}$ heterocyclic group,
5) A and B are each independently a $C_6$-$C_{60}$ aryl group or a $C_2$-$C_{20}$ heterocyclic group, provided that when both A and B are a substituted or unsubstituted $C_6$ aryl group (phenyl group), d is 2, and $R^4$s are bonded to each other to form an aromatic or heterocyclic group,
6) i and i are 0 or 1, with the proviso that i+j is 1 or more, and when i or j is 0, it means a direct bond,
7) $X^1$ and $X^2$ are each independently N-$L^7$-$Ar^6$, O, S, or $CR^6R^7$, wherein $L^7$ is the same as $L^1$ to $L^4$ or $L^6$, wherein $Ar^6$ is the same as $Ar^1$ to $Ar^5$, and $R^6$ and $R^7$ are each independently hydrogen; a $C_6$-$C_{60}$ aryl group; a $C_2$-$C_{60}$ heterocyclic group; or a $C_1$-$C_{50}$ alkyl group and $R^6$ and $R^7$ may combine to each other to form a spiro ring,
wherein, the aryl group, arylene group, heterocyclic group, alkyl group, alkenyl group, may be substituted with one or more substituents selected from the group consisting of deuterium; halogen; cyano group; nitro group; $C_1$-$C_{20}$ alkoxyl group; $C_1$-$C_{20}$ alkyl group; $C_2$-$C_{20}$ alkenyl group; $C_6$-$C_{20}$ aryl group; $C_6$-$C_{20}$ aryl group substituted with deuterium; $C_2$-$C_{20}$ heterocyclic group; wherein the substituents may combine each other and form a saturated or unsaturated ring, wherein the term 'ring' means $C_3$-$C_{60}$ aliphatic ring or $C_6$-$C_{60}$ aromatic ring or a $C_2$-$C_{60}$ heterocyclic group or a fused ring formed by the combination of thereof and includes a saturated or unsaturated ring, and wherein Formula (3-20) has one of the following structures regarding the bonding position of the two amino substituents-N(L¹-Ar₁)(L₂-Ar²) and N(L³Ar³)(L⁴-Ar⁴):

C-3
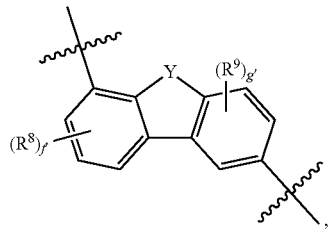

C-6
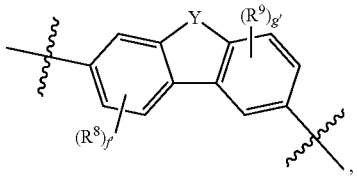

C-9
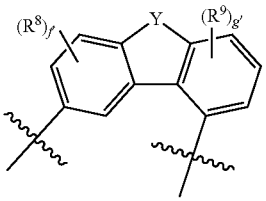

wherein Y is S, and $R^8$, $R^9$, f, g' are the same as defined above for Formula (3-20).

13. A display device comprising the organic electric element of claim 1; and a control part driving the display device.

14. A display device comprising the organic electric element of claim 12; and a control part driving the display device.

15. A display device according to claim 13, wherein the organic electric element is at least one of an OLED, an organic solar cell, an organic photo conductor(OPC), organic transistor(organic TFT) and an element for monochromic or white illumination.

16. A display device according to claim 14, wherein the organic electric element is an OLED, an organic solar cell, an organic photo conductor(OPC), organic transistor(organic TFT), or an element for monochromic or white illumination.

* * * * *